United States Patent
Spiegelman et al.

(10) Patent No.: US 12,194,080 B2
(45) Date of Patent: Jan. 14, 2025

(54) METHODS FOR IDENTIFICATION, ASSESSMENT, PREVENTION, AND TREATMENT OF METABOLIC DISORDERS USING PM20D1 AND N-LIPIDATED AMINO ACIDS

(71) Applicant: Dana-Farber Cancer Institute, Inc., Boston, MA (US)

(72) Inventors: Bruce M. Spiegelman, Waban, MA (US); Jonathan Z. Long, Menlo Park, CA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 820 days.

(21) Appl. No.: 15/770,648

(22) PCT Filed: Oct. 28, 2016

(86) PCT No.: PCT/US2016/059289
§ 371 (c)(1),
(2) Date: Apr. 24, 2018

(87) PCT Pub. No.: WO2017/075329
PCT Pub. Date: May 4, 2017

(65) Prior Publication Data
US 2021/0106661 A1    Apr. 15, 2021

Related U.S. Application Data

(60) Provisional application No. 62/248,007, filed on Oct. 29, 2015, provisional application No. 62/248,365, filed on Oct. 30, 2015, provisional application No. 62/355,120, filed on Jun. 27, 2016, provisional application No. 62/395,735, filed on Sep. 16, 2016.

(51) Int. Cl.
| | | |
|---|---|---|
| *A61K 38/50* | (2006.01) | |
| *A61P 3/10* | (2006.01) | |
| *C12N 9/80* | (2006.01) | |
| *C12Q 1/44* | (2006.01) | |
| *G01N 33/50* | (2006.01) | |

(52) U.S. Cl.
CPC .............. *A61K 38/50* (2013.01); *A61P 3/10* (2018.01); *C12N 9/80* (2013.01); *C12Q 1/44* (2013.01); *G01N 33/502* (2013.01); *C12Y 305/01014* (2013.01); *G01N 2800/04* (2013.01)

(58) Field of Classification Search
None
See application file for complete search history.

(56) References Cited

U.S. PATENT DOCUMENTS

| | | |
|---|---|---|
| 7,541,359 B2 | 6/2009 | Apodaca et al. |
| 2008/0003673 A1 | 1/2008 | Abuin et al. |

FOREIGN PATENT DOCUMENTS

| | | |
|---|---|---|
| WO | WO-2007/100722 A2 | 9/2007 |
| WO | WO-2012/030983 A2 | 3/2012 |
| WO | WO-2013/142571 A2 | 9/2013 |

OTHER PUBLICATIONS

Simmons and Michels (2015) "Type 1 diabetes: A predictable disease", World Journal of Diabetes, 6(3): 380-90. (Year: 2015).*
Shortle (2009) "One sequence plus one mutation equals two folds", Proceedings of the National Academy of Science, USA., 106(50): 21011-12. (Year: 2009).*
Roder, et al. (2016) "Pancreatic regulation of glucose homeostasis", Experimental & Molecular Medicine, 48: e219, 19 pages long. (Year: 2016).*
Winzell and Ahren (2004) "The High-Fat Diet-Fed Mouse: A Model for Studying Mechanisms and Treatment of Impaired Glucose Tolerance and Type 2 Diabetes", Diabetes, 53(S3): S215-19. (Year: 2014).*
Casal and Haskins (2006) "Large animal models and gene therapy", European Journal of Human Genetics, 14: 266-72. (Year: 2006 ).*
Long, et al. (2016) "The Secreted Enzyme PM20D1 Regulates Lipidated Amino Acid Uncouplers of Mitochondria" Cell, 166: 424-35. (Year: 2016).*
Gomez-Uriz et al., "Obesity and ischemic stroke modulate the methylation levels of KCNQ1 in white blood cells," human molecular genetics, 24(5):1432-1440 (2015).
Larrick et al., "Uncoupling mitochondrial respiration for diabesity," Rejuvenation research, 19(4):337-340 (2016).
Long et al., "The secreted enzyme PM20D1 regulates lipidated amino acid uncouplers of mitochondria," Cell, 166(2):424-435 (2016).
Partial European Search Report and Written Opinion received for EP Patent Application No. EP16860861 mailed Mar. 8, 2019.
Smorlesi et al., "The adipose organ: white-brown adipocyte plasticity and metabolic inflammation," Obesity Reviews, 13:83-96 (2012).
Bab et al., "Skeletal Lipidomics: Regulation of Bone Metabolism by Fatty Acid Amide Family," Brit J Pharmacol, 163(7): 1441-1446 (2011).
International Search Report and Written Opinion for International Patent Application No. PCT/US/16/59289 mailed Apr. 12, 2017.
Smoum et al., "Oleoyl Serine, an Endogenous N-acyl Amide, Modulates Bone Remodeling and Mass," P Natl Acad Sci USA, 107(41): 17710-17715 (2010).
Wang et al., "N-Oleoyl Glycine, a Lipoamino Acid, Stimulates Adipogenesis Associated with Activation of CB1 Receptor and Akt Signaling Pathway in 3T3-L1 Adipocyte," Biochem Bioph Res Co, 466(3): 438-443 (2015).
Extended European Search Report and Written Opinion received for EP Patent Application No. EP16860861 mailed May 21, 2019.

(Continued)

*Primary Examiner* — Robert M Kelly
(74) *Attorney, Agent, or Firm* — Foley Hoag LLP

(57) ABSTRACT

The present invention relates to methods for identifying, assessing, preventing, and treating metabolic disorders and modulating metabolic processes using PM20D1 and N-lipidated amino acids.

8 Claims, 27 Drawing Sheets
Specification includes a Sequence Listing.

(56) References Cited

OTHER PUBLICATIONS

Gomez-Uriz et al., "Obesity and ischemic stroke modulate the methylation levels of KCNQ1 in white blood cells," Human Mol Genet 24(5):1432-1440 (2014).
Han et al., "Quantitative LC-MS/MS analysis of arachidonyl amino acids in mouse brain with treatment of FAAH inhibitor," Analyt Biochem 432(2):74-81 (2013).
Hanus et al., "N-Acyl amino acids and their impact on biological processes: N-acyl amino acids," Biofact 40(4):381-388 (2014).
Huang et al., "Identification of a new class of molecules the arachidonyl amino acids, and characterization of one member that inhibits pain," J Bio Chem 276(46):42639-42644 (2001).
Ikeda et al., "Identification of N-arachidonylglycine, U18666A, and 4-androstene-3,17-dione as novel insulin Secretagogues," Biochem Biophys Res Comm 333(3):778-786 (2005).
Connor et al., "N-Acyl amino acids and N-acyl neurotransmitter conjugates: neuromodulators and probes for new drug targets", British journal of pharmacology 160(8): 1857-1871 (2010).

* cited by examiner

A

METHODS FOR IDENTIFICATION, ASSESSMENT, PREVENTION, AND TREATMENT OF METABOLIC DISORDERS USING PM20D1 AND N-LIPIDATED AMINO ACIDS

CROSS-REFERENCE TO RELATED APPLICATIONS

This application claims the benefit of U.S. Provisional Application No. 62/248,007, filed on 29 Oct. 2015; U.S. Provisional Application No. 62/248,365, filed on 30 Oct. 2015; U.S. Provisional Application No. 62/355,120, filed on 27 Jun. 2016; and U.S. Provisional Application No. 62/395,735, filed on 16 Sep. 2016; the entire contents of each of said applications are incorporated herein in their entirety by this reference.

STATEMENT OF RIGHTS

This invention was made with government support under grant numbers K99 DK105203 and DK031405 awarded by the National Institutes of Health. The government has certain rights in the invention.

SEQUENCE LISTING

The present specification makes reference to a Sequence Listing (submitted electronically in a.txt file named "DFS-163_01_Sequence_Listing.txt" on Apr. 24, 2018). The .txt file was generated on Nov. 11, 2016 and is 51,838 bytes in size. The entire contents of the Sequence Listing are herein incorporated by reference.

BACKGROUND OF THE INVENTION

Metabolic disorders comprise a collection of health disorders or risks that increase the risk of morbidity and loss of qualify of life. For example, diabetes, obesity, including central obesity (disproportionate fat tissue in and around the abdomen), atherogenic dyslipidemia (including a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are all metabolic disorders collectively afflicting greater than 50 million people in the United States.

Brown fat has attracted significant interest as an antidiabetic (e.g., anti-type 2 diabetes) and anti-obesity tissue owing to its ability to dissipate energy as heat (Cannon and Nedergaard (2004) *Physiol. Rev.* 84:277-359; Harms and Seale (2013) *Nat. Med.* 19:1252-1263). Activation of brown fat thermogenesis involves the induction of a program of genes, including uncoupling protein 1 (UCP1), which uncouples respiration and increases heat production in fat cells (Kozak and Harper (2000) *Annu. Rev. Nutr.* 20:339-363). Either ablation of brown or beige cells (Cohen et al. (2014) *Cell* 156:304-316; Lowell et al. (1993) *Nature* 366:740-742) or knockout (KO) of the Ucp1 gene (Feldmann et al. (2009) *Cell Metab.* 9:203-209) predisposes mice to obesity and diabetes. Conversely, increasing the number or activity of brown and beige cells is protective against weight gain and metabolic disease (Seale et al. (2011) *J. Clin. Invest.* 121:96-105).

Other, non-UCP1 pathways may also contribute to non-shivering thermogenesis. It is now recognized that at least two types of thermogenic fat cells exist—classical interscapular brown fat, as well as inducible brown-like adipocytes in white fat (also known as beige fat), which tends to be dispersed among white fat depots (Wu et al. (2012) *Cell* 150:366-376; Shinoda et al. (2015) *Nat. Med.* 4:389-394). BAT has high basal levels of UCP1, whereas beige fat has low basal levels that are highly inducible upon stimulation with cold or other agents (Wu et al. (2012) *Cell* 150:366-376). Despite their common ability to exhibit adaptive thermogenesis, brown and beige cells do not derive from the same lineage precursors (Seale et al. (2008) *Nature* 454:961-967) and express different molecular signatures (Wu et al. (2012) *Cell* 150:366-376; Harms and Seale (2013) *Nat. Med.* 19:1252-1263). Mouse models resistant to weight gain through enhanced brown and beige fat content or activity have demonstrated that activation of thermogenesis in fat can be a powerful strategy to improve metabolic health and prevent weight gain (Fisher et al. (2012) *Genes Dev.* 26:271-281; Vegiopoulos et al. (2010) *Science* 328:1158-1161; Ye et al. (2012) *Cell* 151:96-110). As stated above, ablation of UCP1+ cells in transgenic mice have an increased propensity toward obesity and diabetes (Lowell et al. (1993) *Nature* 366:740-742), whereas UCP1 knockout mice develop obesity under thermoneutrality conditions when fed a high fat diet (Feldmann et al. (2009) *Cell Metab.* 9:203-209).

Most studies of adaptive thermogenesis and thermogenic fat have centered upon the expression and function of UCP1. This protein catalyzes a "proton leak" whereby protons that are pumped out of the mitochondrial matrix in the electron transport chain (ETC) are transported back across the inner mitochondrial membrane (Nicholls et al. (1978) *Experientia Suppl.* 32:89-93; Rousset et al. (2004) *Diabetes* 53:S130-S135). This results in oxidative metabolism with no production of ATP, a process referred to as uncoupled respiration. While UCP1 is a very important part of adaptive thermogenesis, in principle, any biochemical process that requires energy and is not linked to energy storage or work can function as a thermogenic event. Indeed, data have emerged indicating that UCP1 is not the only mediator of this process (Kazak et al. (2015) *Cell* 163:643-655; Ukropec et al. (2006) *J. Biol. Chem.* 281:31894-31908). Moreover, other carriers of the mitochondrial SLC25 family, of which UCP1 is only one member (SLC25A7), also have the ability catalyze a proton leak across the inner mitochondrial membrane (Brand et al. (2005) *Biochem. J.* 392:353-362).

In addition to storing chemical energy, adipose cells are now recognized to be important sensors of energy balance and secrete many bioactive proteins, including adipsin, leptin, and adiponectin (Kershaw and Flier (2004) *J. Clin. Endorcinol. Metab.* 89:2548-2556). Proteins secreted by brown and beige fat cells in particular have not been extensively or systematically studied (Svensson et al. (2016) *Cell Metab.* 23:454-466; Wang et al. (2014) Nat. Med. 20:1436-1443). The UCP1-TRAP mouse was recently developed to identify the gene expression signature of brown and beige cells in vivo, regardless of their anatomical localization (Long et al. (2014) *Cell Metab.* 19:810-820). These initial experiments elucidated a smooth muscle-like origin for beige adipocytes, while also providing a comprehensive molecular inventory of the thermogenic fat cell in vivo.

Despite decades of scientific research, few effective therapies have emerged to treat metabolic disorders. The various metabolic benefits of activating brown or beige fat have raised interest in the discovery of hormones and secreted proteins that can act on fat tissue locally or systemically to induce browning. White adipose tissues secrete many protein factors (adipokines) that influence local and systemic metabolism, including adipsin, adiponectin, leptin and TNFα (Rosen and Spiegelman (2014) *Cell.* 156:20-44; Blüther and Mantzoros (2015) *Metabolism.* 64:131.45). However, there is a great need to identify molecular regulators of metabolic disorders, especially those unknown secretory proteins from brown and/or beige fat. In particular, non-classical mechanisms that promote energy dissipation in thermogenic fat cells, such as mechanisms that are independent of UCP1, exist but are not currently understood. Such non-classical thermogenic modulators would also be useful in the generation of diagnostic, prognostic, and therapeutic agents to effectively control metabolic disorders in subjects.

SUMMARY OF THE INVENTION

The present invention is based in part on the discovery that PM20D1 and biologically active fragments thereof are secreted polypeptides that have the ability to modulate many metabolic processes, including modulating adipose thermogenesis, oxygen consumption, energy expenditure, blunted weight gain, and glucose homeostasis. Moreover, PM20D1 is demonstrated herein to be a biosynthetic enzyme for N-lipidated amino acids in vivo and act in a manner independent of UCP1. PM20D1 is also believed to be a biodegradative enzyme for N-lipidated amino acids. N-lipidated amino acids, both natural and synthetic, are also demonstrated herein to recapitulate the metabolic processes modulated by PM20D1. Thus, PM20D1, its biologically active fragments, enzymatic N-lipidated amino acid products, and synthetic N-lipidated amino acids modulate adipose tissue homeostasis and glucose metabolism and they have the therapeutic ability to treat metabolic disorders, especially obesity-induced metabolic disorders.

In one aspect, an agent that modulates expression and/or activity of PM20D1 or a biologically active fragment thereof, or modulates N-lipidated amino acids, in a subject for use in modulating a metabolic response in the subject, is provided.

Numerous embodiments are further provided that can be applied to any aspect of the present invention described herein. For example, in one embodiment, the expression and/or activity of PM20D1 or the biologically active fragment thereof, or N-lipidated amino acids, is upregulated. In another embodiment, the expression and/or activity of PM20D1 or the biologically active fragment thereof, or N-lipidated amino acids, is upregulated using an agent selected from the group consisting of a nucleic acid molecule encoding a PM20D1 polypeptide or fragment thereof, a PM20D1 polypeptide or fragment thereof, and N-lipidated amino acids. In still another embodiment, the medicament further comprises an additional agent that increases the metabolic response. In yet another embodiment, the expression and/or activity of PM20D1 or the biologically active fragment thereof, or N-lipidated amino acids, is downregulated. In another embodiment, the expression and/or activity of PM20D1 or the biologically active fragment thereof, or N-lipidated amino acids, is downregulated using an agent selected from the group consisting of an anti-PM20D1 antisense nucleic acid molecule, an anti-PM20D1 RNA interference molecule, a blocking anti-PM20D1 antibody, a non-activating form of PM20D1 polypeptide or fragment thereof, a small molecule that binds to PM20D1, and a metabolizer of N-lipidated amino acids. In still another embodiment, the medicament further comprises an additional agent that decreases the metabolic response. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified expression of UCP1 protein; and k) modified N-lipidated amino acid amount and/or activity. In another embodiment, the metabolic response is upregulated. In still another embodiment, the metabolic response is downregulated.

In another aspect, a method for modulating a metabolic response comprising contacting a cell with an agent that modulates expression and/or activity of PM20D1 or a biologically active fragment thereof, or modulates N-lipidated amino acids, to thereby modulate the metabolic response, is provided.

As described above, certain embodiments are applicable to any method described herein. For example, in one embodiment the expression and/or activity of PM20D1 or the biologically active fragment thereof, or N-lipidated amino acids, is upregulated. In another embodiment, the expression and/or activity of PM20D1 or the biologically active fragment thereof, or N-lipidated amino acids, is upregulated using an agent selected from the group consisting of a nucleic acid molecule encoding a PM20D1 polypeptide or fragment thereof, a PM20D1 polypeptide or fragment thereof, and N-lipidated amino acids. In still another embodiment, the method further comprises contacting the cell with an additional agent that increases the metabolic response. In yet another embodiment, the expression and/or activity of PM20D1 or the biologically active fragment thereof, or N-lipidated amino acids, is downregulated. In another embodiment, the expression and/or activity of PM20D1 or the biologically active fragment thereof, or N-lipidated amino acids, is downregulated using an agent selected from the group consisting of an anti-PM20D1 antisense nucleic acid molecule, an anti-PM20D1 RNA interference molecule, a blocking anti-PM20D1 antibody, a non-activating form of PM20D1 polypeptide or fragment thereof, a small molecule that binds to PM20D1, and a metabolizer of N-lipidated amino acids. In still another embodiment, the method further comprises contacting the cell with an additional agent that decreases the metabolic response. In yet another embodiment, the step of contacting occurs in vivo. In another embodiment, the step of contacting occurs in vitro. In still another embodiment, the cell is selected from the group consisting of fibroblasts, adipoblasts, preadipocytes, adipocytes, white adipocytes, brown adipocytes, and beige adipocytes. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified expression of UCP1 protein; and k) modified N-lipidated amino acid amount and/or activity. In another embodiment, the metabolic response is upregulated. In still another embodiment, the metabolic response is downregulated.

In still another aspect, a method of preventing or treating a metabolic disorder in a subject comprising administering to the subject an agent that promotes expression and/or activity of PM20D1 or a biologically active fragment thereof, or promotes N-lipidated amino acids, in the subject, thereby preventing or treating the metabolic disorder in the subject, is provided. In one embodiment, the agent is selected from the group consisting of a nucleic acid molecule encoding a PM20D1 polypeptide or fragment thereof, a PM20D1 polypeptide or fragment thereof, and N-lipidated amino acids. In still another embodiment, the agent is administered systemically. In yet another embodiment, the agent is administered in a pharmaceutically acceptable formulation. In another embodiment, the metabolic disorder is selected from the group consisting of pain, insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, and Prader-Labhart-Willi syndrome. In still another embodiment, the subject is a non-human animal or a human, optionally wherein the non-human animal is an animal model of the metabolic disorder.

In yet another aspect, a method for preventing or treating a metabolic disorder in a subject comprising administering to the subject an agent that inhibits PM20D1 expression and/or activity, or reduces N-lipidated amino acids, in the subject, thereby preventing or treating the metabolic disorder in the subject, is provided. In one embodiment, the agent is selected from the group consisting of an anti-PM20D1 antisense nucleic acid molecule, an anti-PM20D1 RNA interference molecule, a blocking anti-PM20D1 antibody, a non-activating form of PM20D1 polypeptide or fragment thereof, a small molecule that binds to PM20D1, and a metabolizer of N-lipidated amino acids. In another embodiment, the agent is administered systemically. In still another embodiment, the agent is administered in a pharmaceutically acceptable formulation. In yet another embodiment, the metabolic disorder is selected from the group consisting of obesity-associated cancer, anorexia, and cachexia. In another embodiment, the subject is a non-human animal or a human, optionally wherein the non-human animal is an animal model of the metabolic disorder.

In another aspect, a cell-based assay for screening for agents that modulate a metabolic response in a cell by modulating the expression and/or activity of PM20D1 or a biologically active fragment, or of N-lipidated amino acids, comprising contacting the cell expressing PM20D1 or the biologically active fragment thereof, or N-lipidated amino acids, with a test agent the modulates the expression and/or activity of PM20D1, or modulates the amount of N-lipidated amino acids, and determining the ability of the test agent to modulate a metabolic response in the cell, is provided.

In still another aspect, a method for assessing the efficacy of an agent that modulates the expression and/or activity of PM20D1 or a biologically active fragment, or of N-lipidated amino acids, for modulating a metabolic response in a subject, comprising: a) detecting in a subject sample at a first point in time, the expression and/or activity of PM20D1 or of N-lipidated amino acids; b) repeating step a) during at least one subsequent point in time after administration of the agent; and c) comparing the expression and/or activity detected in steps a) and b), wherein a significantly lower expression and/or activity of a marker listed in Table 1 or 2 in the first subject sample relative to at least one subsequent subject sample, indicates that the agent increases the metabolic response in the subject and/or wherein a significantly higher expression and/or activity of a marker listed in Table 1 or 2 in the first subject sample relative to at least one subsequent subject sample, indicates that the test agent decreases the metabolic response in the subject.

As described above, certain embodiments are applicable to any method described herein. For example, in one embodiment, expression and/or activity of PM20D1 or the biologically active fragment thereof, or N-lipidated amino acids, is upregulated. In another embodiment, expression and/or activity of PM20D1 or the biologically active fragment thereof, or N-lipidated amino acids, is downregulated. In still another embodiment, the agent is selected from the group consisting of a nucleic acid molecule encoding a PM20D1 polypeptide or fragment thereof, a PM20D1 polypeptide or fragment thereof, a small molecule that binds to PM20D1, an anti-PM20D1 antisense nucleic acid molecule, an anti-PM20D1 RNA interference molecule, an anti-PM20D1 siRNA molecule, a blocking anti-PM20D1 antibody, a non-activating form of PM20D1 polypeptide or fragment thereof, N-lipidated amino acids, and a metabolizer of N-lipidated amino acids. In yet another embodiment, the subject has undergone treatment for the metabolic disorder, has completed treatment for the metabolic disorder, and/or is in remission from the metabolic disorder between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of a metabolic disorder. In yet another embodiment, the first and/or at least one subsequent sample is selected from the group consisting of tissue, whole blood, serum, plasma, buccal scrape, saliva, cerebrospinal fluid, urine, stool, and bone marrow. In another embodiment, the first and/or at least one subsequent sample is a portion of a single sample or pooled samples obtained from the subject. In still another embodiment, a significantly higher expression and/or activity comprises upregulating the expression and/or activity by at least 25% relative to the second sample. In yet another embodiment, a significantly lower expression and/or activity comprises downregulating the expression and/or activity by at least 25% relative to the second sample. In another embodiment, the amount of the marker is compared. In still another embodiment, the amount of the marker is determined by determining the level of protein expression of the marker. In yet another embodiment, the presence of the protein is detected using a reagent which specifically binds with the protein. In another embodiment, the reagent is selected from the group consisting of an antibody, an antibody derivative, and an antibody fragment. In still another embodiment, the level of expression of the marker in the sample is assessed by detecting the presence in the sample of a transcribed polynucleotide or portion thereof. In yet another embodiment, the transcribed polynucleotide is an mRNA or a cDNA. In another embodiment, the step of detecting further comprises amplifying the transcribed polynucleotide. In still another embodiment, the level of expression of the marker in the sample is assessed by detecting the presence in the sample of a transcribed polynucleotide which anneals with the marker or anneals with a portion of a polynucleotide under stringent hybridization conditions. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified expression of UCP1 protein; and k) modified N-lipidated amino acid amount and/or activity. In another embodiment, the metabolic response is upregulated. In still another embodiment, the metabolic response is downregulated.

As described above, certain embodiments are applicable to any method described herein. For example, in one embodiment, PM20D1 is selected from the group of PM20D1 sequences shown in Table 1. In another embodiment, the N-lipidated amino acids are natural or synthetic and has a terminal functional group having a pKa of about 4-5. In still another embodiment, the N-lipidated amino acids comprise a hydrophobic or amphiphilic group derivatized to a main chain alpha, beta, gamma, or delta carbon. In yet another embodiment, the N-lipidated amino acids are N-acyl amino acids. In another embodiment, the N-acyl amino acids comprise a hydrophobic group of C12-C24. In still another embodiment, the hydrophobic group is C14, C16, C16:1, C18, C18:1, C18:2, C20:4, and C22:6. In yet another embodiment, the N-lipidated amino acids comprise N-lipidated phenylalanine, leucine, or isoleucine amino acids. In another embodiment, the N-lipidated amino acids are selected from the group consisting of N-arachidonoyl glycine, N-arachidonoyl phenylalanine, N-arachidonoyl serine, N-arachidonoyl gamma amino butyric acid, N-oleoyl phenylalanine, N-linoleoyl phenylalanine, N-stearoyl phenylalanine, and N-palmitoyl phenylalanine.

Figure 9:
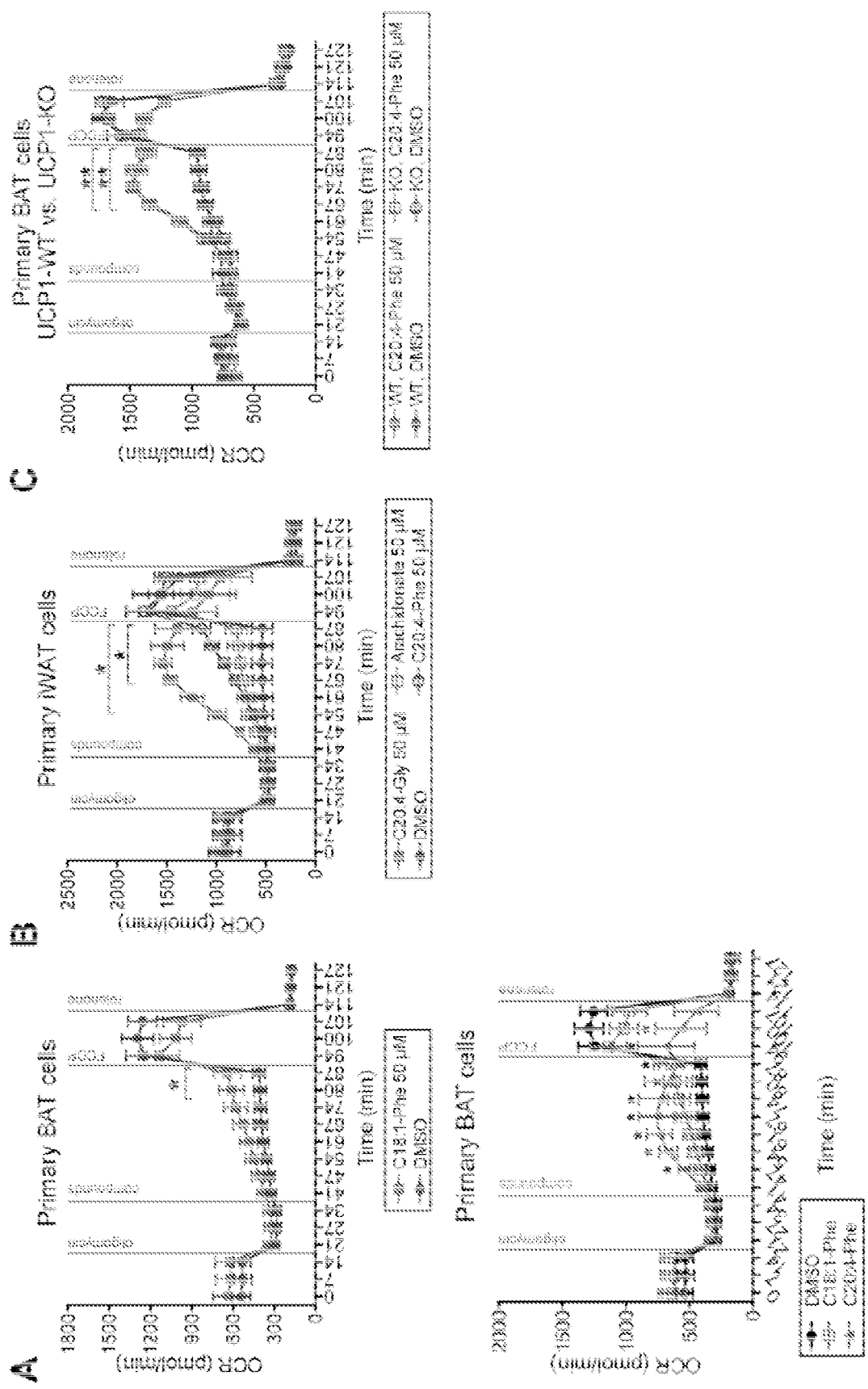
Figure 9:
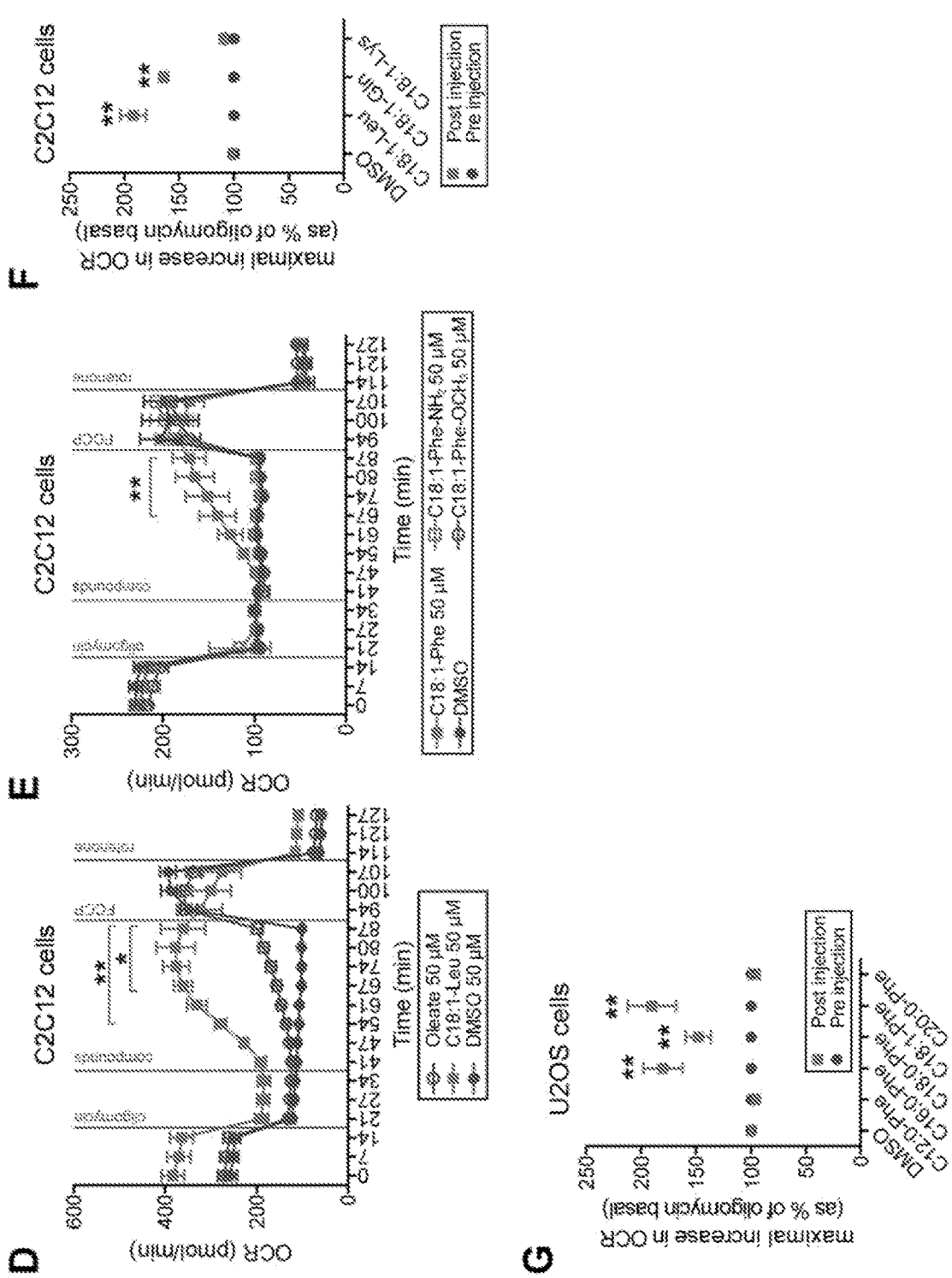
Figure 9:
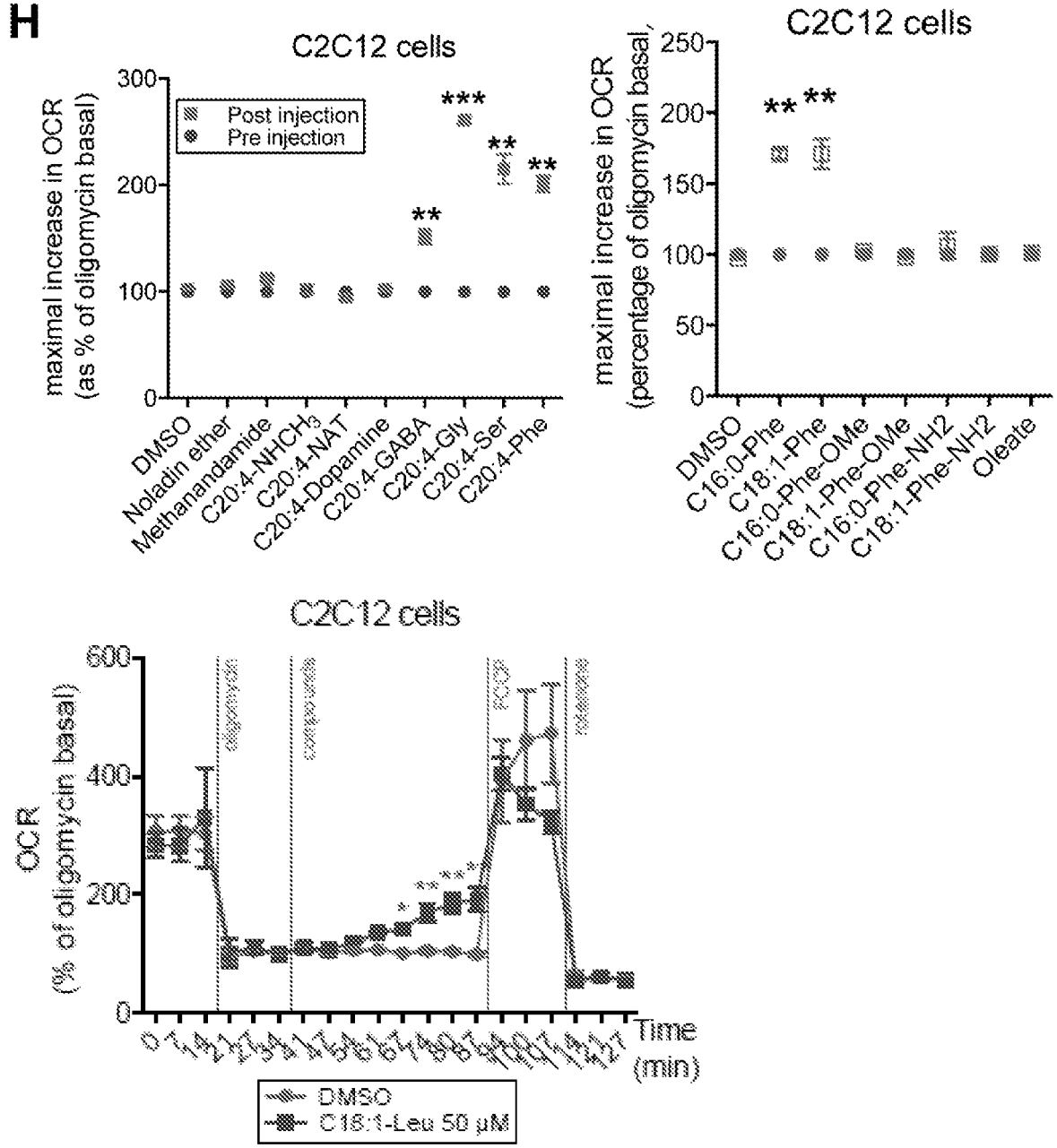

FIG. 9 includes 8 panels, identified as panels A, B, C, D, E, F, G, and H, which show the effects of N-acyl amino acids on respiration in cells. Panels A-C show oxygen consumption rates (OCRs) of differentiated primary BAT cells (Panel A), differentiated primary iWAT cells (Panel B), and differentiated primary BAT cells from UCP1-WT or UCP1-KO mice (Panel C), treated with the indicated compounds for the indicated time. For Panels A-C, adipocytes were differentiated and analyzed on day 5. Panels D-H show OCRs of C2C12 cells (Panels D-F and H) or U2OS cells (Panel G) treated with the indicated compounds for the indicated time, as well as the results of C18:1-Leu increasing uncoupled respiration in C2C12 cells (Panel H). For Panels D-H, cells were seeded and analyzed the following day. For Panels F-H, data are shown as the maximal increase in OCR as a percentage of the oligomycin basal OCR, which is normalized to 100%. For Panels A-H, the following concentrations of compounds were used: oligomycin (1 µM), indicated N-acyl amino acid or fatty acid (50 µM), FCCP (0.2 µM), or rotenone (3 µM). For Panel E, the following non-standard abbreviations are used: C18:1-Phe-$NH_2$ (N-oleoyl phenylalanine amide) and C18:1-Phe-$OCH_3$ (N-oleoyl phenylalanine methyl ester). For Panel H, the following non-standard abbreviations are used: C20:4-$NHCH_3$ (N-arachidonoyl N-methyl amide), C20:4-NAT (N-arachidonoyl taurine), and C20:4-GABA (N-arachidonoyl gamma-amino butyric acid). For Panels A-H, n=3-6/group, mean±SEM, *p<0.05, p<0.01, *p<0.001 for treatment versus DMSO at the same time point.

Figure 10:
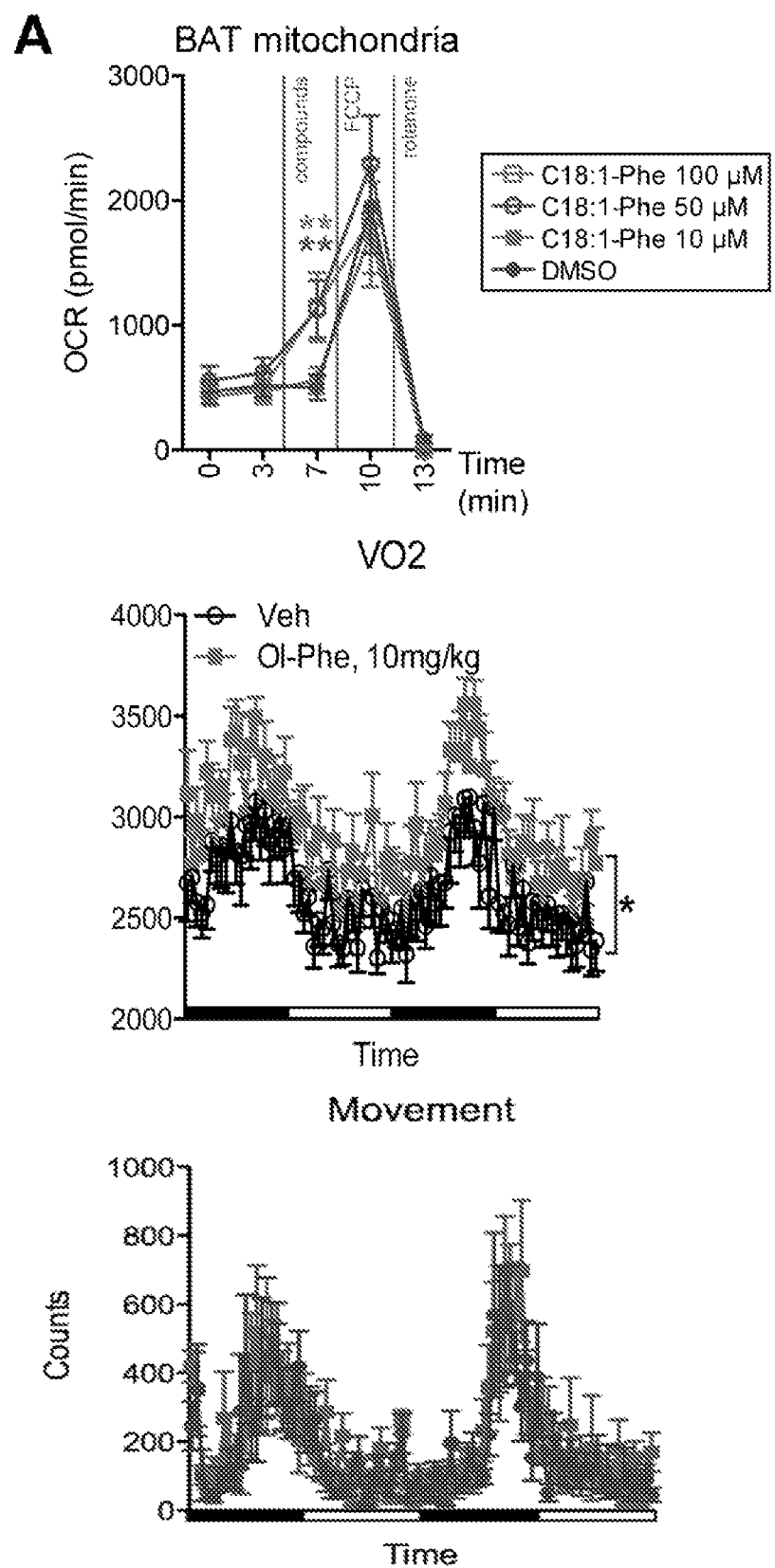
Figure 10:
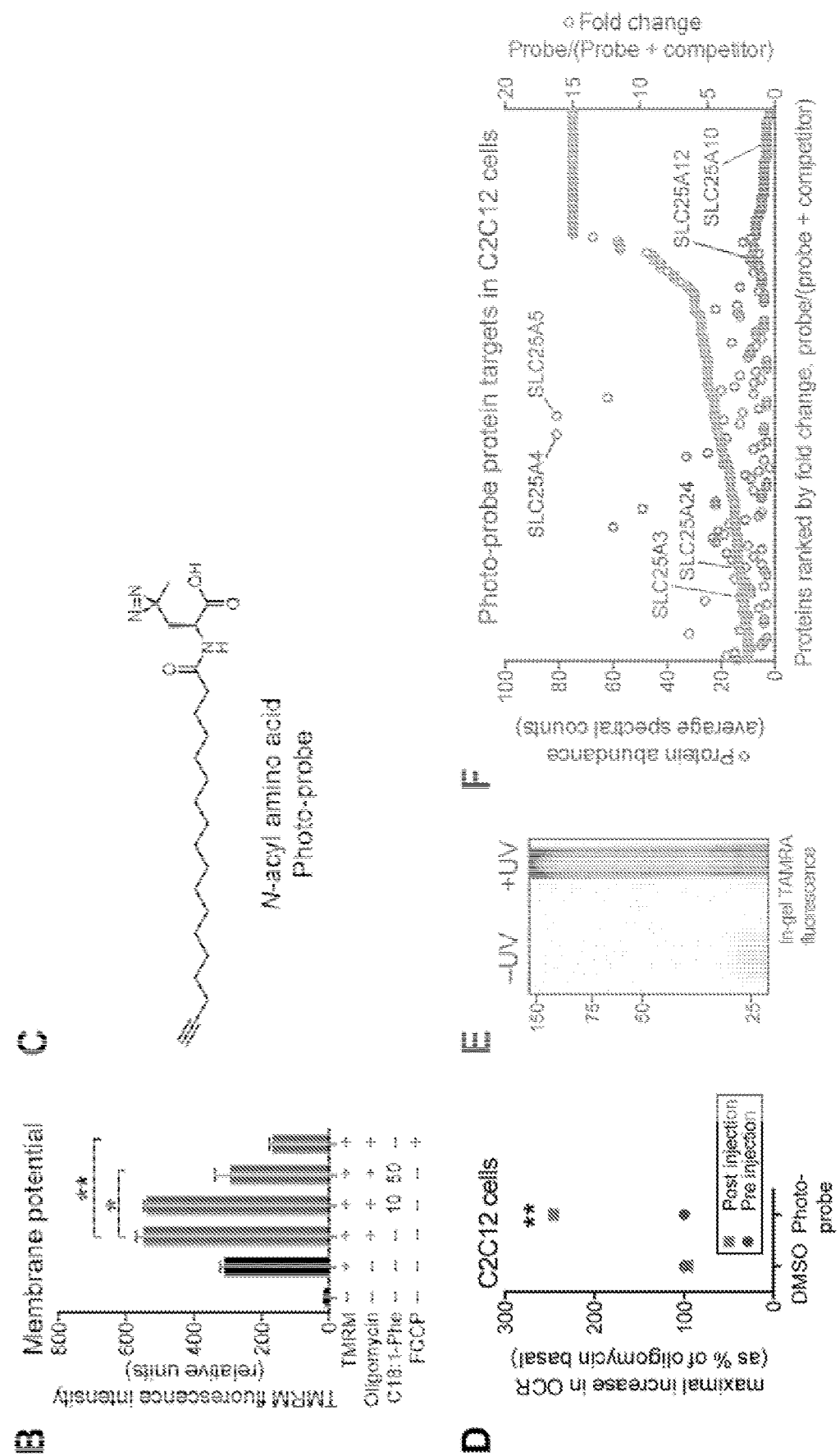

FIG. 10 includes 6 panels, identified as panels A, B, C, D, E, and F, which show the effects of N-acyl amino acids in mitochondria and identification of N-acyl amino acid-interacting proteins. Panel A shows oxygen consumption rates (OCRs) of freshly isolated BAT mitochondria treated with the indicated compounds for the indicated times. Respiration was measured with 10 mM pyruvate and 5 mM malate as substrates, and FCCP and rotenone were used at 2 µM and 3 µM, respectively. n=4-5/group, **p<0.01. Panel A also shows the results of 16-week high fat diet male C57BL/6 mice treated with vehicle (18:1:1 saline:Kolliphor EL:DMSO) or C18:1-Phe (10 mg/kg in vehicle), wherein daily and total body oxygen consumption were measured for days 5 and 6 (n=8 mice per group and mean±SEM), as well as the corresponding results of mouse movement for each mouse cohort showing that the movement of mice between the cohorts were similar. Panel B shows tetramethyl rhodamine methyl ester (TMRM) fluorescence in C2C12 cells following 20 min treatment with oligomycin alone (1 µM), or in combination with C18:1-Phe (10 or 50 µM) or FCCP (0.4 µM). n=3/group, mean±SEM, *p<0.05, p<0.01. Panel C shows the chemical structure of the N-acyl amino acid photocrosslinkable probe ("photo-probe"). Panel D shows the OCR of C2C12 cells treated with DMSO or the photo-probe (50 µM). For Panel D, data are shown as the maximal increase in OCR as a percentage of the oligomycin basal OCR, which is normalized to 100%. n=3-4/group, mean±SEM,  p<0.01. Panel E shows TAMRA in-gel fluorescence of C2C12 cells treated with the photo-probe (50 µM, 20 min), followed by UV irradiation (on ice, 10 min), cell lysis, and click chemistry with TAMRA-$N_3$. For Panel E, control cells that were not UV irradiated were kept under ambient light (on ice, 10 min). Panel F shows proteins in C2C12 cells that showed C20:4-Phe competeable photo-probe labeling. For Panel F, C2C12 cells were incubated with 20 µM photo-probe ("probe only"), or 20 µM photo-probe with 100 µM C20:4-Phe competitor ("probe+competitor"). Cells were then UV irradiated, lysed, subjected to click chemistry with biotin-$N_3$, and analyzed by MS (see Example 1). Proteins satisfying the following filtering criteria are shown: >50% reduction in peptide counts with competitor present versus without competitor, and detection of at least one peptide in all three probe only samples. Comparisons in which no peptides were detected in "probe+competitor" samples were assigned a fold-change of 15.

Figure 11:
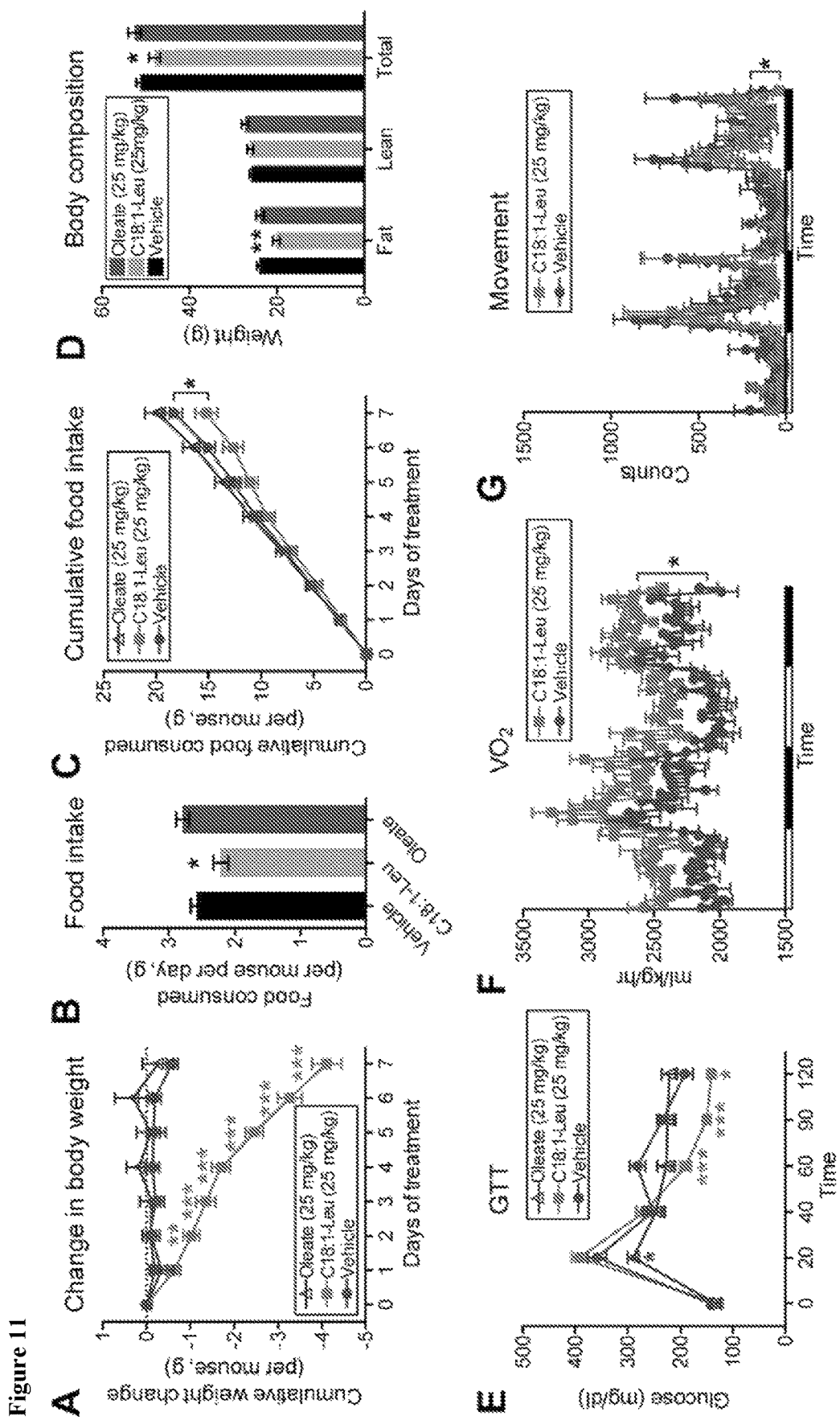

FIG. 11 includes 11 panels, identified as panels A, B, C, D, E, F, and G, which show the in vivo effects of chronic C18:1-Leu administration to mice. Panels A-E show the change in body weight (Panel A), daily and cumulative food intake (Panels B and C), body composition by MRI (Panel D), and GTT (Panel E) of 21 week DIO mice treated daily with vehicle, or C18:1-Leu (25 mg/kg/day, i.p.), or oleate (25 mg/kg/day, i.p.). For Panel D, MRI measurements were taken on day 7. For Panels A-E, the initial weights of the mice were not statistically different (means±SEM: vehicle, 51.9±0.8 g; 25 mg/kg C18:1-Leu, 52.1±1.1 g; 25 mg/kg oleate, 52.9±1.2 g). For Panels A-E, n=9/group, for vehicle and C18:1-Leu, and n=5/group for oleate, mean±SEM, *p<0.05, p<0.01, *p<0.001. For Panel E, after the last dose on day 7, mice were fasted overnight and the GTT was performed the next morning with glucose at a dose of 1.5 g/kg. Panels F and G show $VO_2$ (Panel F) and movement (Panel G) measurements of mice treated with vehicle or C18:1-Leu. For Panels F and G, measurements were recorded for 2 days following 8 days chronic treatment with vehicle or C18:1-Leu (25 mg/kg/day, i.p.); during this time daily administration of the indicated compounds continued. For Panels F and G, n=8/group, mean±SEM, *p<0.05.

Figure 12:
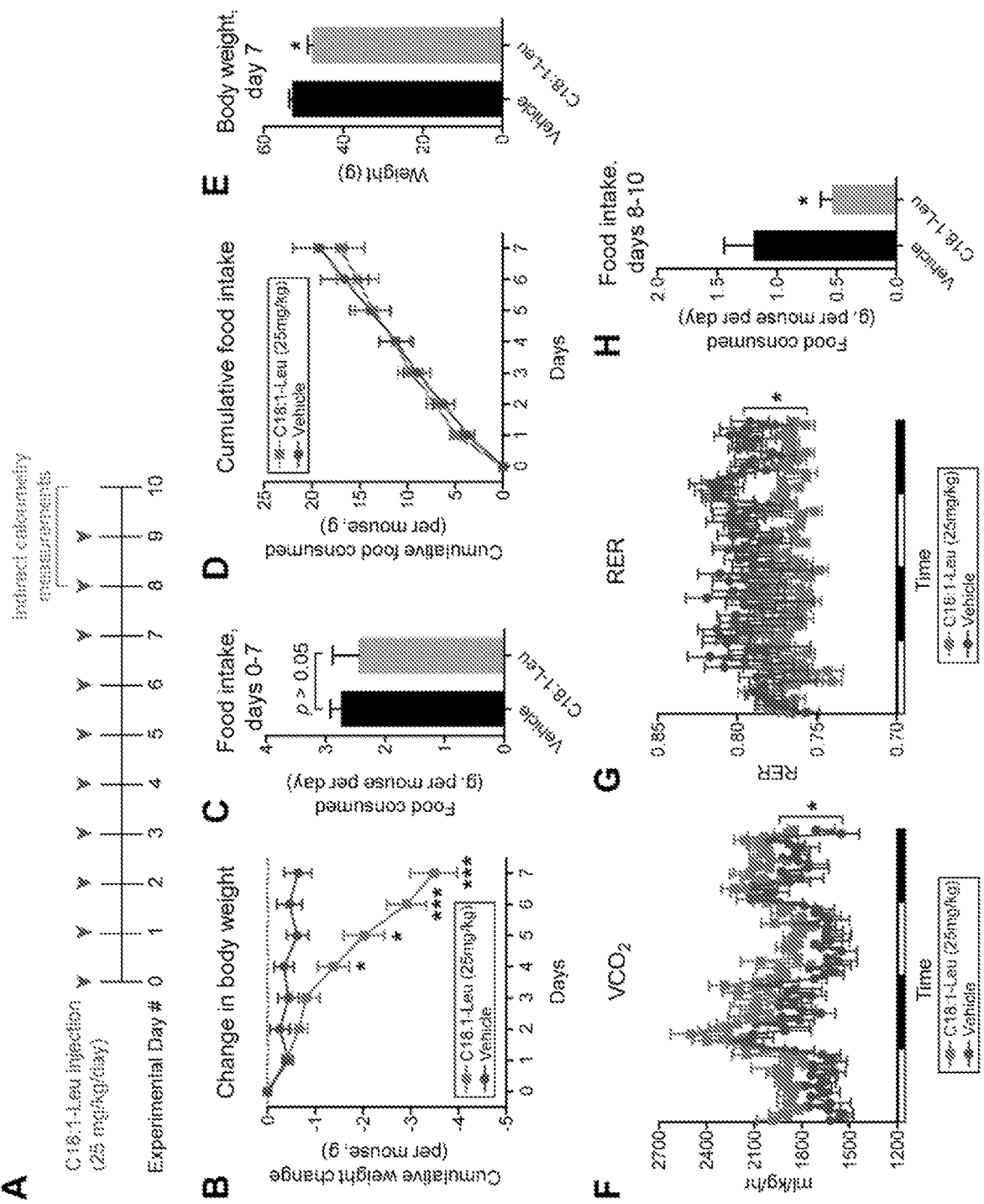

FIG. 12 includes 8 panels, identified as panels A, B, C, D, E, F, G, and H, which show other metabolic parameters of mice chronically treated with C18:1-Leu. Panel A shows a schematic of the experimental design. Panels B-E show the change in body weight (Panel B), daily and cumulative food intake (Panels C and D), and total body weight at day 7 (Panel E) of 23 week DIO mice treated daily with C18:1-Leu (25 mg/kg/day, i.p.) or vehicle. Initial body weights at day 0 were not statistically different between groups (vehicle, 53.2±0.7 g; C18:1-Leu, 52.6±1.0 g; p>0.05, means±SEM). Panels F-H show $VCO_2$ (Panel F), respiratory exchange ratio (Panel G), and food intake (Panel H) of mice treated daily with C18:1-Leu or vehicle, between experimental days 8-10. For Panels B-H, n=8/group, mean±SEM, *p<0.05, **p<0.001.

Figure 13:
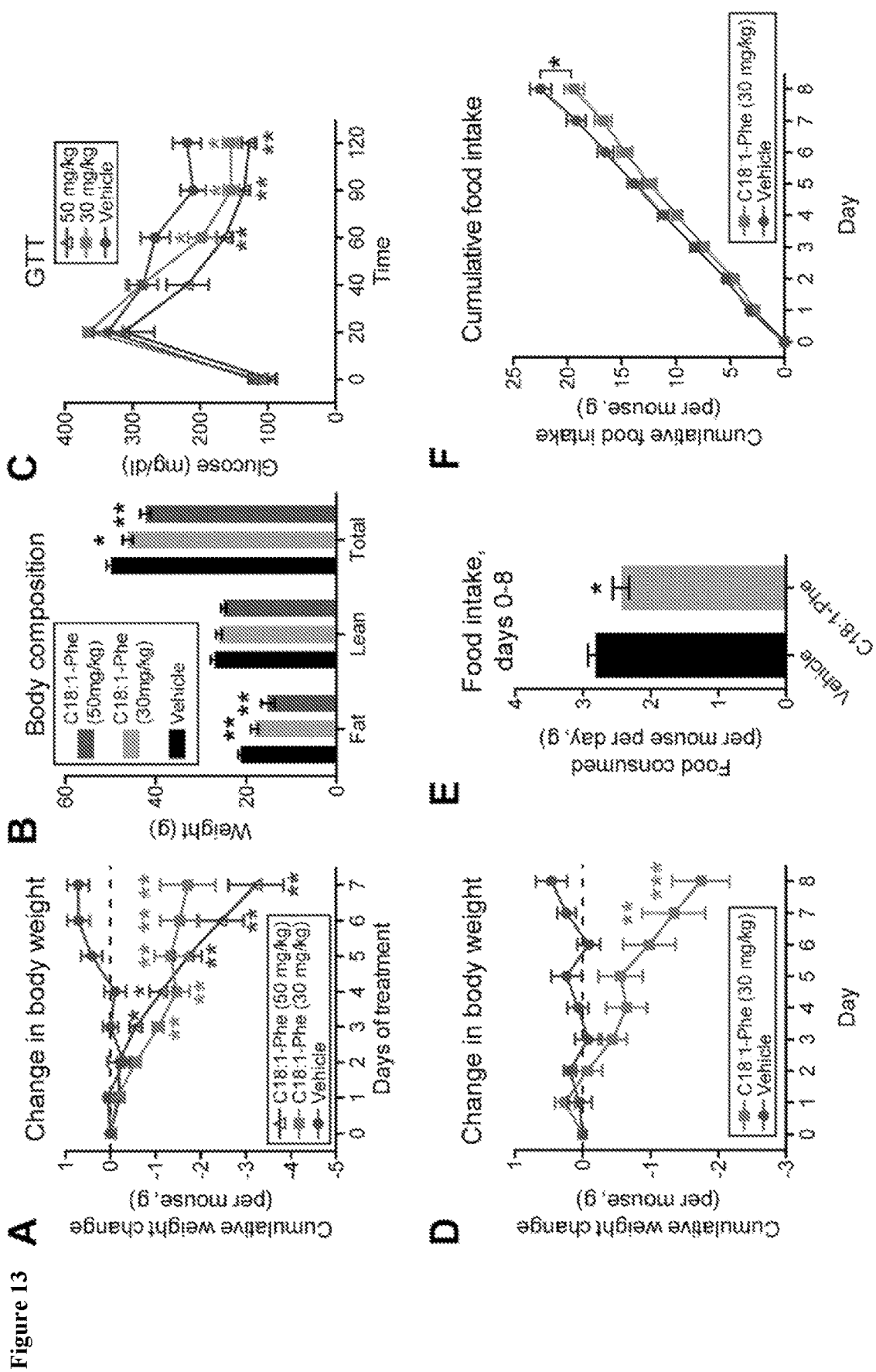
Figure 13:
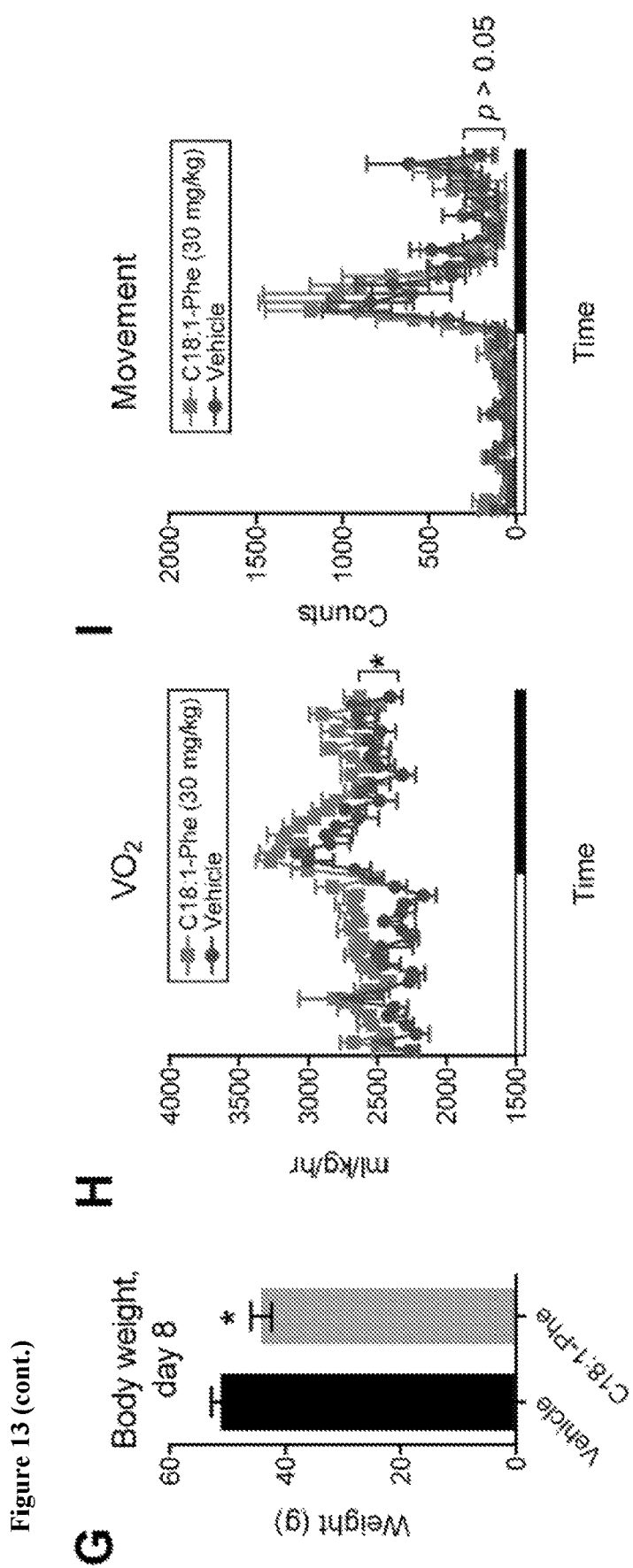

FIG. 13 includes 9 panels, identified as panels A, B, C, D, E, F, G, H, and I, which show the effects of chronic C18:1-Phe administration to mice. Panels A-C show the change in body weight (Panel A), body composition by MRI (Panel B), and GTT (Panel C) of 24 week DIO mice treated daily with vehicle or C18:1-Phe (30 or 50 mg/kg/day, i.p.). For Panel B, MRI measurements were taken the day following the GTT. For Panels A-C, the initial weights of the mice were not statistically different (means±SEM: vehicle, 51.6±0.9 g; 30 mg/kg C18:1-Phe, 50.2±1.2 g; 50 mg/kg C18:1-Phe, 49.7±1.2 g). Panels D-I show the change in body weight (Panel D), daily and cumulative food intake (Panels E and F), body weight on day 8 (Panel G), $VO_2$ (Panel H), and movement (Panel I) of 24 week DIO mice treated daily with vehicle or C18:1-Phe (30 mg/kg/day, i.p.). For Panels D-I, the initial weights of the mice were not statistically different (means±SEM: vehicle, 54.8±1.4 g; 30 mg/kg C18:

l-Phe, 51.4±1.6 g). For Panels H-I, mice were placed into indirect calorimetry chambers on day 8, and measurements were recorded between day 9-10, during which time daily injections of the indicated compounds continued. For Panels A-I, n=8-9/group, mean±SEM, *p<0.05, **p<0.01.

Figure 14:
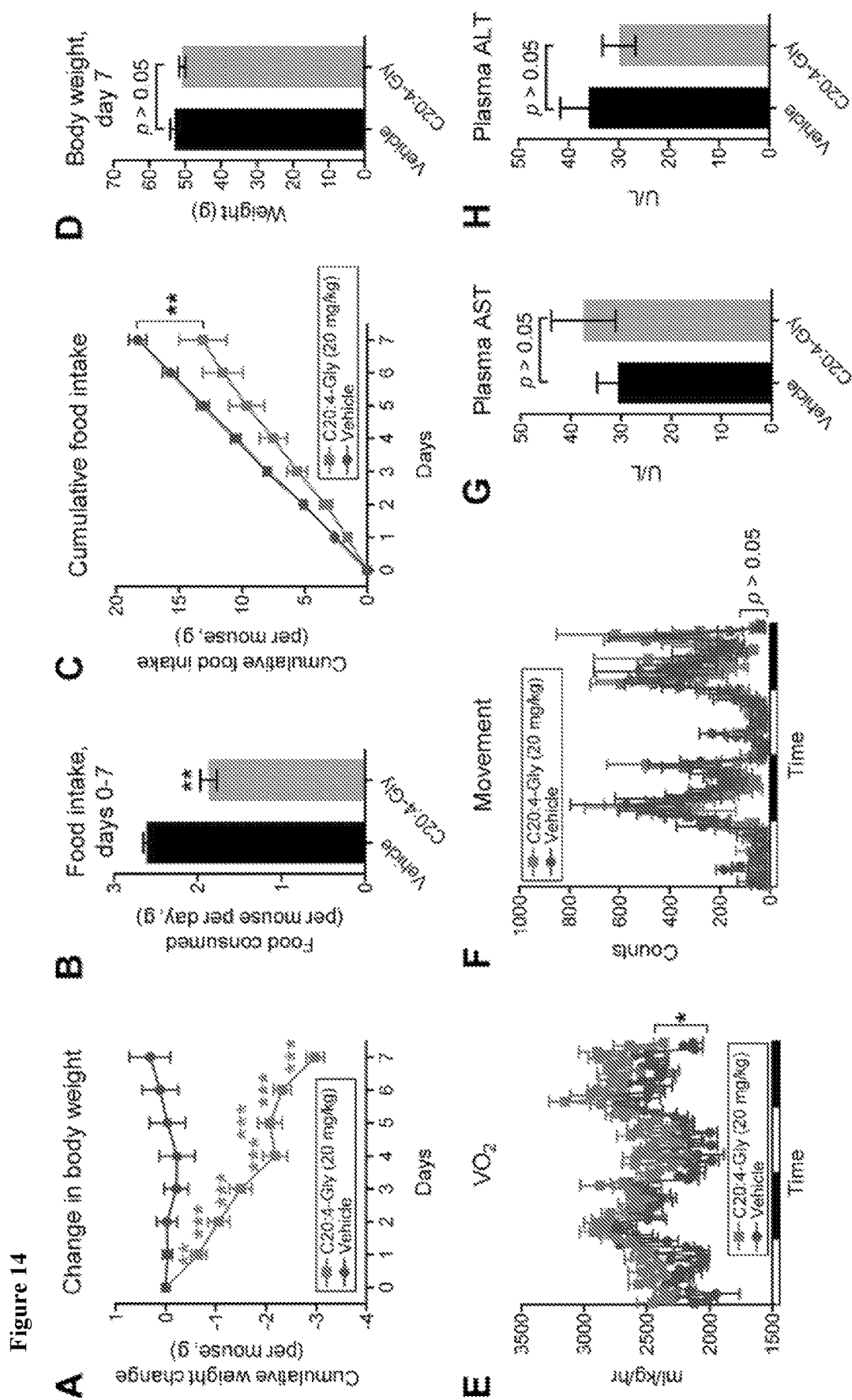
Figure 14:
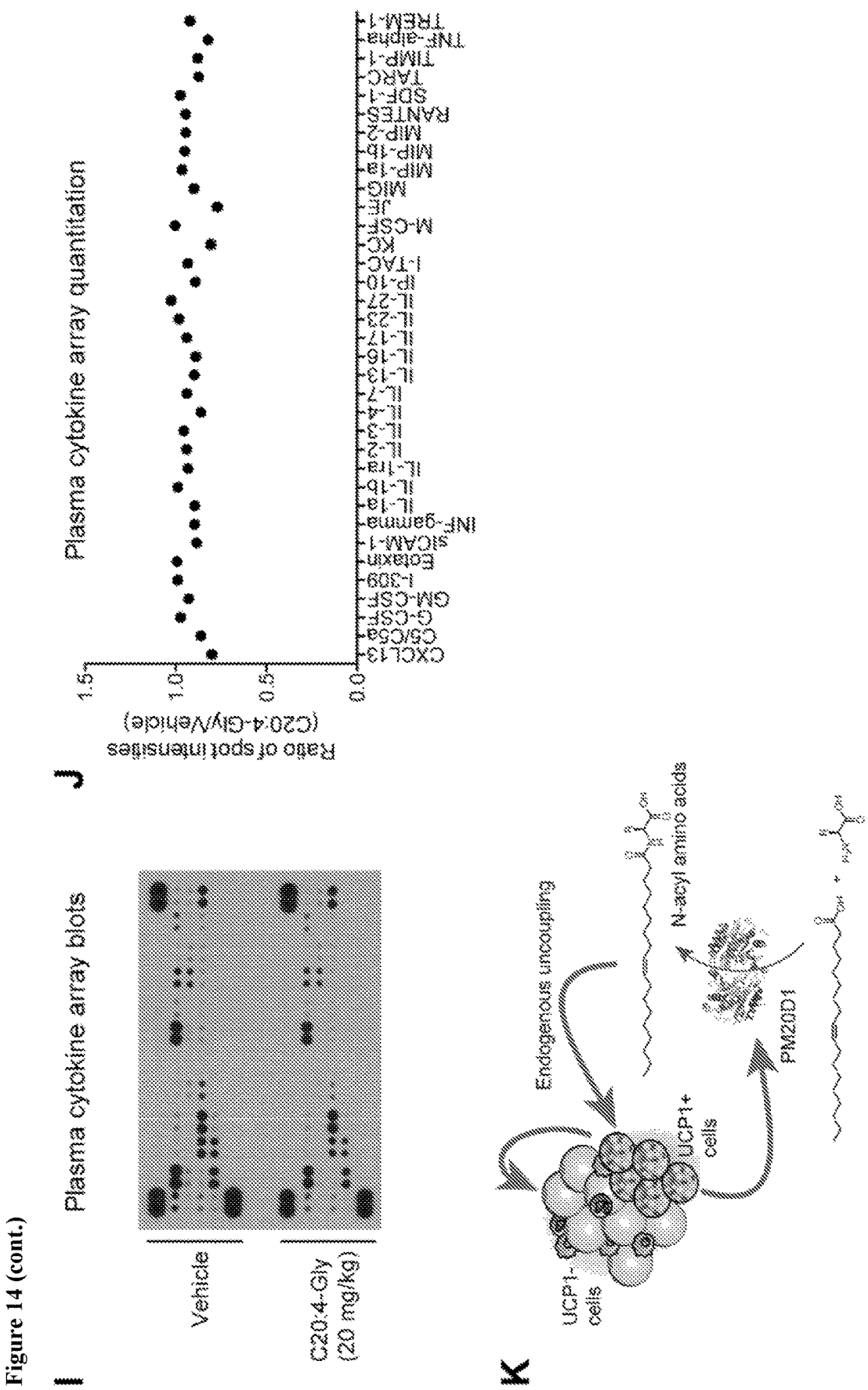

FIG. 14 includes 11 panels, identified as panels A, B, C, D, E, F, G, H, I, J, and K, which show the effects of chronic C20:4-Gly administration to mice. Panels A-F show the change in body weight (Panel A), daily and cumulative food intake (Panels B and C), and total body weight at day 7 (Panel D), $VO_2$ (Panel E), and movement (Panel F) of 14 week DIO mice treated daily with vehicle or C20:4-Gly (20 mg/kg/day, i.p.). For Panels E and F, measurements were recorded for 2 days following 7 days chronic treatment with vehicle or C20:4-Gly (20 mg/kg/day, i.p.); during this time daily administration of the indicated compounds continued. For Panels A-F, the initial weights of the mice were not statistically different (means±SEM: vehicle, 52.6±0.3 g; C20:4-Gly, 52.3±0.2 g). Panels G-J show plasma AST (Panel G), ALT (Panel H), and plasma cytokine array profiling (Panels I and J) following 9 days chronic treatment with vehicle or C20:4-Gly (20 mg/kg/day, i.p.). For Panels G-J, plasma was collected 24 hr following the last dose of vehicle or C20:4-Gly. For Panels A-H, n=8/group, mean±SEM, *p<0.05, **p<0.01. For Panels I and J, plasma from 4 mice/group were pooled for each array. Panel K shows a model of the PM20D1/N-acyl amino acid pathway.

Figure 15:
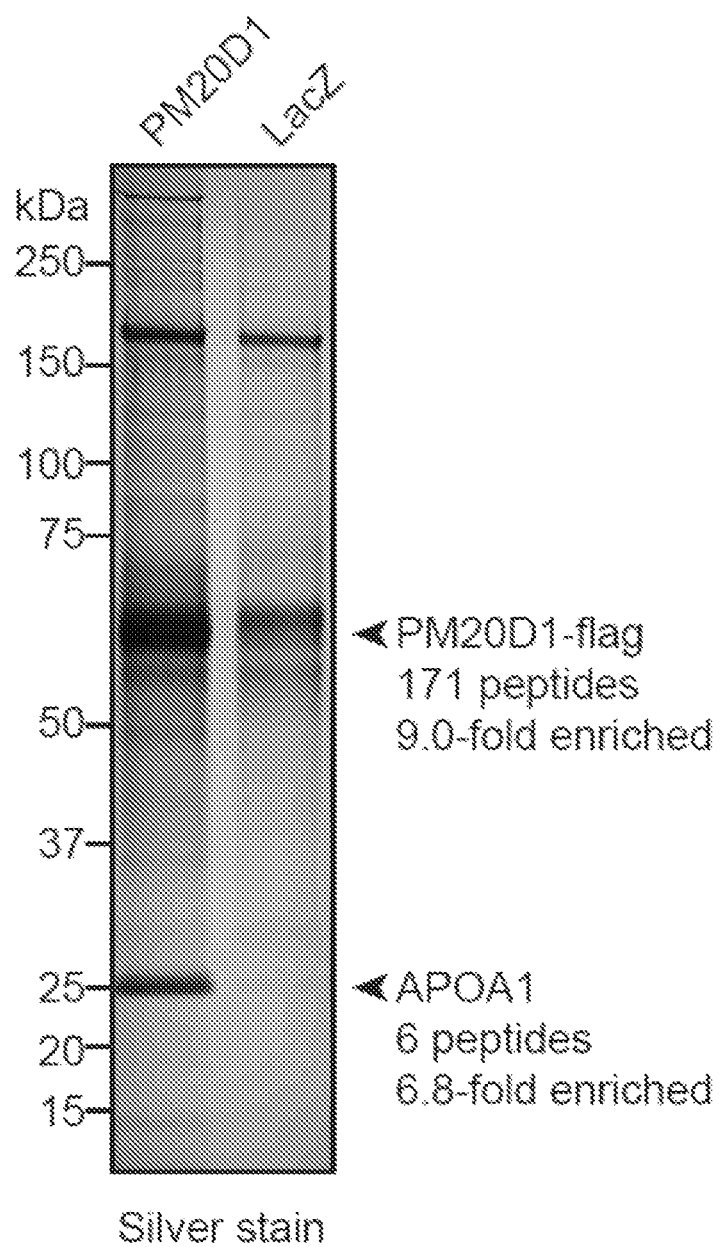

FIG. 15 shows silver stain results of FLAG-immunoprecipitated samples from primary brown fat cells transduced on day 2 with virus overexpressing PM20D1-flag (left) or lacZ control (right). The mass spectrometry identification of the indicated proteins (PM20D1 or APOA1) are indicated to the right of the gel.

Figure 16:
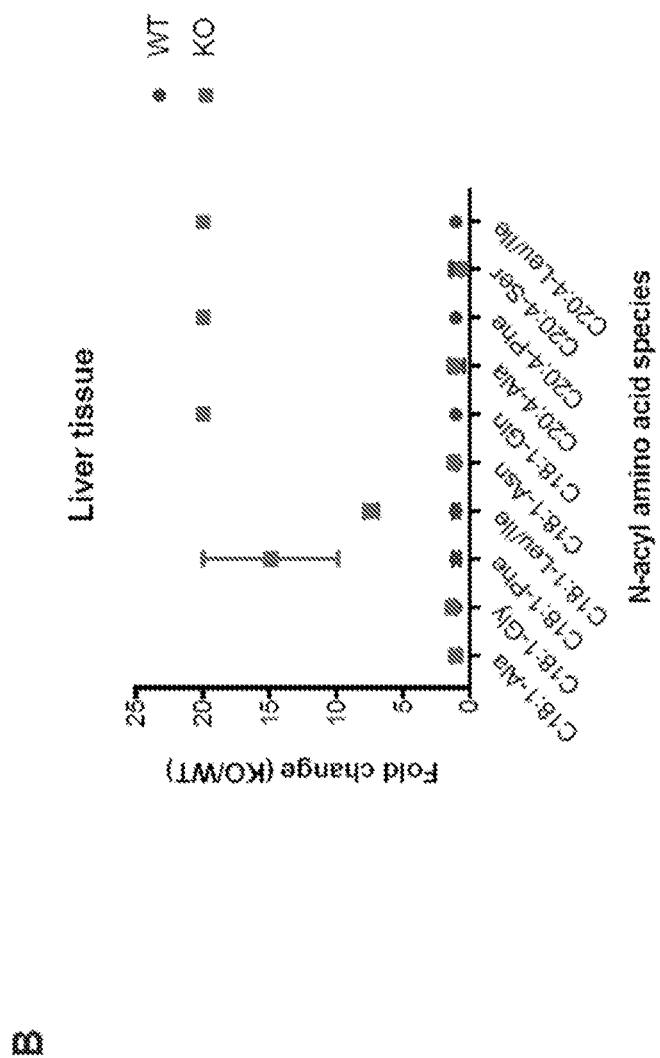

FIG. 16 includes 2 panels, identified as panels A and B, which show the results of analyses of PM20D1 knockout mice. Panel A shows that whole body PM20D1-KO mice were generated by a 6 base pair deletion in exon 1, resulting in a premature stop codon. Panel B shows the fold change of the indicated N-acyl amino acid from whole liver tissue of PM20D1-WT or KO mice. Whole tissue was extracted with ACN/MeOH and metabolites were analyzed by QQQ. N=2 mice per group. Infinite fold changes are arbitrarily set at 20-fold for graphical purposes.

DETAILED DESCRIPTION OF THE INVENTION

The present invention is based in part on the discovery that PM20D1 and biologically active fragments thereof are secreted polypeptides that have the ability to modulate adipose thermogenesis and related metabolic activity (e.g., modulate one or more biological activities of a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; and k) modified amount and/or activity of N-lipidated amino acids. In some embodiments, the metabolic activity modulated is pain.

It is demonstrated herein that PM20D1 and its biologically active cleavage products are secreted by thermogenic fat cells (e.g., beige and brown fat cells) and can act systemically on cells in culture and in vivo to stimulate a broad program of brown fat-like development and/or function. Moreover, it has been determined that PM20D1 and biologically active fragments thereof represent biosynthetic enzymes for the production of certain N-lipidated amino acids, biodegradative enzymes for N-lipidated amino acids, and/or have the ability to stimulate the broad program of brown fat-like development and/or function. This results in improvement in metabolic disorders (e.g., obesity and glucose homeostasis).

In order that the present invention may be more readily understood, certain terms are first defined. Additional definitions are set forth throughout the detailed description. The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The terms "beige fat" or "brite (brown in white) fat" or "iBAT (induced brown adipose tissue)" or "recruitable BAT (brown adipose tissue)" or "wBAT (white adipose BAT)" refer to clusters of UCP1-expressing adipocytes having thermogenic capacity that develop in white adipose tissue (WAT). Beige fat can develop in subcutaneous WAT, such as in inguinal WAT, or in intra-abdominal WAT such as in epididymal WAT. Similar to adipocytes in brown adipose tissue (BAT), beige cells are characterized by a) multilocular lipid droplet morphology, b), high mitochondrial content, and/or c) expression of a core set of brown fat-specific genes, such as Ucp1, Cidea, Pgc1a, and other listed in Table 2. BAT and beige fat both are able to undergo thermogenesis, but these are distinct cell types since beige cells do not derive from Myf5 precursor cells like BAT cells, beige fat express thermogenic genes only in response to activators like beta-adrenergic receptor or PPARgamma agonists unlike constitutive expression in BAT cells (Harms and Seale (2013) *Nat. Med.* 19:1252-1263).

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intracellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

In some embodiments, "pain" is included within the term "metabolic disorder." Pain is a sensation and a perception that is comprised of a complex series of mechanisms. Pain can be experienced both acutely and chronically. Acute pain is the instantaneous onset of a painful sensation in response to a noxious stimulus. It is considered to be adaptive because it can prevent an organism from damaging itself in some instances. Unlike acute pain (e.g., the transient protective physiology pain), persistent pain (also called chronic pain) usually has a delayed onset but can last for hours to days, or even months or years. Persistent pain may involve an amalgamation of physical, social, and psychologic factors. Persistent pain occurs in a variety of forms including, but not limited to, spontaneous pain (painful sensation without an external stimulus), allodynia (painful sensation in response to a normally innocuous stimulus) and hyperalgesia (strong painful sensation to a mildly painful stimulus). Persistent pain can be caused by many different factors. For example, persistent pain can be caused by conditions that accompany the aging process (e.g., conditions that may affect bones and joints in ways that cause persistent pain). In some embodiments, persistent pain can be caused by inflammation or nerve injury (for example, damage to or malfunction of the nervous system). In some embodiments, persistent pain can be inflammatory pain or neuropathic pain (for example, peripheral neuropathic pain and central neuropathic pain). In some embodiments, persistent pain is mediated by hyperexcitable pain-processing neurons in peripheral and central nervous system (e.g., peripheral sensitization or central sensitization). Surrogate indicators of pain are well-known in the art and can be assayed using routine methods, such as hot plate or tail immersion assays to determine thermally-induced pain, electronic von Frey apparatus assays to determine mechanically-induced pain, acetic acid assays to determine chemically-induced pain, adjuvant injection assays to determine inflammatory pain, and the like.

The term "N-lipidated amino acid" includes natural and synthetic amino acids having a hydrophobic or amphiphilic group derivatized to an amine functional group. Natural amino acids comprise an amine ($NH_2$), a carboxylic acid (COOH), and a side chain (R). They are commonly classified according to the location of these core structural groups to core carbon atoms (e.g., alpha, beta, gamma, and delta amino acids). For example, amino acids having both an amine and carboxylic acid groups attached to the first carbon (i.e., alpha carbon) are known as alpha amino acids. The 22 natural proteinogenic amino acids are alpha amino acids (including the 20 natural proteinogenic amino acids encoded directly by triplet codons) and most are present in nature as the L-stereoisomer. By contrast, gamma-amino-butyric acid (GABA) is a gamma amino acid. In some embodiments, the hydrophobic or amphiphilic group is derivatized to the amine functional group of the main chain (i.e., backbone) alpha, beta, gamma, or delta carbon. In organic chemistry, the alpha carbon refers to the first carbon atom that attaches to a function group, whereas the second carbon atom is called the beta carbon, and so forth. For amino acids, the alpha carbon is the backbone carbon before the carbonyl carbon and is the stereo center for every amino acid except glycine. Moreover, L-stereoisomers, D-stereoisomers, and racemic mixtures are also contemplated. The hydrophobic or amphiphilic group can be a fatty acid, a fatty alcohol, a sterol such as cholesterol, and the like. The hydrophobic or amphiphilic group can be saturated, unsaturated, cis, trans, branched, linear, salt form, or any combination thereof, such as a linear fatty acid with 1, 2, 4, or 6 cis or trans carbon-carbon double bonds. The hydrophobic or amphiphilic group can have an even or uneven-number of double bounds or carbon chains. In some embodiments, the hydrophobic or amphiphilic group can have a carbon chain length of C1-C30, such as C1, C2, C3, C4, C5, C6, C7, C8, C9, C10, C11, C12, C13, C14, C15, C16, C17, C18, C19, C20, C21, C22, C23, C24, C25, C26, C27, C28, C29, C30, or longer, or any range in between inclusive, such as C12-C30, C12-C24, C12-C22, C14-C20, C12-C20, C12-C22, and the like. The hydrophobic or amphiphilic group can be derivatized as an acyl group such that the N-lipidated amino acid is an N-acyl amino acid. As described above, the acyl chain can be C12-C22 or any range in between inclusive, such as C14, C16, C16:1, C18, C18:1, C18:2, C20:4, C22:6, and the like (such as N-arachidonoyl glycine, N-arachidonoyl phenylalanine, N-arachidonoyl serine, N-arachidonoyl gamma amino butyric acid, N-oleoyl phenylalanine, N-linoleoyl phenylalanine, N-stearoyl phenylalanine, and N-palmitoyl phenylalanine). Moreover, highly polyunsaturated or completely unsaturated or oxidatively-modified long chain acyl chains (e.g., C24) are contemplated. The carboxylic acid group of the main chain carbon can be a carboxylic group in some embodiments. In other embodiments, the carboxylic acid group of the main chain carbon can be replaced with a terminal functional group having a pKa of approximately 4-5 including, without limitation, a carboxylate group, activated phenol group, phenoylhydrazone group, and the like. Without being bound by theory, it is believed that the terminal functional group having a pKa of approximately 4-5 or carboxylic group acts as a protein carrier in order to generate the UCP1-independent uncoupling effect. Any parameter or combination of parameters described above can be applied to an N-lipidated amino acid of the present invention.

As used herein, "obesity" refers to a body mass index (BMI) of 30 kg/m² or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/m² or more, 26 kg/m² or more, 27 kg/m² or more, 28 kg/m² or more, 29 kg/m² or more, 29.5 kg/m² or more, or 29.9 kg/m² or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

As used herein, the term "PM20D1" or "Peptidase M20 Domain-Containing Protein 1" refers to the D1 family member of the M20A family of secreted peptidases and is intended to include fragments, variants (e.g., allelic variants) and derivatives thereof unless otherwise specified. PM20D1 proteins generally contain a metal ion coordination site and a peptidase domain (Brass et al. (2008) *Science* 319:921-926; Gonzales et al. (2009) *J. Am. Soc. Nephrol.* 20:363-379; Satake et al. (2009) *Nat. Genet.* 41:1303-1307; and Sung et al. (2013) *Hum. Genet.* 132:423-429). PM20D1 has not heretofore been implicated in the regulation of cellular metabolism. Mature PM20D1 proteins lack a signal sequence and PM20D1 sequences of the present invention can comprise a signal sequence, as well as lack a signal sequence. The PM20D1 signal sequence is generally the most N-terminal 20, 21, 22, 23, 24, 25, 26, 27, 28, 29, or 30 amino acids.

Representative PM20D1 nucleic acid and protein sequences are well-known in the art. For example, representative human PM20D1 cDNA and amino acid sequences can be obtained from the National Center for Biotechnology Information (NCBI) under accession numbers NM_152491.4 and NP_689704.4, respectively. The nucleic acid and polypeptide sequences are provided herein as SEQ ID NOs: 1-2, respectively. Nucleic acid and polypeptide sequences of PM20D1 orthologs in organisms other than humans are well-known and include, for example, *Mus musculus* PM20D1 (NM_178079.3 and NP_835180.2); *Pan troglodytes* PM20D1 (XM_514142.4 and XP_514142.2); *Bos taurus* PM20D1 (NM_001038100.1 and NP_001033189.1); *Rattus norvegicus* PM20D1 (NM_001109068.1 and NP_001102538.1); *Gallus gallus* PM20D1 (NM_001030915.1 and NP_001026086.1); and *Xenopus tropicalis* PM20D1 (NM_001127051.1 and NP_001120523.1). The nucleic acid and polypeptide sequences are provided herein as SEQ ID NOs: 3-14, respectively.

In some embodiments, fragments of PM20D1 having one or more biological activities of the full-length PM20D1 protein are described and employed. Such fragments can comprise or consist of at least one domain of a PM20D1 protein without containing the full-length PM20D1 protein sequence. In some embodiments, PM20D1 fragments can comprise, or consist of, an M20 peptidase domain (e.g., residues 53-487 of human PM20D1 or corresponding residues in an ortholog of human PM20D1, such as residues 53-488 of mouse PM20D1, residues 53-488 of rat PM20D1, or residues 65-500 of chicken PM20D1), a metal ion binding site (e.g., coordinated residues 125, 157, 191, 192, 217, and 464 of human PM20D1 or corresponding residues in an ortholog of human PM20D1, such as coordinated residues 125, 157, 191, 192, 218, and 465 of mouse PM20D1, coordinated residues 125, 157, 191, 192, 218, and 465 of rat PM20D1, or coordinated residues 137, 169, 203, 204, 230, and 477 of chicken PM20D1), and the like, without containing the full-length PM20D1 protein sequence. As further indicated in the Examples, PM20D1 orthologs are highly homologous and retain common structural domains well-known in the art. Biologically active fragments, such as N-terminal (N-PM20D1) and/or C-terminal (PM20D1-C), as well as lipidated variants thereof, are also described herein.

TABLE 1

SEQ ID NO: 1 Human PM20D1 cDNA Sequence

```
  1    atggctcagc ggtgcgtttg cgtgctggcc ctggtggcta tgctgctcct agttttccct 61    accgtctcca gatcgatggg cccgaggagc ggggagcatc aaagggcgtc gcgaatccct 121    tctcagttca gcaaagagga acgcgtcgcg atgaaagagg cgctgaaagg tgccatccag 181    attccaacag tgactttag ctctgagaag tccaatacta cagccctggc tgagttcgga 241    aaatacattc ataaagtctt tcctacagtg gtcagcacca gctttatcca gcatgaagtc 301    gtggaagagt atagccacct gttcactatc caaggctcgg accccagctt gcagccctac 361    ctgctgatgg ctcactttga tgtggtgcct gccctgaag aaggctggga ggtgccccca 421    ttctctgggt tggagcgtga tggcatcatc tatggtcggg gcacactgga cgacaagaac
```

TABLE 1-continued

```
 481   tctgtgatgg cattactgca ggccttggag ctcctgctga tcaggaagta catcccccga
 541   agatctttct tcatttctct gggccatgat gaggagtcat cagggacagg ggctcagagg
 601   atctcagccc tgctacagtc aaggggcgtc cagctagcct tcattgtgga cgagggggc
 661   ttcatcttgg atgatttcat tcctaacttc aagaagccca tcgccttgat tgcagtctca
 721   gagaagggtt ccatgaacct catgctgcaa gtaaacatga cttcaggcca ctcttcagct
 781   cctccaaagg agacaagcat tggcatcctt gcagctgctg tcagccgatt ggagcagaca
 841   ccaatgccta tcatatttgg aagcgggaca gtggtgactg tattgcagca actggcaaat
 901   gagtttccct ccctgtcaa tataatcctg agcaacccat ggctatttga accacttata
 961   agcaggttta tggagagaaa tcccttaacc aatgcaataa tcaggaccac cacggcactc
1021   accatattca aagcaggggt caagttcaat gtcatccccc cagtggccca ggccacagtc
1081   aacttccgga ttcaccctgg acagacagtc caagaggtcc tagaactcac gaagaacatt
1141   gtggctgata acagagtcca gttccatgtg ttgagtgcct ttgacccct ccccgtcagc
1201   ccttctgatg acaaggcctt gggctaccag ctgctccgcc agaccgtaca gtccgtcttc
1261   ccggaagtca atattactgc cccagttact tctattggca acacagacag ccgattcttt
1321   acaaacctca ccactggcat ctacaggttc taccccatct acatacagcc tgaagacttc
1381   aaacgcatcc atggagtcaa cgagaaaatc tcagtccaag cctatgagac caagtgaaa
1441   ttcatctttg agttgattca gaatgctgac acagaccagg agccagtttc tcacctgcac
1501   aaactgtga
```

SEQ ID NO: 2 Human PM20D1 Amino Acid Sequence (Signal Peptide: Residues 1-25)
```
   1   maqrcvcvla lvamlllvfp tvsrsmgprs gehqrasrip sqfskeerva mkealkgaiq
  61   iptvtfssek snttalaefg kyihkvfptv vstsfiqhev veeyshlfti qgsdpslqpy
 121   llmahfdvvp apeegwevpp fsglerdgii ygrgtlddkn svmallqale lllirkyipr
 181   rsffislghd eessgtgaqr isallqsrgv qlafivdegg filddfipnf kkpialiavs
 241   ekgsmnlmlq vnmtsghssa ppketsigil aaavsrleqt pmpiifgsgt vvtvlqqlan
 301   efpfpvniil snpwlfepli srfmernplt naiirtttal tifkagvkfn vippvaqatv
 361   nfrihpgqtv qevleltkni vadnrvqfhv lsafdplpvs psddkalgyq llrqtvqsvf
 421   pevnitapvt signtdsrff tnlttgiyrf ypiyiqpedf krihgvneki svqayetqvk
 481   fifeliqnad tdqepvshlh kl
```

SEQ ID NO: 3 Mouse PM20D1 cDNA Sequence
```
   1   atggctgagc tacttgctag cttgcccgcc tgggcagctg tgctccttct cttttttcgct
  61   acggtctccg gatccactgg ccctagaagc agggaaaatc gggggcgtc ccggatccct
 121   tcccagttca gcgaggagga gcgtgtcgct ataaaagagg cgctgaaagg tgccatccag
 181   attcccacag tgtctttcag ccacgaggaa tccaacacca cagccctgc tgagtttgga
 241   gaatatatcc gcaaagcctt ccctacagtg ttccacagca gccttgtcca acatgaagtc
 301   gtggcaaagt atagccacct gttcaccatc caaggctcag accccagttt cagccctac
 361   atgctgatgg ctcacattga tgtggttcct gccccggaag aaggatggga ggtgccccg
 421   ttctcaggcc tggaacgcaa tggcttcatc tatggccggg gtgcgctgga caacaaaaac
 481   tctgtgatgg cgatcctgca tgctttggag ctcctgttga tcagaaacta cagccccaaa
 541   agatctttct tcattgcttt gggccatgat gaggaggtgt ccggggaaaa ggggctcag
 601   aagatctcag cactcttaca ggcaaggggt gtccagctag ccttccttgt ggatgaaggg
```

TABLE 1-continued

```
 661   agctttatct tggaaggctt cattccaaac ctcgagaagc cagttgccat gatttcagtc
 721   actgagaagg gtgcccttga cctcatgctg caagtaaaca tgactccagg ccactcttca
 781   gctccccaa aggagacaag cattggcatt ctttctgccg ctgtcagccg actggagcag
 841   acaccaatgc gaatatgtt tggaggaggg ccattgaaga agacaatgaa gctactggca
 901   aatgagtttt ccttccctat caatatagtc ttgagaaacc tgtggctatt tcatcccatt
 961   gtgagcagga taatggagag gaaccccata acaaatgcgc tggtccgaac taccacagcc
1021   ctcaccatgt tcaatgcagg aatcaaggtg aatgtcatcc ctccattggc tcaggctaca
1081   atcaactgcc gaattcaccc ttcgcagaca gtacatgagg tcctagaact tgtcaagaac
1141   accgtggctg atgacagagt ccagctgcat gtgttgagat cctttgaacc cctgcccatc
1201   agccctctg atgaccaggc catgggctac cagctgcttc aagagaccat acgatctgtc
1261   ttcccggaag tcgacatcgt cgtccccggt atttgtattg ccaatacgga cacccgacac
1321   tatgccaaca tcaccaatgg catgtaccgg ttcaaccccc ttcccctgaa ccctcaggac
1381   ttcagtggtg tccatggaat caatgagaaa gtttccgttc agaactacca gaaccaggtg
1441   aagttcatct ttgagttcat ccaaaatgcc gacacttaca agagccagt cctcatctg
1501   catgaactat ga
```

SEQ ID NO: 4 Mouse PM20D1 Amino Acid Sequence (Signal Peptide: Residues 1-24)

```
  1   maellaslpa waavlllffa tvsgstgprs renrgasrip sqfseeerva ikealkgaiq
 61   iptvsfshee snttalaefg eyirkafptv fhsslvqhev vakyshlfti qgsdpslqpy
121   mlmahidvvp apeegwevpp fsglerngfi ygrgaldnkn svmailhale lllirnyspk
181   rsffialghd eevsgekgaq kisallqarg vqlaflvdeg sfilegfipn lekpvamisv
241   tekgaldlml qvnmtpghss appketsigi lsaavsrleq tpmpnmfggg plkktmklla
301   nefsfpiniv lrnlwlfhpi vsrimernpi tnalvrttta ltmfnagikv nvipplaqat
361   incrihpsqt vhevlelvkn tvaddrvqlh vlrsfeplpi spsddqamgy qllqetirsv
421   fpevdivvpg iciantdtrh yanitngmyr fnplplnpqd fsgvhginek vsvqnyqnqv
481   kfifefiqna dtykepvphl hel
```

SEQ ID NO: 5 Chimpanzee PM20D1 cDNA Sequence

```
  1   atggctcagc ggtgcgtttg cgtgctggcc ctggtggcta tgctgctcct agttttcccc
 61   accgtctcca gatcgatggg cctgaggagc ggggagcatc aaagggcgtc gcgaatccct
121   tctcagttca gcaaagagga acgcgtcgcg atgaaagagg cgctgaaagg tgccatccag
181   attccaacag tgacttttag ctctgagaag tccaatacca cagccctggc tgagttcgga
241   aaatacattc ataaagtctt tcctacagtg gtcagcacca gctttatcca gcatgaagtt
301   gtggaagagt atagccacct gttcactatc caaggctcgg accccagctt gcagccctac
361   ttgctgatgg ctcactttga tgtggtgcct gccctgaag aaggctggga ggtgccccca
421   ttctctgggt tggagcgtga tggcgtcatc tatggtcggg gcacactaga cgacaagaac
481   tctgtgatgg cattactgca ggccttggag ctcctgctga tcaggaagta catccccaa
541   agatctttct tcatttctct gggccatgat gaggagtcgt cagggacagg ggctcagagg
601   atctcagccc tgctacagtc aaggggcgtc cagctagcct tcattgtgga cgagggggc
661   ttcatcttgg atgatttcat tcctaacttc aagaagccca tcgccttgat tgcagtctca
721   gagaagggtt ccatgaacct catgctgcaa gtaaacatga cttcaggcca ctcttcagct
781   cctccaaagg agacgagcat tggcatcctt gcagctgctg tcagccgatt ggagcagaca
841   ccaatgccta tcatatttgg aagcgggaca ttggtgacgg tattgcagca actggcaaat
```

```
 901    gagtttccct tccctgtcaa tataatcctg agcaacccat ggctatttga accacttata
 961    agcaggttta tggagagaaa tcccttaacc aatgcaataa tcaggaccac cacggcactc
1021    accatattca aagcaggggt caagttcaat gtcatccccc cggtggccca ggccacagtc
1081    aacttccgga ttcaccctgg acagacagtc caagaggtcc tagaactcac gaagaacatt
1141    gtggctgata acagagtcca gttccatgtg ttgagtgcct ttgaccccct ccccgtcagc
1201    ccttctgatg acaaggcctt gggctaccag ctgctccgcc agaccgtaca gtccgtcttc
1261    ccggaagtca atattactgc cccagttact tctattggca acacagacag ccgattcttt
1321    acaaacctca ccactggcat ctacaggttc taccccatct acatacagcc tgaagacttc
1381    aaacgcatcc atggagtcaa cgagaaaatc tcagtccaag cctatgagac ccaagtgaaa
1441    ttcatctttg agttgattca gaatgctgac acagaccagg agccagtttc tcacctgcac
1501    aaactgtga
```

SEQ ID NO: 6 Chimpanzee PM20D1 Amino Acid Sequence
```
  1    maqrcvcvla lvamlllvfp tvsrsmglrs gehqrasrip sqfskeerva mkealkgaiq
 61    iptvtfssek snttalaefg kyihkvfptv vstsfiqhev veeyshlfti qgsdpslqpy
121    llmahfdvvp apeegwevpp fsglerdgvi ygrgtlddkn svmallqale lllirkyipq
181    rsffislghd eessgtgaqr isallqsrgv qlafivdegg filddfipnf kkpialiavs
241    ekgsmnlmlq vnmtsghssa ppketsigil aaavsrleqt pmpiifgsgt lvtvlqqlan
301    efpfpvniil snpwlfepli srfmernplt naiirtttal tifkagvkfn vippvaqatv
361    nfrihpgqtv qevleltkni vadnrvqfhv lsafdplpvs psddkalgyq llrgtvgsvf
421    pevnitapvt signtdsrff tnlttgiyrf ypiyiqpedf krihgvneki svqayetqvk
481    fifeliqnad tdqepvshlh kl
```

SEQ ID NO: 7 Cow PM20D1 cDNA Sequence
```
  1    atggctcggc cgtccgtctg cctgctggcc tcgctgtctg cgctgctcct aggtatcgcc
 61    gccgtctcca gatcgaaggg cctgcggggc acggagagtc aaagggagcc gcgaatccct
121    tctcagttca gccaagagca gcgcatcgcc atgaaggaag cgctcaaagg tgccatccag
181    attccaacag tgtctttcag ccccaaggag ctcaacacaa cagccctggc tgagtttgga
241    gaatacattc gtaaagtctt tcctactgtg ttccatacca gctttatccg catgaggtc
301    gtaggaaatt acagccacct gttcactatc aaaggctcag accccagcat gcagccctac
361    attctcctcg ctcacattga cgtggtgcct gccccggaca aaggctggga cgtgccccc
421    ttctctgggt tggagcgtga tggcttcatc tatggtcgag gcacactgga caacaagaac
481    tatcttatgg caatcctgca ggccttggag cttctgctga tcagaaacta catcccccga
541    agatctttct tcattgctct gggccatgat gaggagatat cagggataaa cggggctcag
601    aagatctcag ccctgctaca ggcaaggggt gtccagctag ccttcgtggt ggatgagggg
661    agcttcatct ggacggtttt cattccctac ctcaagaagc cctttgccat ggtttccgtt
721    tctgagaagg gtgcgattaa cctcatgctg caagtcaaca cgactacagg ccactcttca
781    gctcctccaa agaaacaag cataggcatt ctcgcagccg cagtcagccg actggagcag
841    acaccaatgc cgaacatgtt tggaagtggg ccattgatga cggcagtgga gcaactggca
901    aatgagtttc ccttccctac caatatagtc ttgaacaacc tgtggctctt tcgacccctt
961    gtaagcaggt tgatggagag gaattacata accaattcgc tggtcaggac cacaacggcg
1021    ctcaccatgt tcaatgccgg ggtcaaggtg aatgtcatcc ccctgtggc cgaggccatc
1081    atcaacttcc gacttcaccc tgcacagact gttcaggagg ttctaaaatt agccaaggac
```

TABLE 1-continued

```
1141   attgtggctg atgaccgcat ccagttccat gtgttggatg cctttgaccc cctgcccatc
1201   agcccttctg atgatcaggc cttgggttac cagctgctcc gccagaccat acactctgtc
1261   ttcccggaag tcaacattgt tgccccaggt acttgtattg caacacagca cagcagacac
1321   tatctgaatc ttaccactgg catctaccgg ttcaaccca tctacctaca acctcaggac
1381   ttcagtagca tccacggaat caatgagaaa atctcggtcc aagcctacga gacccaggtg
1441   aaattcgtct tcgagtttat ccagaatggt gacacagacg aggagacagt tcctcacctg
1501   catgaactgt ga
```

SEQ ID NO: 8 Cow PM20D1 Amino Acid Sequence (Signal Peptide: Residues 1-25)

```
  1    marpsvclla slsalllgia aysrskglrg tesqreprip sqfsqeqria mkealkgaiq
 61    iptvsfspke lnttalaefg eyirkvfptv fhtsfirhev vgnyshlfti kgsdpsmqpy
121    illahidvvp apdkgwdvpp fsglerdgfi ygrgtldnkn ylmailqale lllirnyipr
181    rsffialghd eeisgingaq kisallqarg vqlafvvdeg sfildgfipy lkkpfamvsv
241    sekgainlml qvntttghss appketsigi laaaysrleq tpmpnmfgsg plmtaveqla
301    nefpfptniv lnnlwlfrpl vsrlmernyi tnslvrttta ltmfnagvkv nvippvaeai
361    infrlhpaqt vqevlklakd ivaddriqfh vldafdplpi spsddqalgy qllrqtihsv
421    fpevnivapg tcigntdsrh ylnittgiyr fnpiylqpqd fssihginek isvqayetqv
481    kfvfefiqng dtdeetvphl hel
```

SEQ ID NO: 9 Rat PM20D1 cDNA Sequence

```
  1    atggctgagc tacttgttat cttgcccacc cgggcagctg tgctccttct ctttttcgct
 61    accgtctcag gatccacggg ccctggcagc agggaaagtc gaggatcgtc gcggatccct
121    tcccagttca gcgaggagga gcgcgtcgct atgaaagagg cgctgaaagg tgccatccgg
181    attccacaag tgtctttcag ccacgaggaa tccaacacca cagcccttgc tgagtttgga
241    gaatatatcc gaaaagcctt tcctacagtg ttccacagca accttatcca acacgaagtc
301    gtgggaagt atagccacct gctcaccgtc cgaggctcgg accccagttt gcagccctac
361    atgctgatgg ctcacttcga cgtggttcct gcctctgaag aaggatggga ggtgccccg
421    ttctcaggcc tggagcaaaa tggcttcatc catggccggg gtgcgctgga caacaaaaac
481    tctgtgatgg cagtcctgca ggctttggag ctcctgttga tcagaaaata cagccccaaa
541    agacctttct tcattgcttt gggccatgat gaggaggtgt ctgggacaaa ggggctcag
601    cagatctcag cactcttaca cgagggggt gtccagctag cttttcttgt ggatgaaggg
661    agctttatct tggaagactt cattccgaac ctcaagaagc cgtttgccat gatttcagtc
721    accgagaagg gtgccccttga cctcatgctg caagtaaaca tgactccagg ccactcttca
781    gctcccccaa aggagacaag cattggaatc ctttctgccg ctgtcagccg actggagcag
841    acaccaatgc caaacatgtt tggaaacggg ccattgaaga agacattgaa gctactggca
901    aatgagtttt ccttccctac caatataatc ttggggaacc tgtggctatt ccgtcccatt
961    gtaagcaggg taatggagag gaatcccata cgaatgcat ggtcagaac taccacagcc
1021   ctcaccatgt tcaatgcagg aatcaaggtg aatgtcatcc cccattggc tcaggcgaca
1081   gtcaacttcc gaattcaccc ttcgcagaca gtacgcgagg tcgtagaact cgtccagaac
1141   attgtggctg atgaccgagt ccagttgcat gtgttgagat cctttgaacc actgcccgtc
1201   agcccctctg atgaccaggc catgggctac cagctgcttc aacagaccat acagtctgtc
1261   ttcccggaag tcaagatcat tgtccccggt atttgtattg caacacgga cacccgacac
```

TABLE 1-continued

```
1321    tatgtcaacc tgaccaatgg cttgtaccgg ttcaaccccg ttttcctgaa gcctcaggac 1381    ttcagtagtg tccatggaat caatgagaaa atctccgttg agagctacca gaaccaggtg 1441    aagttcatct ttgagttgat ccaaaatgct gacacctaca gcaagccagt tcctcatcag 1501    catgaactat ga
```

SEQ ID NO: 10 Rat PM20D1 Amino Acid Sequence (Signal Peptide: Residues 1-24)

```
  1    maellvilpt raavlllffa tvsgstgpgs resrgssrip sqfseeerva mkealkgair 61    iptvsfshee snttalaefg eyirkafptv fhsnliqhev vgkyshlltv rgsdpslqpy 121    mlmahfdvvp aseegwevpp fsgleqngfi hgrgaldnkn svmavlqale lllirkyspk 181    rpffialghd eevsgtkgaq qisallqtrg vqlaflvdeg sfiledfipn lkkpfamisv 241    tekgaldlml qvnmtpghss appketsigi lsaavsrleq tpmpnmfgng plkktlklla 301    nefsfptnii lgnlwlfrpi vsrvmernpi tnalvrttta ltmfnagikv nvipplaqat 361    vnfrihpsqt vhevvelvqn ivaddrvqlh vlisfeplpv spsddqamgy qllqqtiqsv 421    fpevkiivpg icigntdtrh yvnltnglyr fnpvflkpqd fssvhginek isvesyqnqv 481    kfifeliqna dtyskpvphq hel
```

SEQ ID NO: 11 Chicken PM20D1 cDNA Sequence

```
  1    atggcgggtg ggtgcgggcg gcggcgggta gttgtgtgcg cggtggcgtt ggggctgagc 61    gcggcggtgc tggctctaac ggccgtagtg ttgctccgcg cctacgtgct gcgctcccng 121    gccatcccgc ggctgtgggc gcggcgcggg agcaccgccg ctttcagtgc cagcgagagg 181    cggagctga aggaagcgct gcgaggtgct gttcgaatcc cgactgtttc cttgtcttcg 241    gaggacttca acacaactgc catggcagag tttggggatt acattcggaa agccttccca 301    gctgtctttt cttccaagtt cattcaacat gaaatcattg gggagtacag ccacctcttc 361    accgttcagg gttctgactc tgaaatgatg ccctacatgc tgctcgcaca catggatgtt 421    gtgcccgctc cccctgaggg ctgggatttc cctcctttct cagctgcaga gcatgaaggt 481    ttcatctatg gacgaggaac gctggacaac aaaaactctg ccattggcat tctgcaagct 541    ctagaattct tactgagaag aaattacaga ccccgcaggt cttttctatgt tggcattggc 601    catgatgaag aggtgtttgg tcagaaggga gcactgaaga ttgcagctct gctggaatcc 661    agaggagtga aactctcctt cttgctggat gagggaagtg ctatactgga tggcatcatt 721    gcaggtgtga agaagccagt agctctaatt gctgtgacag agaagggttt aatgacactg 781    aacttcaccg tggaaaaaga gccaggacat tcatccttcc ctccaaaaga gacaagtatt 841    ggcattcttg caacagcagt gtccagactg gagcagaatc ccatgcgcag tctgtttggc 901    cgtggtccgg aactcatgac tatggagcac cttgcatcag agttcaattt tcctctcaat 961    ctcatcatga gcaatctctg gctgttttcg cctattgtca gcagagttct tgcctggaaa 1021   ccttccacta atgccttgat tcgaactact acagcagtca aatgtttaa cgcaggaatc 1081   aagttcaatg tcatcccacc atctgcaaga gcaactgtga acttccggat ccactctgga 1141   gagaaggcca agaggtgctg agagacagtt agaaacacag ttgcggatga cagagtgaag 1201   attgatgtca tagaggccct tgaccccta cccatcagcc catgggatga ccagaccttt 1261   ggagtccatg tttttcaaag aaccattctg gatactttcc caaatgttga cagtgtagtc 1321   ccaggcacgt gtattggaaa cacagacagc aggcatttca ctaacgtcac aaatgccatt 1381   tatcgattta acccagtgct cttgaagtca gatgatcttc caggatcca tggggttgaat 1441   gagagaatct cggttgagag ttatgagaaa caggtcgagt ttctctttca gctcattaag 1501   aactgtgatg ttgacaagct tccggagcct cacgcaaact ctcatgagct gtga
```

TABLE 1-continued

SEQ ID NO: 12 Chicken PM20D1 Amino Acid Sequence (Signal Peptide: Residues 1-34)
```
  1   maggcgrrrv vvcavalgls aavlaltavv llrayvlrsp aiprlwarrg staafsaser
 61   relkealrga vriptvslss edfnttamae fgdyirkafp avfsskfiqh eiigeyshlf
121   tvqgsdsemm pymllahmdv vpappegwdf ppfsaaeheg fiygrgtldn knsaigilqa
181   lefllrrnyr prrsfyvgig hdeevfgqkg alkiaalles rgvklsflld egsaildgii
241   agvkkpvali avtekglmtl nftvekepgh ssfppketsi gilatavsrl eqnpmrslfg
301   rgpelmtmeh lasefnfpln limsnlwlfs pivsrvlawk pstnalirtt tavtmfnagi
361   kfnvippsar atvnfrihsg ekakevletv rntvaddrvk idviealdpl pispwddqtf
421   gvhvfqrtil dtfpnvdsvv pgtcigntds rhftnvtnai yrfnpvllks ddlprihgln
481   erisvesyek qveflfqlik ncdvdklpep hanshel
```

SEQ ID NO: 13 Frog PM20D1 cDNA Sequence
```
   1   atggcagtat ctcgctggaa ggctgtgggc agcactctgc ttgctgcgtt tttagtgggg
  61   ctggtagtgc ttatagccgt tttgctcatc agaacttaca ctttgcctac agcggtcagg
 121   aagtggaata ggaatgaaag tctgatcact gaacttgctg agaaagagag aaagcagctg
 181   gtggaggcac tgaaaggtgc cattcgcatt cccactgtct cctttcaga agaggagcag
 241   aataccacag cactcagaga gtttggagaa tacatacaga agtcttccc tcaggttttc
 301   tcctccagtc taatccagca tgaggttttg ggaggttaca gtcacctttt taaagtacaa
 361   ggctctgacc acaatctact tccatacatg ttactggctc acattgatgt tgtaccagct
 421   ccaccagagt cctgggaggt gccacctttc tctggcgagg aacgagatgg ttatatctat
 481   ggaagaggaa ccctagatga caagaactgt gttattggaa ttcttcagtc acttgaattc
 541   ctcctgaaaa gaggtcacaa acctcgccga tctttctaca taggccttgg acatgatgaa
 601   gagatatctg ccacaaaggt tgcccagaag attgtggaga gttgcagtc tcaaggagtt
 661   aagctggcat ttgttttaga tgagggcttg gcagtcctag atggggttat tcaaggcatt
 721   agtcaacctg tcgcactggt tggtaccaca gaaaaaggat cagttacctt ggacctcaca
 781   gtaaatcgtt tacctggtca ttcttctatg ccgccgtctg aaaccagcat tgggatccta
 841   gctgcagctg tgtctagact agagcagaat atgatgccta atatgtttgg aaatggtcca
 901   gaacaagaca tgtttgaaca tctttctaca aagtttgact tccactaaa tattatcatg
 961   gcaaatctat ggctattttc acccatttta agcagaattc tggagctgtc gccttccacc
1021   aatgccatag tacggacaac aactgctctt accatcttca aagcagggat caagtcaaat
1081   gtgatcccac ctacagccac agcaactgtt aatttccggc ttcaccctgc acagacggta
1141   caagaggtcc tggatattgt tcagaacact ataaaggatg aaagagtgga gctatctgtc
1201   ttgaattcat tcgatccttt accagtcagt ccgaatgata tgagtttggg gtaccatatt
1261   cttcagcgta ccattcatga tgtcttttca ggacctccag ttgccccagg tgtttgtgtt
1321   ggcaatacag acagccgcca ttttgtcaac ttgaccaaca gtatctacag atttagccct
1381   gtggtgctca aaaaggagga tgtggatagg attcatgggt tgaatgagcg catttctaaa
1441   gaggcaattg aactccttgt ccagttctac atccagctga ttcaaaattc agatacagat
1501   aacatccctc caccacatct tgacacccat gagctttaa
```

SEQ ID NO: 14 Frog PM20D1 Amino Acid Sequence (Signal Peptide: Residues 1-34)
```
  1   mavsrwkavg stllaaflvg lvvliavlli rtytlptavr kwnrneslit elaekerkql
 61   vealkgairi ptvsfseeeq nttalrefge yiqkvfpqvf sssliqhevl ggyshlfkvq
```

TABLE 1-continued

```
121      gsdhnllpym  llahidvvpa  ppeswevppf  sgeerdgyiy  grgtlddknc  vigilqslef 181      llkrghkprr  sfyiglghde  eisghkgaqk  iveklqsqgv  klafvldegl  avldgviqgi 241      sqpvalvgtt  ekgsvtldlt  vnrlpghssm  ppsetsigil  aaavsrleqn  mmpnmfgngp 301      eqdmfehlst  kfdfpiniim  anlwlfspil  srilelspst  naivrtttal  tifkagiksn 361      vipptatatv  nfrlhpaqtv  qevldivqnt  ikdervelsv  lnsfdplpvs  pndmslgyhi 421      lqrtihdvfs  gppvapgvcv  gntdsrhfvn  ltnsiyrfsp  vvlkkedvdr  ihglnerisk 481      eaiellvqfy  iqliqnsdtd  nippphldth  el
```

Included in Table 1 are variations of 1, 2, 3, 4, 5, 6, 7, 8, 9, 10, 11, 12, 13, 14, 15, 16, 17, 18, 19, 20, or more nucleotides or amino acids on the 5' (N-terminal) end, on the 3' (C-terminal) end, or on both the 5' (N-terminal) and 3' (C-terminal) ends, of the domain sequences as long as the sequence variations encode or maintain the recited function and/or homology Included in Table 1 are nucleic acid and amino acid molecules comprising, consisting essentially of, or consisting of:

1) a nucleic acid or amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a sequence of SEQ ID NO:1-22, or a biologically active fragment thereof;

2) a nucleic acid or amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3500, 4000, 4500, 5000, 5500, 6000, 6500, 7000, 7500, 8000, 8500, 9000, 9500, 10000, or more nucleotides or amino acids, or any range in between, inclusive such as between 110 and 300 nucleotides;

3) a biologically active fragment of a nucleic acid or amino acid sequence of SEQ ID NO:1-22 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1510, 1515, 1520, 1521, 1522, 1523, 1524, 1525, 1526, 1527, 1528, 1529, 1530, or more nucleotides or amino acids, or any range in between, inclusive such as between 110 and 300 nucleotides;

4) a biologically active fragment of a nucleic acid or amino acid sequence of SEQ ID NO:1-22 having 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1510, 1515, 1520, 1521, 1522, 1523, 1524, 1525, 1526, 1527, 1528, 1529, 1530, or fewer nucleotides or amino acids, or any range in between, inclusive such as between 110 and 300 nucleotides;

5) one or more domains selected from the group consisting of a peptidase domain and a metal ion coordination domain;

6) the ability to modulate one or more biological activities of a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; and k) modified N-lipidated amino acid amounts and/or activity;

7) enzymatic products, including natural N-lipidated amino acids and synthetic N-lipidated amino acids that modulate one or more biological activities of 6), of PM20D1 and biologically active fragments thereof; and 8) any combination of 1) through 7), as well as those in the Examples and Figures and modified according to the descriptions provided herein, inclusive.

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein (e.g., cidea, adiponectin (adipoq), adipsin, otopetrin, type II deiodinase, cig30, ppar gamma 2, pgcla, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1)), are well-known in the art and can be used in the embodiments of the invention.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (HIS, H) | CAC, CAT |
| Isoleucineoleucine (ILE, I) | ATA, ATC, ATT |
| Leucine (LEU, L) | CTA, CTC, CTG, CTT, TTA, TTG |
| Lysine (LYS, K) | AAA, AAG |
| Methionine (MET, M) | ATG |
| Phenylalanine (PHE, F) | TTC, TTT |
| Proline (PRO, P) | CCA, CCC, CCG, CCT |
| Serine (SER, S) | AGC, AGT, TCA, TCC, TCG, TCT |
| Threonine (THR, T) | ACA, ACC, ACG, ACT |
| Tryptophan (TRP, W) | TGG |
| Tyrosine (TYR, Y) | TAC, TAT |
| Valine (VAL, V) | GTA, GTC, GTG, GTT |
| Termination signal (END) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the present invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

I. Isolated Nucleic Acids

One aspect of the invention pertains to methods utilizing isolated nucleic acid molecules that encode PM20D1 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PM20D1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of a sequence described in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous or identical to a nucleotide sequence described in Table 1 or a portion thereof (i.e., 100, 200, 300, 400, 450, 500, or more nucleotides), can be isolated using standard molecular biology techniques and the sequence information provided herein. For example, a human PM20D1 cDNA can be isolated from a human beige fat cell line (from Stratagene, LaJolla, CA, or Clontech, Palo Alto, CA) using all or portion of SEQ ID NOs: 1, 3, and 5, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, NY, 1989). Moreover, a nucleic acid molecule encompassing all or a portion of a sequence described in Table 1 or a nucleotide sequence which is at least about 50%, preferably at least about 60%, more preferably at least about 70%, yet more preferably at least about 80%, still more preferably at least about 90%, and most preferably at least about 95% or more homologous to a sequence described in Table 1, or fragment thereof, can be isolated by the polymerase chain reaction using oligonucleotide primers designed based upon the sequence described in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, MD; or AMV reverse transcriptase, available from Seikagaku America, Inc., St. Petersburg, FL). Synthetic oligonucleotide primers for PCR amplification can be designed based upon a sequence described in Table 1, or fragment thereof, or to the homologous nucleotide sequence. A nucleic acid of the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a PM20D1 nucleotide sequence can be prepared by standard synthetic techniques, i.e., using an automated DNA synthesizer.

Probes based on the PM20D1 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a PM20D1 protein, such as by measuring a level of a PM20D1-encoding nucleic acid in a sample of cells from a subject, i.e., detecting PM20D1 mRNA levels.

Nucleic acid molecules encoding other PM20D1 members and thus which have a nucleotide sequence which differs from the PM20D1 sequences of Table 1, or a fragment thereof, are contemplated. Moreover, nucleic acid molecules encoding PM20D1 proteins from different species, and thus which have a nucleotide sequence which differs from the PM20D1 sequences of Table 1 are also intended to be within the scope of the present invention. For example, dog PM20D1 cDNA can be identified based on the nucleotide sequence of a human and/or mouse PM20D1.

In one embodiment, the nucleic acid molecule(s) of the invention encodes a protein or portion thereof which includes an amino acid sequence which is sufficiently homologous to an amino acid sequence of a sequence described in Table 1, or fragment thereof, such that the protein or portion thereof modulates (e.g., enhance), one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; k) modified N-lipidated amino acid amount and/or activity; and l) growth and effects of metabolic disorders, such as obesity-associated cancer, cachexia, anorexia, diabetes, and obesity. As used herein, the language "sufficiently homologous" refers to proteins or portions thereof which have amino acid sequences which include a minimum number of identical or equivalent (e.g., an amino acid residue which has a similar side chain as an amino acid residue in an amino acid sequence described in Table 1, or fragment thereof) amino acid residues to an amino acid sequence of an amino acid sequence described in Table 1, or fragment thereof, such that the protein or portion thereof modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; and k) modified N-lipidated amino acid amount and/or activity; and l) growth and effects of metabolic disorders, such as obesity-associated cancer, cachexia, anorexia, diabetes, and obesity.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of an amino acid sequence described in Table 1, or a fragment thereof.

Portions of proteins encoded by the PM20D1 nucleic acid molecule of the invention are preferably biologically active portions of the PM20D1 protein. As used herein, the term "biologically active portion of PM20D1" is intended to include a portion, e.g., a domain/motif, of PM20D1 that has one or more of the biological activities of the full-length PM20D1 protein. Standard binding assays, e.g., immunoprecipitations and yeast two-hybrid assays, as described herein, or functional assays, e.g., RNAi or overexpression experiments, can be performed to determine the ability of a PM20D1 protein or a biologically active fragment thereof to maintain a biological activity of the full-length PM20D1 protein.

The invention further encompasses nucleic acid molecules that differ from a sequence described in Table 1, or fragment thereof, due to degeneracy of the genetic code and thus encode the same PM20D1 protein as that encoded by a nucleotide sequence described in Table 1, or a fragment thereof. In another embodiment, an isolated nucleic acid molecule of the invention has a nucleotide sequence encoding a protein having an amino acid sequence described in Table 1, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to an amino acid sequence described in Table 1, or a fragment thereof, or differs by at least 1, 2, 3, 5 or 10 amino acids but not more than 30, 20, 15 amino acids from an amino acid sequence described in Table 1.

It will be appreciated by those skilled in the art that DNA sequence polymorphisms that lead to changes in the amino acid sequences of PM20D1 may exist within a population (e.g., a mammalian population, e.g., a human population). Such genetic polymorphism in the PM20D1 gene may exist among individuals within a population due to natural allelic variation. As used herein, the terms "gene" and "recombinant gene" refer to nucleic acid molecules comprising an open reading frame encoding a PM20D1 protein, preferably a mammalian, e.g., human, PM20D1 protein. Such natural allelic variations can typically result in 1-5% variance in the nucleotide sequence of the PM20D1 gene. Any and all such nucleotide variations and resulting amino acid polymorphisms in PM20D1 that are the result of natural allelic variation and that do not alter the functional activity of PM20D1 are intended to be within the scope of the invention. Moreover, nucleic acid molecules encoding PM20D1 proteins from other species, and thus which have a nucleotide sequence which differs from the human or mouse sequences of a sequence described in Table 1, are intended to be within the scope of the invention. Nucleic acid molecules corresponding to natural allelic variants and homologues of the human or mouse PM20D1 cDNAs of the invention can be isolated based on their homology to the human or mouse PM20D1 nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the PM20D1 sequence that may exist in the population, the skilled artisan will further appreciate that changes can be introduced by mutation into a sequence described in Table 1, or fragment thereof, thereby leading to changes in the amino acid sequence of the encoded PM20D1 protein, without altering the functional ability of the PM20D1 protein. For example, nucleotide substitutions leading to amino acid substitutions at "non-essential" amino acid residues can be made in a sequence described in Table 1, or fragment thereof. A "non-essential" amino acid residue is a residue that can be altered from the wild-type sequence of PM20D1 (e.g., an amino acid sequence described in Table 1) without altering the activity of PM20D1, whereas an "essential" amino acid residue is required for PM20D1 activity. Other amino acid residues, however, (e.g., those that are not conserved or only semi-conserved between mouse and human) may not be essential for activity and thus are likely to be amenable to alteration without altering PM20D1 activity. Furthermore, amino acid residues that are essential for PM20D1 functions related to thermogenesis and/or adipogenesis, but not essential for PM20D1 functions related to gluconeogenesis, are likely to be amenable to alteration.

Accordingly, another aspect of the invention pertains to nucleic acid molecules encoding PM20D1 proteins that contain changes in amino acid residues that are not essential for PM20D1 activity. Such PM20D1 proteins differ in amino acid sequence from those amino acid sequences described in Table 1, or fragment thereof, yet retain at least one of the PM20D1 activities described herein. In one embodiment, the isolated nucleic acid molecule comprises a nucleotide sequence encoding a protein, wherein the protein lacks one or more PM20D1 domains. "Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared x 100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

As described herein and below, numerous modifications to PM20D1 polypeptides, and biologically active fragments thereof, can be made in order to, in some embodiments, distinguish the compositions of the present invention (e.g., PM20D1 polypeptides and biologically active fragments thereof, N-lipidated amino acids, etc.) from naturally-occurring compositions.

An isolated nucleic acid molecule encoding a PM20D1 protein homologous to an amino acid sequence described in Table 1, or fragment thereof, can be created by introducing one or more nucleotide substitutions, additions or deletions into a nucleotide sequence described in Table 1, or fragment thereof, or a homologous nucleotide sequence such that one or more amino acid substitutions, additions or deletions are introduced into the encoded protein. Mutations can be introduced into the sequence described in Table 1, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in PM20D1 is preferably replaced with another amino acid residue from the same side chain family. Alternatively, in another embodiment, mutations can be introduced randomly along all or part of a PM20D1 coding sequence, such as by saturation mutagenesis, and the resultant mutants can be screened for a PM20D1 activity described herein to identify mutants that retain PM20D1 activity. Following mutagenesis of a sequence described in Table 1, or fragment thereof, the encoded protein can be expressed recombinantly (as described herein) and the activity of the protein can be determined using, for example, assays described herein.

PM20D1 levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, PM20D1 levels are ascertained by measuring a gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the PM20D1 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well-known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding PM20D1. Other suitable probes for use in the diagnostic assays of the invention are described herein. Hybridization of an mRNA with the probe indicates that PM20D1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the PM20D1 mRNA expression levels.

An alternative method for determining the PM20D1 mRNA expression level in a sample involves the process of nucleic acid amplification, e.g., by rtPCR (the experimental embodiment set forth in Mullis, 1987, U.S. Pat. No. 4,683, 202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854, 033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the PM20D1 mRNA.

As an alternative to making determinations based on the absolute PM20D1 expression level, determinations may be based on the normalized PM20D1 expression level. Expression levels are normalized by correcting the absolute PM20D1 expression level by comparing its expression to the expression of a non-PM20D1 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a PM20D1 protein can also be detected and/or quantified by detecting or quantifying the expressed polypeptide. The PM20D1 polypeptide can be detected and quantified by any of a number of means well-known to those of skill in the art.

These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express PM20D1.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, piwiRNA, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the present invention, including one or more biomarkers listed in Table 1, the Figures, and the Examples, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well-known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA. In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the present invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, piwiRNA, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol.

20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1, the Figures, and the Examples,). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) *Nature* 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

It is to be understood that additional well-known nucleic acid architecture or chemistry can be applied. Different modifications can be placed at different positions to prevent the oligonucleotide from activating RNase H and/or being capable of recruiting the RNAi machinery. In another embodiment, they may be placed such as to allow RNase H activation and/or recruitment of the RNAi machinery. The modifications can be non-natural bases, e.g. universal bases. It may be modifications on the backbone sugar or phosphate, e.g., 2'-O-modifications including LNA or phosphorothioate linkages. As used herein, it makes no difference whether the modifications are present on the nucleotide before incorporation into the oligonucleotide or whether the oligonucleotide is modified after synthesis.

Preferred modifications are those that increase the affinity of the oligonucleotide for complementary sequences, i.e. increases the tm (melting temperature) of the oligonucleotide base paired to a complementary sequence. Such modifications include 2'-O-flouro, 2'-O-methyl, 2'-O-methoxyethyl. The use of LNA (locked nucleic acid) units, phosphoramidate, PNA (peptide nucleic acid) units or INA (intercalating nucleic acid) units is preferred. For shorter oligonucleotides, it is preferred that a higher percentage of affinity increasing modifications are present. If the oligonucleotide is less than 12 or 10 units long, it may be composed entirely of LNA units. A wide range of other non-natural units may also be build into the oligonucleotide, e.g., morpholino, 2'-deoxy-2'-fluoro-arabinonucleic acid (FANA) and arabinonucleic acid (ANA). In a preferred embodiment, the fraction of units modified at either the base or sugar relatively to the units not modified at either the base or sugar is selected from the group consisting of less than less than 99%, 95%, less than 90%, less than 85% or less than 75%, less than 70%, less than 65%, less than 60%, less than 50%, less than 45%, less than 40%, less than 35%, less than 30%, less than 25%, less than 20%, less than 15%, less than 10%, and less than 5%, less than 1%, more than 99%, more than 95%, more than 90%, more than 85% or more than 75%, more than 70%, more than 65%, more than 60%, more than 50%, more than 45%, more than 40%, more than 35%, more than 30%, more than 25%, more than 20%, more than 15%, more than 10%, and more than 5% and more than 1%.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215:327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g., mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well-known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, piwiRNA, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well-known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. Based on the genetic pathway analyses described herein, it is believed that such combinations of agents is especially effective in diagnosing, prognosing, preventing, and treating melanoma. Thus, "single active agents" described herein can be combined with other pharmacologically active compounds ("second active agents") known in the art according to the methods and compositions provided herein. It is believed that certain combinations work synergistically in the treatment of particular types of melanoma. Second active agents can be large molecules (e.g., proteins) or small molecules (e.g., synthetic inorganic, organometallic, or organic molecules). For example, agents that modulate (e.g., promote) brown fat cell-like development and/or activity can be provided as combination agents. Exemplary agents include, without limitation, PRDM16 (U.S. Pat. Publ. 2011/0059051), C/EBPβ (U.S. Pat. Publ. 2012/0022500), FNDC5/Irisin (U.S. Pat. No. 8,969,519 and PCT Publ. No. WO 2013/039996), Meteorin/Meteorin-like (PCT Publ. No. WO 2014/116556), respiration uncoupling agents (e.g., dinitrophenol, CCCP, and FCCP), and the like.

II. Recombinant Expression Vectors and Host Cells

Another aspect of the invention pertains to the use of vectors, preferably expression vectors, containing a nucleic acid encoding PM20D1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a PM20D1 nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of PM20D1 in prokaryotic or eukaryotic cells. For example, PM20D1 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, CA (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein. In one embodiment, the coding sequence of the PM20D1 is cloned into a pGEX expression vector to create a vector encoding a fusion protein comprising, from the N-terminus to the C-terminus, and/or GST-thrombin cleavage site-PM20D1. The fusion protein can be purified by affinity chromatography using glutathione-agarose resin. Recombinant PM20D1 unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, California (1990) 60-89). Target gene expression from the pTrc vector relies on host RNA polymerase transcription from a hybrid trp-lac fusion promoter. Target gene expression from the pET 11d vector relies on transcription from a T7 gn10-1ac fusion promoter mediated by a coexpressed viral RNA polymerase (T7 gni). This viral polymerase is supplied by host strains BL21(DE3) or HMS174 (DE3) from a resident λ prophage harboring a T7 gni gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, California (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the PM20D1 expression vector is a yeast expression vector. Examples of vectors for expression in yeast *S. cerivisae* include pYepSecl (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, CA).

Alternatively, PM20D1 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, NY, 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to PM20D1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, PM20D1 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, NY, 1989), and other laboratory manuals.

A cell culture includes host cells, media and other byproducts. Suitable media for cell culture are well-known in the art. A PM20D1 polypeptide or fragment thereof, may be secreted and isolated from a mixture of cells and medium containing the polypeptide. Alternatively, a PM20D1 polypeptide or fragment thereof, may be retained cytoplasmically and the cells harvested, lysed and the protein or protein complex isolated. A PM20D1 polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of PM20D1 or a fragment thereof. In other embodiments, heterologous tags can be used for purification purposes (e.g., epitope tags and FC fusion tags), according to standards methods known in the art.

Thus, a nucleotide sequence encoding all or a selected portion of a PM20D1 polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant PM20D1 polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well-known in the art and include commercially available kits. Examples of in vitro translation systems include eukaryotic lysates, such as rabbit reticulocyte lysates, rabbit oocyte lysates, human cell lysates, insect cell lysates and wheat germ extracts.

Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the PM20D1 polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding PM20D1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) PM20D1 protein. Accordingly, the invention further provides methods for producing PM20D1 protein using the host cells of the invention. In one embodiment, the method comprises culturing the host cell of invention (into which a recombinant expression vector encoding PM20D1 has been introduced) in a suitable medium until PM20D1 is produced. In another embodiment, the method further comprises isolating PM20D1 from the medium or the host cell.

The host cells of the invention can also be used to produce non-human transgenic animals. The non-human transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which PM20D1 encoding sequences, or fragments thereof, have been introduced. Such host cells can then be used to create non-human transgenic animals in which exogenous PM20D1 sequences have been introduced into their genome or homologous recombinant animals in which endogenous PM20D1 sequences have been altered. Such animals are useful for studying the function and/or activity of PM20D1, or fragments thereof, and for identifying and/or evaluating modulators of PM20D1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PM20D1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding PM20D1, or a fragment thereof, into the male pronuclei of a fertilized oocyte, e.g., by microinjection, retroviral infection, and allowing the oocyte to develop in a pseudopregnant female foster animal. The human PM20D1 cDNA sequence can be introduced as a transgene into the genome of a non-human animal. Alternatively, a non-human homologue of the human PM20D1 gene can be used as a transgene. Intronic sequences and polyadenylation signals can also be included in the transgene to increase the efficiency of expression of the transgene. A tissue-specific regulatory sequence(s) can be operably linked to the PM20D1 transgene to direct expression of PM20D1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the PM20D1 transgene in its genome and/or expression of PM20D1 mRNA in tissues or cells of the animals. A transgenic founder animal can then be used to breed additional animals carrying the transgene. Moreover, transgenic animals carrying a transgene encoding PM20D1 can further be bred to other transgenic animals carrying other transgenes.

To create a homologous recombinant animal, a vector is prepared which contains at least a portion of a PM20D1 gene into which a deletion, addition or substitution has been introduced to thereby alter, e.g., functionally disrupt, the PM20D1 gene. The PM20D1 gene can be a human gene, but more preferably, is a non-human homologue of a human PM20D1 gene. For example, a mouse PM20D1 gene can be used to construct a homologous recombination vector suitable for altering an endogenous PM20D1 gene, respectively, in the mouse genome. In a preferred embodiment, the vector is designed such that, upon homologous recombination, the endogenous PM20D1 gene is functionally disrupted (i.e., no longer encodes a functional protein; also referred to as a "knock out" vector). Alternatively, the vector can be designed such that, upon homologous recombination, the endogenous PM20D1 gene is mutated or otherwise altered but still encodes functional protein (e.g., the upstream regulatory region can be altered to thereby alter the expression of the endogenous PM20D1 protein). In the homologous recombination vector, the altered portion of the PM20D1 gene is flanked at its 5' and 3' ends by additional nucleic acid of the PM20D1 gene to allow for homologous recombination to occur between the exogenous PM20D1 gene carried by the vector and an endogenous PM20D1 gene in an embryonic stem cell. The additional flanking PM20D1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PM20D1 gene has homologously recombined with the endogenous PM20D1 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of Saccharomyces cerevisiae (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Similarly, the CRISPR-Cas system can be used for precise editing of genomic nucleic acids (e.g., for creating null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326: 1509-1512; Moscou and Bogdanove (2009) *Science* 326: 1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

Clones of the non-human transgenic animals, knockout animals, etc. described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated PM20D1 Polypeptides and Anti-PM20D1 Antibodies

The present invention provides soluble, purified and/or isolated forms of PM20D1 polypeptides, or fragments thereof, for use in the present methods or as compositions.

In one aspect, a PM20D1 polypeptide may comprise a full-length PM20D1 amino acid sequence or a full-length PM20D1 amino acid sequence with 1 to about 20 conservative amino acid substitutions. Amino acid sequence of any PM20D1 polypeptide described herein can also be at least 50, 55, 60, 65, 70, 75, 80, 85, 90, 91, 92, 93, 94, 95, 96, 97, 98, 99, or 99.5% identical to a PM20D1 polypeptide sequence of interest, described herein, well-known in the art, or a fragment thereof. In addition, any PM20D1 polypeptide, or fragment thereof, described herein has modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; k) modified N-lipidated amino acid amount and/or activity; and l) growth and effects of metabolic disorders, such as obesity-associated cancer, cachexia, anorexia, diabetes, and obesity. In another aspect, the present invention contemplates a composition comprising an isolated PM20D1 polypeptide and less than about 25%, or alternatively 15%, or alternatively 5%, contaminating biological macromolecules or polypeptides.

The present invention further provides compositions related to producing, detecting, or characterizing a PM20D1 polypeptide, or fragment thereof, such as nucleic acids, vectors, host cells, and the like. Such compositions may serve as compounds that modulate a PM20D1 polypeptide's expression and/or activity, such as antisense nucleic acids.

In certain embodiments, a PM20D1 polypeptide of the invention may be a fusion protein containing a domain which increases its solubility and bioavailability and/or facilitates its purification, identification, detection, and/or structural characterization. Exemplary domains, include, for example, Fc, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a PM20D1 polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 8, 9, 10, 15, 20 amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) a polyG(4)-A-polyG(4) sequence. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, PM20D1 polypeptides, or fragments thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et.al., 2001 Immunity 14:123 133. Fusion to an Fc polypeptide offers the additional advantage of facilitating purification by affinity chromatography over Protein A or Protein G columns.

In still another embodiment, a PM20D1 polypeptide may be labeled with a fluorescent label to facilitate their detection, purification, or structural characterization. In an exemplary embodiment, a PM20D1 polypeptide of the invention may be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated PM20D1 proteins, and biologically active portions thereof, as well as peptide fragments suitable for use as immunogens to raise anti-PM20D1 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of PM20D1 protein in which the protein is separated from cellular components of the cells in which it is naturally or recombinantly produced. In one embodiment, the language "substantially free of cellular material" includes preparations of PM20D1 protein having less than about 30% (by dry weight) of non-PM20D1 protein (also referred to herein as a "contaminating protein"), more preferably less than about 20% of non-PM20D1 protein, still more preferably less than about 10% of non-PM20D1 protein, and most preferably less than about 5% non-PM20D1 protein. When the PM20D1 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PM20D1 protein in which the protein is separated from chemical precursors or other chemicals which are involved in the synthesis of the protein. In one embodiment, the language "substantially free of chemical precursors or other chemicals" includes preparations of PM20D1 protein having less than about 30% (by dry weight) of chemical precursors of non-PM20D1 chemicals, more preferably less than about 20% chemical precursors of non-PM20D1 chemicals, still more preferably less than about 10% chemical precursors of non-PM20D1 chemicals, and most preferably less than about 5% chemical precursors of non-PM20D1 chemicals. In preferred embodiments, isolated proteins or biologically active portions thereof lack contaminating proteins from the same animal from which the PM20D1 protein is derived. Typically, such proteins are produced by recombinant expression of, for example, a human PM20D1 protein in a non-human cell.

In preferred embodiments, the protein or portion thereof comprises an amino acid sequence which is sufficiently homologous to an amino acid sequence described in Table 1, such that the protein or portion thereof maintains one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; k) modified N-lipidated amino acid amount and/or activity; and l) growth and effects of metabolic disorders, such as obesity-associated cancer, cachexia, anorexia, diabetes, and obesity. The portion of the protein is preferably a biologically active portion as described herein. In another preferred embodiment, the PM20D1 protein has an amino acid sequence described in Table 1, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence described in Table 1, or fragment thereof. In yet another preferred embodiment, the PM20D1 protein has an amino acid sequence which is encoded by a nucleotide sequence which hybridizes, e.g., hybridizes under stringent conditions, to a nucleotide sequence described in Table 1, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to a nucleotide sequence described in Table 1, or fragment thereof. The preferred PM20D1 proteins of the present invention also preferably possess at least one of the PM20D1 biological activities, or activities associated with the complex, described herein. For example, a preferred PM20D1 protein of the present invention includes an amino acid sequence encoded by a nucleotide sequence which hybridizes, e.g., hybridizes under stringent conditions, to a nucleotide sequence described in Table 1, or fragment thereof, and which can maintain one or more of the following biological activities or, in complex, modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified expression of UCP1 protein; k) modified N-lipidated amino acid amount and/or activity; and l) growth and effects of metabolic disorders, such as obesity-associated cancer, cachexia, anorexia, diabetes, and obesity.

Biologically active portions of the PM20D1 protein include peptides comprising amino acid sequences derived from the amino acid sequence of the PM20D1 protein, e.g., an amino acid sequence described in Table 1, or fragment thereof, or the amino acid sequence of a protein homologous to the PM20D 1 protein, which include fewer amino acids than the full length PM20D1 protein or the full length protein which is homologous to the PM20D1 protein, and exhibist at least one activity of the PM20D1 protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., signal peptide, peptidase domain, metal ion coordination domain, etc.). In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the PM20D1 protein include one or more selected domains/motifs or portions thereof having biological activity. In an exemplary embodiment, a PM20D1 fragment comprises and/or consists of about 408, 407, 406, 405, 404, 403, 402, 401, 400, 399, 398, 397, 396, 395, 394, 393, 392, 391, 390, 389, 388, 387, 386, 385, 384, 383, 382, 381, 380, 379, 378, 377, 376, 375, 374, 373, 372, 371, 370, 365, 360, 355, 350, 345, 340, 335, 330, 325, 320, 315, 310, 305, 300, 295, 290, 285, 280, 275, 270, 265, 260, 255, 250, 245, 240, 235, 230, 225, 220, 215, 210, 205, 200, or fewer residues of a sequence described in Table 1, or any range in between, inclusive, such as 275 to 408 amino acids in length.

PM20D1 proteins can be produced by recombinant DNA techniques. For example, a nucleic acid molecule encoding the protein is cloned into an expression vector (as described above), the expression vector is introduced into a host cell (as described above) and the PM20D1 protein is expressed in the host cell. The PM20D1 protein can then be isolated from the cells by an appropriate purification scheme using standard protein purification techniques. Alternative to recombinant expression, a PM20D1 protein, polypeptide, or peptide can be synthesized chemically using standard peptide synthesis techniques. Moreover, native PM20D1 protein can be isolated from cells (e.g., brown adipocytes), for example using an anti-PM20D1 antibody (described further below). Similarly, N-lipidated amino acids can be purified or chemically synthesized using well-known methods in the art (e.g., U.S. Pat. Nos. 3,663,459; 5,112,863; U.S. Pat. Publ. 2008/0274124; Huang et al. (2001) *JBC* 276:42639-42644; Milman et al. (2006) *Proc. Natl. Acad. Sci. U.S.A.* 103:2428-2433) and as described further herein.

The present invention also provides PM20D1 chimeric or fusion proteins. As used herein, a PM20D1 "chimeric protein" or "fusion protein" comprises a PM20D1 polypeptide operatively linked to a non-PM20D1 polypeptide. A "PM20D1 polypeptide" refers to a polypeptide having an amino acid sequence corresponding to PM20D1, whereas a "non-PM20D1 polypeptide" refers to a polypeptide having an amino acid sequence corresponding to a protein which is not substantially homologous to the PM20D1 protein, respectively, e.g., a protein which is different from the PM20D1 protein and which is derived from the same or a different organism. Within the fusion protein, the term "operatively linked" is intended to indicate that the PM20D1 polypeptide and the non-PM20D1 polypeptide are fused in-frame to each other. The non-PM20D1 polypeptide can be fused to the N-terminus or C-terminus of the PM20D1 polypeptide, respectively. For example, in one embodiment the fusion protein is a PM20D1-GST and/or PM20D1-Fc fusion protein in which the PM20D1 sequences, respectively, are fused to the N-terminus of the GST or Fc sequences. Such fusion proteins can facilitate the purification, expression, and/or bioavailbility of recombinant PM20D1. In another embodiment, the fusion protein is a PM20D1 protein containing a heterologous signal sequence at its C-terminus. In certain host cells (e.g., mammalian host cells), expression and/or secretion of PM20D1 can be increased through use of a heterologous signal sequence.

Preferably, a PM20D1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PM20D1-encoding nucleic acid can be cloned into such an expression vector such that the fusion moiety is linked in-frame to the PM20D1 protein.

The present invention also pertains to homologues of the PM20D1 proteins which function as either a PM20D1 agonist (mimetic) or a PM20D1 antagonist. In a preferred embodiment, the PM20D1 agonists and antagonists stimulate or inhibit, respectively, a subset of the biological activities of the naturally occurring form of the PM20D1 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the PM20D1 protein.

Homologues of the PM20D1 protein can be generated by mutagenesis, e.g., discrete point mutation or truncation of the PM20D1 protein. As used herein, the term "homologue" refers to a variant form of the PM20D1 protein which acts as an agonist or antagonist of the activity of the PM20D1 protein. An agonist of the PM20D1 protein can retain substantially the same, or a subset, of the biological activities of the PM20D1 protein. An antagonist of the PM20D1 protein can inhibit one or more of the activities of the naturally occurring form of the PM20D1 protein, by, for example, competitively binding to a downstream or upstream member of the PM20D1 cascade which includes the PM20D1 protein. Thus, the mammalia PM20D1 protein and homologues thereof of the present invention can be, for example, either positive or negative regulators of adipocyte differentiation and/or thermogenesis in brown adipocytes.

In an alternative embodiment, homologues of the PM20D1 protein can be identified by screening combinatorial libraries of mutants, e.g., truncation mutants, of the PM20D1 protein for PM20D1 protein agonist or antagonist activity. In one embodiment, a variegated library of PM20D1 variants is generated by combinatorial mutagenesis at the nucleic acid level and is encoded by a variegated gene library. A variegated library of PM20D1 variants can be produced by, for example, enzymatically ligating a mixture of synthetic oligonucleotides into gene sequences such that a degenerate set of potential PM20D1 sequences is expressible as individual polypeptides, or alternatively, as a set of larger fusion proteins (e.g., for phage display) containing the set of PM20D1 sequences therein. There are a variety of methods which can be used to produce libraries of potential PM20D1 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PM20D1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the PM20D1 protein coding can be used to generate a variegated population of PM20D1 fragments for screening and subsequent selection of homologues of a PM20D1 protein. In one embodiment, a library of coding sequence fragments can be generated by treating a double stranded PCR fragment of a PM20D1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the PM20D1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PM20D1 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PM20D1 homologues (Arkin and Youvan (1992) *Proc. Natl. Acad. Sci. USA* 89:7811-7815; Delagrave et al. (1993) *Protein Engineering* 6(3):327-331).

In another aspect, an isolated PM20D1 protein, or a fragment thereof, can be used as an immunogen to generate antibodies that bind PM20D1, or the complex thereof, using standard techniques for polyclonal and monoclonal antibody preparation. The full-length PM20D1 protein can be used or, alternatively, antigenic peptide fragments of PM20D1, or peptides in complex, can be used as immunogens. A PM20D1 immunogen typically is used to prepare antibodies by immunizing a suitable subject, (e.g., rabbit, goat, mouse or other mammal) with the immunogen. An appropriate immunogenic preparation can contain, for example, recombinantly expressed PM20D1 protein or a chemically synthesized PM20D1 peptide. The preparation can further include an adjuvant, such as Freund's complete or incomplete adjuvant, or similar immunostimulatory agent. Immunization of a suitable subject with an immunogenic PM20D1 preparation induces a polyclonal anti-PM20D1 antibody response.

Accordingly, another aspect of the invention pertains to the use of anti-PM20D1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as PM20D1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PM20D1. The term "monoclonal antibody" or "monoclonal antibody composition", as used herein, refers to a population of antibody molecules that contain only one species of an antigen binding site capable of immunoreacting with a particular epitope of PM20D1. A monoclonal antibody composition thus typically displays a single binding affinity for a particular PM20D1 protein with which it immunoreacts.

Polyclonal anti-PM20D1 antibodies can be prepared as described above by immunizing a suitable subject with a PM20D1 immunogen, or fragment thereof. The anti-PM20D1 antibody titer in the immunized subject can be monitored over time by standard techniques, such as with an enzyme linked immunosorbent assay (ELISA) using immobilized PM20D1. If desired, the antibody molecules directed against PM20D1 can be isolated from the mammal (e.g., from the blood) and further purified by well-known techniques, such as protein A chromatography to obtain the IgG fraction. At an appropriate time after immunization, i.e., when the anti-PM20D1 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well-known (see generally R. H. Kenneth, in *Monoclonal Antibodies: A New Dimension In Biological Analyses*, Plenum Publishing Corp., New York, New York (1980); E. A. Lerner (1981) i Yale J. Biol. Med., 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a PM20D1 immunogen as described above, and the culture supernatants of the resulting hybridoma cells are screened to identify a hybridoma producing a monoclonal antibody that binds PM20D1.

Any of the many well-known protocols used for fusing lymphocytes and immortalized cell lines can be applied for the purpose of generating an anti-PM20D1 monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PM20D1, i.e., using a standard ELISA assay.

As an alternative to preparing monoclonal antibody-secreting hybridomas, a monoclonal anti-PM20D1 antibody can be identified and isolated by screening a recombinant combinatorial immunoglobulin library (e.g., an antibody phage display library) with PM20D1 to thereby isolate immunoglobulin library members that bind PM20D1. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-PM20D1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) Proc. Natl. Acad. Sci. USA 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PM20D1 antibody (e.g., monoclonal antibody) can be used to isolate PM20D1 by standard techniques, such as affinity chromatography or immunoprecipitation. An anti-PM20D1 antibody can facilitate the purification of natural PM20D1 from cells and of recombinantly produced PM20D1 expressed in host cells. Moreover, an anti-PM20D1 antibody can be used to detect PM20D1 protein (e.g., in a cellular lysate or cell supernatant) in order to evaluate the abundance and pattern of expression of the PM20D1 protein. Anti-PM20D1 antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In vivo techniques for detection of PM20D1 protein include introducing into a subject a labeled antibody directed against the protein. For example, the antibody can be labeled with a radioactive marker whose presence and location in a subject can be detected by standard imaging techniques.

IV. Identification of Compounds that Modulate PM20D1 and N-Lipidated Amino Acids The PM20D1 nucleic acid and polypeptide molecules described herein may be used to design modulators of one or more of biological activities of PM20D1 polypeptides and/or N-lipidated. In particular, information useful for the design of therapeutic and diagnostic molecules, including, for example, the protein domain, structural information, and the like for polypeptides of the invention is now available or attainable as a result of the ability to prepare, purify and characterize the polypeptides and N-lipidated amino acids, as well as domains, fragments, variants, and derivatives thereof.

In one aspect, modulators, inhibitors, or antagonists against the polypeptides of the invention, biological complexes containing them, or orthologues thereof, may be used to treat any disease or other treatable condition of a patient (including humans and animals), including, for example, metabolic disorders.

Modulators of PM20D1 nucleic acid and polypeptide molecules, may be identified and developed as set forth below using techniques and methods known to those of skill in the art. The modulators of the invention may be employed, for instance, to inhibit and treat PM20D1-mediated diseases or disorders. The modulators of the invention may elicit a change in one or more of the following activities: (a) a change in the level and/or rate of formation of a PM20D1-substrate complex or product (e.g., naturally occurring or synthetic), such as N-lipidated amino acids, (b) a change in the activity of a PM20D1 nucleic acid and/or polypeptide, (c) a change in the stability of a PM20D1 nucleic acid and/or polypeptide, (d) a change in the conformation of a PM20D1 nucleic acid and/or polypeptide, or (e) a change in the activity of at least one polypeptide contained in a PM20D1 complex or substrate/enzyme configuration. A number of methods for identifying a molecule which modulates a PM20D1 nucleic acid and/or polypeptide are known in the art. For example, in one such method, a PM20D1 nucleic acid and/or polypeptide, is contacted with a test compound, and the activity of the PM20D1 nucleic acid and/or polypeptide is determined in the presence of the test compound, wherein a change in the activity of the PM20D1 nucleic acid and/or polypeptide in the presence of the compound as compared to the activity in the absence of the compound (or in the presence of a control compound)

indicates that the test compound modulates the activity of the PM20D1 nucleic acid and/or polypeptide.

Compounds to be tested for their ability to act as modulators of PM20D1 nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of a PM20D1 polypeptide (e.g., a dominant negative form that binds to, but does not activate, PM20D1 enzymatic activity). In other embodiments, the compound promotes (e.g., increases enzymatic activity, such as a substrate having a structure requiring a lower activation energy) or inhibits (e.g., decreases PM20D1 enzymatic activity, such as a reversible or irreversible inhibitor, like a covalent inhibitor).

A variety of assay formats will suffice and, in light of the present disclosure, those not expressly described herein may nevertheless be comprehended by one of ordinary skill in the art based on the teachings herein. Assay formats for analyzing PM20D1-substrate complex formation and/or activity of a PM20D1 nucleic acid and/or polypeptide, may be generated in many different forms, and include assays based on cell-free systems, e.g. purified proteins or cell lysates, as well as cell-based assays, which utilize intact cells. Simple binding assays can also be used to detect agents which modulate a PM20D1, for example, by enhancing the formation of a PM20D1 enzymatic product, by enhancing the rate of PM20D1 enzymatic activity, and/or by enhancing the binding of a PM20D1 polypeptide to a substrate. Another example of an assay useful for identifying a modulator of a PM20D1 is a competitive assay that combines one or more PM20D1 polypeptides with a potential modulator, such as, for example, polypeptides, nucleic acids, natural substrates or ligands, or substrate or ligand mimetics, under appropriate conditions for a competitive inhibition assay. PM20D1 polypeptides can be labeled, such as by radioactivity or a colorimetric compound, such that PM20D1-substrate complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting PM20D1, PM20D1-substrate complexes, complexes comprising PM20D1 polypeptides, and the like, as described above.

Complex formation between a PM20D1 polypeptide, or fragment thereof, and a binding partner (e.g., PM20D1 substrate) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying PM20D1-substrate complexes described above may be incorporated into the detection methods.

In certain embodiments, it may be desirable to immobilize a PM20D1 polypeptide to facilitate separation of PM20D1 complexes from uncomplexed forms, as well as to accommodate automation of the assay. Binding of a PM20D1 polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of PM20D1 polypeptides found in the bead fraction quantified from the gel using standard electrophoretic techniques such as described in the appended examples.

Other techniques for immobilizing proteins on matrices are also available for use in the subject assay. For instance, a PM20D1 polypeptide may be immobilized utilizing conjugation of biotin and streptavidin. For instance, biotinylated polypeptide molecules may be prepared from biotin-NHS (N-hydroxy-succinimide) using techniques well-known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the PM20D1 polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of PM20D1 polypeptide trapped in the PM20D1 complex may be assessed with a chromogenic substrate of the enzyme, e.g. 3,3'-diamino-benzadine terahydrochloride or 4-chloro-1-napthol. Likewise, a fusion protein comprising the PM20D1 polypeptide and glutathione-S-transferase may be provided, and PM20D1 complex formation quantified by detecting the GST activity using 1-chloro-2,4-dinitrobenzene (Habig et al (1974) *J Biol Chem* 249:7130).

Antibodies against the PM20D1 polypeptide can be used for immunodetection purposes. Alternatively, the PM20D1 polypeptide to be detected may be "epitope-tagged" in the form of a fusion protein that includes, in addition to the polypeptide sequence, a second polypeptide for which antibodies are readily available (e.g., from commercial sources). For instance, the GST fusion proteins described above may also be used for quantification of binding using antibodies against the GST moiety. Other useful epitope tags include myc-epitopes (e.g., see Ellison et al. (1991) *J. Biol. Chem.* 266:21150-21157) which includes a 10-residue sequence from c-myc, as well as the pFLAG system (International Biotechnologies, Inc.) or the pEZZ-protein A system (Pharmacia, N. J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, a PM20D1 polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a binding domain of a transcriptional activator may be fused in frame to the coding sequence for a "bait" protein, e.g., a PM20D1 polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a binding domain that recognizes the responsive element on the reporter gene in the host cell, and (b) a bait protein (e.g., a PM20D1 polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The binding domain of the first hybrid protein and the transcriptional activation domain of the second hybrid protein may be derived from transcriptional activators having separable binding and transcriptional activation domains. For instance, these separate binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert binding domains may be used in the subject constructs; such as domains of ACE1, lac repressor, jun or fos. In another embodiment, the binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, PCT Publ. No. WO 1994/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the PM20D1 polypeptide, or substrate-complex or protein-complex thereof, of interest may be generated in whole cells, taking advantage of cell culture techniques to support the subject assay. For example, the PM20D1 polypeptide, or complex thereof, may be constituted in a prokaryotic or eukaryotic cell culture system. Advantages to generating the PM20D1 polypeptide, or complex thereof, in an intact cell includes the ability to screen for modulators of the level and/or activity of the PM20D1 polypeptide, or complex thereof, which are functional in an environment more closely approximating that which therapeutic use of the modulator would require, including the ability of the agent to gain entry into the cell.

Furthermore, certain of the in vivo embodiments of the assay are amenable to high through-put analysis of candidate agents.

The PM20D1 nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high throughput analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of PM20D1 may be detected in a cell-free assay generated by constitution of a functional PM20D1 in a cell lysate. In an alternate format, the assay can be derived as a reconstituted protein mixture which, as described below, offers a number of benefits over lysate-based assays.

The activity of a PM20D1 or a PM20D1 polypeptide may be identified and/or assayed using a variety of methods well-known to the skilled artisan. For example, the activity of a PM20D1 nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of a PM20D1 nucleic acid and/or polypeptide may be assessed by monitoring changes in the phenotype of a targeted cell. For example, the detection means can include a reporter gene construct which includes a transcriptional regulatory element that is dependent in some form on the level and/or activity of a PM20D1 nucleic acid and/or polypeptide. The PM20D1 nucleic acid and/or polypeptide may be provided as a fusion protein with a domain that binds to a DNA element of a reporter gene construct. The added domain of the fusion protein can be one which, through its binding ability, increases or decreases transcription of the reporter gene. Whichever the case may be, its presence in the fusion protein renders it responsive to a PM20D1 nucleic acid and/or polypeptide. Accordingly, the level of expression of the reporter gene will vary with the level of expression of a PM20D1 nucleic acid and/or polypeptide.

Similarly, PM20D1 enzymatic activity can be assessed using well-known enzymatic analysis methods. For example, the rate or amount of PM20D1 catalysis, substrate association, substrate dissociation, product biosynthesis, product catalysis (e.g., breakdown), and the like can be analyzed.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a PM20D1 nucleic acid and/or polypeptide present in the cell. Such embodiments of the subject assay are particularly amenable to high through-put analysis in that proliferation of the cell can provide a simple measure of inhibition of the PM20D1 nucleic acid and/or polypeptide.

Similarly, individual cells or analyses of phenotypes in organisms can be formed to determine effects of test agents on the modulation (e.g., upregulation) of one or more of the following PM20D1-mediated biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity.

V. Methods of the Invention

One aspect of the present invention relates to methods of selecting agents (e.g., antibodies, fusion constructs, peptides, small molecules, small nucleic acids, and N-lipidated amino acids) which bind to, upregulate, downregulate, or modulate one or more biomarkers of the present invention listed in Table 1, the Figures, and the Examples, and/or a metabolic disorder. Such methods can use screening assays, including cell-based and non-cell based assays.

In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

In one embodiment, the invention relates to assays for screening candidate or test compounds which bind to or modulate the expression or activity level of, one or more biomarkers of the present invention, including one or more biomarkers listed in Table 1, the Figures, and the Examples, or a fragment or ortholog thereof. Such compounds include, without limitation, antibodies, proteins, fusion proteins, nucleic acid molecules, small molecules, and N-lipidated amino acids.

In one embodiment, an assay is a cell-based assay, comprising contacting a *cell* expressing one or more biomarkers of the present invention, including one or more biomarkers listed in Table 1, the Figures, and the Examples, or a fragment thereof, with a test compound and determining the ability of the test compound to modulate (e.g., stimulate or inhibit) the level of interaction between the biomarker and its natural binding partners as measured by direct binding or by measuring a parameter related to a metabolic disorder.

For example, in a direct binding assay, the biomarker polypeptide, a binding partner polypeptide of the biomarker, or a fragment(s) thereof, can be coupled with a radioisotope or enzymatic label such that binding of the biomarker polypeptide or a fragment thereof to its natural (or synthetic) binding partner(s) or a fragment(s) thereof can be determined by detecting the labeled molecule in a complex. For example, the biomarker polypeptide, a binding partner polypeptide of the biomarker, or a fragment(s) thereof, can be labeled with $^{125}I$, $^{35}S$, $^{14}C$, or $^{3}H$, either directly or indirectly, and the radioisotope detected by direct counting of radioemission or by scintillation counting. Alternatively, the polypeptides of interest a can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between one or more biomarkers of the present invention, including one or more biomarkers listed in Table 1, the Figures, and the Examples, or a fragment thereof, and its natural (or synthetic) binding partner(s) (e.g., naturally occurring or synthetic N-lipidated amino acids) or a fragment(s) thereof, without the labeling of any of the interactants (e.g., using a microphysiometer as described in McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of blocking agents (e.g., antibodies, fusion proteins, peptides, nucleic acid molecules, small molecules, N-lipidated amino acid mimietics) to antagonize the interaction between a given set of nucleic acid molecules and/or polypeptides can be accomplished by determining the activity of one or more members of the set of interacting molecules. For example, the activity of one or more biomarkers of the present invention, including one or more biomarkers listed in Table 1, the Figures, and the Examples, or a fragment thereof, can be determined by detecting induction of metabolic response, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the biomarker or a fragment thereof (e.g., modulations of biological pathways identified herein, such as modulated cellular respiration, brown/beige fat gene expression, mitochondrial biosynthesis, and the like).

In yet another embodiment, an assay of the present invention is a cell-free assay in which one or more biomarkers of the present invention, including one or more biomarkers listed in Table 1, the Figures, and the Examples, or a fragment thereof, e.g., a biologically active fragment thereof, is contacted with a test compound, and the ability of the test compound to bind to the polypeptide, or biologically active portion thereof, is determined. Binding of the test compound to the biomarker or a fragment thereof, can be determined either directly or indirectly as described above. Determining the ability of the biomarker or a fragment thereof to bind to its natural (or synthetic) binding partner(s) or a fragment(s) thereof can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. One or more biomarkers polypeptide or a fragment thereof can be immobilized on a BIAcore chip and multiple agents, e.g., blocking antibodies, fusion proteins, peptides, small molecules, or N-lipidated amino acids, can be tested for binding to the immobilized biomarker polypeptide or fragment thereof. An example of using the BIA technology is described by Fitz et al. (1997) *Oncogene* 15:613.

The cell-free assays of the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3- cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the biomarker nucleic acid and/or polypeptide, the natural (or synthetic) binding partner(s) of the biomarker, or fragments thereof, to facilitate separation of complexed from uncomplexed forms of the reactants, as well as to accommodate automation of the assay. Binding of a test compound in the assay can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-base fusion proteins, can be adsorbed onto glutathione Sepharose® beads (Sigma Chemical, St. Louis, MO) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

In an alternative embodiment, determining the ability of the test compound to modulate the activity of one or more biomarkers of the present invention, including one or more biomarkers listed in Table 1, the Figures, and the Examples, or a fragment thereof, or of natural (or synthetic) binding partner(s) thereof can be accomplished by determining the ability of the test compound to modulate the expression or activity of a gene, e.g., nucleic acid, or gene product, e.g., polypeptide, that functions downstream of the interaction. For example, cellular migration or invasion can be determined by monitoring cellular movement, matrigel assays, induction of invasion-related gene expression, and the like, as described further herein.

In another embodiment, modulators of one or more biomarkers of the present invention, including one or more biomarkers listed in Table 1, the Figures, and the Examples, or a fragment thereof, are identified in a method wherein a cell is contacted with a candidate compound and the expression or activity level of the biomarker is determined. The level of expression of biomarker RNA or polypeptide or fragments thereof in the presence of the candidate compound is compared to the level of expression of biomarker RNA or polypeptide or fragments thereof in the absence of the candidate compound. The candidate compound can then be identified as a modulator of biomarker expression based on this comparison. For example, when expression of biomarker RNA or polypeptide or fragments thereof is greater (statistically significantly greater) in the presence of the candidate compound than in its absence, the candidate compound is identified as a stimulator of biomarker expression. Alternatively, when expression of biomarker RNA or polypeptide or fragments thereof is reduced (statistically significantly less) in the presence of the candidate compound than in its absence, the candidate compound is identified as an inhibitor of biomarker expression. The expression level of biomarker RNA or polypeptide or fragments, or products thereof such as enzyme catalyzed products, thereof in the cells or produced by the cells can be determined by methods described herein for detecting biomarker mRNA or polypeptide or fragments thereof.

In yet another aspect of the present invention, a biomarker of the present invention, including one or more biomarkers listed in Table 1, the Figures, and the Examples, or a fragment thereof, can be used as "bait" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other nucleic acids and/or polypeptides which bind to or interact with the biomarker or fragments thereof and are involved in activity of the biomarkers. Such biomarker-binding proteins are also likely to be involved in the propagation of signals by the biomarker polypeptides or biomarker natural (or synthetic) binding partner(s) as, for example, downstream elements of one or more biomarkers—mediated signaling pathway.

The two-hybrid system is based on the modular nature of most transcription factors, which consist of separable DNA-binding and activation domains. Briefly, the assay utilizes two different DNA constructs. In one construct, the gene that codes for one or more biomarkers polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming one or more biomarkers—dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with one or more biomarkers polypeptide of the present invention, including one or more biomarkers listed in Table 1, the Figures, and the Examples, or a fragment thereof.

In another aspect, the invention pertains to a combination of two or more of the assays described herein. For example, a modulating agent can be identified using a cell-based or a cell-free assay, and the ability of the agent to modulate the activity of one or more biomarkers polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In other aspects of the present invention, the biomarkers described herein, including the biomarkers listed in Table 1, the Figures, and the Examples, or fragments thereof, can be used in one or more of the following methods: a) screening assays; b) predictive medicine (e.g., diagnostic assays, prognostic assays, and monitoring of clinical trials); and c) methods of treatment (e.g., therapeutic and prophylactic, e.g., by up- or down-modulating the copy number, level of expression, and/or level of activity of the one or more biomarkers).

The biomarkers described herein or agents that modulate the expression and/or activity of such biomarkers can be used, for example, to (a) express one or more biomarkers of the present invention, including one or more biomarkers listed in Table 1, the Figures, and the Examples, or a fragment thereof (e.g., via a recombinant expression vector in a host cell in gene therapy applications or synthetic nucleic acid molecule), (b) detect biomarker RNA or a fragment thereof (e.g., in a biological sample) or a genetic alteration in one or more biomarkers gene, and/or (c) modulate biomarker activity, as described further below. The biomarkers or modulatory agents thereof can be used to treat conditions or disorders characterized by insufficient or excessive production of one or more biomarkers polypeptide or fragment thereof or production of biomarker polypeptide inhibitors. In addition, the biomarker polypeptides or fragments thereof can be used to screen for naturally occurring biomarker binding partner(s), to screen for drugs or compounds which modulate biomarker activity, as well as to treat conditions or disorders characterized by insufficient or excessive production of biomarker polypeptide or a fragment thereof or production of biomarker polypeptide forms which have decreased, aberrant or unwanted activity compared to biomarker wild-type polypeptides or fragments thereof (e.g., amounts in metabolic disorder samples as compared to control samples).

A. Screening Assays

In one aspect, the present invention relates to a method for preventing in a subject, a disease or condition associated with an unwanted, more than desirable, or less than desirable, expression and/or activity of one or more biomarkers described herein. Subjects at risk for a disease that would benefit from treatment with the claimed agents or methods can be identified, for example, by any one or combination of diagnostic or prognostic assays known in the art and described herein (see, for example, agents and assays described above in the section describing methods of selecting agents and compositions).

B. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the expression and/or activity level of biomarkers of the present invention, including biomarkers listed in Table 1, the Figures, and the Examples, or fragments thereof, in the context of a biological sample (e.g., blood, serum, cells, or tissue) to thereby determine whether an individual is afflicted with a disease or disorder, or is at risk of developing a disorder, associated with aberrant or unwanted biomarker expression or activity. The present invention also provides for prognostic (or predictive) assays for determining whether an individual is at risk of developing a disorder associated with biomarker polypeptide and/or nucleic acid expression or activity. For example, mutations in one or more biomarkers gene can be assayed in a biological sample.

Such assays can be used for prognostic or predictive purpose to thereby prophylactically treat an individual prior to the onset of a disorder characterized by or associated with biomarker polypeptide, nucleic acid expression or activity. For example, PM20D1 expression and activity is associated with increased thermogenesis and metabolism such that overexpression of PM20D1 and/or its enzymatic products (e.g., natural or synthetic N-lipidated amino acids) predicts treatment of metabolic disorders, either alone or in combination with additional agents, including nuclear receptor inhibitors. Underexpression and/or reduced activity of PM20D1 and/or its enzymatic products (e.g., natural or synthetic N-lipidated amino acids) indicates reduced thermogenesis and metabolism.

Another aspect of the present invention pertains to monitoring the influence of agents (e.g., drugs, compounds, small nucleic acid-based molecules, N-lipidated amino acids, and the like) on the expression or activity of biomarkers of the present invention, including biomarkers listed in Table 1, the Figures, and the Examples, or fragments thereof, in clinical trials. These and other agents are described in further detail in the following sections.

The term "altered amount" of a marker or "altered level" of a marker refers to increased or decreased copy number of the marker and/or increased or decreased expression level of a particular marker gene or genes in a test sample, as compared to the expression level or copy number of the marker in a control sample. The term "altered amount" of a marker also includes an increased or decreased protein level of a marker in a sample, e.g., a metabolic disorder sample, as compared to the protein level of the marker in a normal, control sample.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker. In some embodiments, the amount of the marker in the subject can be considered "significantly" higher or lower than the normal amount if the amount is 10%, 15%, 20%, 25%, 30%, 35%, 40%, 45%, 50% or more, higher or lower, respectively, than the normal amount of the marker.

The term "altered level of expression" of a marker refers to an expression level or copy number of a marker in a test sample e.g., a sample derived from a subject suffering from a metabolic disorder, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a metabolic disorder sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered cellular localization" of a marker refers to the mislocalization of the marker within a cell relative to the normal localization within the cell e.g., within a healthy and/or wild-type cell. An indication of normal localization of the marker can be determined through an analysis of cellular localization motifs known in the field that are harbored by marker polypeptides. For example, SLNCR is a nuclear transcription factor coordinator and naturally functions to present combinations of nuclear transcription factors within the nucleus such that function is abrogated if nuclear import and/or export is inhibited.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal patient or the patient in need of metabolism modulation, cultured primary cells/tissues isolated from a subject such as a normal subject or the patient in need of metabolism modulation, adjacent normal cells/tissues obtained from the same organ or body location of the patient in need of metabolism modulation, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods of the present invention. In one embodiment, the control may comprise normal or non-metabolic disorder cell/tissue sample. In another preferred embodiment, the control may comprise an expression level for a set of patients, such as a set of metabolic disorder patients, or for a set of metabolic disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with a therapeutic and cells from patients having modulated metabolism. In another embodiment, the control may also comprise a measured value for example, average level of expression of a particular gene in a population compared to the level of expression of a housekeeping gene in the same population. Such a population may comprise normal subjects, metabolic disorder patients who have not undergone any treatment (i.e., treatment naive), or metabolic disorder patients undergoing therapy. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with a metabolic disorder. In one embodiment a control expression product level is established wherein higher or lower levels of expression product relative to, for instance, a particular percentile, are used as the basis for predicting outcome. In another preferred embodiment, a control expression product level is established using expression product levels from metabolic disorder control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-immune checkpoint inhibitor therapy, and/or evaluate the disease state. A pre-determined biomarker amount and/or activity measurement(s) may be determined in populations of patients with or without a metabolic disorder. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

Outcome measures, such as overall survival, increased thermogenesis, and weight loss can be monitored over a period of time for subjects following therapy for whom the measurement values are known. In certain embodiments, the same doses of therapeutic agents are administered to each subject. In related embodiments, the doses administered are standard doses known in the art for therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months or longer. Biomarker threshold values that correlate to outcome of a therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a patient in need of modulated metabolism, comprising carrying out the methods for prognosing a patient according to the different aspects and embodiments of the present invention, and then weighing the results in light of other known clinical and pathological risk factors, in determining a course of treatment for the patient in need of modulated metabolism.

A "kit" is any manufacture (e.g., a package or container) comprising at least one reagent, e.g., a probe, for specifically detecting or modulating the expression of a marker of the present invention. The kit may be promoted, distributed, or sold as a unit for performing the methods of the present invention. Kits comprising compositions described herein are encompassed within the present invention.

1. Diagnostic Assays

The present invention provides, in part, methods, systems, and code for accurately classifying whether a biological sample is associated with a melanoma or a clinical subtype thereof. In some embodiments, the present invention is useful for classifying a sample (e.g., from a subject) as a sample that will respond to metabolic intervention using a statistical algorithm and/or empirical data (e.g., the presence or level of one or biomarkers described herein).

An exemplary method for detecting the level of expression or activity of one or more biomarkers of the present invention, including one or more biomarkers listed in Table 1, the Figures, and the Examples, or fragments thereof, and thus useful for classifying whether a sample is associated with melanoma or a clinical subtype thereof, involves obtaining a biological sample from a test subject and contacting the biological sample with a compound or an agent capable of detecting the biomarker (e.g., polypeptide or nucleic acid that encodes the biomarker or fragments thereof) such that the level of expression or activity of the biomarker is detected in the biological sample. In some embodiments, the presence or level of at least one, two, three, four, five, six, seven, eight, nine, ten, fifty, hundred, or more biomarkers of the present invention are determined in the individual's sample. In certain instances, the statistical algorithm is a single learning statistical classifier system. Exemplary statistical analyses are presented in the Examples and can be used in certain embodiments. In other embodiments, a single learning statistical classifier system can be used to classify a sample as a metabolic disorder sample, a metabolic disorder subtype sample, or a non-metabolic disorder sample based upon a prediction or probability value and the presence or level of one or more biomarkers described herein. The use of a single learning statistical classifier system typically classifies the sample as a metabolic disorder sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the metabolic disorder classification results to a clinician, e.g., an endocrinologist, cardiologist, or hematologist.

In another embodiment, the method of the present invention further provides a diagnosis in the form of a probability that the individual has a metabolic disorder or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having a metabolic disorder or a clinical subtype thereof. In yet another embodiment, the method of the present invention further provides a prognosis of a metabolic disorder in the individual. For example, the prognosis can be surgery, development or progression of a metabolic disorder or a clinical subtype thereof, development of one or more symptoms, or recovery from the metabolic disorder. In some instances, the method of classifying a sample as a metabolic disorder sample is further based on the symptoms (e.g., clinical factors) of the individual from which the sample is obtained. The symptoms or group of symptoms can be, for example, those associated with the metabolic disorder. In some embodiments, the diagnosis of an individual as having a metabolic disorder of interest or a clinical subtype thereof is followed by administering to the individual a therapeutically effective amount of a drug useful for treating one or more symptoms associated with the metabolic disorder or a clinical subtype thereof.

In some embodiments, an agent for detecting biomarker RNA, genomic DNA, or fragments thereof is a labeled nucleic acid probe capable of hybridizing to biomarker RNA, genomic DNA., or fragments thereof. The nucleic acid probe can be, for example, full-length biomarker nucleic acid, or a portion thereof, such as an oligonucleotide of at least 15, 30, 50, 100, 250 or 500 nucleotides in length and sufficient to specifically hybridize under stringent conditions well-known to a skilled artisan to biomarker mRNA or genomic DNA. Other suitable probes for use in the diagnostic assays of the present invention are described herein. In some embodiments, the nucleic acid probe is designed to detect transcript variants (i.e., different splice forms) of a gene.

A preferred agent for detecting PM20D1 bioimarkers in complex with biomarker proteins is an antibody capable of binding to the biomarker, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the present invention can be used to detect biomarker mRNA, polypeptide, genomic DNA, or fragments thereof, in a biological sample in vitro as well as in vivo. For example, in vitro techniques for detection of biomarker mRNA or a fragment thereof include Northern hybridizations and in situ hybridizations. In vitro techniques for detection of biomarker polypeptide include enzyme linked immunosorbent assays (ELISAs), Western blots, immunoprecipitations and immunofluorescence. In vitro techniques for detection of biomarker genomic DNA or a fragment thereof include Southern hybridizations. Furthermore, in vivo techniques for detection of one or more biomarkers polypeptide or a fragment thereof include introducing into a subject a labeled antibiomarker antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain RNA molecules from the test subject or genomic DNA molecules from the test subject. A preferred biological sample is a hematological tissue (e.g., a sample comprising blood, plasma, B cell, bone marrow, etc.) sample isolated by conventional means from a subject.

In another embodiment, the methods further involve obtaining a control biological sample from a control subject, contacting the control sample with a compound or agent capable of detecting polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof of one or more biomarkers listed in Table 1, the Figures, and the Examples, such that the presence of biomarker polypeptide, RNA, genomic DNA, or fragments thereof, is detected in the biological sample, and comparing the presence of biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof in the control sample with the presence of biomarker polypeptide, RNA, cDNA, small RNAs, mature miRNA, pre-miRNA, pri-miRNA, miRNA*, piwiRNA, piwiRNA, anti-miRNA, or a miRNA binding site, or a variant thereof, genomic DNA, or fragments thereof in the test sample.

The invention also encompasses kits for detecting the presence of a polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, of one or more biomarkers listed in Table 1, the Figures, and the Examples, in a biological sample. For example, the kit can comprise a labeled compound or agent capable of detecting one or more biomarkers polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in a biological sample;

means for determining the amount of the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, f in the sample; and means for comparing the amount of the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in the sample with a standard. The compound or agent can be packaged in a suitable container. The kit can further comprise instructions for using the kit to detect the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof.

In some embodiments, therapies tailored to treat stratified patient populations based on the described diagnostic assays are further administered, such as melanoma standards of treatment, immune therapy, and combinations thereof described herein.

2. Prognostic Assays

The diagnostic methods described herein can furthermore be utilized to identify subjects having or at risk of developing a disease or disorder associated with aberrant expression or activity of one or more biomarkers of the present invention, including one or more biomarkers listed in Table 1, the Figures, and the Examples, or a fragment thereof. As used herein, the term "aberrant" includes biomarker expression or activity levels which deviates from the normal expression or activity in a control.

The assays described herein, such as the preceding diagnostic assays or the following assays, can be used to identify a subject that would benefit from metabolic interventions (e.g., low levels of plasma PM20D1 indicates that PM20D1 administration would be differentially beneficial). Alternatively, the prognostic assays can be used to identify a subject having or at risk for developing a disorder associated with a misregulation of biomarker activity or expression. Thus, the present invention provides a method for identifying and/or classifying a disease associated with aberrant expression or activity of one or more biomarkers of the present invention, including one or more biomarkers listed in Table 1, the Figures, and the Examples, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. For example, such methods can be used to determine whether a subject can be effectively treated with an agent for a melanoma. Thus, the present invention provides methods for determining whether a subject can be effectively treated with an agent for a disease associated with aberrant biomarker expression or activity in which a test sample is obtained and biomarker polypeptide or nucleic acid expression or activity is detected (e.g., wherein a significant increase or decrease in biomarker polypeptide or nucleic acid expression or activity relative to a control is diagnostic for a subject that can be administered the agent to treat a disorder associated with aberrant biomarker expression or activity). In some embodiments, significant increase or decrease in biomarker expression or activity comprises at least 1.1, 1.2, 1.3, 1.4, 1.5, 1.6, 1.7, 1.8, 1.9, 2.0, 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

The methods of the present invention can also be used to detect genetic alterations in one or more biomarkers of the present invention, including one or more biomarkers listed in Table 1, the Figures, and the Examples, or a fragment thereof, thereby determining if a subject with the altered biomarker is at risk for melanoma characterized by aberrant biomarker activity or expression levels. In preferred embodiments, the methods include detecting, in a sample of cells from the subject, the presence or absence of a genetic alteration characterized by at least one alteration affecting the integrity of a gene encoding one or more biomarkers, or the mis-expression of the biomarker (e.g., mutations and/or splice variants). For example, such genetic alterations can be detected by ascertaining the existence of at least one of 1) a deletion of one or more nucleotides from one or more biomarkers gene, 2) an addition of one or more nucleotides to one or more biomarkers gene, 3) a substitution of one or more nucleotides of one or more biomarkers gene, 4) a chromosomal rearrangement of one or more biomarkers gene, 5) an alteration in the level of a messenger RNA transcript of one or more biomarkers gene, 6) aberrant modification of one or more biomarkers gene, such as of the methylation pattern of the genomic DNA, 7) the presence of a non-wild type splicing pattern of an RNA transcript of one or more biomarkers gene, 8) a non-wild type level of one or more biomarkers polypeptide, 9) allelic loss of one or more biomarkers gene, and 10) inappropriate post-translational modification of one or more biomarkers polypeptide. As described herein, there are a large number of assays known in the art which can be used for detecting alterations in one or more biomarkers gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in one or more biomarkers gene (see Abravaya et al. (1995) Nucleic Acids Res. 23:675-682). This method can include the steps of collecting a sample of cells from a subject, isolating nucleic acid (e.g., genomic DNA, mRNA, cDNA, small RNA, mature miRNA, pre-miRNA, pri-miRNA, miRNA*, piwiRNA, anti-miRNA, or a miRNA binding site, or a variant thereof) from the cells of the sample, contacting the nucleic acid sample with one or more primers which specifically hybridize to one or more biomarkers gene of the present invention, including the biomarker genes listed in Table 1, the Figures, and the Examples, or fragments thereof, under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in one or more biomarkers gene of the present invention, including one or more biomarkers listed in Table 1, the Figures, and the Examples, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more biomarkers gene of the present invention, including a gene listed in Table 1, the Figures, and the Examples, or a fragment thereof, can be identified by hybridizing a sample and control nucleic acids, e.g., DNA, RNA, mRNA, small RNA, cDNA, mature miRNA, pre-miRNA, pri-miRNA, miRNA*, piwiRNA, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more biomarkers can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence one or more biomarkers gene of the present invention, including a gene listed in Table 1, the Figures, and the Examples, or a fragment thereof, and detect mutations by comparing the sequence of the sample biomarker gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in one or more biomarkers gene of the present invention, including a gene listed in Table 1, the Figures, and the Examples, or fragments thereof, include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker genes of the present invention, including genes listed in Table 1, the Figures, and the Examples, or fragments thereof, obtained from samples of cells. For example, the mutY enzyme of *E. coli* cleaves A at G/A mismatches and the thymidine DNA glycosylase from HeLa cells cleaves Tat G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in biomarker genes of the present invention, including genes listed in Table 1, the Figures, and the Examples, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992)

Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well-known in the art.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more biomarkers of the present invention, including one or more biomarkers listed in Table 1, the Figures, and the Examples, or fragments thereof.

3. Monitoring of Effects During Clinical Trials

Monitoring the influence of agents (e.g., drugs) on the expression or activity of one or more biomarkers of the present invention, including one or more biomarkers listed in Table 1, the Figures, and the Examples, or a fragment thereof (e.g., the modulation of a metabolic state) can be applied not only in basic drug screening, but also in clinical trials. For example, the effectiveness of an agent determined by a screening assay as described herein to increase expression and/or activity of one or more biomarkers of the present invention, including one or more biomarkers listed in Table 1, the Figures, and the Examples, or a fragment thereof, can be monitored in clinical trials of subjects exhibiting decreased expression and/or activity of one or more biomarkers of the present invention, including one or more biomarkers of the present invention, including one or more biomarkers listed in Table 1, the Figures, and the Examples, or a fragment thereof, relative to a control reference. Alternatively, the effectiveness of an agent determined by a screening assay to decrease expression and/or activity of one or more biomarkers of the present invention, including one or more biomarkers listed in Table 1, the Figures, and the Examples, or a fragment thereof, can be monitored in clinical trials of subjects exhibiting decreased expression and/or activity of the biomarker of the present invention, including one or more biomarkers listed in Table 1, the Figures, and the Examples, or a fragment thereof relative to a control reference. In such clinical trials, the expression and/or activity of the biomarker can be used as a "read out" or marker of the phenotype of a particular cell.

In some embodiments, the present invention provides a method for monitoring the effectiveness of treatment of a subject with an agent (e.g., an agonist, antagonist, peptidomimetic, polypeptide, peptide, nucleic acid, small molecule, N-lipidated amino acid, or other drug candidate identified by the screening assays described herein) including the steps of (i) obtaining a pre-administration sample from a subject prior to administration of the agent; (ii) detecting the level of expression and/or activity of one or more biomarkers of the present invention, including one or more biomarkers listed in Table 1, the Figures, and the Examples, or fragments thereof in the pre-administration sample; (iii) obtaining one or more post-administration samples from the subject; (iv) detecting the level of expression or activity of the biomarker in the post-administration samples; (v) comparing the level of expression or activity of the biomarker or fragments thereof in the pre-administration sample with the that of the biomarker in the post administration sample or samples; and (vi) altering the administration of the agent to the subject accordingly. For example, increased administration of the agent may be desirable to increase the expression or activity of one or more biomarkers to higher levels than detected (e.g., to increase the effectiveness of the agent.) Alternatively, decreased administration of the agent may be desirable to decrease expression or activity of the biomarker to lower levels than detected (e.g., to decrease the effectiveness of the agent). According to such an embodiment, biomarker expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder characterized by insufficient or excessive production of biomarkers of the present invention, including biomarkers listed in Table 1, the Figures, and the Examples, or fragments thereof, which have aberrant expression or activity compared to a control. Moreover, agents of the present invention described herein can be used to detect and isolate the biomarkers or fragments thereof, regulate the bioavailability of the biomarkers or fragments thereof, and modulate biomarker expression levels or activity.

1. Prophylactic Methods

In one aspect, the present invention provides a method for preventing in a subject, a disease or condition associated with an aberrant expression or activity of one or more biomarkers of the present invention, including one or more biomarkers listed in Table 1, the Figures, and the Examples, or a fragment thereof, by administering to the subject an agent which modulates biomarker expression or at least one activity of the biomarker. Subjects at risk for a disease or disorder which is caused or contributed to by aberrant biomarker expression or activity can be identified by, for example, any or a combination of diagnostic or prognostic assays as described herein. Administration of a prophylactic agent can occur prior to the manifestation of symptoms characteristic of the biomarker expression or activity aberrancy, such that a disease or disorder is prevented or, alternatively, delayed in its progression.

2. Therapeutic Methods

Another aspect of the present invention pertains to methods of modulating the expression or activity of, or interaction with natural (or synthetic) binding partner(s) of, one or more biomarkers of the present invention, including one or more biomarkers listed in Table 1, the Figures, and the Examples, or fragments thereof, for therapeutic purposes. The biomarkers of the present invention have been demonstrated to correlate with adipose tissue thermogenesis and modulation of metabolism. Accordingly, the activity and/or expression of the biomarker, as well as the interaction between one or more biomarkers or a fragment thereof and its natural (or synthetic) binding partner(s) or a fragment(s) thereof can be modulated in order to modulate the immune response.

Modulatory methods of the present invention involve contacting a cell with one or more biomarkers of the present invention, including one or more biomarkers of the present invention, including one or more biomarkers listed in Table 1, the Figures, and the Examples, or a fragment thereof or agent that modulates one or more of the activities of biomarker activity associated with the cell or produced by the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the present invention, including one or more biomarkers listed in Table 1, the Figures, and the Examples, or a fragment thereof is a nucleic acid molecule described herein, e.g., an antisense nucleic acid molecule, RNAi molecule, shRNA, mature miRNA, pre-miRNA, pri-miRNA, miRNA*, piwiRNA, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the present invention, including one or more biomarkers listed in Table 1, the Figures, and the Examples, or a fragment thereof. Examples of such stimulatory agents include active biomarker polypeptides, or a fragment thereof, such as PM20D1 binding partners, and/or a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, piwiRNA, anti-miRNA, or a miRNA binding site, or a variant thereof, or other functionally equivalent molecule known to a skilled artisan). In another embodiment, stimulatory agents include N-lipidated amino acids. In another embodiment, the agent inhibits one or more biomarker activities. In one embodiment, the agent inhibits or enhances the interaction of the biomarker with its natural (or synthetic) binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1, the Figures, and the Examples, or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., metabolism enhancing agents, such as transplanted brown and/or beige fat cells, hormones, and the like. The preceding treatment methods can be administered in conjunction with other forms of conventional therapy (e.g., standard-of-care treatments for metabolic disorders are well-known to the skilled artisan), either consecutively with, pre- or post-conventional therapy. For example, these modulatory agents can be administered with a therapeutically effective dose of a metabolism modulatory agent.

The methods of the present invention relate to the expression and/or activity of PM20D1 sufficient to modulate (e.g., induce or repress) brown and/or beige fat cell differentiation and/or activity, wherein increases in differentiated brown and/or beige fat cells or activity increase energy expenditure and favorably affect other metabolic processes and can therefore be used to treat metabolic disorders such as obesity, diabetes, decreased thermogenesis and subjects in need of more exercise; and, wherein decreases in differentiated brown and/or beige fat cells or activity decrease energy expenditure and can therefore be used to treat the effects of such conditions as cachexia, anorexia, and obesity-associated cancer.

The invention also relates to methods for increasing energy expenditure in a mammal comprising inducing expression and/or activity of PM20D1 sufficient to activate brown and/or beige fat cell differentiation or activity in the mammal, wherein the differentiated and/or more active brown fat and/or beige fat cells promote energy expenditure thereby increasing energy expenditure in the mammal.

The term "sufficient to activate" is intended to encompass any increase in expression and/or activity of PM20D1 that promotes, activates, stimulates, enhances, or results in brown fat and/or beige fat differentiation or activity.

In another aspect, the invention relates to methods for treating metabolic disorders in a subject comprising administering to the subject an agent that induces expression and/or activity of PM20D1 and/or natural or synthetic N-lipidated amino acids, wherein expression and/or activity of PM20D1 and/or natural or synthetic N-lipidated amino acids increases respiration and energy expenditure to thereby treat the metabolic disorder. In one embodiment, total respiration is increased following the expression and/or activity of PM20D1. In another embodiment, uncoupled respiration is increased following the expression and/or activity of PM20D1. Uncoupled respiration dissipates heat and thereby increases energy expenditure in the subject.

As used herein, the term "agent" and "therapeutic agent" is defined broadly as anything that cells from a subject having a metabolic disorder may be exposed to in a therapeutic protocol. In one embodiment, the agent is a recombinant PM20D1 protein, or fragment thereof, or nucleic acid molecule encoding such a polypeptide. In another embodiment, the agent is an anti-sense nucleic acid molecule having a sequence complementary to PM20D1 (e.g., an RNAi, siRNA, or other RNA inhibiting nucleic acid molecule).

The term "administering" is intended to include routes of administration which allow the agent to perform its intended function of modulating (e.g., increasing or decreasing) expression and/or activity of PM20D1 or of natural or synthetic N-lipidated amino acids. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term "effective amount" of an agent that induces expression and/or activity of PM20D1 or of natural or synthetic N-lipidated amino acids is that amount necessary or sufficient to modulate (e.g., increase or decrease) expression and/or activity of PM20D1 or of natural or synthetic N-lipidated amino acids in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular agent to treat a metabolic disorder can be monitored by comparing two or more samples obtained from a subject undergoing anti-metabolic disorder or metabolic disorder-related disorder treatment. In general, it is preferable to obtain a first sample from the subject prior to begining therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

Another aspect of the invention relates to a method for inducing brown fat and/or beige fat cell differentiation and/or activity in a mammal comprising expressing PM20D1 nucleic acid and/or polypeptide molecules, or of natural or synthetic N-lipidated amino acids, in a mammal and, optionally, monitoring the differentiation of brown fat cells in the mammal. Increased brown and/or beige adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by analyzing a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622;

WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al.(1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant PM20D1 polypeptides, and fragments thereof, can be administered to subjects. In some embodiments, fusion proteins can be constructed and administered which have enhanced biological properties (e.g., Fc fusion proteins discussed above). In addition, the PM20D1 polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VI. Pharmaceutical Compositions

In another aspect, the present invention provides pharmaceutically acceptable compositions which comprise a therapeutically-effective amount of an agent that modulates (e.g., increases or decreases) PM20D1 expression and/or activity or of natural or synthetic N-lipidated amino acids, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) PM20D1 expression and/or activity, or expression and/or activity of a PM20D1 enzyme complex or of natural or synthetic N-lipidated amino acids, or composition comprising an agent that modulates (e.g., enhances) PM20D1 expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) PM20D1 expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) PM20D1 expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) PM20D1 expression and/or activity or expression and/or activity of natural or synthetic N-lipidated amino acids, with the carrier and, optionally, one or more accessory ingredients. In general, the formulations are prepared by uniformly and intimately bringing into association a agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) PM20D1 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) PM20D1 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) PM20D1 expression and/or activity or expression and/or activity of natural or synthetic N-lipidated amino acids, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) PM20D1 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1

Materials and Methods for Examples 2-9

A. Chemicals

The following chemicals were purchased from Sigma Aldrich: N-arachidonoyl dopamine, N-oleoyl ethanolamine, arachidonic acid, sodium oleate, phenylalanine, noladin ether, and R(+)-methanandamide. The following chemicals were purchased from Cayman Chemical Company: N-arachidonoyl glycine, N-arachidonoyl serine, N-arachidonoyl taurine, N-methyl N-arachidonoyl amide. The following chemicals were purchased from Abcam: N-arachidonoyl phenylalanine. The following chemicals were purchased from Santa Cruz Biotechnology: N-arachidonoyl gamma amino butyric acid.

B. Synthesis of N-acyl Amino Acids

The synthesis of non-commercially available N-acyl amino acids is described herein.

Method A: To a solution of amino acid (1 eq.) in acetone and water (1:1) was added $K_2CO_3$ (2 eq.) and oleoyl chloride (1.5 eq.) at 0° C. Then the mixture was stirred at room temperature overnight. The reaction mixture was acidified with HCl (1M) until pH 4.0 before extracted with ethyl acetate. The organic phase was washed with brine and dried over anhydrous $Na_2SO_4$. Then, the solvent was removed under reduced pressure. The residue was purified by flash chromatography on silica gel to give the desired amide.

Method B: To a solution of fatty acid (1 eq.) in DCM was added oxalyl chloride (1.2 eq.) and one drop of DIVIF at 0° C. Then, the mixture was stirred at room temperature for 2 hours. The mixture was concentrated and dissolved in DCM and added to a suspension of amino acid (1.5 eq.) and DIPEA (2 eq.). The reaction mixture was stirred at room temperature overnight before being acidified by HCl (1.0 M) to pH 4.0. The resulting mixture was extracted with DCM, washed with brine, and dried over anhydrous $Na_2SO_4$. Then, the solvent was removed under reduced pressure. The residue was purified by flash chromatography on silica gel to give the desired amide.

Oleoyl-L-phenylalanine, Method A. White solid.
$^1$H NMR (400 MHz, DMSO-$d^6$) δ 0.85 (t, J=5.0 Hz, 3H), 1.09-1.31 (m, 22H), 1.33-1.40 (m, 2H), 1.95-2.04 (m, 6H), 2.82 (dd, J=10.0, 13.8 Hz, 1H), 3.04 (dd, J=4.7, 13.4 Hz, 1H), 4.38-4.44 (m, 1H), 5.29-5.36 (m, 2H), 7.16-7.28 (m, 5H), 8.08 (d, J=8.0 Hz, 1H), 12.61 (brs, 1H)
HRMS (ESI) m/z calcd for $C_{27}H_{44}NO_3$ [M+H]$^+$ 430.3316, found: 430.3317.

Dodecanoyl-L-phenylalanine, Method A. White solid.
$^1$H NMR (400 MHz, DMSO-$d^6$) δ 0.86 (t, J=6.6 Hz, 3H), 1.08-1.31 (m, 16H), 1.34-1.41 (m, 2H), 2.02 (t, J=7.4 Hz, 2H), 2.83 (dd, J=10.2, 13.8 Hz, 1H), 3.05 (dd, J=4.6, 13.8 Hz, 1H), 4.38-4.44 (m, 1H), 7.17-7.28 (m, 5H), 8.08 (d, J=7.0 Hz, 1H), 12.65 (brs, 1H)
HRMS (ESI) m/z calcd for $C_{21}H_{34}NO_3$ [M+H]$^+$ 348.2533, found: 348.2544.

Pentadecanoyl-L-phenylalanine. White solid.
$^1$H NMR (400 MHz, DMSO-$d^6$) δ 0.85 (t, J=7.0 Hz, 3H), 1.08-1.31 (m, 22H), 1.33-1.40 (m, 2H), 2.02 (t, J=7.3 Hz, 2H), 2.82 (dd, J=10.0, 13.8 Hz, 1H), 3.04 (dd, J=4.7, 13.8 Hz, 1H), 4.38-4.44 (m, 1H), 7.16-7.28 (m, 5H), 8.09 (d, J=8.2 Hz, 1H), 12.64 (brs, 1H)
HRMS (ESI) m/z calcd for $C_{24}H_{40}NO_3$ [M+H]$^+$ 390.3003, found: 390.2950.

Palmitoyl-L-phenylalanine, Method A. White solid.
$^1$H NMR (400 MHz, DMSO-$d^6$) δ 0.85 (t, J=6.7 Hz, 3H), 1.08-1.31 (m, 24H), 1.35-1.40 (m, 2H), 2.02 (t, J=7.3 Hz, 2H), 2.83 (dd, J=10.0, 13.8 Hz, 1H), 3.04 (dd, J=4.7, 13.8 Hz, 1H), 4.38-4.44 (m, 1H), 7.17-7.28 (m, 5H), 8.08 (d, J=8.2 Hz, 1H), 12.63 (brs, 1H)
HRMS (ESI) m/z calcd for $C_{25}H_{42}NO_3$ [M+H]$^+$ 404.3159, found: 404.3159.

Stearoyl-L-phenylalanine, Method A. White solid.
$^1$H NMR (400 MHz, DMSO-$d^6$) δ 0.85 (t, J=6.7 Hz, 3H), 1.08-1.31 (m, 28H), 1.33-1.40 (m, 2H), 2.01 (t, J=7.3 Hz, 2H), 2.82 (dd, J=10.0, 13.8 Hz, 1H), 3.04 (dd, J=4.7, 13.8 Hz, 1H), 4.38-4.44 (m, 1H), 7.16-7.28 (m, 5H), 8.09 (d, J=8.2 Hz, 1H), 12.63 (brs, 1H)
HRMS (ESI) m/z calcd for $C_{27}H_{46}NO_3$ [M+H]$^+$ 432.3472, found: 432.3477.

Icosanoyl-L-phenylalanine, Method B. White solid.
$^1$H NMR (400 MHz, DMSO-$d^6$) δ 0.86 (t, J=5.0 Hz, 3H), 1.09-1.31 (m, 32H), 1.33-1.40 (m, 2H), 2.02 (t, J=7.3 Hz, 2H), 2.83 (dd, J=10.2, 13.8 Hz, 1H), 3.05 (dd, J=5.3, 14.2 Hz, 1H), 4.38-4.44 (m, 1H), 7.17-7.28 (m, 5H), 8.08 (d, J=8.0 Hz, 1H), 12.97 (brs, 1H)
HRMS (ESI) m/z calcd for $C_{29}H_{50}NO_3$ [M+H]$^+$ 460.3785, found: 460.3796.

Methyl oleoyl-L-phenylalaninate, Method A. White solid.
$^1$H NMR (400 MHz, CDCl$_3$) δ 0.88 (t, J=7.0 Hz, 3H), 1.21-1.37 (m, 20H), 1.53-1.62 (m, 2H), 1.98-2.06 (m, 4H), 2.17 (t, J=8.4 Hz, 2H), 3.12 (qd, J=5.8, 13.8 Hz, 2H), 3.73 (s, 3H), 4.88-4.93 (m, 1H), 5.32-5.39 (m, 2H), 5.84 (d, J=7.9 Hz, 1H), 7.07-7.10 (m, 2H), 7.22-7.31 (m, 3H)
HRMS (ESI) m/z calcd for $C_{28}H_{46}NO_3$ [M+H]$^+$ 444.3472, found: 444.3482.

(S)-N-(1-amino-1-oxo-3-phenylpropan-2-yl)oleamide, Method A. White solid.
$^1$H NMR (400 MHz, DMSO-$d^6$) δ 0.85 (t, J=6.7 Hz, 3H), 1.04-1.35 (m, 22H), 1.95-2.02 (m, 6H), 2.71 (dd, J=10.0, 13.8 Hz, 1H), 2.98 (dd, J=4.5, 13.8 Hz, 1H), 4.40-4.46 (m, 1H), 5.29-5.36 (m, 2H), 7.02 (brs, 1H), 7.13-7.19 (m, 1H), 7.21-7.26 (m, 4H), 7.39 (brs, 1H), 7.91 (d, J=8.6 Hz, 1H)

HRMS (ESI) m/z calcd for $C_{27}H_{45}NO_3$ [M+H]$^+$ 429.3476, found: 429.3484.

Oleoyl-L-leucine, Method A. White solid.

$^1$H NMR (400 MHz, CDCl$_3$) δ 0.88 (t, J=7.0 Hz, 3H), 0.95 (d, J=3.6 Hz, 3H), 0.97 (d, J=3.6 Hz, 3H), 1.27-1.37 (m, 20H), 1.56-1.77 (m, 5H), 1.98-2.06 (m, 4H), 2.22 (t, J=7.3 Hz, 2H), 4.58-4.64 (m, 1H), 5.31-5.39 (m, 2H), 5.86 (d, J=8.0 Hz, 1H)

HRMS (ESI) m/z calcd for $C_{24}H_{46}NO_3$ [M+H]$^+$ 396.3472, found: 396.3478.

Oleoyl-L-isoleucine $^1$H NMR (400 MHz, DMSO-d$^6$) δ 0.81-0.88 (m, 6H), 1.19-1.32 (m, 22H), 1.34-1.52 (m, 3H), 1.70-1.80 (m, 1H), 1.93-2.03 (m, 4H), 2.06-2.22 (m, 2H), 4.17 (dd, J=6.2, 8.4 Hz, 1H), 5.28-5.36 (m, 2H), 7.92 (d, J=8.4 Hz, 1H), 12.50 (brs, 1H)

HRMS (ESI) m/z calcd for $C_{24}H_{46}NO_3$ [M+H]$^+$ 396.3472, found: 396.3474.

Oleoyl-L-glutamic acid $^1$H NMR (400 MHz, CDCl$_3$) δ 0.88 (t, J=6.7 Hz, 3H), 1.19-1.38 (m, 20H), 1.58-1.68 (m, 2H), 1.93-2.07 (m, 4H), 2.08-2.18 (m, 1H), 2.20-2.30 (m, 3H), 2.42-2.60 (m, 2H), 4.65 (dd, J=6.5, 13.6 Hz, 1H), 5.30-5.38 (m, 2H), 6.53 (d, J=7.2 Hz, 1H), 8.23 (brs, 2H)

HRMS (ESI) m/z calcd for $C_{23}H_{42}NO_5$ [M+H]$^+$ 412.3057, found: 412.3064.

Oleoyl-L-tyrosine $^1$H NMR (400 MHz, CDCl$_3$) δ 0.87 (t, J=6.6 Hz, 3H), 1.19-1.38 (m, 22H), 1.47-1.58 (m, 2H), 1.94-2.04 (m, 4H), 2.07-2.17 (m, 3H), 2.96-3.10 (m, 2H), 4.75 (brs, 1H), 5.29-5.38 (m, 2H), 6.19 (brs, 1H), 6.69 (d, J=6.7 Hz, 2H), 6.95 (d, J=6.7 Hz, 2H)

HRMS (ESI) m/z calcd for $C_{27}H_{44}NO_4$ [M+H]$^+$ 446.3265, found: 446.3270.

Oleoyl-L-tryptophan $^1$H NMR (400 MHz, CDCl$_3$) δ 0.88 (t, J=6.7 Hz, 3H), 1.19-1.38 (m, 22H), 1.47-1.58 (m, 2H), 1.94-2.06 (m, 4H), 2.07-2.17 (m, 2H), 3.30-3.42 (m, 2H), 4.91-4.96 (m, 1H), 5.29-5.38 (m, 2H), 6.00 (d, J=7.4 Hz, 1H), 7.03 (d, J=3.5 Hz, 1H), 7.12 (t, J=8.0 Hz, 1H), 7.21 (t, J=8.0 Hz, 1H), 7.36 (d, J=8.1 Hz, 1H), 7.57 (d, J=8.1 Hz, 1H), 8.22 (brs, 1H)

HRMS (ESI) m/z calcd for $C_{29}H_{45}N_2O_3$ [M+H]$^+$ 469.3425, found: 469.3433./

Oleoyl-L-glutamine $^1$H NMR (400 MHz, CDCl$_3$) δ 0.88 (t, J=6.7 Hz, 3H), 1.19-1.38 (m, 20H), 1.58-1.68 (m, 2H), 1.93-2.07 (m, 5H), 2.25 (d, J=7.6 Hz, 2H), 2.38-2.48 (m, 1H), 2.54-2.65 (m, 1H), 4.46 (dd, J=6.2, 12.0 Hz, 1H), 5.30-5.38 (m, 2H), 6.17 (brs, 1H), 6.48 (brs, 1H), 7.18 (d, J=6.2 Hz, 1H)

HRMS (ESI) m/z calcd for $C_{23}H_{43}N_2O_4$ [M+H]$^+$ 411.3217, found: 411.3224.

Oleoyl-L-lysine $^1$H NMR (400 MHz, CDCl$_3$) δ 0.84 (t, J=6.7 Hz, 3H), 1.17-1.34 (m, 22H), 1.36-1.44 (m, 2H), 1.50-1.58 (m, 2H), 1.63-1.75 (m, 2H), 1.93-1.99 (m, 4H), 2.13-2.24 (m, 2H), 2.84-2.96 (m, 2H), 4.07 (dd, J=6.2, 12.0 Hz, 1H), 5.26-5.34 (m, 2H), 7.12 (d, J=6.6 Hz, 1H)

HRMS (ESI) m/z calcd for $C_{24}H_{47}N_2O_3$ [M+H]$^+$ 411.3581, found: 411.3574.

(S)-3-(3-methyl-3H-diazirin-3-yl)-2-(octadec-17-ynamido)propanoic acid "photo-probe", Method B. White solid.

$^1$H NMR (400 MHz, CDCl$_3$) δ 1.08 (s, 3H), 1.25-1.40 (m, 22H), 1.49-1.56 (m, 2H), 1.61-1.71 (m, 3H), 1.94 (t, J=2.6 Hz, 1H), 2.10-2.15 (m, 1H), 2.17 (td, J=2.6, 6.9 Hz, 2H), 2.17 (t, J=7.3 Hz, 2H), 4.58-4.64 (m, 5H), 6.26 (d, J=6.6 Hz, 1H), 7.52 (brs, 1H)

HRMS (ESI) m/z calcd for $C_{23}H_{40}N_3O_3$ [M+H]$^+$ 406.3064, found: 406.3059.

C. Plasmids and Viruses

Full-length mouse Pm20d1 cDNA (GE Dharmacon) was subcloned with an in-frame C-terminal 6× His and FLAG® tag into pENTR/D-TOPO (Thermo Fisher Scientific) according to the manufacturer's instructions. Mutagenesis was carried out using the QuikChange® II kit (Agilent) according to the manufacturer's instructions. Entry clones were shuttled with Gateway® LR clonase into pAd/CMV/V5-DEST (Thermo Fisher Scientific) for adenovirus production or an in-house-generated Gateway®-compatible variant of pCLHCX-DEST, modified from pCLNCX (Novus), for mammalian expression. PM20D1- or LacZ-expressing adenoviruses were generating according to the manufacturer's instructions (Thermo Fisher Scientific) and purified using Vivapure® AdenoPACK™ 100 (Sartorius). PM20D1- or GFP-expressing retroviruses were generating according to the manufacturer's instructions (Novus) and used directly. The Pm20d1-6× His-Flag construct was cloned into pENN.AAV8.CB7.CI.WPRE.rBG (Penn Vector Core) using the PstI/HindIII sites. AAV-GFP virus (AAV8.CB7.CI.eGFP.WPRE.rBG) was purchased from Penn Vector Core. AAV-PM20D1 virus was generated by Penn Vector Core using the pENN.AAV8-Pm20d1 plasmid.

D. Global Gene Expression Analysis

The following publicly available datasets were used for the comparisons: UCP1-TRAP (GSE56248), brown versus white adipose tissues (GSE8044), inguinal fat following 1 or 5 weeks cold exposure (GSE13432). For the UCP1-TRAP dataset (GSE56248), genes were considered expressed if the average signal intensity >1 FPKM and the FPKM>0.3 in all replicates (n=7230). For the brown versus white adipose tissues dataset (GSE8044), genes were considered enriched in UCP1$^+$ cells if the BAT versus WAT fold change>4, and the adjusted p<0.05 (n=494). For the 1- or 5-week cold exposure of the inguinal fat (GSE13432), genes were considered cold-induced if the 4° C. versus 30° C. fold change>4, and the adjusted p<0.05 (n=200 and 96, respectively).

E. Animals

Animal experiments were performed according to procedures approved by the Beth Israel Deaconess Medical Center IACUC. Mice were maintained in 12 h light-dark cycles at 22° C. and fed a standard irradiated rodent chow diet. All experiments on wild-type mice were performed with male C57BL/6 mice purchased from Jackson Laboratories, except for the AAV experiments, which were performed with male C57BL/6 mice from Charles River. UCP1-KO (stock #017476) and 16-20 week DIO mice (stock #380050) were obtained from Jackson Laboratories. For AAV injection experiments, mice were gently warmed using a 250 W clear infrared heat lamp, immobilized, and injected via tail vein with 10$^{10}$ virus/mouse (diluted in saline) in a total volume of 100 μl/mouse. Where indicated, mice were placed on high-fat diet (60% fat, Research Diets). For cold exposure experiments, mice were group housed and placed at 4° C. for the indicated times. For the preparation of C18:1-Phe for in vivo injections, compounds were dissolved in 18:1:1 v/v/v saline: Kolliphor® EL (Sigma Aldrich):DMSO and sonicated until homogeneous. Mice were administered compounds at 5 μl/g body weight at the indicated doses. For all injection experiments, mice were mock injected with saline daily for 3 days prior to the start of the experiments. For glucose tolerance tests (GTTs), mice received their final dose of compound the day prior to the assay and were then fasted overnight. Glucose was administered at 1.5 g/kg.

F. Indirect Calorimetry and Body Composition Measurements

Energy expenditure, $O_2$ consumption, $CO_2$ production, respiratory exchange ratio, total locomotor activity, and food intake measurements were made with a 16-cage Columbus Instruments Oxymax Comprehensive Lab Animal Monitoring System (CLAMS) at ambient room temperature (21-23° C.). Mice were acclimated for one day in metabolic cages prior to data collection. Whole-body composition was assessed with an EchoMRI™ 3-in-1 on conscious mice.

G. Molecular Studies

Quantitative PCR (qPCR) and Western blotting were performed according to standard methods. For qPCR from whole tissues, all values were normalized by the AACt method to Rps18, where indicated, or Tbp otherwise. The following antibodies were used: anti-Flag M2-HRP (Sigma Aldrich, A8592), anti-UCP1 (Abcam, ab10983), and total OXPHOS rodent antibody cocktail (Abcam, ab110413). Coomassie staining was performed using SimplyBlue™ SafeStain (Thermo Fisher Scientific) according to the manufacturer's instructions.

The following primers, written 5' to 3', were used for measuring the indicated genes: Tbp, ACCCTTCAC-CAATGACTCCTATG (SEQ ID NO: 15) and TGACTGCAGCAAATCGCTTGG (SEQ ID NO: 16); aP2, AAGGTGAAGAGCATCATAACCCT (SEQ ID NO: 17) and TCACGCCTTTCATAACACATTCC (SEQ ID NO: 18); Ucp1, ACTGCCACACCTCCAGTCATT (SEQ ID NO: 19) and CTTTGCCTCACTCAGGATTGG (SEQ ID NO: 20); Ppargc1a, CCCTGCCATTGTTAAGACC (SEQ ID NO: 21) and TGCTGCTGTTCCTGTTTTC (SEQ ID NO: 22); Cox2, GCCGACTAAATCAAGCAACA (SEQ ID NO: 23) and CAATGGGCATAAAGCTATGG (SEQ ID NO: 24); Cox4, GCACATGGGAGTGTTGTGA (SEQ ID NO: 25) and CCTTCTCCTTCTCCTTCAGC (SEQ ID NO: 26); Erra, CAAGAGCATCCCAGGCTT (SEQ ID NO: 27) and GCACTTCCATCCACACACTC (SEQ ID NO: 28); Ckmt1, TGAGGAGACCTATGAGGTATTTGC (SEQ ID NO: 29) and TCATCAAAGTAGCCAGAACGGA (SEQ ID NO: 30); Ckmt2, GCATGGTGGCTGGTGATGAG (SEQ ID NO: 31) and AAACTGCCCGTGAGTAATCTTG (SEQ ID NO: 32). The following mutagenesis primers were used for the indicated PM20D1 mutants: H125A, GCAGGAACCA-CATCAATGGCAGCCATCAGCATGTAGGG (SEQ ID NO: 33) and CCCTACATGCTGATGGCTGCCATT-GATGTGGTTCCTGC (SEQ ID NO: 34); D127A, GGGGCAGGAACCACAGCAATGTGAGCCATCA (SEQ ID NO: 35) and TGATGGCTCACAT-TGCTGTGGTTCCTGCCCC (SEQ ID NO: 36); H465A, AAACTTTCTCATTGATTCCAGCGACACCACT-GAAGTCCTGAG (SEQ ID NO: 37) and CTCAGGACTTCAGTGGTGTCGCTGGAATCAAT-GAGAAAGTTT (SEQ ID NO: 38).

H. Detection of Endogenous, Circulating PM20D1 by Shotgun LC-MS/MS

Murine plasma specimens (50 µl) were depleted of albumin and IgG using Proteome Purify™ 2 Mouse Serum Protein Immunodepletion Resin (R&D Systems) and subsequently concentrated by 3 kDa molecular weight cut-off spin-filter columns (Millipore). One hundred µg of plasma were deglycosylated using Protein Deglycosylation Mix (New England Biolabs) as per the manufacturer's denaturing protocol. Deglycosylated plasma samples were further reduced with 10 mM DTT prior to being resolved by SDS-PAGE using 4-12% NuPAGE Bis-Tris precast gels (Life Technologies). Gels were Coomassie stained and fragments were excised from the 50-80 kDa region. Gel pieces were destained with 40% ACN/0.5% formic acid, dehydrated with 100% ACN, vacuumed dried, and resuspended with 25 mM HEPES, pH 8.5 containing 1 µg of sequencing grade trypsin (Promega) for an overnight incubation at 37° C. Digests were quenched after 12 h with 1% formic acid and de-salted using homemade stage tips (Rappsilber et al. (2007) Nat. Protoc. 2:1896-1906).

Isobaric labeling of peptides was performed using a 10-plex tandem mass tag (TMT) reagents (Thermo Fisher Scientific). TMT reagents (5 mg) were dissolved in 250 µl dry acetonitrile and 3 µl was added to digested peptides dissolved in 25 µl of 200 mM HEPES, pH 8.5. After 1 hour at room temperature (RT), the reaction was quenched by adding 2 µl of 5% hydroxylamine. Labeled peptides were combined, acidified with 40 µl of 10% FA (pH ~2), and de-salted using homemade stage tips.

All MS analysis was performed on an Oribtrap Fusion™ (Thermo Fisher Scientific) coupled to a Proxeon EASY-nLC™ 1200 ultra-high pressure liquid chromatography (UPLC) pump (Thermo Fisher Scientific). Peptides were re-suspended in 12 µl of 5% formic acid and separated (2 µl) onto a packed 100 µM inner diameter column containing 0.5 cm of Magic C4 resin (5 µm, 100 Å, Michrom Bioresources) followed by 40 cm of Sepax Technologies GP-C18 resin (1.8 µm 120 Å) and a gradient consisting of 6-27% (ACN, 0.125% formic acid) over 165 min at ~500 nl/min. The instrument was operated in data-dependent mode with a 60 s (±5 ppm window) expiration time, with FTMS1 spectra collected at 120,000 resolution with an AGC target of 500,000 and a max injection time of 100 ms. The ten most intense ions were selected for MS/MS and precursors were filtered according to charge state (required >1 z). Monoisotopic precursor selection was enabled, isolation width was set at 0.7 m/z, ITMS2 spectra were collected at an AGC of 18,000, max injection time of 120 ms and CID collision energy of 35%. For the FTMS3 acquisition, the Orbitrap was operated at 60,000 resolution with an AGC target of 50,000 and a max injection time of 250 ms and an HCD collision energy of 55%. Synchronous-precursor-selection (SPS) was enabled to include 7 MS2 fragment ions in the FTMS3 spectrum.

A collection of in-house software was used to convert .raw files to mzXML format, as well as to correct monoisotopic m/z measurements. Assignment of MS/MS spectra was performed using the Sequest algorithm. A protein sequence database containing Mouse Uniprot database (downloaded 12/2015), as well as known contaminants, such as human keratins and reverse protein sequences, was used. Sequest searches were performed using a 10 ppm precursor ion tolerance, requiring trypsin protease specificity, while allowing up to two missed cleavages. TMT tags on peptide N termini/lysine residues (+229.162932 Da) were set as static modifications while methionine oxidation (+15.99492 Da) and deamidation of asparagine (0.984016) were set as variable modifications. An MS2 spectra assignment false discovery rate (FDR) of less than 1% was achieved by applying the target-decoy database search strategy and filtered using an in-house linear discrimination analysis algorithm with the following peptide ion and MS2 spectra metrics: XCorr, peptide ion mass accuracy, charge state, peptide length and missed-cleavages. Peptides were further filtered a 1% protein-level false discovery rate for the final dataset. Two tryptic peptides were identified for PM20D1: 39-48 R.IP-SQFSEEER.V (SEQ ID NO: 39) and 313-323 R.NLWLFH-PIVSR.I (SEQ ID NO: 40).

For quantification, a 0.003 m/z (10-plex TMT) window centered on the theoretical m/z value of each reporter ion, with the maximum signal intensity from the theoretical m/z value was recorded. Reporter ion intensities were adjusted based on the overlap of isotopic envelopes of all reporter ions (manufacturer specifications). Total signal to noise values for all peptides were summed for each TMT channel (150 minimum) and all values were normalized to account for variance in sample preparation.

I. Purification of Mammalian Recombinant PM20D1

293A cells were infected with retrovirus expressing PM20D1-6× His-Flag or GFP-Flag in the presence of polybrene (8 μg/ml). After two days, cells were selected with hygromycin (150m/ml, Sigma Aldrich). The stable 293A cells were then grown in complete media. At confluence, the media (~500 ml) was changed, harvested 24 h later, and concentrated ~10-fold in 30 kDa MWCO filters (EMD Millipore) according to the manufacturer's instructions.

The concentrated media was centrifuged to remove debris (600×g, 10 min, 4° C.) and the supernatant containing PM20D1-flag was decanted into a new tube. PM20D1-Flag was immunoaffinity purified overnight at 4° C. from the concentrated media using magnetic Flag-M2 beads (Sigma Aldrich). The beads were collected, washed three times in PBS, eluted with 3× Flag peptide (0.1m/m1 in PBS, Sigma Aldrich), aliquoted, and stored at −80° C. For the purification of human PM20D1-flag, hPM20D1-flag plasmid (Origene) was transiently transfected into 293A cells. After two days, the media was changed, harvested 24 h later, concentrated, and purified exactly as described above.

J. In Vitro Activity Assays

In vitro PM20D1-catalyzed synthesis of N-acyl amino acids was measured by incubating purified PM20D1 protein with oleate (1.5 mM) and phenylalanine (0.1 mM) in PBS (to 100 μl final volume) at 37° C. for 1.5 hrs. In vitro PM20D1-catalyzed N-acyl amino acid hydrolysis was measured by incubating purified PM20D1 protein with the indicated N-acyl amino acid (0.1 mM) in PBS (to 100 μl final volume) at 37° C. for 1.5 hrs. Reactions were terminated by placing the vials at −80° C. and the products generated in vitro were analyzed by mass spectroscopy (MS).

Briefly, frozen serum (30 μl) for polar metabolomic analyses were extracted in 160 μl of 1:1 acetonitrile/methanol with inclusion of internal standard $D_3$, $^{15}N$-serine (1 nmol). Activity assays (100 μl) were extracted in 400 μl 1:1 acetonitrile/methanol. Following 30 s of thorough vortexing and 1 min of bath sonication, the polar metabolite fraction (supernatant) was isolated by centrifugation at 13,000×g for 10 min. Ten μl of this supernatant was analyzed by SRM-based targeted LC-MS/MS, or untargeted LC-MS.

For separation of polar metabolites, normal-phase chromatography was performed with a Luna-5 mm $NH_2$ column (50 mm×4.60 mm, Phenomenex). Mobile phases were as follows: Buffer A, acetonitrile; Buffer B, 95:5 water/acetonitrile with 0.1% formic acid or 0.2% ammonium hydroxide with 50 mM ammonium acetate for positive and negative ionization mode, respectively. The flow rate for each run started at 0.2 ml/min for 2 min, followed by a gradient starting at 0% B and increasing linearly to 100% B over the course of 15 min with a flow rate of 0.7 ml/min, followed by an isocratic gradient of 100% B for 10 min at 0.7 ml/min before equilibrating for 5 min at 0% B with a flow rate of 0.7 ml/min. MS analysis was performed with an electrospray ionization (ESI) source on an Agilent 6430 QQQ LC—MS/MS. The capillary voltage was set to 3.5 kV, and the fragmentor voltage was set to 100 V. The drying gas temperature was 325° C., the drying gas flow rate was 10 l/min, and the nebulizer pressure was 45 psi. For polar targeted and untargeted metabolomic analysis, representative metabolites were quantified by SRM of the transition from precursor to product ions (corresponding to amino acid fragment) at associated collision energies. Several representative fragmentation ions are as follows: C18:1-Ala, 352>88; C18:1-Gly, 338>74; C18:1-Phe, 428>164; C18:1-Leu/Ile, 394>130; C20:4-Phe, 450>164; C20:4-Leu/Ile, 416>130. Untargeted LC-MS was performed by scanning a mass range of m/z 50-1200, and data were exported as mzdata files and uploaded to XCMSOnline (xcmsserver.nutr.berkeley.edu) to identify metabolites that were differentially changed. For targeted metabolomics analysis, metabolites were quantified by integrating the area under the peak and were normalized to internal standard values corresponding to 1 nmol $D_3$, $^{15}N$-serine.

K. Cell Culture

C2C12, U2O5, and 293A cells were cultured in DMEM with 10% FBS and pen/strep. Primary inguinal (iWAT) and brown (BAT) adipocytes were obtained as follows. The stromal-vascular fraction of inguinal (iWAT) pad from 4-12 week old male mice was dissected, minced, and digested for 45 min. at 37° C. in PBS containing 10 mM $CaCl_2$, 2.4 U/ml dispase II (Roche), and 1.5 U/ml collagenase D (Roche). The stromal-vascular fraction of brown fat (BAT) pads from newborn (P1-P14) pups was dissected, minced, and digested for 45 min at 37° C. in PBS containing 1.3 mM $CaCl_2$, 120 mM NaCl, 5 mM KCl, 5 mM glucose, 100 mM HEPES, 4% BSA, and 1.5 mg/ml collagenase B (Roche). Digested tissue was diluted with adipocyte culture media (DMEM/F-12, GlutaMAX™ supplement, Life Technologies, with 10% FBS and pen/strep) and centrifuged (600×g for 10 min.). The pellet was resuspended in 10 ml adipocyte culture media, strained through a 40 μm filter, and plated. Differentiation was induced by application of an adipogenic cocktail containing 5 μg/ml insulin (Sigma), 5 μM dexamethasone (Sigma), 250 μM isobutylmethylxanthine (Sigma), and 1 μM rosiglitazone (Cayman) for 2 days. Two days after induction, cells were maintained in adipocyte culture media containing 5 μg/ml insulin and 1 μM rosiglitazone.

L. Cellular Respiration Measurements

Cellular oxygen consumption rates were determined using an XF24 Extracellular Flux Analyzer (Seahorse Biosciences). Oligomycin was purchased from EMD Millipore, and FCCP and rotenone were purchased from Sigma. C2C12 or U2OS cells were seeded at 30,000 or 50,000 cells/well, respectively in an XF24 cell culture microplate (V7-PS, Seahorse Bioscience) and analyzed the following day. Primary iWAT or BAT adipocytes were seeded at 15,000 cells/well, differentiation was induced the following day as described, and the cells were analyzed on day 5. On the day of analysis, the cells were washed once with Seahorse respiration buffer (8.3 g/l DMEM, 1.8 g/l NaCl, 1 mM pyruvate, 20 mM glucose, pen/strep), placed in 0.5 ml Seahorse respiration buffer, and incubated in a $CO_2$-free incubator for 1 hr. Port injection solutions were prepared as follows (final concentrations in assay in parentheses): 10 μM oligomycin (1 μM final), 500 N-acyl amino acid (50 μM final), 2 μM FCCP (0.2 μM final), and 30 μM rotenone (3 μM final). The Seahorse program was run as follows: basal measurement, 3 cycles; inject port A (oligomycin), 3 cycles; inject port B (compounds), 8 cycles; inject port C (FCCP), 3 cycles; inject port D (rotenone), 3 cycles. Each cycle consisted of mix 4 min, wait 0 min, and measure 2 min. For data expressed as a percentage of oligomycin-treated basal, the respiration at cycle 6 was normalized to 100%, and the maximum respiration at any time point between cycles 7 and 15 inclusive was used.

M. Isolation of Crude Mitochondria from BAT and Respiration Measurements

BAT pads from ten 6-12 week old male mice were harvested and minced on ice in isolation buffer (250 mM sucrose, 5 mM HEPES, and 1 mM EGTA) supplemented with 2% fatty acid-free BSA (Sigma). The tissue was then homogenized in a Teflon homogenizer and centrifuged (8,500×g, 10 min, 4° C.). The supernatant was discarded, the pellet was re-suspended in 20 ml isolation buffer supplemented with 1% fatty acid-free BSA, and centrifuged (700× g, 10 min, 4° C.). The supernatant was centrifuged one final time (8,500×g, 10 min, 4° C.). The pellet was re-suspended in isolation buffer supplemented with 1% fatty acid-free BSA (200 µl) to yield crude BAT mitochondria at 50-80 mg/ml. For respiration measurements, BAT mitochondria were diluted to in mitochondria respiration buffer (5 mM KCl, 4 mM $KH_2PO_4$, 5 mM HEPES, 1 mM EGTA, 1% fatty acid free BSA, 10 mM pyruvate, 5 mM malate, and 1 mM GDP) and plated at 15 µg/well (50 µl total volume) in an XF24 cell culture microplate. The plate was centrifuged (1000×g, 20 min, 4° C.), additional pre-warmed mitochondrial respiration buffer was added (450 µl), and respiration was measured on a XF24 Extracellular Flux Analyzer. The Seahorse program was run as follows: basal measurement, 2 cycles; inject port A (compounds), 1 cycle, inject port B (FCCP), 1 cycle, inject port C (rotenone), 1 cycle. Each cycle consisted of mix 0.5 min, wait 0 min, measure 2 min. FCCP and rotenone were used at final concentrations of 2 µM and 3 µM, respectively.

N. Measurement of Mitochondrial Membrane Potential

Mitochondrial membrane potential was measured using tetramethylrhodamine methyl ester (TMRM, Life Technologies) fluorescence. C2C12 cells were plated in 6-well plates and grown to 80-90% confluence. Cells were then washed once with PBS and switched into Seahorse respiration buffer with the indicated compounds at the indicated concentrations: TMRM (100 nM), oligomycin (1 µM), FCCP (0.4 µM), and C18:1-Phe (10 or 50 µM). After 20 min. incubation at 37° C., the media was aspirated, cells were washed once with PBS, and trypsinized. Trypsinized cells were directly resuspended in PBS (total volume 300 µl), stored on ice, and analyzed on a FACSCanto™ II (BD Biosciences) with 20,000 events per sample.

O. UV Crosslinking and Identification of N-acyl Amino Acid Protein Targets

Confluent 6-cm plates of C2C12 cells were washed twice with PBS and then treated with photo-probe (20 µM) with or without competitor (C20:4-Phe, 100 µM) in serum free media at 37° C. for 20 min. The media was aspirated. Cells were then placed on ice and UV-irradiated (10 min, UV Stratalinker 2400). Control samples were left on ice under ambient light.

Following UV irradiation, cells were then scraped, centrifuged (5 min, 1,400×g), washed once with cold PBS, and centrifuged again (5 min, 1,400×g). The cell pellets were resuspended in 0.3 ml PBS and sonicated. Click chemistry was performed as follows: To 50 µl cell lysate at 1 mg/ml was added 3 µl TBTA (stock solution: 1.7 mM in 4:1 v/v DMSO:t-BuOH), 1 ul CuSO4 (stock solution: 50 mM in water), 1 ul TCEP (freshly prepared, stock solution: 50 mM), and 1 ul TAMRA-$N_3$ (stock solution: 1.25 mM in DMSO). Reactions were incubated at room temperature for 1 h, and then quenched with 4× SDS loading buffer (17 ul). In-gel TAMRA fluorescence was visualized on a Typhoon™ FLA 9000 scanner (GE Healthcare Life Sciences).

For LC-MS/MS identification of photo-probe labeled proteins, click chemistry was performed using biotin-PEG3-azide (100 mM stock, Click Chemistry Tools). Samples were mixed and the reaction was allowed to proceed for 1 h at room temperature. After click reactions, proteomes were precipitated by centrifugation at 6,500×g, washed twice in ice-cold methanol, then denatured and resolubilized by heating in 1.2% SDS/PBS to 80° C. for 5 minutes. Insoluble components were precipitated by centrifugation at 6,500×g and soluble proteome was diluted in 5 ml 0.2% SDS/PBS. Labeled proteins were bound to avidin-agarose beads (170 ml resuspended beads/sample, Thermo Pierce) while rotating overnight at 4° C. Bead-linked proteins were enriched by washing three times each in PBS and water, then resuspended in 6 M urea/PBS (Sigma-Aldrich) and reduced in dithiothreitol (1 mM, Sigma-Aldrich), alkylated with iodoacetamide (18 mM, Sigma-Aldrich), then washed and resuspended in 2 M urea and trypsinized overnight with 0.5 ug/ul sequencing grade trypsin (Promega). Tryptic peptides were diluted in PBS, acidified with formic acid (1.2 M, Spectrum) and prepared for MS analysis, as described in Nomura et al. (2010) Cell 140:49-61.

P. Statistics

The Student's t-test was used for pair-wise comparisons, and ANOVA was used for indirect calorimetry experiments. Unless otherwise specified, statistical significance was set at p<0.05.

Q. Representative Brown and Beige Fat Markers

Table 2 below provides representative gene expression markers for brown and/or beige fat. In addition, assays for analyzing quantitative RT-PCR, mitochondrial biogenesis, oxygen consumption, glucose uptake, energy intake, energy expenditure, weight loss, multilocular lipid droplet morphology, mitochondrial content, and the like modulated by PM20D1 and exhibited by brown and/or beige fat cells are well-known in the art (see, at least Harms and Seale (2013) Nat. Med. 19:1252-1263 and U.S. Pat. Publ. 2013/0074199).

TABLE 2

| Gene Symbol | Gene Name | GenBank Gene Accession Number | GenBank Protein Accession Number | Gene ID |
|---|---|---|---|---|
| adipsin | complement factor D | e.g., NM_013459.2 and NM_001928.2 | e.g., NP_038487.1 and NP_001919.2 | e.g., 11537 and 1675 |
| fatty acid transporter cd36 | fatty acid transporter/cd36 | e.g., NM_007643.3 and NM_000072.3 and NM_001001547.2 and NM_001001548.2 and NM_001127443.1 and NM_001127444.1 | e.g., NP_031669.2 and NP_000063.2 and NP_001001547.1 and NP_001001548.1 and NP_001120915.1 and NP_001120916.1 | e.g., 12491 and 948 |
| adiponectin | adiponectin | e.g., NM_009605.4 and NM_004797.2 | e.g., NP_0033735.3 and NP_004788.1 | e.g., 11450 and 9370 |

TABLE 2-continued

| Gene Symbol | Gene Name | GenBank Gene Accession Number | GenBank Protein Accession Number | Gene ID |
|---|---|---|---|---|
| UCP-1 | uncoupling protein 1 | e.g., NM_009463.3 and NM_021833.4 | e.g., NP_033489.1 and NP_068605.1 | e.g., 22227 and 7350 |
| cidea | cell death-inducing DFFA-like effector a | e.g., NM_007702.2 and NM_001279.3 and NM_198289.2 | e.g., NP_031728.1 and NP_001270.1 and NP_938031.1 | e.g., 12683 and 1149 |
| PGC1a | Peroxisome proliferative activated receptor, gamma, coactivator 1 alpha | e.g., NM_008904.2 and NM_013261.3 | e.g., NP_032930.1 and NP_037393.1 | e.g., 19017 and 10891 |
| Elovl3 | elongation of very long chain fatty acids (FEN1/Elo2, SUR4/Elo3, yeast)-like 3 | e.g., NM_007703.2 and NM_152310.1 | e.g., NP_031729.1 and NP_689523.1 | e.g., 12686 and 83401 |
| C/EBPbeta | CCAAT/enhancer binding protein beta | e.g., NM_009883.3 and NM_005194.2 | e.g., NP_034013.1 and NP_005185.2 | e.g., 12608 and 1051 |
| Cox7a1 | cytochrome c oxidase subunit VIIa polypeptide 1 | e.g., NM_009944.3 and NM_001864.2 | e.g., NP_034074.1 and NP_001855.1 | e.g., 12865 and 1346 |
| Otopetrin | Otopetrin 1 | e.g., NM_172709.3 and NM_177998.1 | e.g., NP_766297.2 and NP_819056.1 | e.g., 21906 and 133060 |
| Type II deiodinase | Deiodinase, iodothyronine, type II | e.g., NM_010050.2 and NM_000793.4 and NM_001007023.2 and NM_013989.3 | e.g., NP_034180.1 and NP_000784.2 and NP_001007024.1 and NP_054644.1 | e.g., 13371 and 1734 |
| cytochrome C | cytochrome c | e.g., NM_009989.2 and NM_018947.4 | e.g., NP_034119.1 and NP_061820.1 | e.g., 13067 and 54205 |
| cox4i1 | cytochrome c oxidase subunit IV isoform 1 | e.g., NM_009941.2 and NM_001861.2 | e.g., NP_034071.1 and NP_001852.1 | e.g., 12857 and 1327 |
| coxIII | mitochondrially encoded cytochrome c oxidase III | e.g., NC_005089.1 and ENST00000362079 | e.g., NP_904334.1 and ENSP00000354982 | e.g., 17705 and 4514 |
| cox5b | cytochrome c oxidase subunit Vb | e.g., NM_009942.2 and NM_001862.2 | e.g., NP_034072.2 and NP_001853.1 | e.g., 12859 and 1329 |
| cox8b | cytochrome c oxidase subunit 8B, mitochondrial precursor | e.g., NM_007751.3 | e.g., NP_031777.1 | e.g., 12869 and 404544 |
| glut4 | solute carrier family 2 (facilitated glucose transporter), member 4 | e.g., NM_009204.2 and NM_001042.2 | e.g., NP_033230.2 and NP_001033.1 | e.g., 20528 and 6517 |
| atpase b2 | ATPase, H+ transportying, lysosomal 56/58kDa, V1 subunit B2 | e.g., NM_057213.2 and NM_001693.3 | e.g., NP_476561.1 and NP_001684.2 | e.g., 117596 and 526 |
| coxII | mitochondrially encoded cytochrome c oxidase II | e.g., NC_005089.1 and ENST00000361739 | e.g., NP_904331 and ENSP00000354876 | e.g., 17709 and 4513 |
| atp5o | ATP synthase, H+ transporting, mitochondrial F1 complex, O subunit | e.g., NM_138597.2 and NM_001697.2 | e.g., NP_613063.1 and NP_001688.1 | e.g., 28080 and 539 |
| ndufb5 | NADH dehydrogenase (ubiquinone) 1 beta subcomplex, 5, 16kDa | e.g., NM_025316.2 and NM_002492.2 | e.g., NP_079592.2 and NP_002483.1 | e.g., 66046 and 4711 |
| Rarres2 | retinoic acid receptor responder (tazarotene induced) 2 | e.g., NM_027852.2 and NM_002889.3 | e.g., NP_082128.1 and NP_002880.1 | e.g., 71660 and 5919 |
| Car3 | carbonic anhydrase 3 | e.g., NM_007606.3 and NM_005181.3 | e.g., NP_031632.2 and NP_005172.1 | e.g., 12350 and 761 |
| Peg10 | paternally expressed 10 | e.g., NM_001040611.1 and NM_001040152.1 and NM_001172437.1 and NM_001172438.1 and NM_015068.3 | e.g., NP_001035701.1 and NP_001035242.1 and NP_001165908.1 and NP_001165909.1 and NP_055883.2 | e.g., 170676 and 23089 |
| Cidec | Cidec cell death-inducing DFFA-like effector c | e.g., NM_178373.3 and NM_022094.2 | e.g., NP_848460.1 and NP_071377.2 | e.g., 14311 and 63924 |
| Cd24a | CD24a antigen | e.g., NM_009846.2 and NM_013230.2 | e.g., NP_033976.1 and NP_037362.1 | e.g., 12484 and 100133941 |

TABLE 2-continued

| Gene Symbol | Gene Name | GenBank Gene Accession Number | GenBank Protein Accession Number | Gene ID |
|---|---|---|---|---|
| Nr1d2 | nuclear receptor subfamily 1, group D, member 2 | e.g., NM_011584.4 and NM_001145425.1 and NM_005126.4 | e.g., NP_035714.3 and NP_001138897.1 and NP_005117.3 | e.g., 353187 and 9975 |
| Ddx17 | DEAD (Asp-Glu-Ala-Asp) box polypeptide 17 | e.g., NM_001040187.1 and NM_001098504.1 and NM_001098505.1 and NM_006386.4 and NM_030881.3 | e.g., NP_001035277.1 and NP_001091974.1 and NP_001091975.1 and NP_006377.2 and NP_112020.1 | e.g., 67040 and 10521 |
| Ap1p2 | amyloid beta (A4) precursor-like protein 2 | e.g., NM_001102455.1 and NM_001142276.1 and NM_001142277.1 and NM_001142278.1 and NM_001642.2 | e.g., NP_001095925.1 and NP_001135748.1 and NP_001135749.1 and NP_001135750.1 and NP_001633.1 | e.g., 11804 and 334 |
| Nr3c1 | nuclear receptor subfamily 3, group C, member 1 | e.g., NM_008173.3 and NM_000176.2 and NM_001018074.1 and NM_001018075.1 and NM_001018076.1 and NM_001018077.1 and NM_001020825.1 and NM_001024094.1 | e.g., NP_032199.3 and NP_000167.1 and NP_001018084.1 and NP_001018085.1 and NP_001018086.1 and NP_001018087.1 and NP_001018661.1 and NP_001019265.1 | e.g., 14815 and 2908 |
| Rybp | RING1 and YY1 binding protein | e.g., NM_019743.3 and NM_012234.4 | e.g., NP_062717.2 and NP_036366.3 | e.g., 56353 and 23429 |
| Txnip | thioredoxin interacting protein | e.g., NM_001009935.2 and NM_006472.3 | e.g., NP_001009935.1 and NP_006463.3 | e.g., 56338 and 10628 |
| Cig30 | Elongation of very long chain fatty acids-like 3 | e.g., NM_152310.1 and NM_007703.1[1] | e.g., NP_689523.1 and NP_031729.1[1] | e.g., 83401 and 12686 |
| Ppar gamma 2 | Peroxisome proliferator-activated receptor gamma 2 | e.g., NM_015869.4 and NM_011146.2[1] | e.g., NP_056953 and NP_035276.1[1] | e.g., 5468 and 19016 |
| Prdm16 | PR domain containing 16 protein | e.g., NM_022114.3 and NM_199454.2 and NM_027504.3 | e.g., NP_071397.3 and NP_955533.2 and NP_081780.3 | e.g., 63976 and 70673 |
| Ap2 | Fatty acid binding protein 4 | e.g., NM_001442.2 and NM_024406.1 | e.g., NP_001433.1 and NP_077717.1 | e.g., 2167 and 11770 |
| Ndufs2 | NADH dehydrogenase (ubiquinone) Fe-S protein 2, 49kDa (NADH-coenzyme Q reductase | e.g., NM_001166159.1 and NM_004550.4 and NM_153064.4 | e.g., NP_001159631.1 and NP_004541.1 and NP_694704.1 | e.g., 4720 and 226646 |
| Grp109A | Hydroxycarboxylic acid receptor 2 | e.g., NM_177551 and NM_030701.3 | e.g., NP_808219 and NP_109626.1 | e.g., 338442 and 80885 |
| AcylCoA-thioesterase 4 | Acyl-coenzyme A thioesterase 4 | e.g., NM_152331 and NM_134247.3 | e.g., NP_689544 and NP_599008.3 | e.g., 122970 and 171282 |
| Claudin1 | Claudin1 | e.g., NM_021101.4 and NM_016674.4 | e.g., NP_066924.1 and NP_057883.1 | e.g., 9076 and 12737 |
| PEPCK | Phosphoenolpyruvate carboxykinase (mitochondrial) | e.g., NM_001018073.1 and NM_004563.2 and NM_028994.2 | e.g., NP_001018083.1 and NP_004554.2 and NP_083270.1 | e.g., 5106 and 74551 |
| Fgf21 | Fibroblast growth factor 21 | e.g., NM_019113 and NM_020013.4 | e.g., NP_061986 and NP_064397.1 | e.g., 26291 and 56636 |
| AcyCoA-thioesterase 3 | Acyl-coenzyme A thioesterase 4 | e.g., NM_001037161.1 and NM_134246.3 | e.g., NP_001032238.1 and NP_599007.1 | e.g., 641371 and 171281 |
| Dio2 | Type II iodothyronine deiodinase | e.g., NM_00793.5 and NM_010050.2 | e.g., NP_000784.2 and NP_034180.1 | e.g., 1734 and 13371 |

Example 2

Figure 1:
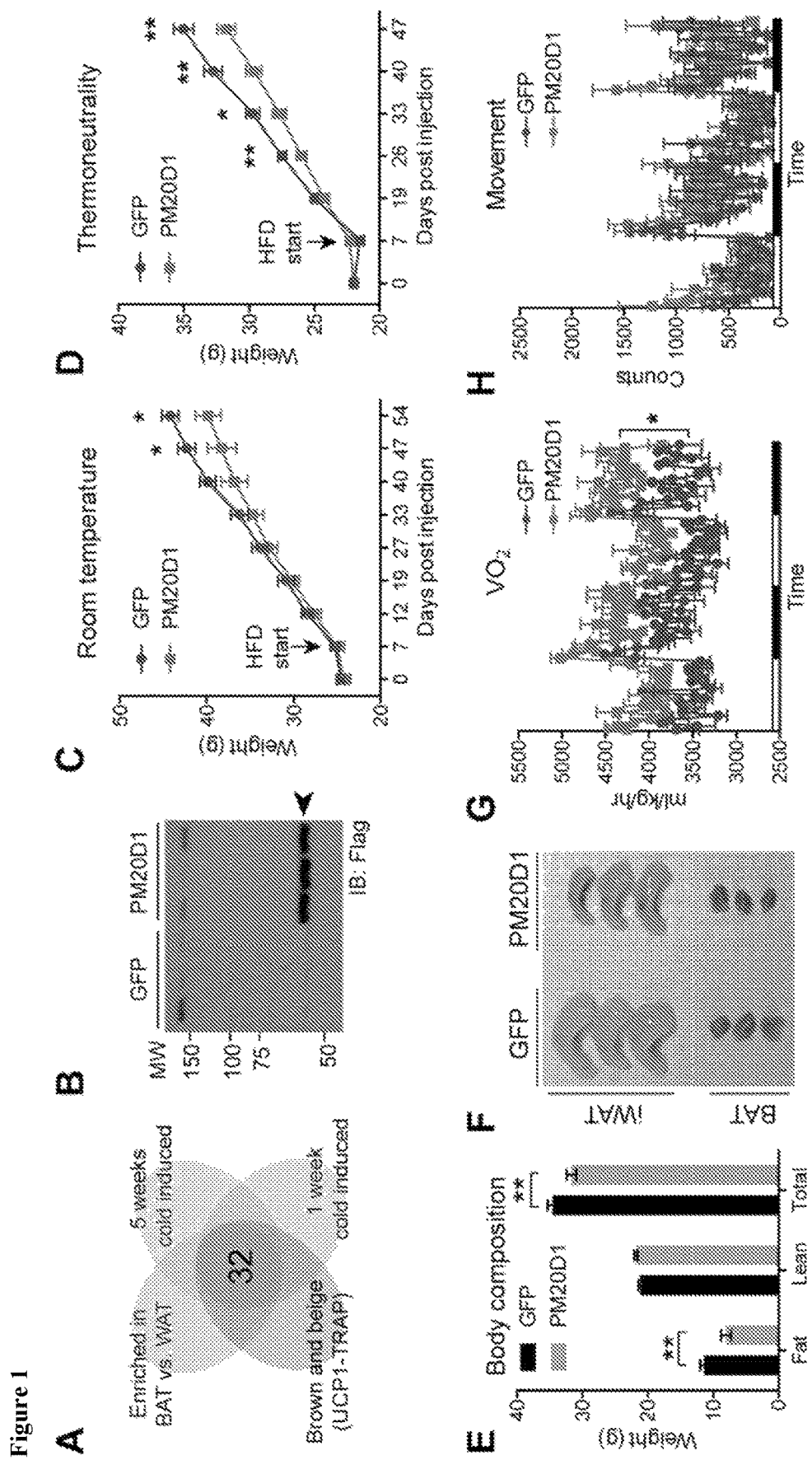
FIG. 1 includes 8 panels, identified as panels A, B, C, D, E, F, G, and H, which show that increased circulating PM20D1 augments whole body energy expenditure. Panel A shows a schematic diagram of the search strategy used to identify factors expressed by UCP1+ cells. The following publicly available datasets were used for the comparisons: UCP1-TRAP (GSE56248), brown versus white adipose tissues (GSE8044), and inguinal fat following 1 or 5 weeks cold exposure (GSE13432). Panels B-C show the results of anti-flag Western blot of plasma 40 days post-injection (Panel B) and whole body weight curves (Panel C) from male C57BL/6 mice after tail vein injection of AAV-GFP or AAV-PM20D1 fed high fat diet (HFD) at room temperature. Mice were 7 weeks old at the time of injection, HFD was started 7 days post-injection, and mice were maintained at room temperature for the duration of the experiment. For Panel B, the arrow indicates band corresponding to PM20D1-flag. For Panel C, n=8-10/group, mean±SEM, *p<0.05. Panels D-F show whole body weight curves (Panel D), MM analysis of total body composition (Panel E), and representative images of adipose tissues (Panel F) from male C57BL/6 mice after tail vein injections of AAV-GFP or AAV-PM20D1 fed HFD at thermoneutrality. Mice were placed into thermoneutrality (30° C.) at 6 weeks old, injected with virus at 7 weeks old, and HFD was started 7 days post-injection. Mice were maintained at 30° C. for the duration of the experiment. For Panels E-F, data are from 47 days post-injection. n=8-10/group, mean±SEM, *p<0.05, **p<0.01. Panels G-H show $VO_2$ (Panel G) and movement (Panel H) of male C57BL/6 mice over a period of two days. Mice were 7 weeks old at the time of injection, high fat diet (HFD) was started 7 days post-injection, and mice were maintained at room temperature for the duration of the experiment. For Panels G-H, measurements were taken at 4 weeks post-injection, a time point prior to any sigificant divergence of body weight (body weight means±SEM: GFP 33.3±1.3 g, PM20D1 31.6±1.3 g,p>0.05). n=8/group, mean±SEM, *p<0.05.
Figure 2:
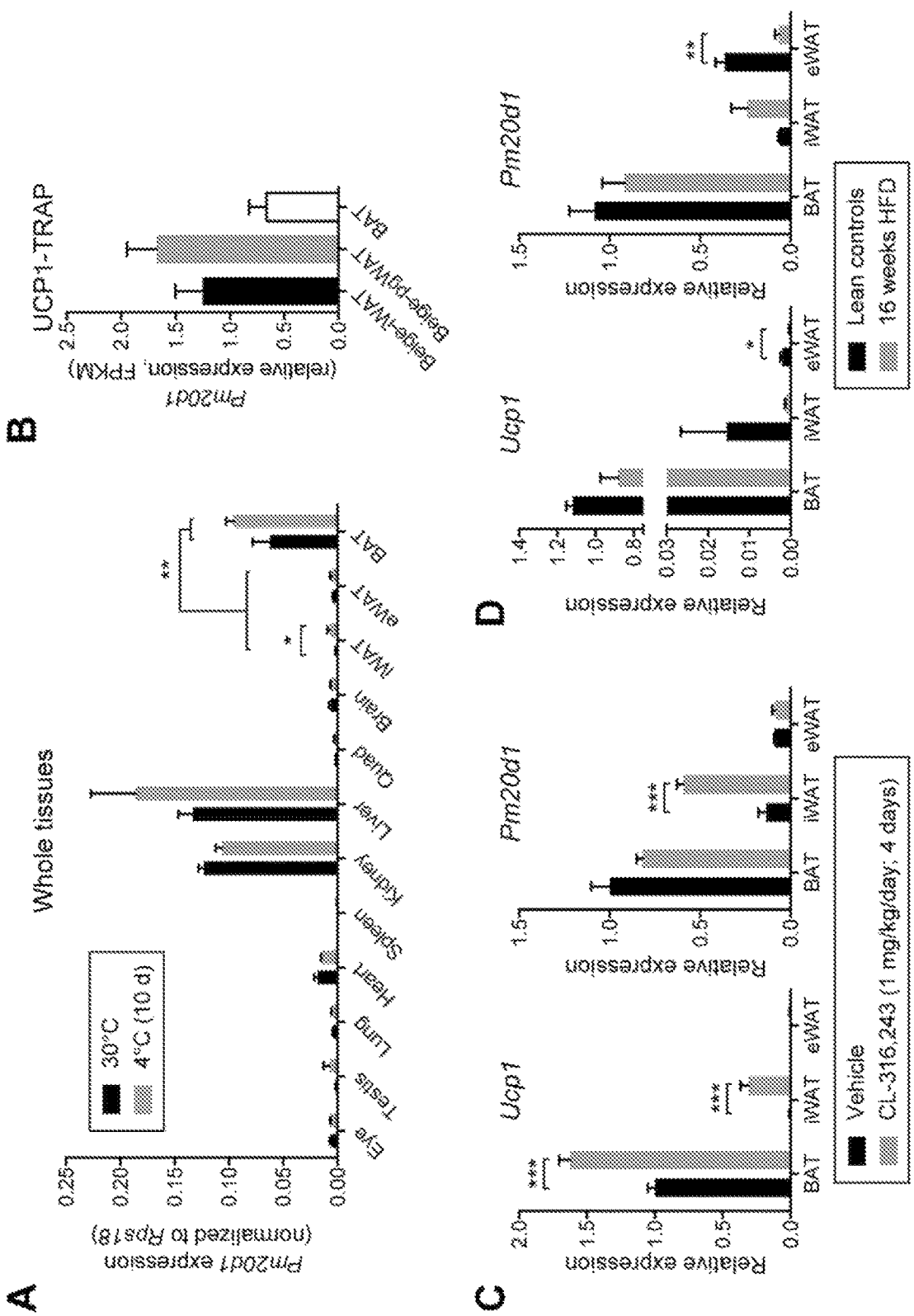
FIG. 2 includes 7 panels, identified as panels A, B, C, D, E, F, and G, which show Pm20d1 expression profiles and detection of circulating PM20D1 in Blood. Panel A shows Pm20d1 mRNA expression levels in various tissues of 8-week old male C57BL/6 mice following 10 days at thermoneutrality (30° C.) or cold (4° C.) (n=3/group, mean±SEM, *p<0.05, **p<0.01). Panel B shows Pm20d1 mRNA expression levels in the UCP1+ cells of various adipose depots of 6-week old female UCP1-TRAP mice following 2-weeks at 4° C. (n=2-3/group, mean±SEM). These values are extracted from GSE56248. Panel C shows Ucp1 (left panels) and Pm20d1 (right panels) mRNA levels in the indicated fat depots following CL-316,243 treatment (1 mg/kg/day for 4 days) versus vehicle treatment. For Panel C, tissues were harvested 6 hr after the final injection. Panel D shows Ucp1 (left panels) and Pm20d1 (right panels) mRNA levels in the indicated fat depots in mice fed 16-week high fat diet (HFD) or 16-week chow diet (lean controls). For Panels C and D, n=4-5/group, mean±SEM, *p<0.05, p<0.01, *p<0.001. Panel E shows fold changes of 50-70 kDa plasma proteins from TMT shotgun plasma proteomics of mice at thermoneutrality or cold (10 days, 4° C.). The point corresponding to PM20D1 protein is indicated. Panel F shows quantification of the TMT peak area for the identified peptides in plasma mapping to PM20D1. For Panels E and F, n=4-5/group. Panel G shows an anti-flag Western blot of cells and conditioned media from 293A cells two days after transfection with C-terminal flag-tagged GFP or PM20D1. The following abbreviations are used for the adipose depots: iWAT, inguinal white adipose tissue; eWAT, epididymal white adipose tissue; pgWAT, perigonadal white adipose tissue (in females); BAT, brown adipose tissue.
Figure 2:
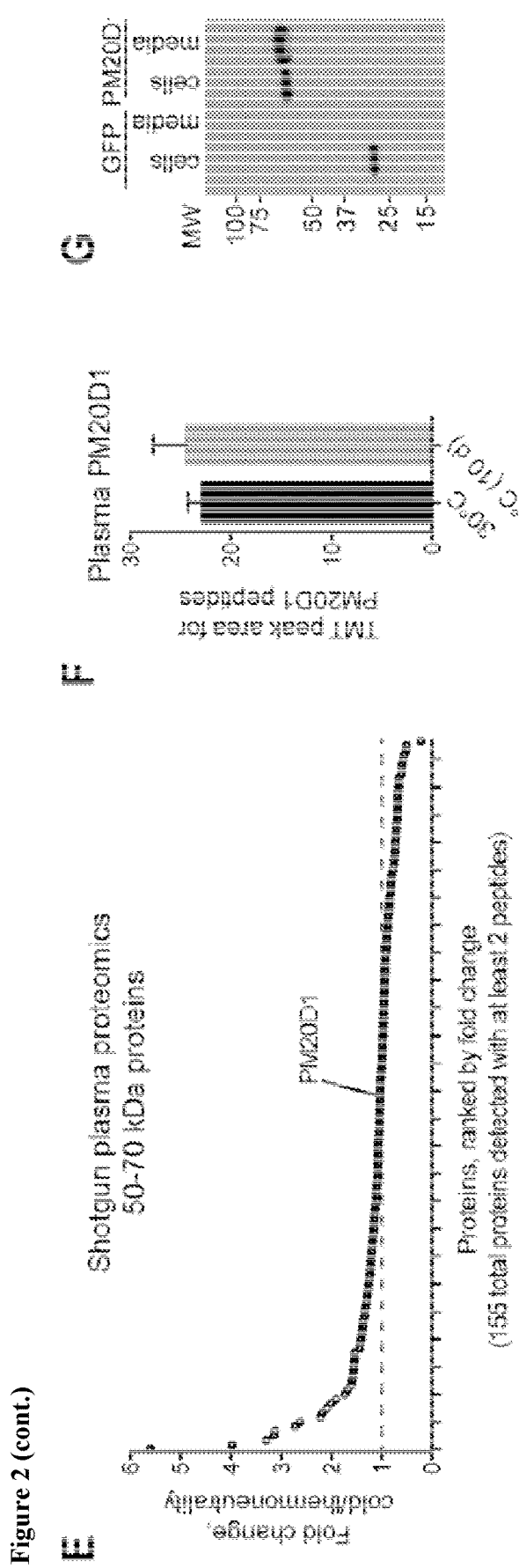

PM20D1 is a Secreted Enzyme that Promotes Thermogenesis in a UCP1-Independent Manner and Modulates Metabolic Disorders PM20D1 is highly enriched in thermogenic versus non-thermogenic adipocytes and thermogenic adipocytes secrete an enzyme called PM20D1 into the blood (FIGS. 1-2). In mice rendered diabetic by high fat diet feeding, the overexpression of PM20D1 by adenoviral vectors or adeno-associated vectors increased circulating PM20D1 levels and improved metabolic outcomes. In particular, PM20D1 improved whole body glucose tolerance, whole body energy expenditure, and control of weight gain (FIG. 1). For example, increasing circulating PM20D1 reduced blood glucose levels as determined using standard glucose tolerance tests.

Biochemically, PM20D1 is the biosynthetic enzyme that produces a class of N-lipidated amino acids in vivo, including oleoyl-phenylalanine. PM20D1 is also believed to be a biodegradative enzyme for N-lipidated amino acids. Increased circulating PM20D1 by adeno-associated virus increases the plasma levels of various N-acyl phenylalanine in vivo (FIG. 2). These natural increases also extend out of the phenylalanine head group class to at least N-acyl leucine/isoleucine. In cells, overexpression of PM20D1 increases the levels of some N-acyl amino acids and depletes the levels of others, thereby demonstrating that PM20D1 can regulate a wide variety of N-acyl amino acids. Based on the results of in vitro analyses, PM20D1 can catalyze both the hydrolysis of N-acyl amino acids to free fatty acid and free amino acid, as well as the synthesis of N-acyl amino acids by conjugation of free fatty acid and free amino acid. These reactions do not require high-energy intermediates, such as ATP or fatty acyl-CoA. Moreover, these reactions do not require the metal ion coordination domain of PM20D1 since both the hydrolysis and synthase reactions can be performed directly in PBS without the addition of any additional ions, such as Zn. The addition of $Zn(OAc)_2$ at 2 mM does not augment reaction rate and may decrease the rate.

For the synthesis reaction, for example, PM20D1 can generate N-oleoyl phenylalanine using roughly physiologic concentrations of oleate (300 uM or higher) and phenylalanine (100 uM). For the hydrolysis reaction, for example, PM20D1 can accept a variety of N-acyl amino acids as substrates, including C18:1-Phe, C18:1-Gly, and C18:1-Ser. However, PM20D1 does not hydrolyze another N-acyl amide, N-oleoyl ethanolamine, which is a physiologic substrate of fatty acid amide hydrolase (FAAH). Thus, PM20D1 generally uses the carboxylate in the substrate for the hydrolysis reaction, and this demonstrates that PM20D1 and FAAH have distinct enzymatic activities (FIG. 2).

The experiments were performed using full-length cDNA encoding mouse PM20D1 with an in-frame C-terminal 6×HIS/Flag tag. Protein modification of PM20D1, such as C-terminal tagging, did not affect enzymatic activity.

Example 3

N-Lipidated Amino Acids Promote Thermogenesis and Modulate Metabolic Disorders

Figure 5:
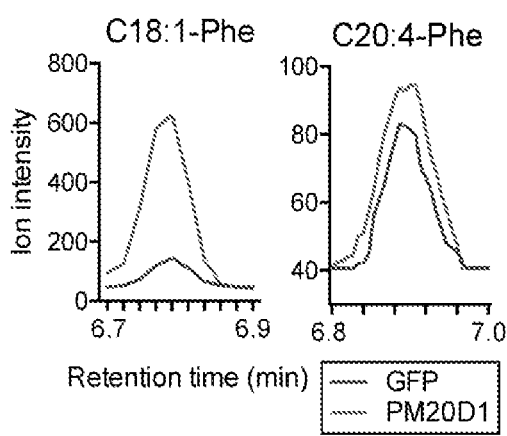
FIG. 5 includes 5 panels, identified as panels A, B, C, D, and E, which show that PM20D1 regulates the levels of N-acyl amino acids in vivo. Panels A-D show chromatograms (Panels A and C) and quantitation of fold change (Panels B and D) of various N-acyl Phes (Panels A and B) or various oleoyl/C18:1-amino acids (Panels C and D) in plasma of male C57BL/6 mice in thermoneutrality after tail vein injection of AAV-GFP or AAV-PM20D1 by targeted MRM. Mice were placed into 30° C. at 6 weeks old, injected with virus at 7 weeks old, and high fat diet (HFD) was started 7 days post-injection. Mice were maintained at 30° C. for the duration of the experiment. The comparative targeted metabolomics was performed on plasma harvested 47 days post-injection. For Panels A and C, chromatograms are from one representative mouse per group. For Panels B and D, the absolute quantitation in AAV-GFP versus AAV-PM20D1 is as follows: C16-Phe, 6 versus 15 nM, respectively; C18:2-Phe, 2 versus 7 nM, respectively; C18:1-Phe, 4 versus 10 nM, respectively; C18:1-Leu, 6 versus 29 nM, respectively. Panel E shows the fold change (cold/room temperature) of the indicated plasma N-acyl amino acids following cold exposure for the indicated times by targeted MRM. For Panels B, D, and E, n=4-5/group, mean±SEM, *p<0.05, **p<0.01.
Figure 5:
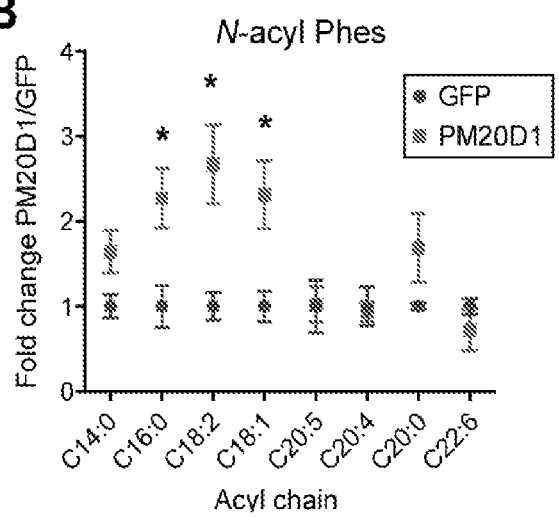
Figure 5:
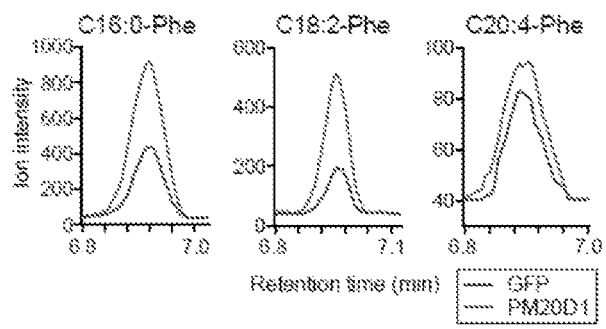
Figure 5:
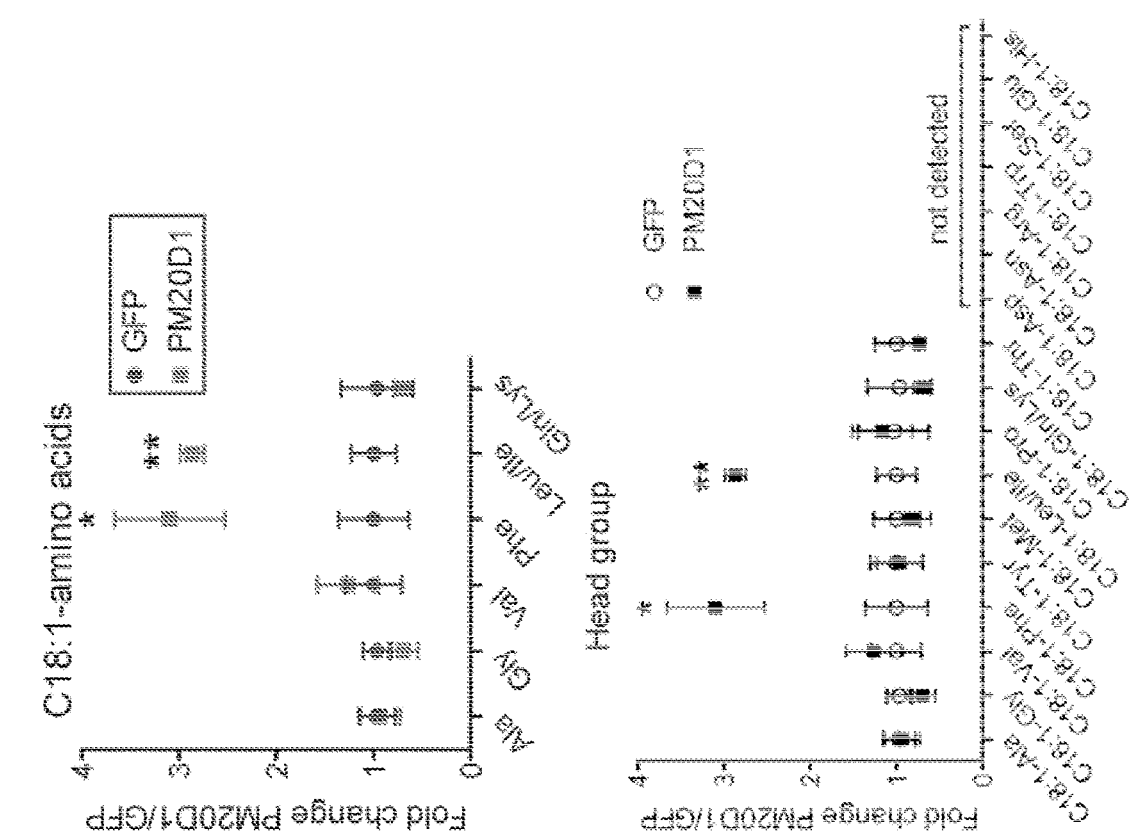
Figure 5:
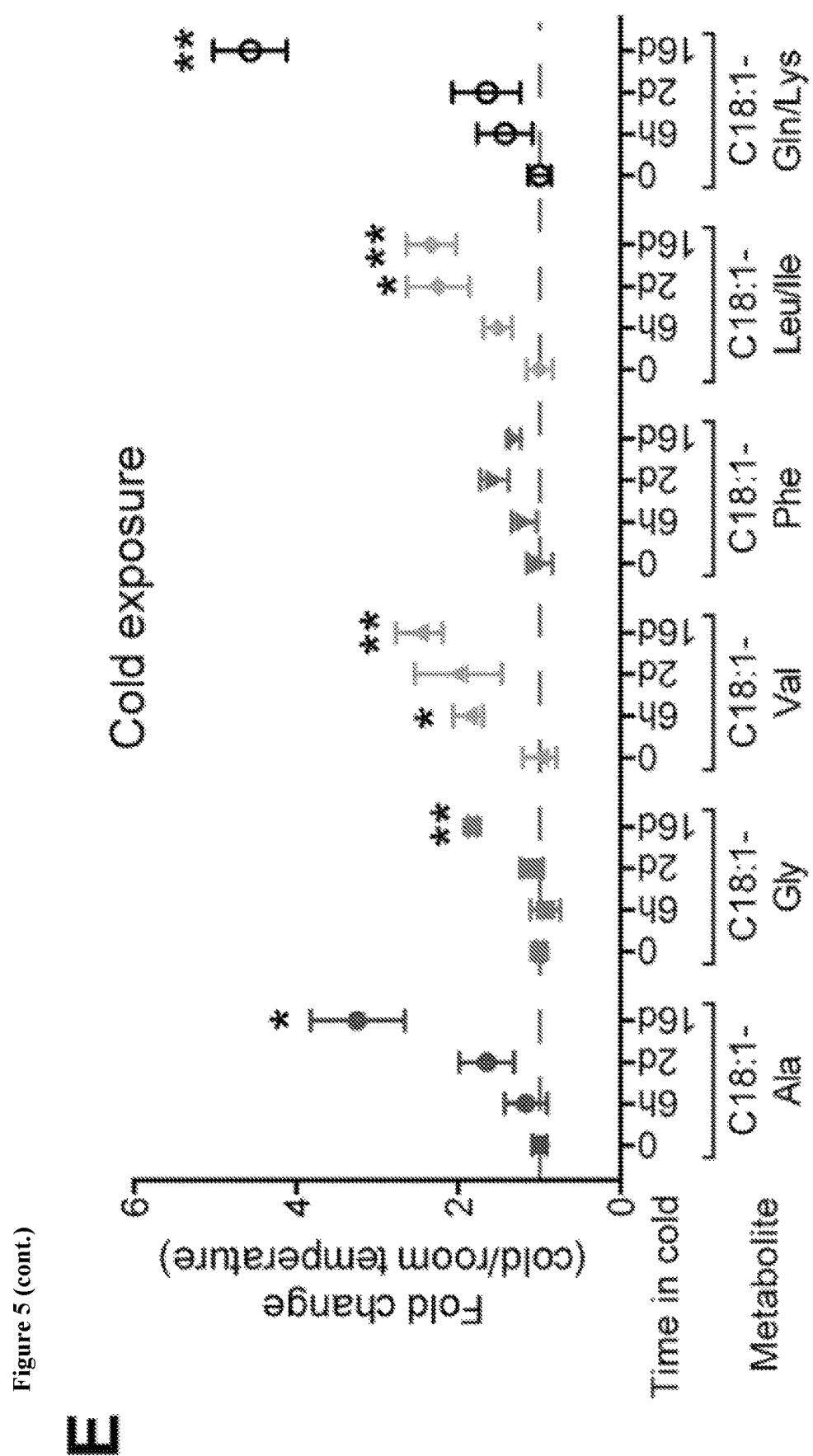

Direct treatment of adipocytes with N-lipidated amino acids promotes thermogenesis, such as promoting an increasing in oxygen consumption. For example, direct treatment of a variety of cell types (e.g., primary inguinal fat cells, primary BAT cells, C2C12 cells, and U2OS cells) with N-acyl amino acids at 10-100 uM increased uncoupled respiration (FIG. 5). For example, the following N-lipidated amino acids increased uncoupled respiration in cells: N-arachidonoyl glycine, N-arachidonoyl phenylalanine, N-arachidonoyl serine, N-arachidonoyl gamma amino butyric acid, N-oleoyl phenylalanine, N-linoleoyl phenylalanine, N-stearoyl phenylalanine, and N-palmitoyl phenylalanine. The following compounds were inactive in uncouple respiration cellular assays: noladin ether, methanandamide, N-arachidonoyl N-methyl amide, N-arachidonoyl taurine, N-arachidonoyl dopamine, N-oleoyl ethanolamine, oleate, N-palmitoyl phenylalanine methyl ester, N-palmitoyl phenylalanine amide, N-oleoyl phenylalanine methyl ester, N-oleoyl phenylalanine amide, N-lauroyl phenylalanine, N-arachidoyl phenylalanine, and (S)-alpha-methylbenzyl ricinoleamide. These data provide important structure-activity relationships (SAR) for the modulation of metabolic disorders. A terminal functional group having a pKa of about 4-5 is required since loss of the carboxylate abolished activity. Other N-lipidated amino acids lacking standard amino acid head groups also showed activity, such as N-arachidonoyl-gamma-amino butyric acid (C20:4-GABA). This result is consistent with GABA having a terminal carboxylate and only differeing from glycine by two additional methylene groups. The effects on uncoupled respiration are identical in adipocytes from UCP1 WT or knockout mice, demonstrating that the action of N-acyl amino acids does not require UCP1.

Consistent with a direct effect on uncoupled respiration, N-acyl amino acids significantly reduce the mitochondrial membrane potential to nearly the same levels of other known chemical uncouplers, such as FCCP. Also, N-acyl amino acids stimulate respiration directly on mitochondria from BAT and liver mitochondria, demonstrating that N-acyl amino acids can act directly on the mitochondria themselves. Moreover, daily injection of N-acyl amino acids to 16-week high fat diet mice augmented whole body energy expenditure.

Based on the foregoing, the data presented herein demonstrate a previously uncharacterized role for PM20D1 and N-lipidated amino acids in fat biology and the modulation of metabolic processes, including thermogenesis.

Example 4

Peptidase M20 Domain Containing 1 (PM20D1) is Expressed in UCP1+ Adipocytes and Promotes Energy Expenditure In Vivo To identify secreted factors from brown and beige adipocytes, a list was generated of "core thermogenesis" genes enriched in all types of thermogenic (UCP1+) versus non-thermogenic (UCP1−) adipocytes. To this end, the overlapping gene set were identified from the following publicly available microarray/RNAseq datasets: 1) enrichment in the classical brown adipose tissue (BAT) versus the epididymal white fat (eWAT); 2) roughly equivalent expression in both brown and beige cells in vivo using the TRAP method; and 3) induction in the cold in the subcutaneous inguinal white fat (iWAT) following 1 or 5 weeks cold exposure (Long et al. (2014) *Cell Metab.* 19:810-820; Seale et al. (2007) *Cell Metab.* 6:38-54; Xue et al. (2009) *Cell Metab.* 9:99-109) (FIG. 1A). Thirty-two genes passed these filters (Table 3). Consistent with the original search strategy, cross-referencing of these 32 genes with the Universal Protein Resource (UniProt) demonstrated that half of these candidates (16 out of 32) were mitochondrial in subcellular localization (Table 3). Of the remainder, only one, peptidase M20 domain containing 1 (PM20D1), contained a signal peptide without any transmembrane domains, two features characteristic of a classically secreted protein. The original microarray/RNAseq datasets were validated in a new cohort of mice, and it was found that Pm20d1 mRNA was higher in BAT versus the other fat depots and cold-inducible in the subcutaneous inguinal (iWAT) depot (FIGS. 2A-2B).

TABLE 3

List of genes common to all four brown/beige datasets

| Gene symbol | UCP1-TRAP (avg. FPKM) | BAT vs WAT (logFC) | 1 week cold iWAT (logFC) | 5 weeks cold iWAT (logFC) | Subcellular compartment |
|---|---|---|---|---|---|
| 1300010F03Rik | 32.7 | 2.4 | 2.6 | 2.3 | Mitochondria |
| Acaa2 | 321.1 | 3.7 | 2.5 | 2.1 | Mitochondria |
| Acot11 | 38.0 | 5.7 | 5.4 | 5.2 | Mitochondria |
| AI317395 | 2.1 | 3.9 | 3.0 | 3.8 | Membrane |
| Clic5 | 4.3 | 4.0 | 2.6 | 2.2 | Cytoplasm |
| Cox7a1 | 653.5 | 6.4 | 5.2 | 4.5 | Mitochondria |
| Cyp2b10 | 6.0 | 2.2 | 3.2 | 2.7 | ER |

TABLE 3-continued

List of genes common to all four brown/beige datasets

| Gene symbol | UCP1-TRAP (avg. FPKM) | BAT vs WAT (logFC) | 1 week cold iWAT (logFC) | 5 weeks cold iWAT (logFC) | Subcellular compartment |
| --- | --- | --- | --- | --- | --- |
| Dio2 | 26.0 | 5.5 | 2.5 | 3.5 | Membrane |
| Dlat | 74.0 | 2.2 | 2.2 | 2.0 | Mitochondria |
| Elovl3 | 63.2 | 5.2 | 9.2 | 7.9 | ER |
| Etfdh | 105.7 | 2.1 | 2.3 | 2.4 | Mitochondria |
| Fabp3 | 435.3 | 5.6 | 5.8 | 5.4 | Cytoplasm |
| Gpd2 | 78.8 | 3.6 | 2.1 | 2.5 | Mitochondria |
| Gyk | 48.6 | 3.6 | 3.2 | 3.4 | Mitochondria |
| Gys2 | 15.9 | 3.6 | 3.2 | 2.6 | Cytoplasm |
| Idh3a | 247.1 | 3.1 | 3.0 | 2.8 | Mitochondria |
| Lace1 | 14.8 | 2.7 | 2.6 | 2.2 | Mitochondria |
| Ldhb | 198.1 | 3.2 | 2.5 | 2.4 | Cytoplasm |
| Ldhd | 5.3 | 2.4 | 2.2 | 2.5 | Cytoplasm |
| Letmd1 | 84.3 | 2.8 | 3.5 | 2.8 | Mitochondria |
| LOC100048085 | 53.4 | 2.6 | 2.0 | 2.2 | Golgi |
| Ndufab1 | 183.3 | 2.4 | 2.3 | 2.5 | Mitochondria |
| Otop1 | 33.0 | 8.3 | 3.8 | 3.7 | Mitochondria |
| Pank1 | 51.9 | 5.8 | 3.5 | 3.9 | Cytoplasm |
| Pdk4 | 257.4 | 4.0 | 3.2 | 4.1 | Mitochondria |
| Plin5 | 34.8 | 3.9 | 3.5 | 3.3 | Cytoplasm |
| Pm20d1 | 1.1 | 3.4 | 2.2 | 2.7 | Secreted |
| Ppara | 10.1 | 4.4 | 2.8 | 3.3 | Nuclear |
| S100b | 16.2 | 5.0 | 3.8 | 5.2 | Cytoplasm |
| Slc25a20 | 73.7 | 3.0 | 3.4 | 2.7 | Mitochondria |
| Slc27a2 | 31.1 | 4.8 | 3.6 | 5.3 | ER |
| Ucp1 | 1310.5 | 8.1 | 7.7 | 7.7 | Mitochondria |

\* The accession numbers are as follows: UCP1-TRAP (GSE56248); BAT versus WAT (GSE8044); and cold exposure 1 and 5 weeks in iWAT (GSE13432).
For the UCP1-TRAP column, numbers indicate average FPKM across all 8 samples.
For the BAT versus WAT columns, numbers indicate the log2(fold change) for expression in BAT versus expression in epididymal WAT.
Higher numbers indicate greater enrichment in BAT vs. epididymal WAT.
For the cold exposure columns, numbers indicate the log2(fold change) for expression at 4° C. versus expression at 30° C. for the indicated time (1 or 5 weeks).
Higher numbers indicate greater enrichment in cold vs. thermoneutrality.
Genes are sorted alphabetically by gene symbol.

Further supporting Pm20d1 co-expression with Ucp1 in vivo, Pm20d1 and Ucp1 mRNA were coordinately upregulated regulated in the iWAT following treatment of mice with the β-adrenergic receptor agonist CL-316,243 (FIG. 2C), and coordinately downregulated in the eWAT following high fat diet (FIG. 2D). Shotgun proteomics with tandem mass tag (TMT) labeling confirmed the presence of PM20D1 in blood, though its circulating levels were unchanged following 10 days of cold exposure (FIGS. 2E-2F). This is presumably because, in addition to UCP1$^+$ fat cells, liver and kidney also highly express PM20D1 (FIG. 2A).

To confirm that PM20D1 can be secreted, a C-terminal flag-tagged PM20D1 cDNA construct was generated and transfected this plasmid into HEK293A cells. PM20D1 was detected both in cells and in conditioned media, whereas flag-tagged GFP was found exclusively in the cellular fraction (FIG. 2G). These data demonstrate that PM20D1 is a bona fide secreted factor enriched in thermogenic fat and induced by cold exposure.

Figure 3:
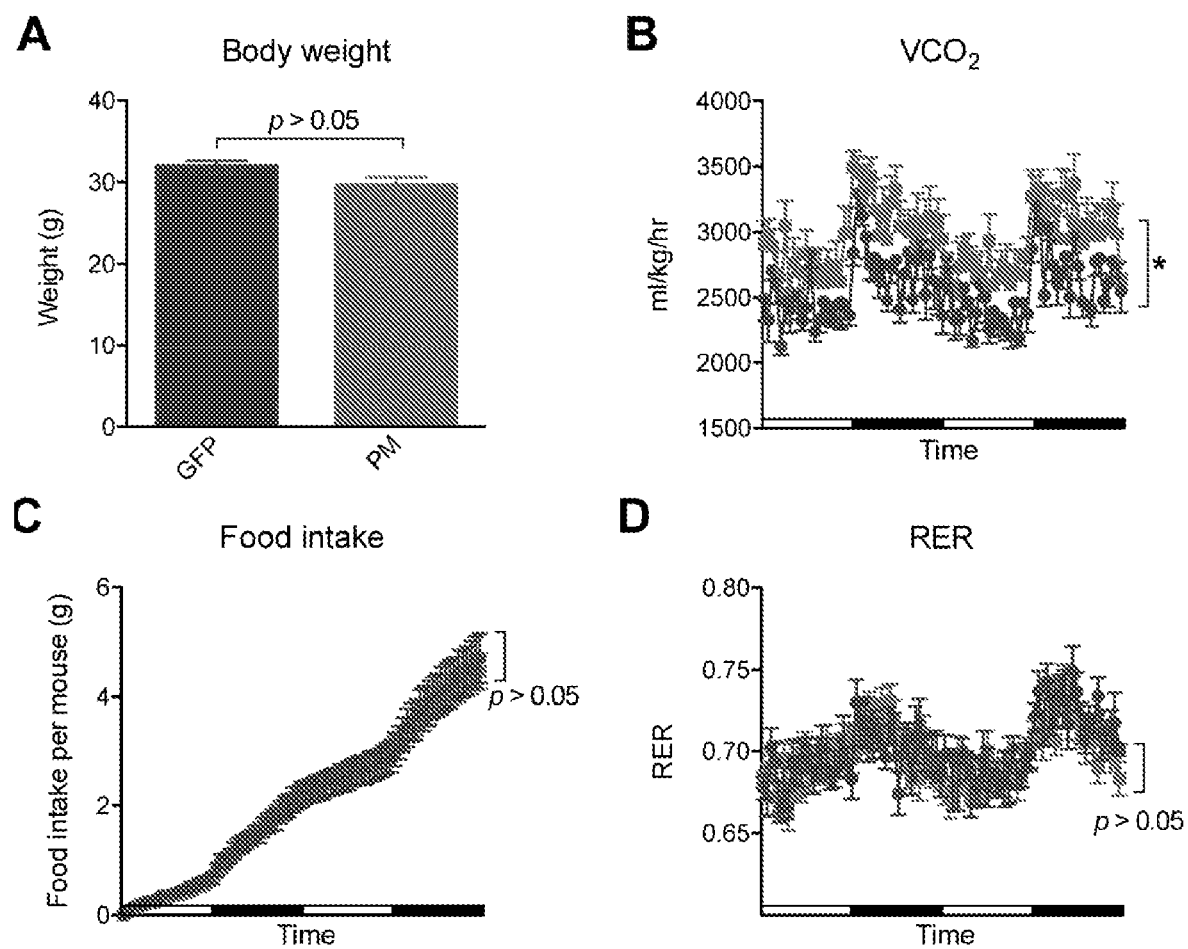
FIG. 3 includes 4 panels, identified as panels A, B, C, and D, which show other metabolic parameters of mice injected with AAV-PM20D1. Panels A-D show body weights (Panel A), $VCO_2$ (Panel B), accumulated feed (Panel C), and RER (Panel D) of male C57BL/6 mice after tail vein injection of AAV-GFP or AAV-PM20D1. Mice were 7 weeks old at the time of injection, high fat diet (HFD) was started 7 days post-injection, and mice were maintained at room temperature for the duration of the experiment. All metabolic measurements were taken at 4 weeks post injection, a time point prior to divergence of body weight. n=8/group, mean±SEM, *p<0.05.

To assess the functions of PM20D1 in vivo, mice were tail vein-injected with adeno-associated viral vectors (serotype AAV8) expressing PM20D1 or GFP. These vectors are primarily taken up and expressed by the liver, though other tissues may also express them (Zincarelli et al. (2008) Mol. Ther. 16:1073-1080). One week following the injections, the mice were placed on high fat diet (HFD). Increased circulating PM20D1 was observed by Western blots of the plasma at 40 days post-injection (FIG. 1B). At room temperature (22° C.), mice with augmented circulating PM20D1 showed blunted weight gain (final weight means±SEM: GFP, 44.2±1.0 g; PM20D1, 39.8±1.5 g; 10% weight difference) compared to the control animals (FIG. 1C). Mice were also studied at thermoneutralty (30° C.), where the sympathetic nervous input to adipose tissues is decreased (Virtue et al. (2013) Front Physiol 4:128). A similar blunting of weight gain was observed under these conditions (final weight means±SEM: GFP, 35.0±0.8 g; PM20D1, 31.8±0.7 g; 9% weight difference; FIG. 1D). Body composition analysis by MRI at the end of the experiment at thermoneutrality revealed that the weight difference was due exclusively to a 30% reduction in fat mass in those animals receiving PM20D1 compared to GFP (FIG. 1E). Gross inspection of the adipose pads confirmed a reduction in iWAT pad size, with no obvious changes in the classical BAT (FIG. 1F). In a separate cohort of mice treated with AAV-PM20D1 or AAV-GFP at room temperature, whole body energy expenditure measurements at a time point was performed prior to the divergence in weights (4 weeks HFD, FIG. 3A). These analyses revealed significantly augmented VO$_2$ (FIG. 1G) and VCO$_2$ (FIG. 3B), indicative of increased energy expenditure. Most importantly, this occurred with no changes in movement (FIG. 1H) or food intake (FIG. 3C).

Example 5

PM20D1 Regulates N-Lipidated Amino Acids In Vivo

Changes in energy expenditure with no change in physical movement are usually indicative of activation of a thermogenic gene program in the classical brown fat, subcutaneous inguinal fat (termed browning), or both. In addition, recent work has indicated the presence of an additional thermogenic pathway based upon a futile cycle of creatine phosphorylation (Kazak et al. (2015) Cell 163:643-655). Surprisingly, the increased metabolic rates observed here were not accompanied by any obvious molecular change corresponding to these processes, such as an induction of UCP1 (FIGS. 3A-3B), or changes in gene expression related to creatine metabolism (FIG. 3A). These data suggest that PM20D1 increases whole body energy expenditure through some unusual mechanism.

To further investigate how PM20D1 augmented energy expenditure, the detailed molecular consequences of PM20D1 actions in the blood were examined. PM20D1 is one of five members of the mammalian M20 peptidase family, but remains entirely uncharacterized with respect to its endogenous substrates and products. Despite their annotation as metallopeptidases, the other four other mammalian M20 family members do not appear to act on protein substrates, but instead possess peptidase activity on a variety of small molecule substrates (i.e., molecular weight<500 g/mol) (Teufel et al. (2003) J Biol. Chem. 278:6521-6531; Van Coster et al. (2005) Biochem. Biophys. Res. Commun. 338:1322-1326; Veiga-da-Cunha et al. (2014) J. Biol. Chem. 289:19726-19736). Untargeted polar small molecule mass spectrometry (MS) of plasma from mice injected with AAV-GFP or AAV-PM20D1 viral vectors (Smith et al. (2006) Anal. Chem. 78:779-797) were performed. In this assay, aqueous-soluble compounds were extracted from plasma using a mixture of methanol, acetonitrile, and water. Next, these polar metabolites were analyzed by liquid chromatography-MS in scanning mode for peaks with mass-to-charge (m/z) ratios between 50-1200 (see Example 1). Each metabolite corresponds to a peak of a specific m/z ratio and retention time, and XCMS software (Smith et al. (2006) Anal. Chem. 78:779-797; Tautenhahn et al. (2012) Anal.

Chem. 84:5035-5039) was used to align the chromatograms and identify differentially regulated peaks (Table 4).

Figure 4:
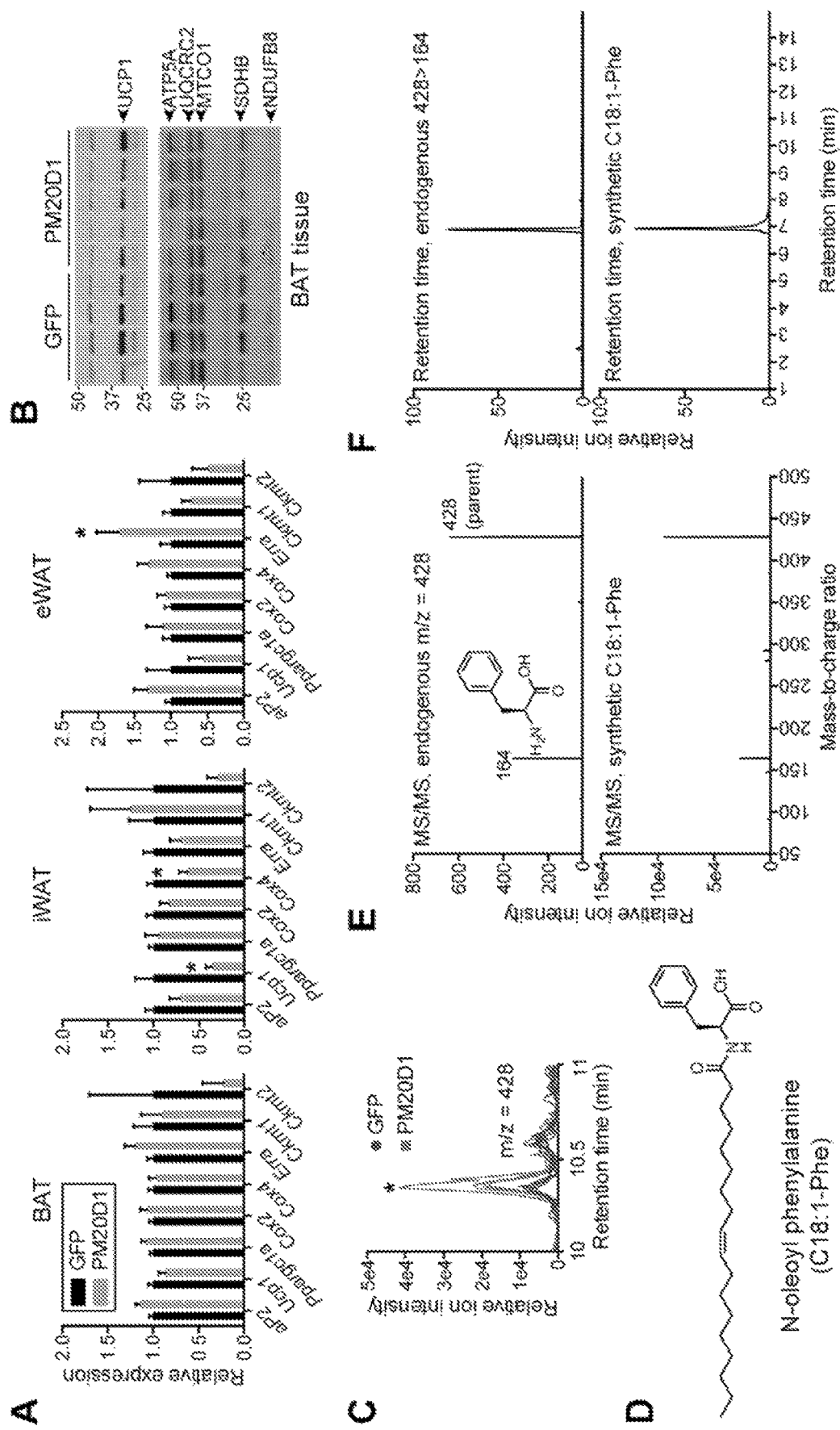
FIG. 4 includes 6 panels, identified as panels A, B, C, D, E, and F, which show a lack of classical browning and the identification of increased N-oleoyl phenylalanine in mice injected with AAV-PM20D1. Panels A shows mRNA expression results of the indicated genes in BAT, iWAT, and eWAT and Panel B shows Western blot results of UCP1 and mitochondrial proteins, respectively, from male C57BL/6 mice at thermoneutrality after tail vein injections of AAV-GFP or AAV-PM20D1. Mice were placed into thermoneutrality (30° C.) at 6 weeks old, injected with virus at 7 weeks old, and high fat diet (HFD) was started 7 days post-injection. Mice were maintained at 30° C. for the duration of the experiment. For Panels A-B, data are from 47 days post-injection. For Panel A, n=8/group, mean±SEM, *p<0.05. For Panel B, n=4-5/group. Panel C shows a chromatogram at m/z=428 from plasma of male C57BL/6 mice after tail vein injection of AAV-GFP or AAV-PM20D1. For Panel C, mice were 7 weeks old at the time of injection, high fat diet (HFD) was started 7 days post-injection, and mice were maintained at room temperature for the duration of the experiment. The comparative metabolomics was performed on plasma harvested 54 days post-injection. n=4/group, *p<0.05. Panel D shows the chemical structure of N-oleoyl phenylalanine (C18:1-Phe). Panels E and F show MS/MS spectra (Panel E) and retention time (Panel F) of endogenous (top) or synthetic (bottom) C18:1-Phe.

Manual inspection of these features revealed the most robust difference occurred in a metabolite with an m/z=428, which was increased in mice injected with AAV-PM20D1 versus AAV-GFP (FIGS. 4C and Table 4). The m/z=428 peak as the EM-Hf ion of N-oleoyl phenylalanine (C18:1-Phe, chemical formula $C_{27}H_{42}NO_3^-$, expected m/z=428) (FIG. 4D) was identified. This identification was confirmed by MS/MS experiments, which revealed a predominant product ion of m/z=164 for both synthetic C18:1-Phe and the endogenous m/z=428 precursor peak (FIG. 4C). This product ion corresponds to the phenylalanine anion fragment (chemical formula $C_9H_{10}NO_2$, expected m/z=164). Further supporting this identification, both synthetic C18:1-Phe and the endogenous m/z=428 peak eluted at similar retention times by liquid chromatography (FIG. 4F).

TABLE 4

List of features changed by untargeted metabolomics in mice injected with AAV-PM20D1 versus AAV-GFP

| m/z med | Retention time (min) | Fold change | P-value | Max peak intensity |
|---|---|---|---|---|
| 280.8 | 8.4 | 2.2 | 0.023 | 33561 |
| 368.3 | 10.4 | 3.4 | 0.020 | 23881 |
| 369.0 | 7.3 | 3.4 | 0.043 | 29711 |
| 397.0 | 7.7 | 2.3 | 0.038 | 40157 |
| 426.3 | 10.4 | 4.2 | 0.001 | 22158 |
| 428.4 | 10.3 | 5.4 | 0.025 | 41266 |
| 430.5 | 10.3 | 7.3 | 0.039 | 24105 |
| 501.3 | 10.9 | 2.4 | 0.036 | 244608 |
| 545.4 | 12.1 | 2.7 | 0.028 | 25597 |
| 583.3 | 11.0 | 2.0 | 0.017 | 47876 |
| 696.6 | 4.9 | 3.4 | 0.003 | 25206 |
| 780.9 | 11.0 | 2.8 | 0.027 | 26735 |
| 781.1 | 11.1 | 2.8 | 0.027 | 31249 |
| 784.6 | 9.9 | 2.0 | 0.035 | 67703 |
| 887.4 | 11.6 | 3.3 | 0.035 | 73182 |

* Untargeted metabolomics from male C57BL/6 mice after tail vein injection of AAV-GFP or AAV-PM20D1 ($10^{10}$ virus/mouse).
Mice were 7 weeks old at the time of injection, high fat diet (HFD) was started 7 days post-injection, and mice were maintained at room temperature for the duration of the experiment.
The comparative metabolomics was performed in negative ionization mode on plasma harvested 54 days post-injection (n = 4/group).
The features listed here were identified by XCMS and satisfy $p < 0.05$, fold change > 2, and max intensity > 20000 between AAV-PM20D1 versus AAV-GFP groups.

Figure 6:
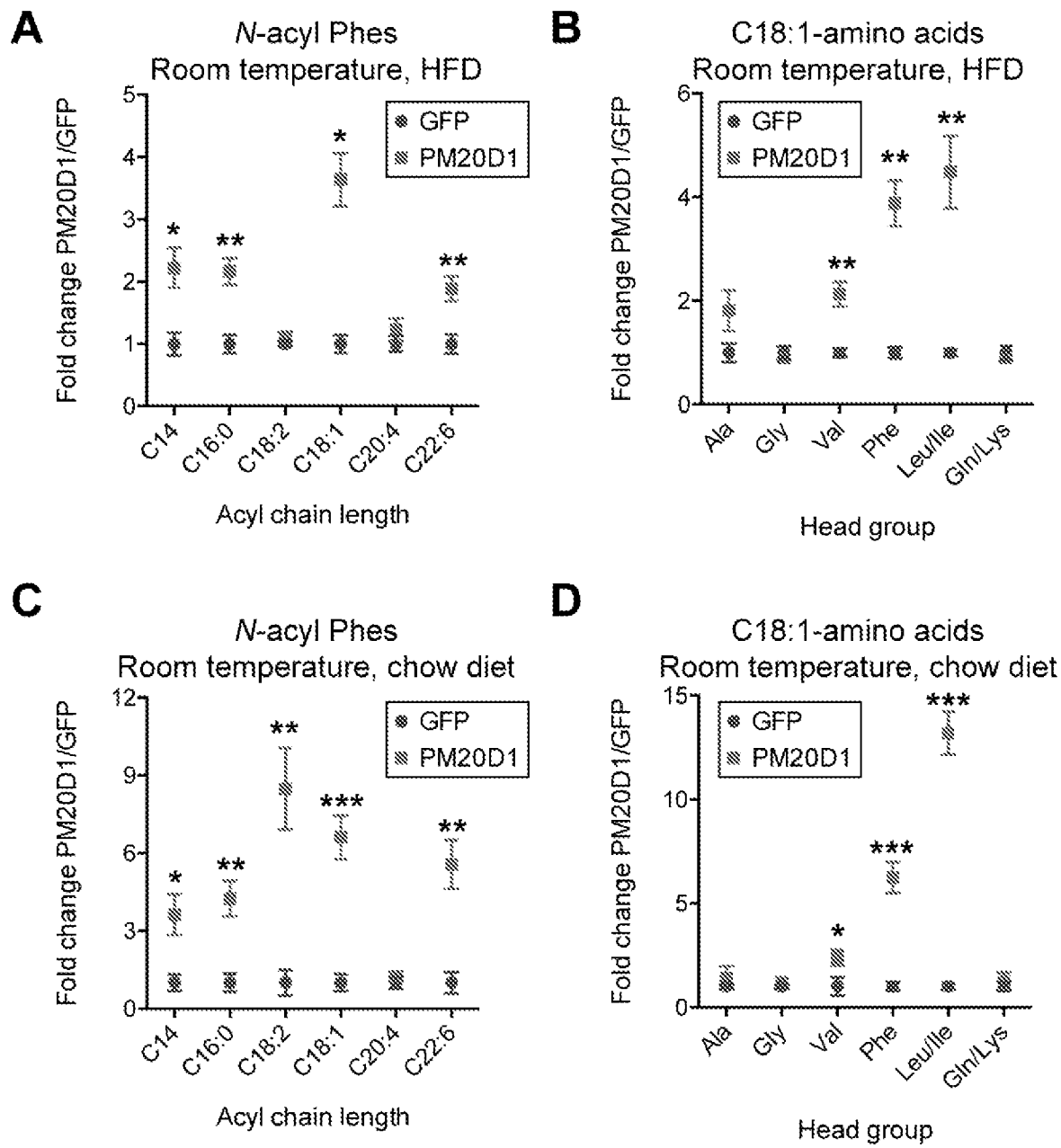
FIG. 6 includes 4 panels, identified as panels A, B, C, and D, which show metabolite changes in mice injected with AAV-PM20D1 under different environmental conditions. Panels A-D show quantitation of fold changes of various N-acyl Phes (Panels A and C) or various C18:1-amino acids (Panels B and D) in plasma of male C57BL/6 mice at room temperature after AAV-GFP or AAV-PM20D1 injection by tail vein by targeted MRM. For Panels A and B, mice were injected with virus at 7 weeks old, and high fat diet (HFD) was started 7 days post-injection at room temperature. The comparative targeted metabolomics was performed on plasma harvested at 54 days post injection. For Panels C and D, mice were injected with virus at 7 weeks old and maintained on a standard chow diet at room temperature. The comparative targeted metabolomics was performed on plasma harvested at 28 days post-injection. For Panels A-D, n=4-5/group, mean±SEM, *p<0.05, p<0.01, *p<0.001.

A targeted multiple reaction monitoring (MRM) program was developed to assess the scope of scope of N-acyl amino acids regulated by PM20D1 in plasma in vivo. By absolute quantitation using a C15-Phe internal standard, the plasma concentrations of specific members of the N-acyl amino acids were found to be in the 1-100 nM range (Table 5). PM20D1 predominantly elevates medium and long (C14-18; FIGS. 5A-5B), but not very long chain (C20-22) N-acyl Phes. Next, N-oleoyl amino acids was measured of varying head groups. Several such metabolites were robustly detected in plasma, and PM20D1 predominantly increased the large and hydrophobic N-acyl amino acid subset (C18: 1-Phe and C18:1-Leu/Ile; FIGS. 5C-5D), but not C18:1-Ala, Gly, Val, or Gln/Lys. Similar changes in N-acyl amino acids were observed for mice injected with AAV-PM20D1 at room temperature (FIG. 6).

TABLE 5

Absolute quantitation of N-acyl amino acids in plasma

| Metabolite | Plasma levels (nM) |
|---|---|
| C14-Phe | 0.4 ± 0.1 |
| C16:0-Phe | 6.0 ± 1.5 |

TABLE 5-continued

Absolute quantitation of N-acyl amino acids in plasma

| Metabolite | Plasma levels (nM) |
|---|---|
| C18:2-Phe | 2.4 ± 0.4 |
| C18:1-Phe | 3.8 ± 0.4 |
| C20:5-Phe | 0.3 ± 0.1 |
| C20:4-Phe | 0.6 ± 0.1 |
| C20:0-Phe | 0.3 ± 0.0 |
| C22:6-Phe | 0.6 ± 0.1 |
| C18:1-Ala | 1.9 ± 0.2 |
| C18:1-Gly | 65.0 ± 14.2 |
| C18:1-Val | 2.9 ± 0.6 |
| C18:1-Phe | 3.8 ± 0.4 |
| C18:1-Leu/Ile | 6.2 ± 0.7 |
| C18:1-Gln/Lys | 0.5 ± 0.1 |

* Targeted metabolomics from male C57BL/6 mice after tail vein injection of AAV-GFP ($10/\backslash 10$ virus/mouse).
Mice were 7 weeks old at the time of injection, high fat diet (HFD) was started 7 days post-injection, and mice were maintained at room temperature for the duration of the experiment.
Targeted MRM was performed in negative ionization mode on plasma harvested 54 days post-injection (n = 4/group).
Absolute quantitation was determined by normalizing to 100 pmol of C15-Phe internal standard, and numbers indicate the abundance in plasma from AAV-GFP mice.

Since Pm20d1 mRNA is induced in the iWAT following cold exposure (FIG. 1A and 2A), plasma levels of the N-oleoyl amino acids was assessed following 6 hours, 2 days, or 16 days of cold exposure by targeted MS. While acute cold exposure did not consistently affect plasma N-oleoyl amino acid levels, 6 hours or 2 days of cold increased specific members of this class (C18:1-Leu/Ile and C18:1-Val, FIG. 5E). Long-term cold exposure (16 days) significantly elevated the levels of most N-oleoyl amino acids that were measured (FIG. 5E). Therefore, both PM20D1 and its N-acyl amino acid products are physiologically co-regulated by cold exposure.

Example 6

PM20D1 is a Bidirectional N-acyl Amino Acid Synthase and Hydrolase In Vitro

Figure 7:
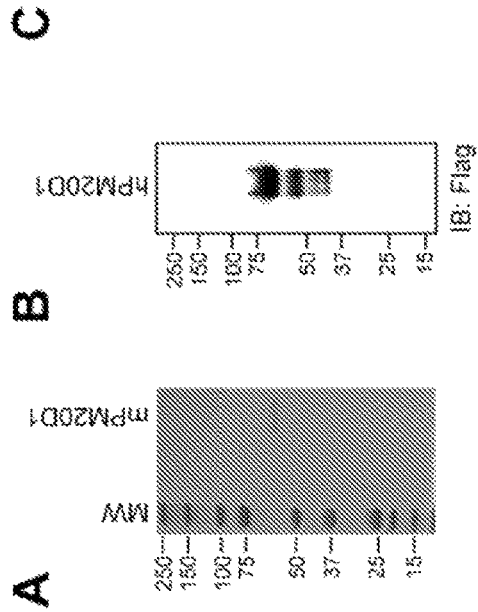
FIG. 7 includes 3 panels, identified as panels A, B, and C, which describe the generation of mammalian recombinant PM20D1. Panel A shows a Coomassie stained gel of purified C-terminal flag-tagged mouse PM20D1 (mPM20D1) from HEK293A cells stably expressing the PM20D1-flag. Panel B shows an anti-flag immunoblot of purified C-terminal flag-tagged human PM20D1 (hPM20D1) from transiently transfected HEK293A cells. Panel C shows an alignment of hPM20D1 and mPM20D1 protein sequences. Residues required for synthase and hydrolase activities are highlighted.
Figure 8:
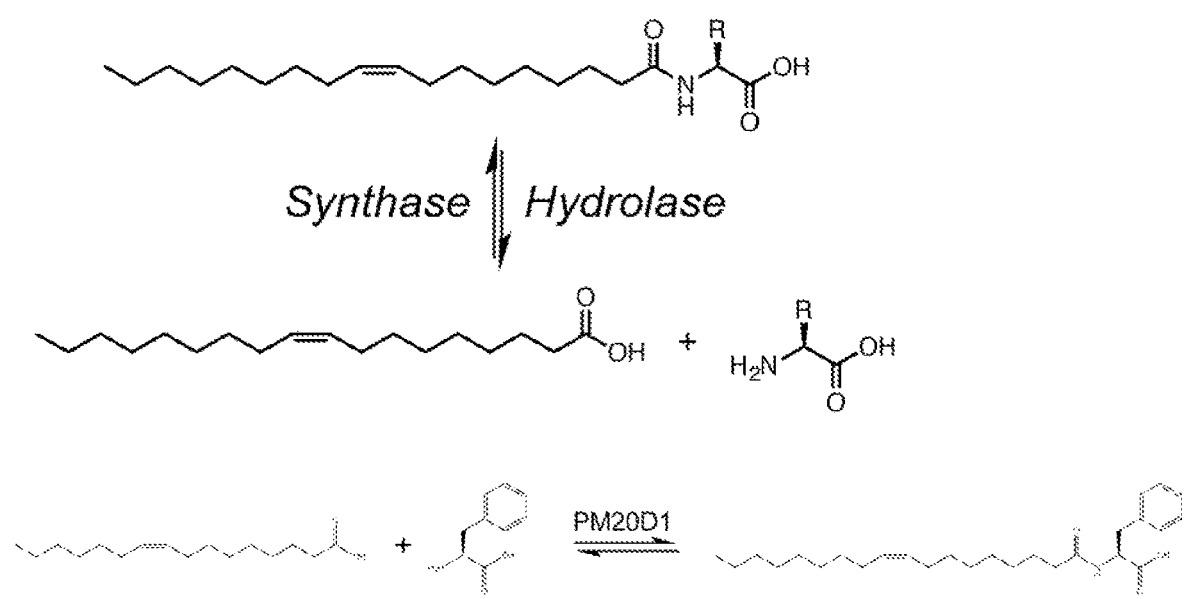
FIG. 8 includes 11 panels, identified as panels A, B, C, D, E, F, G, H, I, J, and K, which show enzymatic activity of PM20D1 in vitro. Panel A shows a schematic of synthase and hydrolase reaction of free fatty acid and free amino acid to N-acyl amino acid, as well as the forward and reverse reaction of oleic acid and free phenylalanine to C18:1-Phe. Panel B shows the relative levels of C18:1-Phe generated in vitro from Phe (100 μM), oleate (0.03-1.5 mM), and purified mouse PM20D1-flag. Reactions were carried out in PBS at 37° C. for 1.5 hours (n=3 mice per group; mean±SEM; *p<0.05; and **p<0.01 for treatment versus reaction with PM20D1 omitted). The relative levels of oleate generated in vitro from the indicated N-acyl amide substrates (100 μM) and purified PM20D1-flag are also shown. Reactions were carried out in PBS at 37° C. for 1.5 hours (n=3 mice per group; mean±SEM; *p<0.05; and **p<0.01 for treatment versus corresponding reaction with PM20D1 omitted). C18:1-EA refers to N-oleoyl ethanolamine and the mRNA expression of the indicated genes in BAT and iWAT is shown. Also shown are the relative levels of C18:1-amino acid generated from the indicated amino acid (100 μM), oleate (1.5 mM), and purified PM20D1-flag. The relative levels of oleate generated in vitro from the indicated N-acyl amide substrates (100 μM) and purified PM20D1-flag are shown. Panels C-E show the relative levels of C18:1-amino acid generated in vitro from the indicated head group (100 μM) and purified mouse PM20D1-flag using either oleate (1.5 mM; Panel C), arachidonate (1.5 mM; Panel D), or oleoyl-coenzyme A (C18:1-CoA, 0.7 mM; Panel E). For Panel C, EA refers to ethanolamine. Panel F shows the relative levels of oleate generated in vitro from the indicated N-acyl amide substrates (100 μM) and purified mouse PM20D1-flag. C18:1-EA, N-oleoyl ethanolamine. Panel G shows an anti-flag Western blot of immunoaffinity purified mouse PM20D1-flag or the indicated point mutants. Panel H shows the relative levels of C18:1-Phe generated in vitro from Phe (100 μM), oleate (1.5 mM), and the indicated wild-type (WT) or mutant PM20D1-flag protein. Panel I shows the relative levels of oleate generated in vitro from C18:1-Phe (100 μM) and the indicated wild-type (WT) or mutant PM20D1-flag protein. Panel J shows the relative levels of C18:1-amino acid generated in vitro from the indicated head group (100 μM), oleate (1.5 mM), and purified human PM20D1-flag. Panel K shows the relative levels of oleate generated in vitro from the indicated N-acyl amide substrate (100 μM) and purified human PM20D1-flag. For Panels B-F and Panels H-K, enzymatic assays were carried out in PBS at 37° C. for 1.5 hours, n=3/group, mean±SEM, *p<0.05, **p<0.01, for reaction with PM20D1 versus reaction omitting PM20D1, or reaction with PM20D1 versus reaction with heat-denatured PM20D1. The Y-axes indicate relative ion intensity normalized to 1 nmol of a $D_3$, $^{15}N$-serine internal standard that was doped in during the extraction process prior to MS analysis.
Figure 8:
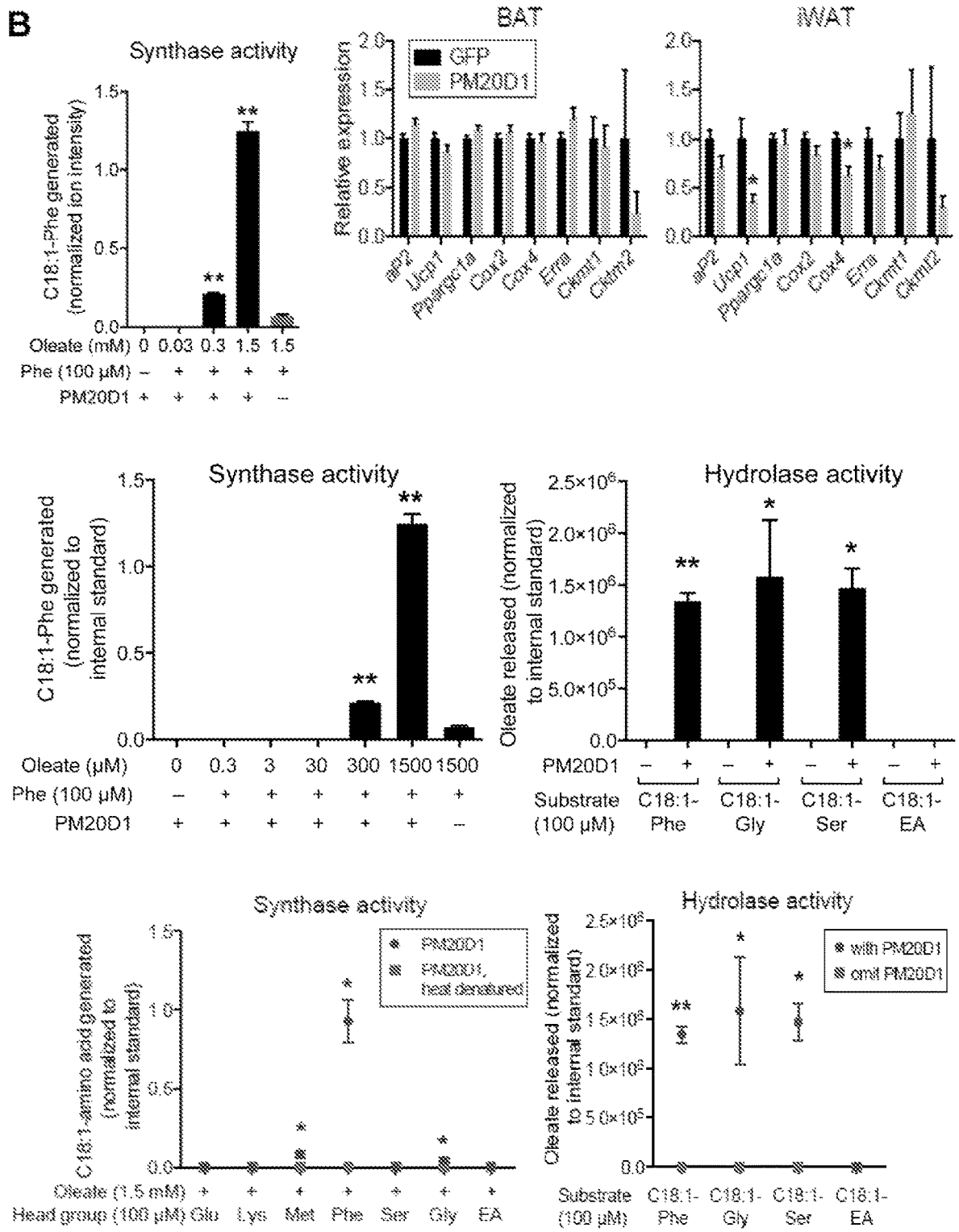
Figure 8:
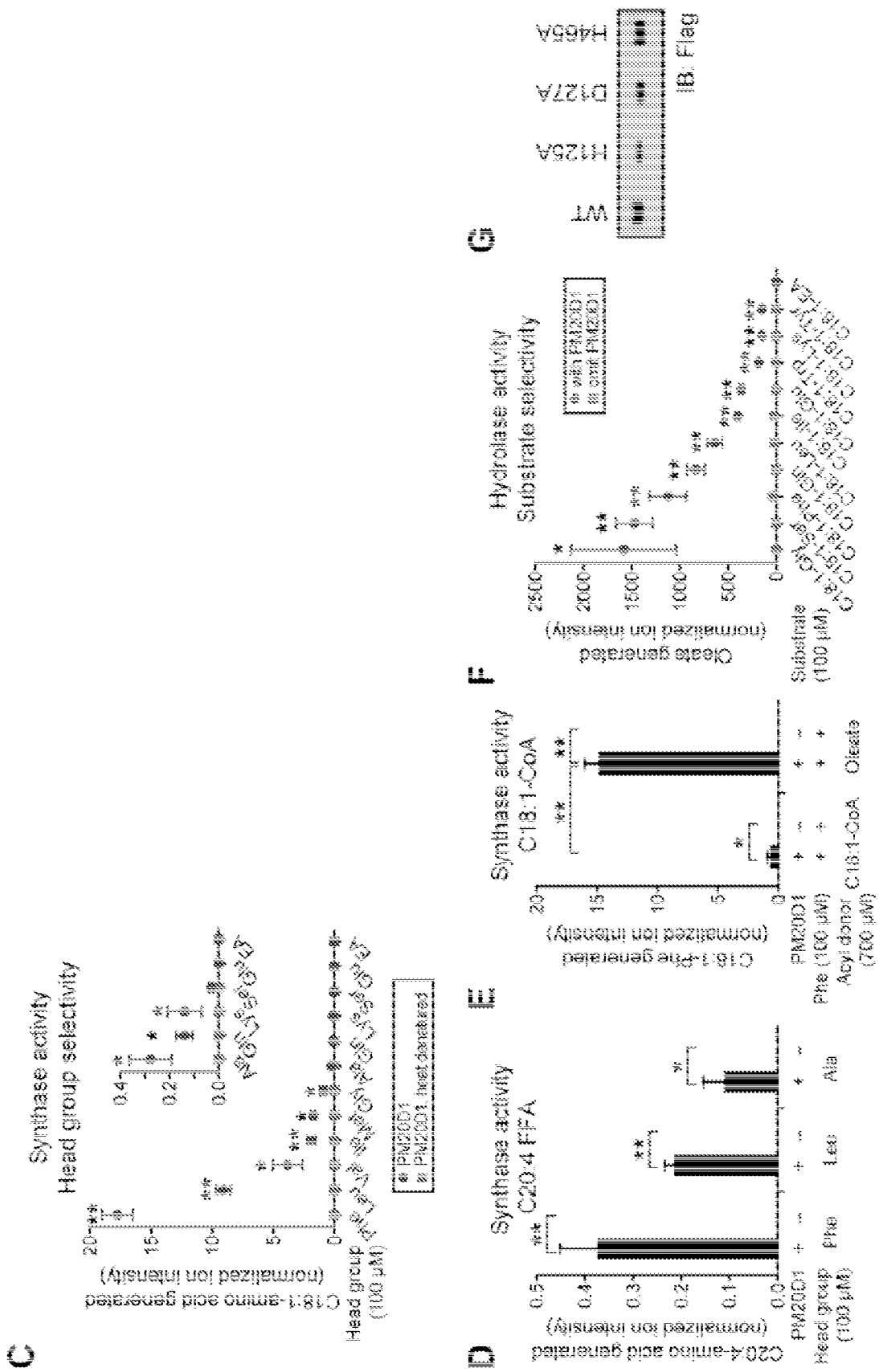
Figure 8:
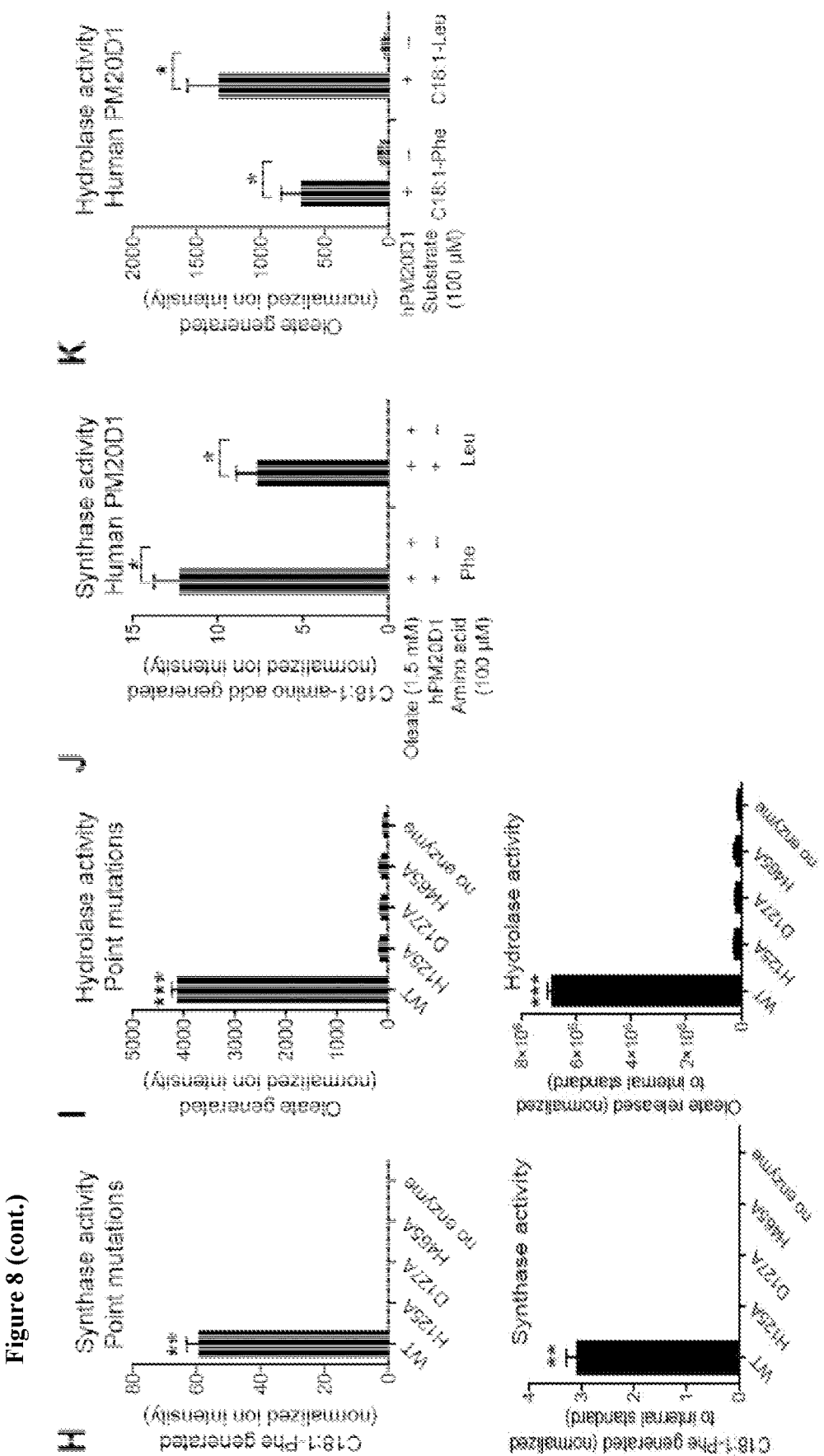

Although the endogenous presence of N-acyl amino acids has been previously described (Connor et al. (2010) *Br J Pharmacol* 160:1857-1871; Huang et al. (2001) *J Biol Chem* 276:42639-42644; Tan et al. (2010) *J Lipid Res* 51:112-119), their biosynthesis has remained a long-standing mystery. The increase of these metabolites in AAV-PM20D1 mice suggested that PM20D1 might be the enzyme responsible for N-acyl amino acid biosynthesis in vivo. To investigate this process in vitro, purified, mammalian recombinant PM20D1 was generated for enzymatic assays. As expected, purified PM20D1 migrated as a single ~60 kDa band by Coomassie staining (FIG. 7A). Significant formation of C18:1-Phe was observed by LC-MS when recombinant PM20D1 was incubated in the reaction mixture with physiologically relevant concentrations of free oleate and Phe (300 μM and 100 μM, respectively; FIGS. 8A-8B). Among different amine head groups, Phe was the amino acid most efficiently converted to its corresponding N-acyl amino acid product (FIG. 8C). PM20D1 could also condense other amino acids with oleate, although less efficiently than Phe (FIG. 8C). The negatively charged amino acid glutamate, as well as ethanolamine (EA), were not substrates for the synthase reaction (FIG. 8C). PM20D1 was also capable of using arachidonate as a fatty acid donor (FIG. 8D), and showed strong preference for free oleate over oleoyl-coenzyme A (C18:1-CoA, FIG. 8E). Thus, free fatty acids and free amino acids are substrates for PM20D1, and its N-acyl amino acid synthase activity shows selectivity for specific amino groups and acyl donors.

It was observed that incubation of C18:1-Phe with PM20D1 liberated free oleate, indicating that PM20D1 can also act as an N-acyl amino acid hydrolase (FIGS. 8A and 8F). The hydrolase activity was apparently more promiscuous than the synthase activity since PM20D1 hydrolyzed all N-oleoyl amino acids tested (FIG. 8F). In contrast, N-oleoyl ethanolamine (C18:1-EA), a well-characterized substrate for fatty acid amide hydrolase (FAAH) (Cravatt et al. (1996) Nature 384:83-87; Saghatelian et al. (2004) Biochemistry 43:14332-14339), was not a PM20D1 substrate under these conditions.

Based on sequence homology with the other members of the mammalian M20 family and Uniprot annotations, three point mutations in PM20D1 were generated that were anticipated to disrupt catalytic activity. Two of these residues, H125 and H465, are predicted to coordinate zinc cations (Lindner et al. (2003) J Biol Chem 278:44496-44504); a third residue, D127, is predicted to act as a general base for H125 (Herga et al. (2005) Biochem Biophys Res Commun 330:540-546). Due to differences in protein stability and expression, following Flag-immunoaffinity purification, each construct was titrated such that approximately equivalent protein amounts were used in the subsequent enzymatic activity assays (FIG. 8G). Under synthase activity reaction conditions using oleate and Phe as substrates, or hydrolyase activity reaction conditions using C18:1-Phe, only wild-type (WT) PM20D1 possessed enzymatic activity, whereas no activity was observed for any of the mutants (FIGS. 8H-8I). In these in vitro assays, 1.2±0.1% and 94.0±0.8% conversion (means±SEM, n=3) in the synthase and hydrolase direction, respectively, were observed for the wild-type enzyme. Therefore, the synthase and hydrolase activities are embodied within the PM20D1 polypeptide and not a co-purifying protein. PM20D1 appears to require residues predicted to coordinate divalent cations, and both synthase and hydrolase activities are coordinately disrupted by point mutations in the cation binding sites. Notably, all enzymatic assays were performed in PBS buffer without the addition of exogenous zinc, suggesting that the divalent cations required for activity are likely tightly associated with PM20D1 during the purification process.

Finally, purified, recombinant human PM20D1, which shares 71% identity and 86% similarity with the mouse enzyme, was generated. The human protein also shows complete conservation of the H125, D127, and H465 residues required for catalysis (FIGS. 7B-7C). Human PM20D1 also possessed N-acyl amino acid synthase and hydrolase activities (FIGS. 8J-8K), demonstrating the conservation of this enzymatic activity in the PM20D1 polypeptide from these two mammalian species.

Taken together, these studies indicate that PM20D1 is a bidirectional enzyme that can generate N-acyl amino acids from amino acids and free fatty acids, and can also hydrolyze N-acyl amino acids into amino acids and free fatty acids. The changes in the various species of N-acyl amino acids in plasma from AAV-PM20D1 injected mice are therefore likely to reflect a balance of the relative synthase and hydrolase activities on, as well as the relative concentrations of, the particular substrates and products. Differences between N-acyl amino acids regulated by PM20D1 overexpression and cold exposure (FIG. 5) likely reflect different levels of fatty acid or amino acid substrates under various physiologic conditions.

Example 7

N-acyl Amino Acids are Endogenous Uncouplers of Mitochondrial Respiration

The increased plasma N-acyl amino acid levels and increased whole body energy expenditure in AAV-PM20D1 mice suggested that N-acyl amino acids might directly affect uncoupled respiration. To directly test this possibility, differentiated primary BAT adipocytes were acutely treated first with the ATP synthase inhibitor oligomycin to block coupled respiration, and then with C18:1-Phe (50 µM). Cellular oxygen consumption was significantly augmented by C18:1-Phe treatment (maximal OCR of 198%, versus oligomycin-treated basal respiration; and 156% versus DMSO at the same time point, FIG. 9A). Similarly, in differentiated primary iWAT adipocytes, both C20:4-Gly and C20:4-Phe augmented respiration in the presence of oligomycin (maximal OCR of 295% and 243%, respectively, versus oligomycin-treated basal respiration; and 285% and 214%, respectively, versus DMSO at the same time point, FIG. 9B). That these effects occurred in the presence of oligomycin indicates that multiple members of the N-acyl amino acid family can increase uncoupled respiration. As a control, arachidonate itself also increased the oxygen consumption rate very modestly, but not nearly as much in magnitude as the N-acyl amino acids (FIG. 9B).

The major biological mechanism currently understood for inducing uncoupled respiration in adipocytes is through the action of UCP1 (Rousset et al. (2004) Diabetes 53:S130-S135). This intramembrane protein uses long chain fatty acids to transport protons across the inner mitochondrial membrane in a "flip-flop" mechanism (Fedorenko et al. (2012) Cell 151:400-413). It was therefore determined whether N-acyl amino acids might be direct activators and/or ligands for UCP1. To test this hypothesis, primary BAT adipocytes were generated from UCP1-WT or KO mice (Enerback et al. (1997) Nature 387, 90-94). C20:4-Phe produced virtually identical increases in uncoupled respiration in both UCP1-WT and KO cells (maximal OCR of 221% and 214%, in UCP1-WT and UCP1-KO cells, respectively, versus the oligomycin-treated basal respiration, $p>0.05$ between genotypes, FIG. 9C), establishing that UCP1 is not required for this effect. Consistent with these observations, N-acyl amino acids were also competent inducers of uncoupled respiration in cell types that completely lack UCP1, including the mouse myoblast cell line, C2C12 (FIGS. 9D-9F), and the human osteosarcoma cell line, U2OS (FIG. 9G). These data show that N-acyl amino acids are endogenous chemical uncouplers of mitochondrial respiration in a UCP1-independent manner.

The structural requirements for N-acyl amino acids to exert their effects on uncoupled respiration were explored next. A direct comparison of C18:1-Leu and oleate demonstrated that the N-acyl amino acid conjugate was significantly more potent than the free fatty acid alone (FIG. 9D). Modification of the free amino acid carboxylate of C18:1-Phe, either by methyl esterification (C18:1-Phe-OCH$_3$), or by primary amidation (C18:1-Phe-NH$_2$), completely abrogated uncoupling activity (FIG. 9E), indicating that the amino acid carboxylate moiety is required for activity. Some amino acid head group selectivity to the respiration effects was observed, as C18:1-Gln, but not C18:1-Lys, possessed the uncoupling activity (FIG. 9F).

Modification of the lipid chain revealed that only C16-, C18-, and C18:1-Phe possessed uncoupling activity, whereas saturated acyl chains that were too short (C12:0-Phe) or too long (C20:0-Phe) completely lacked uncoupling activity (FIG. 9G). The difference in uncoupling capacity between the long chain saturated (e.g., C20:0-Phe) and polyunsaturated (e.g., C20:4-Phe) lipids, together with the acyl chain selectivity, is consistent with highly specific binding interactions between N-acyl amino acids and mitochondrial protein targets that mediate their effects. Further supporting these structure activity relationships, testing of multiple commercially available fatty acid amides revealed that most (e.g., methanandamide, arachidonoyl amide, N-arachidonoyl taurine, N-arachidonoyl dopamine) did not stimulate uncoupled respiration, unless they possessed these general structural features outlined above (e.g., N-arachidonoyl gamma-amino butyric acid).

Example 8

N-acyl Amino Acids Directly Uncouple Mitochondria and Interact with Mitochondrial Proteins To directly assess the ability of N-acyl amino acids to uncouple mitochondria, two approaches were employed. First, mitochondria from the BAT tissues were isolated and treated with increasing concentrations of C18:1-Phe (10-100 µM). Isolated BAT mitochondria increased respiration in a dose-dependent manner following C18:1-Phe treatment (FIG. 10A), indicating that N-acyl amino acids do not require any other cellular components or organelles for their uncoupling effects. Second, tetramethylrhodamine methyl ester (TMRM) fluorescence was used to directly measure the mitochondrial membrane potential in live cells. As expected, treatment of C2C12 cells with oligomycin increased the membrane potential (FIG. 10B). Co-treatment of oligomycin with C18:1-Phe (50 µM) decreased the TMRM fluorescence by ~45% (FIG. 10B). As a positive control, the well-known chemical uncoupler FCCP (0.4 µM) also reduced TMRM fluorescence by an even larger magnitude (~70% reduction). Therefore, N-acyl amino acids can directly augment uncoupled respiration in isolated mitochondria, resulting in a decreased mitochondrial membrane potential.

The structure activity relationships (SAR) observed with N-acyl amino acids-induced uncoupling (FIG. 9), and the direct effects of N-acyl amino acids on isolated mitochondria (FIG. 10A), are consistent with specific binding interactions between these metabolites and mitochondrial proteins (Niphakis et al. (2015) Cell 161:1668-1680). To identify the proteins that may be mediating the uncoupling by N-acyl amino acid, a photo-crosslinkable version was synthesized (FIG. 10C). This molecule, termed "photo-probe," contains a modified Met amino acid with a photo-crosslinking diazarine side chain, and a fatty acid-alkyne for downstream click chemistry applications. Photo-probe (50 µM) was a competent inducer of uncoupled respiration in C2C12 cells, demonstrating that the alkyne and diazarine modifications did not affect the bioactivity (FIG. 10D). Moreover, photo-probe demonstrated robust, UV-dependent crosslinking as assessed by in-gel TAMRA fluorescence (FIG. 10E).

C2C12 cells were selected for LC-MS/MS analysis of photo-probe targets since they demonstrate robust N-acyl amino acid induced uncoupling. To this end, C2C12 cells were incubated with photo-probe (20 µM, "probe only" samples), or co-incubated with both photo-probe (20 µM) and a C20:4-Phe competitor at 5-fold excess (100 µM, "probe+competitor" samples). Cells were then UV irradiated on ice and lysed by sonication. Probe-labeled proteins were conjugated to biotin-$N_3$ by click chemistry, streptavidin-enriched, and subject to LC-MS/MS analysis with spectral counting. In total, 149 proteins were identified that showed >50% competition by C20:4-Phe (Table 6 and FIG. 10F). Of these, 31 proteins (21%) are localized to the mitochondria by Uniprot annotation, including 6 members of the SLC25 carrier family (Table 6 and FIG. 10F). Notably, the two most abundantly detected proteins in the entire dataset were the mitochondrial SLC25A4 and SLC25A5 (also known as ANT1 and 2) proteins. In addition to their ADP/ATP symport activity, these transporters have previously been demonstrated to translocate protons across the inner membrane (Brand et al. (2005) Biochem. 1 392:353-362). Taken together, these data are consistent with a model where N-acyl amino acids increase uncoupled respiration by liganding SLC25 family members, including SLC25A4 and SLC25A5, and increasing SLC25-mediated proton flux into the matrix.

TABLE 6

List of proteins crosslinked by N-acyl amino acid photo-probe in C2C12 cells

| Protein name | Probe only | | | Probe + competitor | | | Avg. signal in probe only | Fold change, probe only/ (probe + competitor) |
|---|---|---|---|---|---|---|---|---|
| | Rep 1 | Rep 2 | Rep 3 | Rep 1 | Rep 2 | Rep 3 | | |
| LOC100046302 | 13 | 26 | 4 | 10 | 0 | 12 | 14 | 2.0 |
| Flnb | 22 | 29 | 4 | 11 | 2 | 15 | 18 | 2.0 |
| Gm5506;Eno1; LOC100044223 | 25 | 14 | 7 | 7 | 3 | 13 | 15 | 2.0 |
| Ipo5 | 12 | 10 | 4 | 9 | 0 | 4 | 9 | 2.0 |
| Pfn1 | 4 | 9 | 3 | 0 | 0 | 8 | 5 | 2.0 |
| Npm1 | 2 | 7 | 3 | 0 | 2 | 4 | 4 | 2.0 |
| Gdi2 | 2 | 4 | 2 | 2 | 0 | 2 | 3 | 2.0 |
| Pdia3 | 30 | 45 | 21 | 19 | 5 | 23 | 32 | 2.0 |
| Mccc1 | 8 | 22 | 8 | 8 | 3 | 7 | 13 | 2.1 |
| Vcp | 14 | 14 | 6 | 6 | 0 | 10 | 11 | 2.1 |
| Sdha | 6 | 5 | 2 | 2 | 0 | 4 | 4 | 2.2 |
| Tm9sf4 | 4 | 5 | 2 | 0 | 2 | 3 | 4 | 2.2 |

TABLE 6-continued

List of proteins crosslinked by N-acyl amino acid photo-probe in C2C12 cells

| Protein name | Probe only | | | Probe + competitor | | | Avg. signal in probe only | Fold change, probe only/ (probe + competitor) |
|---|---|---|---|---|---|---|---|---|
| | Rep 1 | Rep 2 | Rep 3 | Rep 1 | Rep 2 | Rep 3 | | |
| Slc3a2 | 11 | 14 | 6 | 4 | 2 | 8 | 10 | 2.2 |
| Cyb5r3 | 14 | 20 | 2 | 4 | 2 | 10 | 12 | 2.3 |
| Cct4 | 6 | 10 | 2 | 0 | 2 | 6 | 6 | 2.3 |
| Praf2 | 4 | 3 | 2 | 2 | 0 | 2 | 3 | 2.3 |
| Lrrc59 | 21 | 37 | 21 | 11 | 5 | 18 | 26 | 2.3 |
| Cltc | 7 | 22 | 11 | 4 | 6 | 7 | 13 | 2.4 |
| Far1 | 10 | 12 | 4 | 4 | 2 | 5 | 9 | 2.4 |
| Rpn2 | 19 | 5 | 2 | 2 | 2 | 7 | 9 | 2.4 |
| Cct8 | 3 | 7 | 2 | 3 | 0 | 2 | 4 | 2.4 |
| Zmpste24 | 16 | 10 | 6 | 4 | 0 | 9 | 11 | 2.5 |
| Slc25a3 | 12 | 23 | 10 | 7 | 0 | 11 | 15 | 2.5 |
| Idh2 | 3 | 5 | 2 | 4 | 0 | 0 | 3 | 2.5 |
| Aco2 | 7 | 4 | 2 | 0 | 2 | 3 | 4 | 2.6 |
| Rab7 | 10 | 16 | 6 | 6 | 0 | 6 | 11 | 2.7 |
| Hnrnpu | 7 | 7 | 2 | 0 | 0 | 6 | 5 | 2.7 |
| Rtn4 | 15 | 16 | 16 | 4 | 3 | 10 | 16 | 2.8 |
| Sacm1l | 5 | 14 | 6 | 3 | 0 | 6 | 8 | 2.8 |
| Atp1a1 | 16 | 28 | 9 | 5 | 4 | 10 | 18 | 2.8 |
| Hnrnpf | 2 | 9 | 3 | 3 | 0 | 2 | 5 | 2.8 |
| Rab1 | 9 | 11 | 11 | 2 | 3 | 6 | 10 | 2.8 |
| Surf4 | 12 | 27 | 26 | 5 | 7 | 11 | 22 | 2.8 |
| P4hb | 40 | 18 | 10 | 7 | 3 | 14 | 23 | 2.8 |
| Phb | 27 | 22 | 8 | 10 | 0 | 10 | 19 | 2.9 |
| Hadha | 24 | 23 | 16 | 7 | 4 | 11 | 21 | 2.9 |
| Tuba1b | 40 | 96 | 43 | 0 | 0 | 62 | 60 | 2.9 |
| Pkm2 | 18 | 25 | 8 | 0 | 5 | 12 | 17 | 3.0 |
| Slc25a24 | 12 | 14 | 7 | 2 | 3 | 6 | 11 | 3.0 |
| no | 2 | 14 | 2 | 2 | 0 | 4 | 6 | 3.0 |
| Xpo1 | 4 | 7 | 4 | 0 | 2 | 3 | 5 | 3.0 |
| Tubb2a | 58 | 68 | 22 | 49 | 0 | 0 | 49 | 3.0 |
| Por | 22 | 29 | 16 | 8 | 3 | 11 | 22 | 3.0 |
| Vdac2 | 32 | 26 | 9 | 10 | 0 | 12 | 22 | 3.0 |
| Aldh3a2 | 4 | 7 | 5 | 3 | 0 | 2 | 5 | 3.2 |
| Cyp51 | 4 | 10 | 2 | 3 | 0 | 2 | 5 | 3.2 |
| Tmem43 | 12 | 8 | 3 | 3 | 0 | 4 | 8 | 3.3 |
| Agps | 3 | 5 | 2 | 0 | 0 | 3 | 3 | 3.3 |
| Mcm7 | 3 | 4 | 3 | 0 | 0 | 3 | 3 | 3.3 |
| Copa | 8 | 14 | 5 | 4 | 0 | 4 | 9 | 3.4 |
| Stt3a | 9 | 21 | 4 | 6 | 0 | 4 | 11 | 3.4 |
| Gmps | 5 | 8 | 4 | 0 | 3 | 2 | 6 | 3.4 |
| Prpf8 | 3 | 2 | 2 | 0 | 0 | 2 | 2 | 3.5 |
| Phb2 | 14 | 33 | 11 | 6 | 3 | 7 | 19 | 3.6 |
| Cand1 | 6 | 3 | 2 | 3 | 0 | 0 | 4 | 3.7 |
| Ckap4 | 32 | 43 | 23 | 8 | 4 | 14 | 33 | 3.8 |
| Rpn1 | 35 | 28 | 11 | 9 | 3 | 7 | 25 | 3.9 |
| Kpnb1 | 7 | 13 | 4 | 3 | 0 | 3 | 8 | 4.0 |
| Tomm22 | 7 | 6 | 3 | 2 | 0 | 2 | 5 | 4.0 |
| Ptgs1 | 2 | 4 | 2 | 2 | 0 | 0 | 3 | 4.0 |
| Esyt1 | 21 | 20 | 13 | 4 | 4 | 5 | 18 | 4.2 |
| Slc25a5 | 74 | 106 | 62 | 22 | 10 | 26 | 81 | 4.2 |
| mt-Co2 | 6 | 4 | 3 | 0 | 0 | 3 | 4 | 4.3 |
| Wls | 3 | 8 | 2 | 0 | 0 | 3 | 4 | 4.3 |
| Vdac3 | 18 | 18 | 4 | 4 | 0 | 5 | 13 | 4.4 |
| Hsp90ab1 | 24 | 21 | 13 | 6 | 3 | 4 | 19 | 4.5 |
| Slc25a4 | 60 | 121 | 61 | 22 | 11 | 21 | 81 | 4.5 |
| Atl3 | 16 | 15 | 5 | 2 | 2 | 4 | 12 | 4.5 |
| Myadm | 9 | 6 | 3 | 4 | 0 | 0 | 6 | 4.5 |
| Fkbp8 | 2 | 4 | 3 | 2 | 0 | 0 | 3 | 4.5 |
| Hist3h2bb | 3 | 3 | 3 | 0 | 0 | 2 | 3 | 4.5 |
| Atp2a2 | 95 | 59 | 31 | 9 | 11 | 19 | 62 | 4.7 |
| Acsl3 | 7 | 14 | 3 | 3 | 0 | 2 | 8 | 4.8 |
| Tln1 | 17 | 35 | 7 | 8 | 4 | 0 | 20 | 4.9 |
| Hsd17b12 | 21 | 18 | 6 | 4 | 2 | 3 | 15 | 5.0 |
| Hsp90aa1 | 16 | 5 | 4 | 0 | 2 | 3 | 8 | 5.0 |
| Ppia | 3 | 9 | 3 | 0 | 0 | 3 | 5 | 5.0 |
| Gpd2 | 19 | 18 | 3 | 2 | 2 | 4 | 13 | 5.0 |
| Rab18 | 5 | 11 | 4 | 4 | 0 | 0 | 7 | 5.0 |
| Aaas | 5 | 3 | 2 | 0 | 0 | 2 | 3 | 5.0 |
| Ergic1 | 3 | 3 | 4 | 0 | 0 | 2 | 3 | 5.0 |
| Txndc5 | 3 | 5 | 2 | 0 | 0 | 2 | 3 | 5.0 |

TABLE 6-continued

List of proteins crosslinked by N-acyl amino acid photo-probe in C2C12 cells

| Protein name | Probe only | | | Probe + competitor | | | Avg. signal in probe only | Fold change, probe only/ (probe + competitor) |
|---|---|---|---|---|---|---|---|---|
| | Rep 1 | Rep 2 | Rep 3 | Rep 1 | Rep 2 | Rep 3 | | |
| Acadvl | 10 | 14 | 7 | 2 | 0 | 4 | 10 | 5.2 |
| Pigu | 3 | 13 | 10 | 0 | 2 | 3 | 9 | 5.2 |
| Tmed10 | 9 | 10 | 7 | 2 | 0 | 3 | 9 | 5.2 |
| Atp2b1 | 4 | 12 | 5 | 2 | 0 | 2 | 7 | 5.3 |
| Esyt2 | 11 | 23 | 14 | 0 | 2 | 7 | 16 | 5.3 |
| Copg | 7 | 7 | 2 | 3 | 0 | 0 | 5 | 5.3 |
| Eif4a1 | 9 | 10 | 3 | 4 | 0 | 0 | 7 | 5.5 |
| Soat1 | 9 | 11 | 2 | 4 | 0 | 0 | 7 | 5.5 |
| Ggcx | 3 | 4 | 4 | 0 | 0 | 2 | 4 | 5.5 |
| Pcyox1 | 3 | 5 | 3 | 0 | 0 | 2 | 4 | 5.5 |
| Tmem48 | 3 | 4 | 4 | 0 | 0 | 2 | 4 | 5.5 |
| Mybbp1a | 11 | 16 | 12 | 0 | 5 | 2 | 13 | 5.6 |
| Atp5b | 24 | 11 | 6 | 3 | 0 | 4 | 14 | 5.9 |
| Vdac1 | 24 | 28 | 14 | 3 | 0 | 8 | 22 | 6.0 |
| Actn4 | 15 | 24 | 3 | 7 | 0 | 0 | 14 | 6.0 |
| C230096C10Rik | 6 | 4 | 2 | 2 | 0 | 0 | 4 | 6.0 |
| Cct6a | 4 | 5 | 3 | 2 | 0 | 0 | 4 | 6.0 |
| Sptlc2 | 5 | 5 | 2 | 0 | 0 | 2 | 4 | 6.0 |
| Srprb | 9 | 8 | 2 | 3 | 0 | 0 | 6 | 6.3 |
| Tm9sf2 | 16 | 20 | 3 | 2 | 0 | 4 | 13 | 6.5 |
| Spnb2 | 2 | 10 | 2 | 0 | 0 | 2 | 5 | 7.0 |
| Hsd17b4 | 5 | 8 | 2 | 0 | 0 | 2 | 5 | 7.5 |
| Sec63 | 3 | 9 | 3 | 2 | 0 | 0 | 5 | 7.5 |
| Rab1b | 8 | 10 | 6 | 0 | 0 | 3 | 8 | 8.0 |
| Lass2 | 6 | 9 | 2 | 0 | 0 | 2 | 6 | 8.5 |
| Sec23a | 4 | 11 | 2 | 2 | 0 | 0 | 6 | 8.5 |
| Acaa2 | 7 | 15 | 5 | 0 | 0 | 3 | 9 | 9.0 |
| Sqrdl | 11 | 10 | 6 | 0 | 0 | 3 | 9 | 9.0 |
| Ano10 | 9 | 7 | 3 | 2 | 0 | 0 | 6 | 9.5 |
| Letm1 | 9 | 10 | 4 | 0 | 0 | 2 | 8 | 11.5 |
| Slc25a12 | 12 | 6 | 5 | 2 | 0 | 0 | 8 | 11.5 |
| Atp13a1 | 9 | 19 | 7 | 0 | 0 | 3 | 12 | 11.7 |
| Sgpl1 | 11 | 9 | 7 | 0 | 0 | 2 | 9 | 13.5 |
| Fam114a1 | 10 | 9 | 3 | 0 | 0 | 0 | 7 | 15.0 |
| Lman1 | 9 | 9 | 3 | 0 | 0 | 0 | 7 | 15.0 |
| Sfxn3 | 7 | 8 | 6 | 0 | 0 | 0 | 7 | 15.0 |
| Atp2b4 | 5 | 11 | 4 | 0 | 0 | 0 | 7 | 15.0 |
| Mtdh | 9 | 8 | 3 | 0 | 0 | 0 | 7 | 15.0 |
| Man2a1 | 3 | 13 | 2 | 0 | 0 | 0 | 6 | 15.0 |
| Lbr | 2 | 7 | 8 | 0 | 0 | 0 | 6 | 15.0 |
| Clptm1 | 4 | 10 | 2 | 0 | 0 | 0 | 5 | 15.0 |
| Lman2 | 8 | 4 | 4 | 0 | 0 | 0 | 5 | 15.0 |
| Adpgk | 5 | 7 | 3 | 0 | 0 | 0 | 5 | 15.0 |
| Cds2 | 6 | 4 | 4 | 0 | 0 | 0 | 5 | 15.0 |
| Ap2b1 | 3 | 5 | 5 | 0 | 0 | 0 | 4 | 15.0 |
| Slc25a10 | 4 | 4 | 5 | 0 | 0 | 0 | 4 | 15.0 |
| Acaa1b;Acaa1a | 4 | 6 | 2 | 0 | 0 | 0 | 4 | 15.0 |
| Acad9 | 7 | 3 | 2 | 0 | 0 | 0 | 4 | 15.0 |
| Cct2 | 4 | 6 | 2 | 0 | 0 | 0 | 4 | 15.0 |
| Tmpo | 3 | 6 | 3 | 0 | 0 | 0 | 4 | 15.0 |
| Eprs | 3 | 6 | 2 | 0 | 0 | 0 | 4 | 15.0 |
| Gnai2 | 4 | 5 | 2 | 0 | 0 | 0 | 4 | 15.0 |
| Hmox2 | 5 | 4 | 2 | 0 | 0 | 0 | 4 | 15.0 |
| Immt | 3 | 5 | 3 | 0 | 0 | 0 | 4 | 15.0 |
| March5 | 3 | 5 | 2 | 0 | 0 | 0 | 3 | 15.0 |
| 2900073G15Rik | 4 | 4 | 2 | 0 | 0 | 0 | 3 | 15.0 |
| Asna1 | 4 | 4 | 2 | 0 | 0 | 0 | 3 | 15.0 |
| Gna11 | 4 | 4 | 2 | 0 | 0 | 0 | 3 | 15.0 |
| Ncstn | 3 | 5 | 2 | 0 | 0 | 0 | 3 | 15.0 |
| Sec31a | 2 | 5 | 3 | 0 | 0 | 0 | 3 | 15.0 |
| Pgrmc2 | 3 | 3 | 3 | 0 | 0 | 0 | 3 | 15.0 |
| Ugcg | 2 | 5 | 2 | 0 | 0 | 0 | 3 | 15.0 |
| Dpy19l1 | 2 | 4 | 2 | 0 | 0 | 0 | 3 | 15.0 |
| Gm5619 | 3 | 3 | 2 | 0 | 0 | 0 | 3 | 15.0 |
| P4ha1 | 3 | 3 | 2 | 0 | 0 | 0 | 3 | 15.0 |

TABLE 6-continued

List of proteins crosslinked by N-acyl amino acid photo-probe in C2C12 cells

| | Probe only | | | Probe + competitor | | | Avg. signal in probe only | Fold change, probe only/ (probe + competitor) |
|---|---|---|---|---|---|---|---|---|
| Protein name | Rep 1 | Rep 2 | Rep 3 | Rep 1 | Rep 2 | Rep 3 | | |
| Hk1 | 2 | 3 | 2 | 0 | 0 | 0 | 2 | 15.0 |
| Ptplad1 | 2 | 3 | 2 | 0 | 0 | 0 | 2 | 15.0 |

* Proteins identified from C2C12 cells after incubation with photo-probe alone (20 µM, "probe only") or photo-probe (20 µM) with 5-fold excess C20:4-Phe (100 µM, "probe + competitor"). Following UV irradiation on ice (10 min), cells were harvested, lysed, and click chemistry was performed with biotin-N3. Probe-bound protein targets were enriched by streptavidin and analyzed by mass spectrometry with spectral counting (see Methods). The numbers indicate spectral counts for the indicated protein in the indicated sample. Proteins satisfying the following criteria were included: at least one peptide in each of the probe only samples and > 50% reduction in signal in probe + competitor versus probe only samples; n = 3. The subset of 31 mitochondrial proteins, as determined by manual curation with Uniprot, is shown in the tab marked "mito subset." Comparisons in which no peptides were detected in "probe + competitor" samples were assigned a fold-change of 15.

Example 9

Administration of N-acyl Amino Acids to Mice Increases Energy Expenditure and Improves Glucose Homeostasis It was next sought to determine the physiologic effects of N-lipidated amino acid administration to mice, such as whether N-lipidated amino acids could stimulate energy expenditure in vivo. Diet induced obese (DIO) mice were treated daily with vehicle, oleate, or C18:1-Leu (25 mg/kg, i.p.). After 8 days treatment, mice receiving C18:1-Leu lost 4.1±0.3 g, whereas mice treated with oleate or vehicle only lost 0.3±0.2 g and 0.6±0.1 g, respectively (means±SEM, FIG. 11A). Over this time course, food intake was slightly but significantly reduced in mice receiving C18:1-Leu (17% reduction versus vehicle-treated mice, FIGS. 11B-11C). Body composition analysis at the end of this experiment showed the weight loss induced by C18:1-Leu was entirely accounted for by a difference in fat mass (FIG. 11D). Lastly, C18:1-Leu treated mice also showed improvements in GTT versus either vehicle- or oleate-treated mice (FIG. 11E).

To assess the effects of C18:1-Leu on whole body energy expenditure, indirect calorimetry measurements were performed in a separate cohort of mice treated daily with vehicle or C18:1-Leu (25 mg/kg/day, i.p.). After 8 daily injections, mice were placed into metabolic cages and injected for an additional two days (FIG. 12). Mice treated with C18:1-Leu showed significantly augmented $VO_2$ (FIG. 11F) and $VCO_2$ (FIG. 12F) compared with vehicle-treated mice, and also slightly reduced movement (FIG. 11G). In this cohort, C18:1-Leu treated mice also showed a reduced food intake over the final two days of the experiment (FIG. 12H), but not during the earlier time period (days 0-7; FIGS. 12C-12D). Finally, the RER was significantly lower in mice receiving C18:1-Leu, indicating a switch to fats as a metabolic fuel type (FIG. 12G).

The uncoupling activity of N-acyl amino acids appears to be a property of this entire class of metabolites, at least in cells. To explore the generality of N-acyl amino acid bioactivity in vivo, additional cohorts of DIO mice treated daily with C18:1-Phe (30 or 50 mg/kg/day, i.p.) or C20:4-Gly (15 mg/kg/day, i.p.) were analyzed. Blood levels of C18:1-Phe were 3.0±0.3 µM and 0.4±0.1 µM (means±SEM, n=3) at 2 h and 6 h post-injection, respectively, following a single 30 mg/kg i.p. dose. While chronic treatment of mice with C18:1-Phe or C20:4-Gly reduced food intake, these compounds nevertheless significantly augmented $VO_2$, with no effects on movement (FIGS. 13-14). Measurements of plasma AST and ALT, as well as plasma cytokines, revealed no sigificant elevations in mice treated with C20:4-Gly versus vehicle (FIGS. 14G-14J). Taken together, these data demonstrate that N-acyl amino acids can directly augment whole body energy expenditure, reduce fat mass, and improve glucose clearance in mice.

Based on the foregoing, the previously unstudied enzyme, PM20D1, has been determined to be enriched in UCP1+ versus UCP1− cells and catalyze the condensation of fatty acids and certain amino acids to form N-acyl amino acids. It has been demonstrated herein that N-acyl amino acids function as endogenous uncouplers of mitochondrial respiration, even in cells lacking UCP1. The experiments demonstrating in vitro and in vivo augmentation of respiration by N-acyl amino acids have been performed in two independent laboratories. These data thus suggest a new model of brown and beige fat thermogenesis, whereby UCP1+ adipocytes can stimulate uncoupled respiration in neighboring cells that are not specialized to dissipate chemical energy as heat (i.e., UCP1− cells). In this model, brown and beige fat cells are not only the terminal effectors of thermogenesis via UCP1 and a creatine futile cycle, but also are the initiators of a broader cascade of UCP1-independent thermogenic events (FIG. 14K). This model also suggests that the thermogenic and metabolic benefits of brown and beige fat extend beyond their own intracellular functions. Based on the N-acyl amino acid concentrations observed in blood, the PM20D1/N-acyl amino acid pathway likely endogenously occurs in a local, paracrine manner. However, the in vivo experiments with viral vectors indicate that this mechanism can potentially function with systemic administration of the protein as well.

These data further indicate that either PM20D1, or N-acyl amino acids themselves, might be used therapeutically for the treatment of obesity and other obesity-associated disorders. The therapeutic use of synthetic chemical uncouplers has been limited by untoward and even fatal side effects (Grundlingh et al. (2011) *J Med. Toxicol.* 7:205-212). Although administration of several distinct N-acyl amino acids to mice augments energy expenditure and promotes weight loss, a small but significant reduction in food intake was observed, at least under the chronic dosing regime. The total weight loss observed in the DIO mice treated with N-acyl amino acids is likely due to a combination of both reduced food intake and augmented energy expenditure.

Further exploration of other naturally occurring lipidated amino acids or chemical modifications of such molecules might identify compounds that can dissociate the beneficial from any potential undesired effects. Alternatively, PM20D1 protein injections might also be used to augment N-acyl amino acid levels in vivo.

Besides potential therapeutic applications, these studies on the enzymology of PM20D1 address long-standing questions regarding biosynthetic pathways for N-acyl amino acids. Historically, an enzymatic activity involving the condensation of fatty acids and amino acids has been previously reported in tissues (Fukui and Axelrod (1961) *J Biol. Chem.* 236:811-816), but its molecular identity has remained unclear. The data here provide strong evidence that PM20D1 is an enzyme responsible for these activities. From an chemical equilibrium point of view, a thermodynamic equilibrium of ~1% conversion to N-acyl amino acid is calculated, based on the in vitro synthase reactant concentrations (1.5 mM oleate and 100 µM Phe) and the equilibrium constant for a related amide condensation and hydrolysis reaction (Katayama et al. (1999) *Biochim. Biophys. Acta* 1440:205-214). The experimentally observed N-acyl amino acid generation in the synthase direction (1.2±0.1% conversion; mean±SEM) is consistent with these calculations. Moreover, such concentrations of fatty acid and amino acid reactants are within the physiologic range (Stegink et al. (1991) *Am. J Clin. Nutr.* 53:670-675). The energetic driving force of the synthase reaction in vivo is likely to arise from a disequilibrium of the fatty acid and amino acid reactants and their N-acyl amino acid products, analogous to the proton-motive force that drives ATP production by ATP synthase.

An outstanding issue is the molecular target(s) responsible for the uncoupling activity of N-acyl amino acids. The photo-crosslinking experiments provide direct evidence that N-acyl amino acids engage members of the SLC25 family of inner mitochondrial carriers, including ANT1 and 2. Notably, the function of this photo-probe reagent requires both diazarine and alkyne "ends" of the molecule. Consequently, the intact photo-probe, and not a hydrolyzed product, interacts with proteins. The proton conductance activity of the ANTs, or other SLC carriers, might be directly or allosterically activated by N-acyl amino acid binding. Moreover, it has been determined that PM20D1 is believed to interact with high-density lipoprotein (HDL) particles since it interacts with apolipoprotein 1 (APOA1), which is the major protein component of HDL in plasma (FIG. 15). In addition, the loss of PM20D1 due to a genetic knockout of PM20D1 protein in mice, results in significant changes to many N-acyl amino acid species in such mice as compared to those mice normally expressing PM20D1 protein (FIG. 16).

In summary, these data identify a new enzymatic node and a class of lipidated metabolites that might be used for the treatment of human obesity and diabetes, and to modulate thermogenesis more generally.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for decoupling mitochondrial respiration in a cell comprising contacting the cell with an agent that increases expression and/or activity of PM20D1 polypeptide comprising the sequence of SEQ ID NO: 2, wherein the step of contacting occurs in vitro, thereby decoupling mitochondrial respiration in the cell.

2. The method of claim 1, wherein the agent is selected from the group consisting of a nucleic acid molecule encoding the PM20D1 polypeptide and the PM20D1 polypeptide.

3. The method of claim 1, wherein the cell is selected from the group consisting of fibroblasts, adipoblasts, preadipocytes, adipocytes, white adipocytes, brown adipocytes, and beige adipocytes.

4. The method of claim 2, further comprising contacting the cell with an additional agent that increases decoupled mitochondrial respiration in the cell.

5. The method of claim 2, wherein the step of contacting occurs in vivo.

6. The method of claim 2, wherein the step of contacting occurs in vitro.

7. The method of claim 2, wherein the cell is selected from the group consisting of fibroblasts, adipoblasts, preadipocytes, adipocytes, white adipocytes, brown adipocytes, and beige adipocytes.

8. The method of claim 1, further comprising contacting the cell with an additional agent that increases decoupled mitochondrial respiration in the cell.

* * * * *

SEQUENCE LISTING

```
<160> NUMBER OF SEQ ID NOS: 44

<210> SEQ ID NO 1
<211> LENGTH: 1509
<212> TYPE: DNA
<213> ORGANISM: Homo sapiens

<400> SEQUENCE: 1
atggctcagc ggtgcgtttg cgtgctggcc ctggtggcta tgctgctcct agttttccct      60
accgtctcca gatcgatggg cccgaggagc ggggagcatc aaagggcgtc gcgaatccct     120
tctcagttca gcaaagagga acgcgtcgcg atgaaagagg cgctgaaagg tgccatccag     180
attccaacag tgacttttag ctctgagaag tccaatacta cagccctggc tgagttcgga     240
aaatacattc ataaagtctt tcctacagtg gtcagcacca gctttatcca gcatgaagtc     300
gtggaagagt atagccacct gttcactatc caaggctcgg accccagctt gcagccctac     360
ctgctgatgg ctcactttga tgtggtgcct gcccctgaag aaggctggga ggtgccccca     420
ttctctgggt tggagcgtga tggcatcatc tatggtcggg gcacactgga cgacaagaac     480
tctgtgatgg cattactgca ggccttggag ctcctgctga tcaggaagta catccccga      540 agatctttct tcatttctct gggccatgat gaggagtcat cagggacagg ggctcagagg     600
```

```
atctcagccc tgctacagtc aaggggcgtc cagctagcct tcattgtgga cgagggggc      660 ttcatcttgg atgatttcat tcctaacttc aagaagccca tcgccttgat tgcagtctca     720
gagaagggtt ccatgaacct catgctgcaa gtaaacatga cttcaggcca ctcttcagct     780
cctccaaagg agacaagcat tggcatcctt gcagctgctg tcagccgatt ggagcagaca     840
ccaatgccta tcatatttgg aagcgggaca gtggtgactg tattgcagca actggcaaat     900
gagtttccct tccctgtcaa tataatcctg agcaacccat ggctatttga accacttata     960
agcaggttta tggagagaaa tcccttaacc aatgcaataa tcaggaccac cacggcactc    1020
accatattca aagcaggggt caagttcaat gtcatccccc cagtggccca ggccacagtc    1080
aacttccgga ttcaccctgg acagacagtc aagaggtcc tagaactcac gaagaacatt     1140
gtggctgata cagagtcca gttccatgtg ttgagtgcct tgacccccct ccccgtcagc     1200
ccttctgatg acaaggcctt gggctaccag ctgctccgcc agaccgtaca gtccgtcttc    1260
ccggaagtca atattactgc cccagttact tctattggca acacagacag ccgattcttt    1320
acaaacctca ccactggcat ctacaggttc taccccatct acatacagcc tgaagacttc    1380
aaacgcatcc atggagtcaa cgagaaaatc tcagtccaag cctatgagac ccaagtgaaa    1440
ttcatctttg agttgattca gaatgctgac acagaccagg agccagtttc tcacctgcac    1500
aaactgtga                                                            1509
```

<210> SEQ ID NO 2
<211> LENGTH: 502
<212> TYPE: PRT
<213> ORGANISM: Homo sapiens

<400> SEQUENCE: 2

```
Met Ala Gln Arg Cys Val Cys Val Leu Ala Leu Val Ala Met Leu Leu
1               5                   10                  15

Leu Val Phe Pro Thr Val Ser Arg Ser Met Gly Pro Arg Ser Gly Glu
            20                  25                  30

His Gln Arg Ala Ser Arg Ile Pro Ser Gln Phe Ser Lys Glu Glu Arg
        35                  40                  45

Val Ala Met Lys Glu Ala Leu Lys Gly Ala Ile Gln Ile Pro Thr Val
    50                  55                  60

Thr Phe Ser Ser Glu Lys Ser Asn Thr Thr Ala Leu Ala Glu Phe Gly
65                  70                  75                  80

Lys Tyr Ile His Lys Val Phe Pro Thr Val Ser Thr Ser Phe Ile
                85                  90                  95

Gln His Glu Val Val Glu Glu Tyr Ser His Leu Phe Thr Ile Gln Gly
            100                 105                 110

Ser Asp Pro Ser Leu Gln Pro Tyr Leu Leu Met Ala His Phe Asp Val
        115                 120                 125

Val Pro Ala Pro Glu Glu Gly Trp Glu Val Pro Pro Phe Ser Gly Leu
    130                 135                 140

Glu Arg Asp Gly Ile Ile Tyr Gly Arg Gly Thr Leu Asp Asp Lys Asn
145                 150                 155                 160

Ser Val Met Ala Leu Leu Gln Ala Leu Glu Leu Leu Ile Arg Lys
                165                 170                 175

Tyr Ile Pro Arg Arg Ser Phe Phe Ile Ser Leu Gly His Asp Glu Glu
            180                 185                 190

Ser Ser Gly Thr Gly Ala Gln Arg Ile Ser Ala Leu Leu Gln Ser Arg
        195                 200                 205
```

Gly Val Gln Leu Ala Phe Ile Val Asp Glu Gly Phe Ile Leu Asp
    210             215                 220

Asp Phe Ile Pro Asn Phe Lys Lys Pro Ile Ala Leu Ile Ala Val Ser
225                 230                 235                 240

Glu Lys Gly Ser Met Asn Leu Met Leu Gln Val Asn Met Thr Ser Gly
                245                 250                 255

His Ser Ser Ala Pro Pro Lys Glu Thr Ser Ile Gly Ile Leu Ala Ala
            260                 265                 270

Ala Val Ser Arg Leu Glu Gln Thr Pro Met Pro Ile Ile Phe Gly Ser
        275                 280                 285

Gly Thr Val Val Thr Val Leu Gln Gln Leu Ala Asn Glu Phe Pro Phe
    290                 295                 300

Pro Val Asn Ile Ile Leu Ser Asn Pro Trp Leu Phe Glu Pro Leu Ile
305                 310                 315                 320

Ser Arg Phe Met Glu Arg Asn Pro Leu Thr Asn Ala Ile Ile Arg Thr
                325                 330                 335

Thr Thr Ala Leu Thr Ile Phe Lys Ala Gly Val Lys Phe Asn Val Ile
            340                 345                 350

Pro Pro Val Ala Gln Ala Thr Val Asn Phe Arg Ile His Pro Gly Gln
        355                 360                 365

Thr Val Gln Glu Val Leu Glu Leu Thr Lys Asn Ile Val Ala Asp Asn
    370                 375                 380

Arg Val Gln Phe His Val Leu Ser Ala Phe Asp Pro Leu Pro Val Ser
385                 390                 395                 400

Pro Ser Asp Asp Lys Ala Leu Gly Tyr Gln Leu Leu Arg Gln Thr Val
                405                 410                 415

Gln Ser Val Phe Pro Glu Val Asn Ile Thr Ala Pro Val Thr Ser Ile
            420                 425                 430

Gly Asn Thr Asp Ser Arg Phe Phe Thr Asn Leu Thr Thr Gly Ile Tyr
        435                 440                 445

Arg Phe Tyr Pro Ile Tyr Ile Gln Pro Glu Asp Phe Lys Arg Ile His
    450                 455                 460

Gly Val Asn Glu Lys Ile Ser Val Gln Ala Tyr Glu Thr Gln Val Lys
465                 470                 475                 480

Phe Ile Phe Glu Leu Ile Gln Asn Ala Asp Thr Asp Gln Glu Pro Val
                485                 490                 495

Ser His Leu His Lys Leu
            500

<210> SEQ ID NO 3
<211> LENGTH: 1512
<212> TYPE: DNA
<213> ORGANISM: Mus musculus

<400> SEQUENCE: 3
atggctgagc tacttgctag cttgcccgcc tgggcagctg tgctccttct cttttttcgct    60 acggtctccg gatccactgg ccctagaagc aggaaaatc gggggggcgtc ccggatccct   120 tcccagttca gcgaggagga gcgtgtcgct ataaaagagg cgctgaaagg tgccatccag   180 attccacag tgtctttcag ccacgaggaa tccaacacca cagcccttgc tgagtttgga   240
gaatatatcc gcaaagcctt ccctacagtg ttccacagca gccttgtcca acatgaagtc   300
gtggcaaagt atagccacct gttcaccatc caaggctcag accccagttt gcagccctac   360
atgctgatgg ctcacattga tgtggttcct gccccggaag aaggatggga ggtgccccg    420

```
ttctcaggcc tggaacgcaa tggcttcatc tatggccggg gtgcgctgga caacaaaaac    480
tctgtgatgg cgatcctgca tgctttggag ctcctgttga tcagaaacta cagccccaaa    540
agatctttct tcattgcttt gggccatgat gaggaggtgt ccggggaaaa gggggctcag    600
aagatctcag cactcttaca ggcaagggt gtccagctag ccttccttgt ggatgaaggg     660
agctttatct tggaaggctt cattccaaac ctcgagaagc cagttgccat gatttcagtc    720
actgagaagg gtgcccttga cctcatgctg caagtaaaca tgactccagg ccactcttca    780
gctcccccaa aggagacaag cattggcatt ctttctgccg ctgtcagccg actggagcag    840
acaccaatgc cgaatatgtt tggaggaggg ccattgaaga agacaatgaa gctactggca    900
aatgagtttt ccttccctat caatatagtc ttgagaaacc tgtggctatt tcatcccatt    960
gtgagcagga taatggagag gaacccccata acaaatgcgc tggtccgaac taccacagcc   1020
ctcaccatgt tcaatgcagg aatcaaggtg aatgtcatcc ctccattggc tcaggctaca   1080
atcaactgcc gaattcaccc ttcgcagaca gtacatgagg tcctagaact tgtcaagaac   1140
accgtggctg atgacagagt ccagctgcat gtgttgagat cctttgaacc cctgcccatc   1200
agccctctg atgaccaggc catgggctac cagctgcttc aagagaccat acgatctgtc   1260
ttcccggaag tcgacatcgt cgtccccggt atttgtattg ccaatacgga cacccgacac   1320
tatgccaaca tcaccaatgg catgtaccgg ttcaacccc ttcccctgaa ccctcaggac   1380
ttcagtggtg tccatggaat caatgagaaa gtttccgttc agaactacca gaaccaggtg   1440
aagttcatct ttgagttcat ccaaaatgcc gacacttaca agagccagt tcctcatctg    1500
catgaactat ga                                                        1512

<210> SEQ ID NO 4
<211> LENGTH: 503
<212> TYPE: PRT
<213> ORGANISM: Mus musculus

<400> SEQUENCE: 4

Met Ala Glu Leu Leu Ala Ser Leu Pro Ala Trp Ala Ala Val Leu Leu
1               5                   10                  15

Leu Phe Phe Ala Thr Val Ser Gly Ser Thr Gly Pro Arg Ser Arg Glu
                20                  25                  30

Asn Arg Gly Ala Ser Arg Ile Pro Ser Gln Phe Ser Glu Glu Glu Arg
            35                  40                  45

Val Ala Ile Lys Glu Ala Leu Lys Gly Ala Ile Gln Ile Pro Thr Val
        50                  55                  60

Ser Phe Ser His Glu Glu Ser Asn Thr Thr Ala Leu Ala Glu Phe Gly
65                  70                  75                  80

Glu Tyr Ile Arg Lys Ala Phe Pro Thr Val Phe His Ser Ser Leu Val
                85                  90                  95

Gln His Glu Val Val Ala Lys Tyr Ser His Leu Phe Thr Ile Gln Gly
            100                 105                 110

Ser Asp Pro Ser Leu Gln Pro Tyr Met Leu Met Ala His Ile Asp Val
        115                 120                 125

Val Pro Ala Pro Glu Glu Gly Trp Glu Val Pro Phe Ser Gly Leu
        130                 135                 140

Glu Arg Asn Gly Phe Ile Tyr Gly Arg Gly Ala Leu Asp Asn Lys Asn
145                 150                 155                 160

Ser Val Met Ala Ile Leu His Ala Leu Glu Leu Leu Ile Arg Asn
                165                 170                 175
```

Tyr Ser Pro Lys Arg Ser Phe Phe Ile Ala Leu Gly His Asp Glu Glu
            180                 185                 190

Val Ser Gly Glu Lys Gly Ala Gln Lys Ile Ser Ala Leu Leu Gln Ala
        195                 200                 205

Arg Gly Val Gln Leu Ala Phe Leu Val Asp Glu Gly Ser Phe Ile Leu
210                 215                 220

Glu Gly Phe Ile Pro Asn Leu Glu Lys Pro Val Ala Met Ile Ser Val
225                 230                 235                 240

Thr Glu Lys Gly Ala Leu Asp Leu Met Leu Gln Val Asn Met Thr Pro
                245                 250                 255

Gly His Ser Ser Ala Pro Pro Lys Glu Thr Ser Ile Gly Ile Leu Ser
            260                 265                 270

Ala Ala Val Ser Arg Leu Glu Gln Thr Pro Met Pro Asn Met Phe Gly
        275                 280                 285

Gly Gly Pro Leu Lys Lys Thr Met Lys Leu Leu Ala Asn Glu Phe Ser
290                 295                 300

Phe Pro Ile Asn Ile Val Leu Arg Asn Leu Trp Leu Phe His Pro Ile
305                 310                 315                 320

Val Ser Arg Ile Met Glu Arg Asn Pro Ile Thr Asn Ala Leu Val Arg
                325                 330                 335

Thr Thr Thr Ala Leu Thr Met Phe Asn Ala Gly Ile Lys Val Asn Val
            340                 345                 350

Ile Pro Pro Leu Ala Gln Ala Thr Ile Asn Cys Arg Ile His Pro Ser
        355                 360                 365

Gln Thr Val His Glu Val Leu Glu Leu Val Lys Asn Thr Val Ala Asp
370                 375                 380

Asp Arg Val Gln Leu His Val Leu Arg Ser Phe Glu Pro Leu Pro Ile
385                 390                 395                 400

Ser Pro Ser Asp Asp Gln Ala Met Gly Tyr Gln Leu Leu Gln Glu Thr
                405                 410                 415

Ile Arg Ser Val Phe Pro Glu Val Asp Ile Val Pro Gly Ile Cys
            420                 425                 430

Ile Ala Asn Thr Asp Thr Arg His Tyr Ala Asn Ile Thr Asn Gly Met
        435                 440                 445

Tyr Arg Phe Asn Pro Leu Pro Leu Asn Pro Gln Asp Phe Ser Gly Val
450                 455                 460

His Gly Ile Asn Glu Lys Val Ser Val Gln Asn Tyr Gln Asn Gln Val
465                 470                 475                 480

Lys Phe Ile Phe Glu Phe Ile Gln Asn Ala Asp Thr Tyr Lys Glu Pro
                485                 490                 495

Val Pro His Leu His Glu Leu
            500

<210> SEQ ID NO 5
<211> LENGTH: 1509
<212> TYPE: DNA
<213> ORGANISM: Pan troglodytes

<400> SEQUENCE: 5
atggctcagc ggtgcgtttg cgtgctggcc ctggtggcta tgctgctcct agttttcccc      60
accgtctcca gatcgatggg cctgaggagc ggggagcatc aaagggcgtc gcgaatccct     120
tctcagttca gcaaagagga acgcgtcgcg atgaaagagg cgctgaaagg tgccatccag     180
attccaacag tgacttttag ctctgagaag tccaatacca cagccctggc tgagttcgga     240

-continued

```
aaatacattc ataaagtctt tcctacagtg gtcagcacca gctttatcca gcatgaagtt    300
gtggaagagt atagccacct gttcactatc caaggctcgg accccagctt gcagccctac    360
ttgctgatgg ctcactttga tgtggtgcct gcccctgaag aaggctggga ggtgccccca    420
ttctctgggt tggagcgtga tggcgtcatc tatggtcggg gcacactaga cgacaagaac    480
tctgtgatgg cattactgca ggccttggag ctcctgctga tcaggaagta catcccccaa    540
agatctttct tcatttctct gggccatgat gaggagtcgt cagggacagg ggctcagagg    600
atctcagccc tgctacagtc aaggggcgtc cagctagcct tcattgtgga cgaggggggc    660
ttcatcttgg atgatttcat tcctaacttc aagaagccca tcgccttgat tgcagtctca    720
gagaagggtt ccatgaacct catgctgcaa gtaaacatga cttcaggcca ctcttcagct    780
cctccaaagg agacgagcat tggcatcctt gcagctgctg tcagccgatt ggagcagaca    840
ccaatgccta tcatatttgg aagcgggaca ttggtgacgg tattgcagca actggcaaat    900
gagtttccct tccctgtcaa tataatcctg agcaacccat ggctatttga accacttata    960
agcaggttta tggagagaaa tcccttaacc aatgcaataa tcaggaccac cacggcactc   1020
accatattca aagcagggt caagttcaat gtcatccccc cggtggccca ggccacagtc   1080
aacttccgga ttcaccctgg acagacagtc caagaggtcc tagaactcac gaagaacatt   1140
gtggctgata cagagtcca gttccatgtg ttgagtgcct ttgaccccct ccccgtcagc   1200
ccttctgatg acaaggcctt gggctaccag ctgctccgcc agaccgtaca gtccgtcttc   1260
ccggaagtca atattactgc cccagttact tctattggca acacagacag ccgattcttt   1320
acaaacctca ccactggcat ctacaggttc taccccatct acatacagcc tgaagacttc   1380
aaacgcatcc atggagtcaa cgagaaaatc tcagtccaag cctatgagac ccaagtgaaa   1440
ttcatctttg agttgattca gaatgctgac acagaccagg agccagtttc tcacctgcac   1500
aaactgtga                                                          1509
```

<210> SEQ ID NO 6
<211> LENGTH: 502
<212> TYPE: PRT
<213> ORGANISM: Pan troglodytes

<400> SEQUENCE: 6

```
Met Ala Gln Arg Cys Val Cys Val Leu Ala Leu Val Ala Met Leu Leu
1               5                   10                  15

Leu Val Phe Pro Thr Val Ser Arg Ser Met Gly Leu Arg Ser Gly Glu
            20                  25                  30

His Gln Arg Ala Ser Arg Ile Pro Ser Gln Phe Ser Lys Glu Glu Arg
        35                  40                  45

Val Ala Met Lys Glu Ala Leu Lys Gly Ala Ile Gln Ile Pro Thr Val
    50                  55                  60

Thr Phe Ser Ser Glu Lys Ser Asn Thr Thr Ala Leu Ala Glu Phe Gly
65                  70                  75                  80

Lys Tyr Ile His Lys Val Phe Pro Thr Val Val Ser Thr Ser Phe Ile
                85                  90                  95

Gln His Glu Val Val Glu Glu Tyr Ser His Leu Phe Thr Ile Gln Gly
            100                 105                 110

Ser Asp Pro Ser Leu Gln Pro Tyr Leu Leu Met Ala His Phe Asp Val
        115                 120                 125

Val Pro Ala Pro Glu Glu Gly Trp Glu Val Pro Pro Phe Ser Gly Leu
    130                 135                 140
```

```
Glu Arg Asp Gly Val Ile Tyr Gly Arg Gly Thr Leu Asp Asp Lys Asn
145                 150                 155                 160

Ser Val Met Ala Leu Leu Gln Ala Leu Glu Leu Leu Ile Arg Lys
            165                 170                 175

Tyr Ile Pro Gln Arg Ser Phe Phe Ile Ser Leu Gly His Asp Glu Glu
            180                 185                 190

Ser Ser Gly Thr Gly Ala Gln Arg Ile Ser Ala Leu Leu Gln Ser Arg
            195                 200                 205

Gly Val Gln Leu Ala Phe Ile Val Asp Glu Gly Phe Ile Leu Asp
210                 215                 220

Asp Phe Ile Pro Asn Phe Lys Lys Pro Ile Ala Leu Ile Ala Val Ser
225                 230                 235                 240

Glu Lys Gly Ser Met Asn Leu Met Leu Gln Val Asn Met Thr Ser Gly
            245                 250                 255

His Ser Ser Ala Pro Pro Lys Glu Thr Ser Ile Gly Ile Leu Ala Ala
            260                 265                 270

Ala Val Ser Arg Leu Glu Gln Thr Pro Met Pro Ile Ile Phe Gly Ser
            275                 280                 285

Gly Thr Leu Val Thr Val Leu Gln Gln Leu Ala Asn Glu Phe Pro Phe
290                 295                 300

Pro Val Asn Ile Ile Leu Ser Asn Pro Trp Leu Phe Glu Pro Leu Ile
305                 310                 315                 320

Ser Arg Phe Met Glu Arg Asn Pro Leu Thr Asn Ala Ile Ile Arg Thr
            325                 330                 335

Thr Thr Ala Leu Thr Ile Phe Lys Ala Gly Val Lys Phe Asn Val Ile
            340                 345                 350

Pro Pro Val Ala Gln Ala Thr Val Asn Phe Arg Ile His Pro Gly Gln
            355                 360                 365

Thr Val Gln Glu Val Leu Glu Leu Thr Lys Asn Ile Val Ala Asp Asn
370                 375                 380

Arg Val Gln Phe His Val Leu Ser Ala Phe Asp Pro Leu Pro Val Ser
385                 390                 395                 400

Pro Ser Asp Asp Lys Ala Leu Gly Tyr Gln Leu Leu Arg Gln Thr Val
            405                 410                 415

Gln Ser Val Phe Pro Glu Val Asn Ile Thr Ala Pro Thr Ser Ile
            420                 425                 430

Gly Asn Thr Asp Ser Arg Phe Phe Thr Asn Leu Thr Thr Gly Ile Tyr
            435                 440                 445

Arg Phe Tyr Pro Ile Tyr Ile Gln Pro Glu Asp Phe Lys Arg Ile His
            450                 455                 460

Gly Val Asn Glu Lys Ile Ser Val Gln Ala Tyr Glu Thr Gln Val Lys
465                 470                 475                 480

Phe Ile Phe Glu Leu Ile Gln Asn Ala Asp Thr Asp Gln Glu Pro Val
            485                 490                 495

Ser His Leu His Lys Leu
            500

<210> SEQ ID NO 7
<211> LENGTH: 1512
<212> TYPE: DNA
<213> ORGANISM: Bos taurus

<400> SEQUENCE: 7
atggctcggc cgtccgtctg cctgctggcc tcgctgtctg cgctgctcct aggtatcgcc    60
```

```
gccgtctcca gatcgaaggg cctgcggggc acggagagtc aaagggagcc gcgaatccct    120
tctcagttca gccaagagca gcgcatcgcc atgaaggaag cgctcaaagg tgccatccag    180
attccaacag tgtctttcag ccccaaggag ctcaacacaa cagccctggc tgagtttgga    240
gaatacattc gtaaagtctt tcctactgtg ttccatacca gctttatccg gcatgaggtc    300
gtaggaaatt acagccacct gttcactatc aaaggctcag accccagcat gcagccctac    360
attctcctcg ctcacattga cgtggtgcct gccccggaca aaggctggga cgtgccccc     420 ttctctgggt tggagcgtga tggcttcatc tatggtcgag gcacactgga caacaagaac    480
tatcttatgg caatcctgca ggccttggag cttctgctga tcagaaacta catccccga     540 agatctttct tcattgctct gggccatgat gaggagatat cagggataaa cggggctcag    600
aagatctcag ccctgctaca ggcaagggg gtccagctag ccttcgtggt ggatgagggg    660
agcttcatct tggacggttt cattccctac ctcaagaagc cctttgccat ggtttccgtt    720
tctgagaagg gtgcgattaa cctcatgctg caagtcaaca cgactacagg ccactcttca    780
gctcctccaa agaaacaag cataggcatt ctcgcagccg cagtcagccg actggagcag    840
acaccaatgc cgaacatgtt tggaagtggg ccattgatga cggcagtgga gcaactggca    900
aatgagtttc ccttccctac caatatagtc ttgaacaacc tgtggctctt cgaccccttt    960
gtaagcaggt tgatggagag gaattacata accaattcgc tggtcaggac acaacggcg   1020 ctcaccatgt tcaatgccgg ggtcaaggtg aatgtcatcc ccctgtggc cgaggccatc   1080 atcaacttcc gacttcaccc tgcacagact gttcaggagg ttctaaaatt agccaaggac   1140
attgtggctg atgaccgcat ccagttccat gtgttggatg cctttgaccc cctgcccatc   1200
agcccttctg atgatcaggc cttgggttac cagctgctcc gccagaccat acactctgtc   1260
ttcccggaag tcaacattgt tgccccaggt acttgtattg caacacaga cagcagacac   1320 tatctgaatc ttaccactgg catctaccgg ttcaacccca tctacctaca acctcaggac   1380
ttcagtagca tccacggaat caatgagaaa atctcggtcc aagcctacga gacccaggtg   1440
aaattcgtct tcgagtttat ccagaatggt gacacagacg aggagacagt tcctcacctg   1500
catgaactgt ga                                                       1512

<210> SEQ ID NO 8
<211> LENGTH: 503
<212> TYPE: PRT
<213> ORGANISM: Bos taurus

<400> SEQUENCE: 8

Met Ala Arg Pro Ser Val Cys Leu Leu Ala Ser Leu Ser Ala Leu Leu
1               5                   10                  15

Leu Gly Ile Ala Ala Val Ser Arg Ser Lys Gly Leu Arg Gly Thr Glu
            20                  25                  30

Ser Gln Arg Glu Pro Arg Ile Pro Ser Gln Phe Ser Gln Glu Gln Arg
        35                  40                  45

Ile Ala Met Lys Glu Ala Leu Lys Gly Ala Ile Gln Ile Pro Thr Val
    50                  55                  60

Ser Phe Ser Pro Lys Glu Leu Asn Thr Thr Ala Leu Ala Glu Phe Gly
65                  70                  75                  80

Glu Tyr Ile Arg Lys Val Phe Pro Thr Val Phe His Thr Ser Phe Ile
                85                  90                  95

Arg His Glu Val Val Gly Asn Tyr Ser His Leu Phe Thr Ile Lys Gly
            100                 105                 110
```

Ser Asp Pro Ser Met Gln Pro Tyr Ile Leu Leu Ala His Ile Asp Val
        115                 120                 125

Val Pro Ala Pro Asp Lys Gly Trp Asp Val Pro Phe Ser Gly Leu
    130                 135                 140

Glu Arg Asp Gly Phe Ile Tyr Gly Arg Gly Thr Leu Asp Asn Lys Asn
145                 150                 155                 160

Tyr Leu Met Ala Ile Leu Gln Ala Leu Glu Leu Leu Ile Arg Asn
                165                 170                 175

Tyr Ile Pro Arg Arg Ser Phe Phe Ile Ala Leu Gly His Asp Glu Glu
                180                 185                 190

Ile Ser Gly Ile Asn Gly Ala Gln Lys Ile Ser Ala Leu Leu Gln Ala
        195                 200                 205

Arg Gly Val Gln Leu Ala Phe Val Asp Glu Gly Ser Phe Ile Leu
        210                 215                 220

Asp Gly Phe Ile Pro Tyr Leu Lys Lys Pro Phe Ala Met Val Ser Val
225                 230                 235                 240

Ser Glu Lys Gly Ala Ile Asn Leu Met Leu Gln Val Asn Thr Thr Thr
                245                 250                 255

Gly His Ser Ser Ala Pro Pro Lys Glu Thr Ser Ile Gly Ile Leu Ala
            260                 265                 270

Ala Ala Val Ser Arg Leu Glu Gln Thr Pro Met Pro Asn Met Phe Gly
        275                 280                 285

Ser Gly Pro Leu Met Thr Ala Val Glu Gln Leu Ala Asn Glu Phe Pro
    290                 295                 300

Phe Pro Thr Asn Ile Val Leu Asn Asn Leu Trp Leu Phe Arg Pro Leu
305                 310                 315                 320

Val Ser Arg Leu Met Glu Arg Asn Tyr Ile Thr Asn Ser Leu Val Arg
                325                 330                 335

Thr Thr Thr Ala Leu Thr Met Phe Asn Ala Gly Val Lys Val Asn Val
            340                 345                 350

Ile Pro Pro Val Ala Glu Ala Ile Ile Asn Phe Arg Leu His Pro Ala
        355                 360                 365

Gln Thr Val Gln Glu Val Leu Lys Leu Ala Lys Asp Ile Val Ala Asp
    370                 375                 380

Asp Arg Ile Gln Phe His Val Leu Asp Ala Phe Asp Pro Leu Pro Ile
385                 390                 395                 400

Ser Pro Ser Asp Asp Gln Ala Leu Gly Tyr Gln Leu Leu Arg Gln Thr
                405                 410                 415

Ile His Ser Val Phe Pro Glu Val Asn Ile Val Ala Pro Gly Thr Cys
            420                 425                 430

Ile Gly Asn Thr Asp Ser Arg His Tyr Leu Asn Leu Thr Thr Gly Ile
        435                 440                 445

Tyr Arg Phe Asn Pro Ile Tyr Leu Gln Pro Gln Asp Phe Ser Ser Ile
    450                 455                 460

His Gly Ile Asn Glu Lys Ile Ser Val Gln Ala Tyr Glu Thr Gln Val
465                 470                 475                 480

Lys Phe Val Phe Glu Phe Ile Gln Asn Gly Asp Thr Asp Glu Glu Thr
                485                 490                 495

Val Pro His Leu His Glu Leu
            500

<210> SEQ ID NO 9
<211> LENGTH: 1512

```
<212> TYPE: DNA
<213> ORGANISM: Rattus norvegicus

<400> SEQUENCE: 9
atggctgagc tacttgttat cttgcccacc cgggcagctg tgctccttct ctttttcgct      60
accgtctcag gatccacggg ccctggcagc agggaaagtc gaggatcgtc gcggatccct     120
tcccagttca gcgaggagga gcgcgtcgct atgaagagg cgctgaaagg tgccatccgg      180
attcccacag tgtctttcag ccacgaggaa tccaacacca cagcccttgc tgagtttgga     240
gaatatatcc gaaaagcctt tcctacagtg ttccacagca accttatcca cacgaagtc      300
gtggggaagt atagccacct gctcaccgtc cgaggctcgg accccagttt gcagccctac     360
atgctgatgg ctcacttcga cgtggttcct gcctctgaag aaggatggga ggtgcccccg     420
ttctcaggcc tggagcaaaa tggcttcatc catggccggg gtgcgctgga caacaaaaac     480
tctgtgatgg cagtcctgca ggctttggag ctcctgttga tcagaaaata cagccccaaa     540
agacctttct tcattgcttt gggccatgat gaggaggtgt ctgggacaaa gggggctcag     600
cagatctcag cactcttaca gacgaggggt gtccagctag cttttcttgt ggatgaaggg     660
agctttatct tggaagactt cattccgaac ctcaagaagc cgtttgccat gatttcagtc     720
accgagaagg gtgcccttga cctcatgctg caagtaaaca tgactccagg ccactcttca     780
gctcccccaa aggagacaag cattggaatc ctttctgccg ctgtcagccg actggagcag     840
acaccaatgc caaacatgtt tggaaacggg ccattgaaga gacattgaa gctactggca      900
aatgagtttt ccttccctac caatataatc ttggggaacc tgtggctatt ccgtcccatt     960
gtaagcaggg taatggagag gaatcccata cgaatgcat tggtcagaac taccacagcc     1020
ctcaccatgt tcaatgcagg aatcaaggtg aatgtcatcc ccccattggc tcaggcgaca    1080
gtcaacttcc gaattcaccc ttcgcagaca gtacacgagg tcgtagaact cgtccagaac    1140
attgtggctg atgaccgagt ccagttgcat gtgttgagat cctttgaacc actgcccgtc    1200
agcccctctg atgaccaggc catgggctac cagctgcttc aacagaccat acagtctgtc    1260
ttcccggaag tcaagatcat tgtccccggt atttgtattg caacacggga cacccgacac    1320
tatgtcaacc tgaccaatgg cttgtaccgg ttcaaccccg ttttcctgaa gcctcaggac    1380
ttcagtagtg tccatggaat caatgagaaa atctccgttg agagctacca gaaccaggtg    1440
aagttcatct tgagttgat ccaaaatgct gacacctaca gcaagccagt tcctcatcag     1500
catgaactat ga                                                       1512

<210> SEQ ID NO 10
<211> LENGTH: 503
<212> TYPE: PRT
<213> ORGANISM: Rattus norvegicus

<400> SEQUENCE: 10

Met Ala Glu Leu Leu Val Ile Leu Pro Thr Arg Ala Ala Val Leu Leu
1               5                   10                  15

Leu Phe Phe Ala Thr Val Ser Gly Ser Thr Gly Pro Gly Ser Arg Glu
                20                  25                  30

Ser Arg Gly Ser Ser Arg Ile Pro Ser Gln Phe Ser Glu Glu Glu Arg
            35                  40                  45

Val Ala Met Lys Glu Ala Leu Lys Gly Ala Ile Arg Ile Pro Thr Val
        50                  55                  60

Ser Phe Ser His Glu Glu Ser Asn Thr Thr Ala Leu Ala Glu Phe Gly
65                  70                  75                  80
```

-continued

```
Glu Tyr Ile Arg Lys Ala Phe Pro Thr Val Phe His Ser Asn Leu Ile
                 85                  90                  95
Gln His Glu Val Val Gly Lys Tyr Ser His Leu Leu Thr Val Arg Gly
                100                 105                 110
Ser Asp Pro Ser Leu Gln Pro Tyr Met Leu Met Ala His Phe Asp Val
                115                 120                 125
Val Pro Ala Ser Glu Glu Gly Trp Glu Val Pro Pro Phe Ser Gly Leu
            130                 135                 140
Glu Gln Asn Gly Phe Ile His Gly Arg Gly Ala Leu Asp Asn Lys Asn
145                 150                 155                 160
Ser Val Met Ala Val Leu Gln Ala Leu Glu Leu Leu Ile Arg Lys
                165                 170                 175
Tyr Ser Pro Lys Arg Pro Phe Phe Ile Ala Leu Gly His Asp Glu Glu
                180                 185                 190
Val Ser Gly Thr Lys Gly Ala Gln Gln Ile Ser Ala Leu Leu Gln Thr
            195                 200                 205
Arg Gly Val Gln Leu Ala Phe Leu Val Asp Glu Gly Ser Phe Ile Leu
            210                 215                 220
Glu Asp Phe Ile Pro Asn Leu Lys Lys Pro Phe Ala Met Ile Ser Val
225                 230                 235                 240
Thr Glu Lys Gly Ala Leu Asp Leu Met Leu Gln Val Asn Met Thr Pro
                245                 250                 255
Gly His Ser Ser Ala Pro Pro Lys Glu Thr Ser Ile Gly Ile Leu Ser
                260                 265                 270
Ala Ala Val Ser Arg Leu Glu Gln Thr Pro Met Pro Asn Met Phe Gly
            275                 280                 285
Asn Gly Pro Leu Lys Lys Thr Leu Lys Leu Leu Ala Asn Glu Phe Ser
            290                 295                 300
Phe Pro Thr Asn Ile Ile Leu Gly Asn Leu Trp Leu Phe Arg Pro Ile
305                 310                 315                 320
Val Ser Arg Val Met Glu Arg Asn Pro Ile Thr Asn Ala Leu Val Arg
                325                 330                 335
Thr Thr Thr Ala Leu Thr Met Phe Asn Ala Gly Ile Lys Val Asn Val
                340                 345                 350
Ile Pro Pro Leu Ala Gln Ala Thr Val Asn Phe Arg Ile His Pro Ser
            355                 360                 365
Gln Thr Val His Glu Val Val Glu Leu Val Gln Asn Ile Val Ala Asp
            370                 375                 380
Asp Arg Val Gln Leu His Val Leu Arg Ser Phe Glu Pro Leu Pro Val
385                 390                 395                 400
Ser Pro Ser Asp Asp Gln Ala Met Gly Tyr Gln Leu Leu Gln Gln Thr
                405                 410                 415
Ile Gln Ser Val Phe Pro Glu Val Lys Ile Val Pro Gly Ile Cys
                420                 425                 430
Ile Gly Asn Thr Asp Thr Arg His Tyr Val Asn Leu Thr Asn Gly Leu
            435                 440                 445
Tyr Arg Phe Asn Pro Val Phe Leu Lys Pro Gln Asp Phe Ser Ser Val
450                 455                 460
His Gly Ile Asn Glu Lys Ile Ser Val Glu Ser Tyr Gln Asn Gln Val
465                 470                 475                 480
Lys Phe Ile Phe Glu Leu Ile Gln Asn Ala Asp Thr Tyr Ser Lys Pro
                485                 490                 495
```

Val Pro His Gln His Glu Leu
        500

<210> SEQ ID NO 11
<211> LENGTH: 1554
<212> TYPE: DNA
<213> ORGANISM: Gallus gallus

<400> SEQUENCE: 11

| | | | | | |
|---|---|---|---|---|---|
| atggcgggtg | ggtgcgggcg | gcggcgggta | gttgtgtgcg | cggtggcgtt | ggggctgagc | 60 |
| gcggcggtgc | tggctctaac | ggccgtagtg | ttgctccgcg | cctacgtgct | gcgctccccg | 120 |
| gccatcccgc | ggctgtgggc | gcggcgcggg | agcaccgccg | ctttcagtgc | cagcgagagg | 180 |
| cgggagctga | aggaagcgct | gcgaggtgct | gttcgaatcc | cgactgtttc | cttgtcttcg | 240 |
| gaggacttca | cacaactgc | catggcagag | tttggggatt | acattcggaa | agccttccca | 300 |
| gctgtctttt | cttccaagtt | cattcaacat | gaaatcattg | gggagtacag | ccacctcttc | 360 |
| accgttcagg | gttctgactc | tgaaatgatg | ccctacatgc | tgctcgcaca | catggatgtt | 420 |
| gtgcccgctc | ccctgaggg | ctgggatttc | cctcctttct | cagctgcaga | gcatgaaggt | 480 |
| ttcatctatg | gacgaggaac | gctggacaac | aaaaactctg | ccattggcat | ctgcaagct | 540 |
| ctagaattct | tactgagaag | aaattacaga | ccccgcaggt | ctttctatgt | tggcattggc | 600 |
| catgatgaag | aggtgtttgg | tcagaaggga | gcactgaaga | ttgcagctct | gctgaatcc | 660 |
| agaggagtga | aactctcctt | cttgctggat | gagggaagtg | ctatactgga | tggcatcatt | 720 |
| gcaggtgtga | agaagccagt | agctctaatt | gctgtgacag | agaagggttt | aatgacactg | 780 |
| aacttcaccg | tggaaaaaga | gccaggacat | tcatccttcc | ctccaaaaga | gacaagtatt | 840 |
| ggcattcttg | caacagcagt | gtccagactg | gagcagaatc | ccatgcgcag | tctgtttggc | 900 |
| cgtggtccgg | aactcatgac | tatggagcac | cttgcatcag | agttcaattt | tcctctcaat | 960 |
| ctcatcatga | gcaatctctg | gctgttttcg | cctattgtca | gcagagttct | tgcctggaaa | 1020 |
| ccttccacta | atgccttgat | tcgaactact | acagcagtca | caatgtttaa | cgcaggaatc | 1080 |
| aagttcaatg | tcatcccacc | atctgcaaga | gcaactgtga | acttccggat | ccactctgga | 1140 |
| gagaaggcca | agaggtgct | agagacagtt | agaaacacag | ttgcggatga | cagagtgaag | 1200 |
| attgatgtca | tagaggccct | tgaccccca | cccatcagcc | catgggatga | ccagaccttt | 1260 |
| ggagtccatg | tttttcaaag | aaccattctg | gatactttcc | caaatgttga | cagtgtagtc | 1320 |
| ccaggcacgt | gtattggaaa | cacagacagc | aggcatttca | ctaacgtcac | aaatgccatt | 1380 |
| tatcgattta | acccagtgct | cttgaagtca | gatgatcttc | ccaggatcca | tgggttgaat | 1440 |
| gagagaatct | cggttgagag | ttatgagaaa | caggtcgagt | ttctctttca | gctcattaag | 1500 |
| aactgtgatg | ttgacaagct | tccggagcct | cacgcaaact | ctcatgagct | gtga | 1554 |

<210> SEQ ID NO 12
<211> LENGTH: 517
<212> TYPE: PRT
<213> ORGANISM: Gallus gallus

<400> SEQUENCE: 12

Met Ala Gly Gly Cys Gly Arg Arg Val Val Val Cys Ala Val Ala
1               5                   10                  15

Leu Gly Leu Ser Ala Ala Val Leu Ala Leu Thr Ala Val Val Leu Leu
                20                  25                  30

Arg Ala Tyr Val Leu Arg Ser Pro Ala Ile Pro Arg Leu Trp Ala Arg
            35                  40                  45

```
Arg Gly Ser Thr Ala Ala Phe Ser Ala Ser Glu Arg Glu Leu Lys
 50                  55                  60

Glu Ala Leu Arg Gly Ala Val Arg Ile Pro Thr Val Ser Leu Ser Ser
 65                  70                  75                  80

Glu Asp Phe Asn Thr Thr Ala Met Ala Glu Phe Gly Asp Tyr Ile Arg
                 85                  90                  95

Lys Ala Phe Pro Ala Val Phe Ser Ser Lys Phe Ile Gln His Glu Ile
                100                 105                 110

Ile Gly Glu Tyr Ser His Leu Phe Thr Val Gln Gly Ser Asp Ser Glu
            115                 120                 125

Met Met Pro Tyr Met Leu Leu Ala His Met Asp Val Val Pro Ala Pro
130                 135                 140

Pro Glu Gly Trp Asp Phe Pro Pro Phe Ser Ala Ala Glu His Glu Gly
145                 150                 155                 160

Phe Ile Tyr Gly Arg Gly Thr Leu Asp Asn Lys Asn Ser Ala Ile Gly
                165                 170                 175

Ile Leu Gln Ala Leu Glu Phe Leu Leu Arg Arg Asn Tyr Arg Pro Arg
            180                 185                 190

Arg Ser Phe Tyr Val Gly Ile Gly His Asp Glu Glu Val Phe Gly Gln
        195                 200                 205

Lys Gly Ala Leu Lys Ile Ala Ala Leu Leu Glu Ser Arg Gly Val Lys
210                 215                 220

Leu Ser Phe Leu Leu Asp Glu Gly Ser Ala Ile Leu Asp Gly Ile Ile
225                 230                 235                 240

Ala Gly Val Lys Lys Pro Val Ala Leu Ile Ala Val Thr Glu Lys Gly
                245                 250                 255

Leu Met Thr Leu Asn Phe Thr Val Glu Lys Glu Pro Gly His Ser Ser
            260                 265                 270

Phe Pro Pro Lys Glu Thr Ser Ile Gly Ile Leu Ala Thr Ala Val Ser
        275                 280                 285

Arg Leu Glu Gln Asn Pro Met Arg Ser Leu Phe Gly Arg Gly Pro Glu
290                 295                 300

Leu Met Thr Met Glu His Leu Ala Ser Glu Phe Asn Phe Pro Leu Asn
305                 310                 315                 320

Leu Ile Met Ser Asn Leu Trp Leu Phe Ser Pro Ile Val Ser Arg Val
                325                 330                 335

Leu Ala Trp Lys Pro Ser Thr Asn Ala Leu Ile Arg Thr Thr Thr Ala
            340                 345                 350

Val Thr Met Phe Asn Ala Gly Ile Lys Phe Asn Val Ile Pro Pro Ser
        355                 360                 365

Ala Arg Ala Thr Val Asn Phe Arg Ile His Ser Gly Glu Lys Ala Lys
370                 375                 380

Glu Val Leu Glu Thr Val Arg Asn Thr Val Ala Asp Arg Val Lys
385                 390                 395                 400

Ile Asp Val Ile Glu Ala Leu Asp Pro Leu Pro Ile Ser Pro Trp Asp
                405                 410                 415

Asp Gln Thr Phe Gly Val His Val Phe Gln Arg Thr Ile Leu Asp Thr
            420                 425                 430

Phe Pro Asn Val Asp Ser Val Val Pro Gly Thr Cys Ile Gly Asn Thr
        435                 440                 445

Asp Ser Arg His Phe Thr Asn Val Thr Asn Ala Ile Tyr Arg Phe Asn
450                 455                 460
```

Pro Val Leu Leu Lys Ser Asp Asp Leu Pro Arg Ile His Gly Leu Asn
465                 470                 475                 480

Glu Arg Ile Ser Val Glu Ser Tyr Glu Lys Gln Val Glu Phe Leu Phe
            485                 490                 495

Gln Leu Ile Lys Asn Cys Asp Val Asp Lys Leu Pro Glu Pro His Ala
        500                 505                 510

Asn Ser His Glu Leu
        515

<210> SEQ ID NO 13
<211> LENGTH: 1539
<212> TYPE: DNA
<213> ORGANISM: Xenopus laevis

<400> SEQUENCE: 13

```
atggcagtat ctcgctggaa ggctgtgggc agcactctgc ttgctgcgtt tttagtgggg      60
ctggtagtgc ttatagccgt tttgctcatc agaacttaca ctttgcctac agcggtcagg     120
aagtggaata ggaatgaaag tctgatcact gaacttgctg agaaagagag aaagcagctg     180
gtggaggcac tgaaaggtgc cattcgcatt cccactgtct cctttcaga agaggagcag      240
aataccacag cactcagaga gtttggagaa tacatacaga aagtcttccc tcaggttttc     300
tcctccagtc taatccagca tgaggttttg ggaggttaca gtcacctttt taaagtacaa     360
ggctctgacc acaatctact ccatacatg ttactggctc acattgatgt tgtaccagct      420
ccaccagagt cctgggaggt gccacctttc tctggcgagg aacgagatgg ttatatctat     480
ggaagaggaa ccctagatga caagaactgt gttattggaa ttcttcagtc acttgaattc     540
ctcctgaaaa gaggtcacaa acctcgccga tctttctaca taggccttgg acatgatgaa     600
gagatatctg gccacaaagg tgcccagaag attgtggaga gttgcagtc tcaaggagtt      660
aagctggcat ttgttttaga tgagggcttg gcagtcctag atggggttat tcaaggcatt     720
agtcaacctg tcgcactggt tggtaccaca gaaaaaggat cagttacctt ggacctcaca     780
gtaaatcgtt tacctggtca ttcttctatg ccgccgtctg aaaccagcat gggatccta     840
gctgcagctg tgtctagact agagcagaat atgatgccta atatgtttgg aaatggtcca     900
gaacaagaca tgtttgaaca tcttttctaca aagtttgact ttccactaaa tattatcatg     960
gcaaatctat ggctattttc acccatttta agcagaattc tggagctgtc gccttccacc    1020
aatgccatag tacggacaac aactgctctt accatcttca aagcagggat caagtcaaat    1080
gtgatcccac ctacagccac agcaactgtt aatttccggc ttcaccctgc acagacggta    1140
caagaggtcc tggatattgt tcagaacact ataaaggatg aaagagtgga gctatctgtc    1200
ttgaattcat tcgatccttt accagtcagt ccgaatgata tgagtttggg gtaccatatt    1260
cttcagcgta ccattcatga tgtctttttca ggacctccag ttgccccagg tgtttgtgtt    1320
ggcaatacag acagccgcca tttgtcaac ttgaccaaca gtatctacag atttagccct     1380
gtggtgctca aaaaggagga tgtggatagg attcatgggt gaatgagcg catttctaaa    1440
gaggcaattg aactccttgt ccagttctac atccagctga ttcaaaattc agatacagat    1500
aacatccctc caccacatct tgacacccat gagctttaa                           1539
```

<210> SEQ ID NO 14
<211> LENGTH: 512
<212> TYPE: PRT
<213> ORGANISM: Xenopus laevis

<400> SEQUENCE: 14

-continued

```
Met Ala Val Ser Arg Trp Lys Ala Val Gly Ser Thr Leu Leu Ala Ala
1               5                   10                  15
Phe Leu Val Gly Leu Val Leu Ile Ala Val Leu Leu Ile Arg Thr
            20                  25                  30
Tyr Thr Leu Pro Thr Ala Val Arg Lys Trp Asn Arg Asn Glu Ser Leu
            35                  40                  45
Ile Thr Glu Leu Ala Glu Lys Glu Arg Lys Gln Leu Val Glu Ala Leu
    50                  55                  60
Lys Gly Ala Ile Arg Ile Pro Thr Val Ser Phe Ser Glu Glu Glu Gln
65                  70                  75                  80
Asn Thr Thr Ala Leu Arg Glu Phe Gly Glu Tyr Ile Gln Lys Val Phe
                85                  90                  95
Pro Gln Val Phe Ser Ser Leu Ile Gln His Glu Val Leu Gly Gly
            100                 105                 110
Tyr Ser His Leu Phe Lys Val Gln Gly Ser Asp His Asn Leu Leu Pro
            115                 120                 125
Tyr Met Leu Leu Ala His Ile Asp Val Val Pro Ala Pro Pro Glu Ser
    130                 135                 140
Trp Glu Val Pro Pro Phe Ser Gly Glu Glu Arg Asp Gly Tyr Ile Tyr
145                 150                 155                 160
Gly Arg Gly Thr Leu Asp Asp Lys Asn Cys Val Ile Gly Ile Leu Gln
                165                 170                 175
Ser Leu Glu Phe Leu Leu Lys Arg Gly His Lys Pro Arg Arg Ser Phe
            180                 185                 190
Tyr Ile Gly Leu Gly His Asp Glu Glu Ile Ser Gly His Lys Gly Ala
            195                 200                 205
Gln Lys Ile Val Glu Lys Leu Gln Ser Gln Gly Val Lys Leu Ala Phe
    210                 215                 220
Val Leu Asp Glu Gly Leu Ala Val Leu Asp Gly Val Ile Gln Gly Ile
225                 230                 235                 240
Ser Gln Pro Val Ala Leu Val Gly Thr Thr Glu Lys Gly Ser Val Thr
                245                 250                 255
Leu Asp Leu Thr Val Asn Arg Leu Pro Gly His Ser Ser Met Pro Pro
            260                 265                 270
Ser Glu Thr Ser Ile Gly Ile Leu Ala Ala Val Ser Arg Leu Glu
            275                 280                 285
Gln Asn Met Met Pro Asn Met Phe Gly Asn Gly Pro Glu Gln Asp Met
    290                 295                 300
Phe Glu His Leu Ser Thr Lys Phe Asp Phe Pro Leu Asn Ile Ile Met
305                 310                 315                 320
Ala Asn Leu Trp Leu Phe Ser Pro Ile Leu Ser Arg Ile Leu Glu Leu
                325                 330                 335
Ser Pro Ser Thr Asn Ala Ile Val Arg Thr Thr Thr Ala Leu Thr Ile
            340                 345                 350
Phe Lys Ala Gly Ile Lys Ser Asn Val Ile Pro Pro Thr Ala Thr Ala
            355                 360                 365
Thr Val Asn Phe Arg Leu His Pro Ala Gln Thr Val Gln Glu Val Leu
    370                 375                 380
Asp Ile Val Gln Asn Thr Ile Lys Asp Glu Arg Val Glu Leu Ser Val
385                 390                 395                 400
Leu Asn Ser Phe Asp Pro Leu Pro Val Ser Pro Asn Asp Met Ser Leu
                405                 410                 415
```

Gly Tyr His Ile Leu Gln Arg Thr Ile His Asp Val Phe Ser Gly Pro
            420                 425                 430

Pro Val Ala Pro Gly Val Cys Val Gly Asn Thr Asp Ser Arg His Phe
        435                 440                 445

Val Asn Leu Thr Asn Ser Ile Tyr Arg Phe Ser Pro Val Val Leu Lys
    450                 455                 460

Lys Glu Asp Val Asp Arg Ile His Gly Leu Asn Glu Arg Ile Ser Lys
465                 470                 475                 480

Glu Ala Ile Glu Leu Leu Val Gln Phe Tyr Ile Gln Leu Ile Gln Asn
                485                 490                 495

Ser Asp Thr Asp Asn Ile Pro Pro His Leu Asp Thr His Glu Leu
            500                 505                 510

<210> SEQ ID NO 15
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 15
acccttcacc aatgactcct atg                                             23

<210> SEQ ID NO 16
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 16
tgactgcagc aaatcgcttg g                                               21

<210> SEQ ID NO 17
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 17
aaggtgaaga gcatcataac cct                                             23

<210> SEQ ID NO 18
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 18
tcacgccttt cataacacat tcc                                             23

<210> SEQ ID NO 19
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

-continued

```
<400> SEQUENCE: 19
actgccacac ctccagtcat t                                              21

<210> SEQ ID NO 20
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 20
ctttgcctca ctcaggattg g                                              21

<210> SEQ ID NO 21
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 21
ccctgccatt gttaagacc                                                 19

<210> SEQ ID NO 22
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 22
tgctgctgtt cctgttttc                                                 19

<210> SEQ ID NO 23
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 23
gccgactaaa tcaagcaaca                                                20

<210> SEQ ID NO 24
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 24
caatgggcat aaagctatgg                                                20

<210> SEQ ID NO 25
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 25
```
gcacatggga gtgttgtga                                               19

<210> SEQ ID NO 26
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 26
ccttctcctt ctccttcagc                                              20

<210> SEQ ID NO 27
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 27
caagagcatc ccaggctt                                                18

<210> SEQ ID NO 28
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 28
gcacttccat ccacacactc                                              20

<210> SEQ ID NO 29
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 29
tgaggagacc tatgaggtat ttgc                                         24

<210> SEQ ID NO 30
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 30
tcatcaaagt agccagaacg ga                                           22

<210> SEQ ID NO 31
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 31

```
gcatggtggc tggtgatgag                                              20

<210> SEQ ID NO 32
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 32
aaactgcccg tgagtaatct tg                                           22

<210> SEQ ID NO 33
<211> LENGTH: 38
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 33
gcaggaacca catcaatggc agccatcagc atgtaggg                          38

<210> SEQ ID NO 34
<211> LENGTH: 38
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 34
ccctacatgc tgatggctgc cattgatgtg gttcctgc                          38

<210> SEQ ID NO 35
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 35
ggggcaggaa ccacagcaat gtgagccatc a                                 31

<210> SEQ ID NO 36
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 36
tgatggctca cattgctgtg gttcctgccc c                                 31

<210> SEQ ID NO 37
<211> LENGTH: 42
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 37
aaactttctc attgattcca gcgacaccac tgaagtcctg ag                     42
```

```
<210> SEQ ID NO 38
<211> LENGTH: 42
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 38
ctcaggactt cagtggtgtc gctggaatca atgagaaagt tt                          42

<210> SEQ ID NO 39
<211> LENGTH: 12
<212> TYPE: PRT
<213> ORGANISM: Artificial Sequence
<220> FEATURE:
<223> OTHER INFORMATION: /note="Description of Artificial Sequence:
      PM20D1 tryptic peptide sequence"

<400> SEQUENCE: 39

Arg Ile Pro Ser Gln Phe Ser Glu Glu Glu Arg Val
1               5                   10

<210> SEQ ID NO 40
<211> LENGTH: 13
<212> TYPE: PRT
<213> ORGANISM: Artificial Sequence
<220> FEATURE:
<223> OTHER INFORMATION: /note="Description of Artificial Sequence:
      PM20D1 tryptic peptide sequence"

<400> SEQUENCE: 40

Arg Asn Leu Trp Leu Phe His Pro Ile Val Ser Arg Ile
1               5                   10

<210> SEQ ID NO 41
<211> LENGTH: 138
<212> TYPE: DNA
<213> ORGANISM: Mus musculus

<400> SEQUENCE: 41
atggctgagc tacttgctag cttgcccgcc tgggcagctg tgctccttct cttttttcgct      60 acggtctccg gatccactgg ccctagaagc agggaaaatc ggggggcgtc ccggatccct      120
tcccagttca gcgaggag                                                    138

<210> SEQ ID NO 42
<211> LENGTH: 46
<212> TYPE: PRT
<213> ORGANISM: Mus musculus

<400> SEQUENCE: 42

Met Ala Glu Leu Leu Ala Ser Leu Pro Ala Trp Ala Ala Val Leu Leu
1               5                   10                  15

Leu Phe Phe Ala Thr Val Ser Gly Ser Thr Gly Pro Arg Ser Arg Glu
                20                  25                  30

Asn Arg Gly Ala Ser Arg Ile Pro Ser Gln Phe Ser Glu Glu
            35                  40                  45

<210> SEQ ID NO 43
<211> LENGTH: 132
<212> TYPE: DNA
<213> ORGANISM: Artificial Sequence
<220> FEATURE:
```

```
<223> OTHER INFORMATION: /note="Description of Artificial Sequence:
      Synthetic mouse PM20D1 knockout nucleic acid sequence"

<400> SEQUENCE: 43
atggctgagc tacttgctag cttgcccgcc tgggcagctg tgctccttct cttttcgct      60 acggtctccg gatccactgg ccctagaagc agggaaaatc gggggcgtc ccggatccct     120 tcccagtagg ag                                                        132

<210> SEQ ID NO 44
<211> LENGTH: 42
<212> TYPE: PRT
<213> ORGANISM: Artificial Sequence
<220> FEATURE:
<223> OTHER INFORMATION: /note="Description of Artificial Sequence:
      Synthetic mouse PM20D1 knockout protein sequence"

<400> SEQUENCE: 44

Met Ala Glu Leu Leu Ala Ser Leu Pro Ala Trp Ala Ala Val Leu Leu
1               5                   10                  15

Leu Phe Phe Ala Thr Val Ser Gly Ser Thr Gly Pro Arg Ser Arg Glu
            20                  25                  30

Asn Arg Gly Ala Ser Arg Ile Pro Ser Gln
        35                  40
```